(12) United States Patent
Deutsch et al.

(10) Patent No.: US 12,002,566 B2
(45) Date of Patent: Jun. 4, 2024

(54) ATTACHMENT SYSTEM FOR MOUNTING APPARATUS

(71) Applicant: Smith & Nephew, Inc., Memphis, TN (US)

(72) Inventors: Kealoha Young Deutsch, Odessa, FL (US); William W. Gregory, Gainesville, FL (US); Kory A. Gunnerson, Cincinnati, OH (US); Kathryn Ann Leigh, Saint Petersburg, FL (US); Andrew P. Muser, Saint Pete Beach, FL (US); Karl W. Vanderbeek, Cincinnati, OH (US)

(73) Assignee: Smith & Nephew, Inc., Memphis, TN (US)

( * ) Notice: Subject to any disclaimer, the term of this patent is extended or adjusted under 35 U.S.C. 154(b) by 1070 days.

(21) Appl. No.: 16/447,509

(22) Filed: Jun. 20, 2019

(65) Prior Publication Data
US 2019/0328943 A1    Oct. 31, 2019

Related U.S. Application Data

(63) Continuation of application No. 14/775,339, filed as application No. PCT/US2014/026692 on Mar. 13, 2014, now Pat. No. 10,328,188.
(Continued)

(51) Int. Cl.
*A61M 1/00* (2006.01)
*F16M 11/04* (2006.01)
(Continued)

(52) U.S. Cl.
CPC ............ *G16H 20/40* (2018.01); *A61M 1/732* (2021.05); *A61M 1/74* (2021.05); *A61M 1/96* (2021.05);
(Continued)

(58) Field of Classification Search
CPC ........ A61M 1/0023; A61M 1/86; A61M 1/90; A61M 2205/3553; A61M 2205/42; A61M 2209/08; A61M 2209/082; F16M 13/022
See application file for complete search history.

(56) References Cited

U.S. PATENT DOCUMENTS

| 695,270 A | 3/1902 | Beringer |
|---|---|---|
| 3,187,601 A | 6/1965 | Glenn |

(Continued)

FOREIGN PATENT DOCUMENTS

| CA | 2 819 475 | 6/2012 |
|---|---|---|
| CN | 201921164 U | 8/2011 |

(Continued)

OTHER PUBLICATIONS

International Preliminary Report on Patentability and Written Opinion, re PCT/US2014/026692, mailed Sep. 24, 2015.
(Continued)

*Primary Examiner* — Kai H Weng
(74) *Attorney, Agent, or Firm* — Knobbe, Martens, Olson & Bear, LLP

(57) ABSTRACT

Embodiments of reduced pressure systems and methods for operating the systems are disclosed. In some embodiments, a system can include a source of negative pressure and a controller configured to present GUI screens for controlling and monitoring operation of the system. The controller can be configured to receive, via the GUI, an adjustment of a negative pressure therapy parameter and adjust (or cause adjustment) of the operation of the negative pressure source based on received adjustment. The controller can be further configured to record historical data parameters associated with negative pressure therapy parameters. The controller can also be configured to transmit (or cause transmission) over a communication channel at least some of recorded historical data. The system can be configured to provide
(Continued)

external connectivity for accomplishing various activities, such as location tracking, compliance monitoring, tracking of operational data, remote selection and adjustment of therapy settings, etc.

18 Claims, 105 Drawing Sheets

Related U.S. Application Data

(60) Provisional application No. 61/860,809, filed on Jul. 31, 2013, provisional application No. 61/785,384, filed on Mar. 14, 2013.

(51) Int. Cl.
*F16M 13/02* (2006.01)
*G16H 20/40* (2018.01)
*G16H 40/63* (2018.01)

(52) U.S. Cl.
CPC .............. *A61M 1/98* (2021.05); *F16M 11/04* (2013.01); *F16M 13/022* (2013.01); *G16H 40/63* (2018.01); *A61M 1/982* (2021.05); *A61M 2205/3553* (2013.01); *A61M 2209/08* (2013.01); *A61M 2209/082* (2013.01)

(56) References Cited

U.S. PATENT DOCUMENTS

| | | |
|---|---|---|
| 3,194,239 A | 7/1965 | Sullivan |
| 4,832,299 A | 5/1989 | Gorton et al. |
| 4,969,880 A | 11/1990 | Zamierowski |
| 5,100,396 A | 3/1992 | Zamierowski |
| 5,158,528 A | 10/1992 | Walker et al. |
| 5,174,533 A | 12/1992 | Pryor et al. |
| 5,215,523 A | 6/1993 | Williams et al. |
| 5,219,146 A | 6/1993 | Thompson |
| 5,219,428 A | 6/1993 | Stern |
| 5,261,893 A | 11/1993 | Zamierowski |
| 5,419,768 A | 5/1995 | Kayser |
| 5,449,347 A | 9/1995 | Preen et al. |
| D364,679 S | 11/1995 | Heaton et al. |
| 5,466,229 A | 11/1995 | Elson |
| 5,473,536 A | 12/1995 | Wimmer |
| 5,527,293 A | 6/1996 | Zamierowski |
| 5,582,601 A | 12/1996 | Wortrich et al. |
| 5,584,824 A | 12/1996 | Gillette et al. |
| 5,599,308 A | 2/1997 | Krupa |
| 5,622,429 A | 4/1997 | Heinze |
| 5,636,643 A | 6/1997 | Argenta et al. |
| 5,645,081 A | 7/1997 | Argenta et al. |
| 5,656,027 A | 8/1997 | Ellingboe |
| 5,669,892 A | 9/1997 | Keogh et al. |
| 5,687,717 A | 11/1997 | Halpern et al. |
| 5,693,013 A | 12/1997 | Geuder |
| 5,779,207 A | 7/1998 | Danby |
| 5,829,723 A * | 11/1998 | Brunner .............. A61M 5/1413 248/222.13 |
| D408,625 S | 4/1999 | Barker |
| 5,956,023 A | 9/1999 | Lyle et al. |
| 5,960,403 A | 9/1999 | Brown et al. |
| 5,989,234 A | 11/1999 | Valerio et al. |
| 6,055,506 A | 4/2000 | Frasca et al. |
| 6,071,267 A | 6/2000 | Zamierowski |
| 6,174,306 B1 | 1/2001 | Fleischmann |
| 6,228,056 B1 | 5/2001 | Boehringer et al. |
| 6,241,739 B1 | 6/2001 | Waldron |
| 6,250,482 B1 | 6/2001 | Want et al. |
| 6,336,900 B1 | 1/2002 | Alleckson et al. |
| 6,353,445 B1 | 3/2002 | Babula et al. |
| 6,375,614 B1 | 4/2002 | Braun et al. |
| 6,385,622 B2 | 5/2002 | Bouve et al. |
| 6,406,426 B1 | 6/2002 | Reuss et al. |
| 6,434,572 B2 | 8/2002 | Derzay et al. |
| 6,460,041 B2 | 10/2002 | Lloyd et al. |
| 6,572,530 B1 | 6/2003 | Araki et al. |
| 6,574,518 B1 | 6/2003 | Lounsberry et al. |
| 6,579,231 B1 | 6/2003 | Phipps |
| 6,605,032 B2 | 8/2003 | Benkowski et al. |
| 6,640,145 B2 | 10/2003 | Hoffberg et al. |
| 6,640,246 B1 | 10/2003 | Gary, Jr. et al. |
| 6,675,131 B2 | 1/2004 | Hahn et al. |
| 6,681,003 B2 | 1/2004 | Linder et al. |
| 6,723,046 B2 | 4/2004 | Lichtenstein et al. |
| 6,738,052 B1 | 5/2004 | Manke et al. |
| 6,747,556 B2 | 6/2004 | Medema et al. |
| 6,779,024 B2 | 8/2004 | Delahuerga et al. |
| 6,782,285 B2 | 8/2004 | Birkenbach et al. |
| 6,868,528 B2 | 3/2005 | Roberts et al. |
| 6,871,211 B2 | 3/2005 | Labounty et al. |
| 6,909,974 B2 | 6/2005 | Yung et al. |
| 6,912,481 B2 | 6/2005 | Breunissen et al. |
| 6,936,037 B2 | 8/2005 | Bubb et al. |
| 6,961,731 B2 | 11/2005 | Holbrook et al. |
| 7,004,915 B2 | 2/2006 | Boynton et al. |
| 7,022,113 B2 | 4/2006 | Lockwood et al. |
| 7,051,012 B2 | 5/2006 | Cole et al. |
| 7,066,883 B2 | 6/2006 | Schmidt et al. |
| 7,103,578 B2 | 9/2006 | Beck et al. |
| 7,108,683 B2 | 9/2006 | Zamierowski et al. |
| 7,120,488 B2 | 10/2006 | Nova et al. |
| 7,128,735 B2 | 10/2006 | Weston |
| 7,133,869 B2 | 11/2006 | Bryan et al. |
| 7,167,858 B2 | 1/2007 | Naeymi-Rad et al. |
| 7,212,829 B1 | 5/2007 | Lau et al. |
| 7,216,651 B2 | 5/2007 | Argenta et al. |
| 7,264,591 B2 | 9/2007 | Brown et al. |
| 7,304,573 B2 | 12/2007 | Postma et al. |
| 7,311,665 B2 | 12/2007 | Hawthorne et al. |
| 7,333,002 B2 | 2/2008 | Bixler et al. |
| D565,177 S | 3/2008 | Locke et al. |
| 7,353,179 B2 | 4/2008 | Ott et al. |
| 7,361,184 B2 | 4/2008 | Joshi |
| 7,384,267 B1 | 6/2008 | Franks et al. |
| 7,430,598 B2 | 9/2008 | Raden et al. |
| D581,042 S | 11/2008 | Randolph et al. |
| D581,522 S | 11/2008 | Randolph et al. |
| 7,451,002 B2 | 11/2008 | Choubey et al. |
| 7,457,804 B2 | 11/2008 | Uber et al. |
| 7,460,872 B2 | 12/2008 | Millard et al. |
| D590,934 S | 4/2009 | Randolph et al. |
| 7,534,240 B1 | 5/2009 | Johnson et al. |
| 7,546,993 B1 | 6/2009 | Walker |
| 7,553,306 B1 | 6/2009 | Hunt et al. |
| 7,569,742 B2 | 8/2009 | Haggstrom et al. |
| 7,594,901 B2 | 9/2009 | Hopkins et al. |
| D602,582 S | 10/2009 | Pidgeon et al. |
| D602,583 S | 10/2009 | Pidgeon et al. |
| 7,598,855 B2 | 10/2009 | Scalisi et al. |
| 7,611,500 B1 | 11/2009 | Lina et al. |
| 7,615,036 B2 | 11/2009 | Joshi et al. |
| 7,627,334 B2 | 12/2009 | Cohen et al. |
| 7,649,449 B2 | 1/2010 | Fenske et al. |
| 7,671,733 B2 | 3/2010 | Mcneal et al. |
| 7,684,999 B2 | 3/2010 | Brown et al. |
| 7,699,823 B2 | 4/2010 | Haggstrom et al. |
| 7,723,560 B2 | 5/2010 | Lockwood et al. |
| 7,734,764 B2 | 6/2010 | Weiner et al. |
| 7,749,164 B2 | 7/2010 | Davis et al. |
| 7,753,894 B2 | 7/2010 | Blott et al. |
| 7,770,855 B2 | 8/2010 | Locke et al. |
| 7,776,028 B2 | 8/2010 | Miller et al. |
| 7,779,153 B2 | 8/2010 | Van Den Heuvel et al. |
| 7,789,828 B2 | 9/2010 | Clapp et al. |
| D625,801 S | 10/2010 | Pidgeon et al. |
| 7,827,148 B2 | 11/2010 | Mori et al. |
| 7,846,141 B2 | 12/2010 | Weston |
| 7,857,806 B2 | 12/2010 | Karpowicz et al. |
| 7,865,375 B2 | 1/2011 | Lancaster et al. |
| 7,889,069 B2 | 2/2011 | Fifolt et al. |
| 7,890,887 B1 | 2/2011 | Linardos et al. |
| 7,912,823 B2 | 3/2011 | Ferrari et al. |

(56) References Cited

U.S. PATENT DOCUMENTS

| | | |
|---|---|---|
| D635,588 S | 4/2011 | Sprules |
| 7,925,603 B1 | 4/2011 | Laidig et al. |
| 7,927,319 B2 | 4/2011 | Lawhorn |
| 7,933,817 B2 | 4/2011 | Radl et al. |
| 7,945,452 B2 | 5/2011 | Fathallah et al. |
| 7,976,519 B2 | 7/2011 | Bubb et al. |
| 7,981,098 B2 | 7/2011 | Boehringer et al. |
| D644,250 S | 8/2011 | Barber et al. |
| 7,988,850 B2 | 8/2011 | Roncadi et al. |
| 8,007,481 B2 | 8/2011 | Schuessler et al. |
| 8,015,443 B2 | 9/2011 | Adachi et al. |
| 8,015,972 B2 | 9/2011 | Pirzada et al. |
| 8,019,618 B2 | 9/2011 | Brown et al. |
| 8,048,046 B2 | 11/2011 | Hudspeth et al. |
| 8,054,950 B1 | 11/2011 | Hung et al. |
| 8,061,360 B2 | 11/2011 | Locke et al. |
| 8,066,243 B2 | 11/2011 | Svedman et al. |
| 8,094,009 B2 | 1/2012 | Allen et al. |
| 8,096,515 B2 | 1/2012 | Locke et al. |
| 8,100,873 B2 | 1/2012 | Jaeb et al. |
| 8,105,295 B2 | 1/2012 | Blott et al. |
| 8,126,735 B2 | 2/2012 | Dicks et al. |
| 8,130,095 B2 | 3/2012 | Allen et al. |
| 8,131,472 B2 | 3/2012 | Chow et al. |
| 8,180,750 B2 | 5/2012 | Wilmering et al. |
| 8,190,445 B2 | 5/2012 | Kuth et al. |
| 8,190,448 B2 | 5/2012 | Bajars et al. |
| 8,216,198 B2 | 7/2012 | Heagle et al. |
| 8,228,188 B2 | 7/2012 | Key et al. |
| 8,235,955 B2 | 8/2012 | Blott et al. |
| 8,240,470 B2 | 8/2012 | Pidgeon et al. |
| 8,246,606 B2 | 8/2012 | Stevenson et al. |
| 8,246,607 B2 | 8/2012 | Karpowicz et al. |
| 8,249,894 B2 | 8/2012 | Brown et al. |
| 8,255,241 B2 | 8/2012 | Cafer et al. |
| 8,257,328 B2 | 9/2012 | Augustine et al. |
| 8,260,630 B2 | 9/2012 | Brown et al. |
| 8,280,682 B2 | 10/2012 | Vock et al. |
| 8,284,046 B2 | 10/2012 | Allen et al. |
| 8,290,792 B2 | 10/2012 | Sekura et al. |
| 8,291,337 B2 | 10/2012 | Gannin et al. |
| 8,298,200 B2 | 10/2012 | Vess et al. |
| 8,308,714 B2 | 11/2012 | Weston et al. |
| 8,317,752 B2 | 11/2012 | Cozmi et al. |
| 8,323,263 B2 | 12/2012 | Wood et al. |
| 8,332,233 B2 | 12/2012 | Ott et al. |
| 8,333,744 B2 | 12/2012 | Hartwell et al. |
| 8,334,768 B2 | 12/2012 | Eaton et al. |
| 8,337,482 B2 | 12/2012 | Wood et al. |
| 8,360,975 B1 | 1/2013 | Schwieterman et al. |
| 8,361,043 B2 | 1/2013 | Hu et al. |
| 8,366,692 B2 | 2/2013 | Weston |
| 8,372,050 B2 | 2/2013 | Jaeb et al. |
| 8,377,016 B2 | 2/2013 | Argenta et al. |
| 8,377,018 B2 | 2/2013 | Bendele et al. |
| 8,400,295 B1 | 3/2013 | Khaira |
| 8,403,902 B2 | 3/2013 | Locke et al. |
| 8,409,170 B2 | 4/2013 | Locke et al. |
| 8,422,377 B2 | 4/2013 | Weiner et al. |
| 8,424,517 B2 | 4/2013 | Sutherland et al. |
| 8,436,871 B2 | 5/2013 | Alberte et al. |
| 8,439,882 B2 | 5/2013 | Kelch |
| 8,444,392 B2 | 5/2013 | Turner et al. |
| 8,457,740 B2 | 6/2013 | Osche et al. |
| 8,480,641 B2 | 7/2013 | Jacobs |
| 8,494,349 B2 | 7/2013 | Gordon |
| 8,495,074 B2 | 7/2013 | Weber et al. |
| 8,515,776 B2 | 8/2013 | Schoenberg et al. |
| 8,529,548 B2 | 9/2013 | Blott et al. |
| 8,532,764 B2 | 9/2013 | Duke et al. |
| 8,535,296 B2 | 9/2013 | Blott et al. |
| 8,540,688 B2 | 9/2013 | Eckstein et al. |
| 8,545,483 B2 | 10/2013 | Schwabe et al. |
| 8,552,880 B2 | 10/2013 | Kopp et al. |
| 8,554,195 B2 | 10/2013 | Rao et al. |
| 8,558,964 B2 | 10/2013 | Bedingfield |
| 8,560,082 B2 | 10/2013 | Wei et al. |
| 8,577,694 B2 | 11/2013 | Kanaan et al. |
| 8,595,553 B2 | 11/2013 | Goertler et al. |
| 8,604,265 B2 | 12/2013 | Locke et al. |
| 8,617,129 B2 | 12/2013 | Hartwell |
| 8,622,981 B2 | 1/2014 | Hartwell et al. |
| 8,626,342 B2 | 1/2014 | Williams, Jr. et al. |
| 8,626,526 B2 | 1/2014 | Lemke et al. |
| 8,628,258 B2 | 1/2014 | Vogt |
| 8,632,485 B2 | 1/2014 | Schlaeper et al. |
| 8,641,693 B2 | 2/2014 | Locke et al. |
| 8,652,111 B2 | 2/2014 | Pratt et al. |
| 8,659,420 B2 | 2/2014 | Salvat et al. |
| 8,668,677 B2 | 3/2014 | Eckstein et al. |
| 8,676,597 B2 | 3/2014 | Buehler et al. |
| 8,689,008 B2 | 4/2014 | Rangadass et al. |
| 8,694,600 B2 | 4/2014 | Gaines et al. |
| 8,706,537 B1 | 4/2014 | Young et al. |
| 8,747,376 B2 | 6/2014 | Locke et al. |
| 8,756,078 B2 | 6/2014 | Collins et al. |
| 8,757,485 B2 | 6/2014 | Drees et al. |
| 8,758,315 B2 | 6/2014 | Chen et al. |
| 8,768,441 B2 | 7/2014 | De Zwart et al. |
| 8,771,259 B2 | 7/2014 | Karpowicz et al. |
| 8,781,847 B2 | 7/2014 | Simms et al. |
| 8,791,315 B2 | 7/2014 | Lattimore et al. |
| 8,791,316 B2 | 7/2014 | Greener |
| 8,795,171 B2 | 8/2014 | Adamczyk et al. |
| 8,795,244 B2 | 8/2014 | Randolph et al. |
| 8,795,257 B2 | 8/2014 | Coulthard et al. |
| 8,798,284 B2 | 8/2014 | Cartwright et al. |
| 8,814,841 B2 | 8/2014 | Hartwell |
| 8,814,842 B2 | 8/2014 | Coulthard et al. |
| 8,838,136 B2 | 9/2014 | Carnes et al. |
| 8,843,327 B2 | 9/2014 | Vernon-Harcourt et al. |
| 8,845,603 B2 | 9/2014 | Middleton et al. |
| 8,845,604 B2 | 9/2014 | Croizat et al. |
| 8,852,149 B2 | 10/2014 | Weston et al. |
| 8,858,517 B2 | 10/2014 | Pan et al. |
| 8,862,393 B2 | 10/2014 | Zhou et al. |
| 8,868,794 B2 | 10/2014 | Masoud et al. |
| 8,870,812 B2 | 10/2014 | Alberti et al. |
| 8,874,035 B2 | 10/2014 | Sherman et al. |
| 8,887,100 B1 | 11/2014 | Cook et al. |
| 8,890,656 B2 | 11/2014 | Pendse et al. |
| 8,897,198 B2 | 11/2014 | Gaines et al. |
| 8,902,278 B2 | 12/2014 | Pinter et al. |
| 8,905,959 B2 | 12/2014 | Basaglia |
| 8,905,985 B2 | 12/2014 | Allen et al. |
| 8,909,595 B2 | 12/2014 | Gandy et al. |
| 8,912,897 B2 | 12/2014 | Carnes et al. |
| 8,922,377 B2 | 12/2014 | Carnes et al. |
| 8,926,574 B2 | 1/2015 | Croizat et al. |
| 8,943,168 B2 | 1/2015 | Wiesner et al. |
| 8,945,073 B2 | 2/2015 | Croizat et al. |
| 8,945,074 B2 | 2/2015 | Buan et al. |
| 8,947,237 B2 | 2/2015 | Margon et al. |
| 8,961,497 B2 | 2/2015 | Ryu et al. |
| 8,974,429 B2 | 3/2015 | Gordon et al. |
| 8,978,026 B2 | 3/2015 | Charlton et al. |
| 8,996,393 B2 | 3/2015 | Sobie |
| 9,017,286 B2 | 4/2015 | Kamen et al. |
| 9,019,681 B2 | 4/2015 | Locke et al. |
| 9,023,002 B2 | 5/2015 | Robinson et al. |
| 9,047,648 B1 | 6/2015 | Lekutai et al. |
| 9,087,141 B2 | 7/2015 | Huang et al. |
| 9,092,705 B2 | 7/2015 | Zhuang et al. |
| 9,098,114 B2 | 8/2015 | Potter et al. |
| 9,105,006 B2 | 8/2015 | Williamson et al. |
| 9,135,398 B2 | 9/2015 | Kaib et al. |
| 9,141,270 B1 | 9/2015 | Stuart et al. |
| 9,159,148 B2 | 10/2015 | Boyer et al. |
| 9,215,516 B2 | 12/2015 | Carnes et al. |
| 9,215,581 B2 | 12/2015 | Julian et al. |
| 9,220,821 B2 | 12/2015 | Croizat et al. |
| 9,220,822 B2 | 12/2015 | Hartwell et al. |
| 9,230,420 B2 | 1/2016 | Lee et al. |
| 9,268,827 B2 | 2/2016 | Fernandez et al. |

(56) References Cited

U.S. PATENT DOCUMENTS

| | | |
|---|---|---|
| 9,286,443 B2 | 3/2016 | Ford et al. |
| 9,323,893 B2 | 4/2016 | Berry et al. |
| 9,332,363 B2 | 5/2016 | Jain et al. |
| 9,338,819 B2 | 5/2016 | Meng et al. |
| 9,424,020 B2 | 8/2016 | Borges et al. |
| 9,427,159 B2 | 8/2016 | Chang et al. |
| 9,436,800 B2 | 9/2016 | Forrester et al. |
| 9,460,431 B2 | 10/2016 | Curry et al. |
| 9,483,614 B2 | 11/2016 | Ash et al. |
| 9,539,373 B2 | 1/2017 | Jones et al. |
| 9,558,331 B2 | 1/2017 | Orona et al. |
| 9,585,565 B2 | 3/2017 | Carnes et al. |
| 9,602,952 B2 | 3/2017 | Kang et al. |
| 9,658,066 B2 | 5/2017 | Yuen et al. |
| 9,662,438 B2 | 5/2017 | Kamen et al. |
| 9,687,618 B2 | 6/2017 | Steinhauer et al. |
| 9,693,691 B2 | 7/2017 | Johnson et al. |
| 9,716,757 B2 | 7/2017 | Fernandes et al. |
| 9,740,825 B2 | 8/2017 | Sansale et al. |
| 9,741,084 B2 | 8/2017 | Holmes et al. |
| 9,792,660 B2 | 10/2017 | Cannon et al. |
| 9,818,164 B2 | 11/2017 | Nolte et al. |
| 9,838,645 B2 | 12/2017 | Hyde et al. |
| 9,864,066 B2 | 1/2018 | Park et al. |
| 9,878,081 B2 | 1/2018 | Leiendecker et al. |
| 9,928,478 B2 | 3/2018 | Ragusky et al. |
| 9,990,466 B2 | 6/2018 | Debusk et al. |
| 9,996,681 B2 | 6/2018 | Suarez et al. |
| 10,049,346 B2 | 8/2018 | Jensen et al. |
| 10,061,894 B2 | 8/2018 | Sethumadhavan et al. |
| 10,173,008 B2 | 1/2019 | Simpson et al. |
| 10,185,834 B2 | 1/2019 | Adam et al. |
| 2001/0013822 A1 | 8/2001 | Nazarian et al. |
| 2001/0031944 A1 | 10/2001 | Peterson et al. |
| 2001/0041831 A1 | 11/2001 | Starkweather et al. |
| 2001/0049609 A1 | 12/2001 | Girouard et al. |
| 2002/0002326 A1 | 1/2002 | Causey, III et al. |
| 2002/0002368 A1 | 1/2002 | Tomita et al. |
| 2002/0013516 A1 | 1/2002 | Freyre et al. |
| 2002/0015034 A1 | 2/2002 | Malmborg |
| 2002/0026160 A1 | 2/2002 | Takahashi et al. |
| 2002/0049562 A1 | 4/2002 | Hahn |
| 2002/0065685 A1 | 5/2002 | Sasaki et al. |
| 2002/0082568 A1 | 6/2002 | Yam |
| 2002/0087360 A1 | 7/2002 | Pettit |
| 2002/0128804 A1 | 9/2002 | Geva |
| 2002/0128869 A1 | 9/2002 | Kuth |
| 2002/0135336 A1 | 9/2002 | Zhou et al. |
| 2002/0161317 A1 | 10/2002 | Risk et al. |
| 2002/0177757 A1 | 11/2002 | Britton |
| 2002/0184055 A1 | 12/2002 | Naghavi et al. |
| 2002/0193679 A1 | 12/2002 | Malave et al. |
| 2002/0198505 A1 | 12/2002 | Want et al. |
| 2003/0009244 A1 | 1/2003 | Engleson et al. |
| 2003/0018395 A1 | 1/2003 | Crnkovich et al. |
| 2003/0018736 A1 | 1/2003 | Christ et al. |
| 2003/0028175 A1 | 2/2003 | D'Antonio |
| 2003/0040687 A1 | 2/2003 | Boynton et al. |
| 2003/0093041 A1 | 5/2003 | Risk, Jr. et al. |
| 2003/0105389 A1 | 6/2003 | Noonan et al. |
| 2003/0105649 A1 | 6/2003 | Sheiner et al. |
| 2003/0128125 A1 | 7/2003 | Burbank et al. |
| 2003/0164600 A1 | 9/2003 | Dunn et al. |
| 2003/0176183 A1 | 9/2003 | Drucker et al. |
| 2003/0182158 A1 | 9/2003 | Sor |
| 2003/0214412 A1 | 11/2003 | Ho et al. |
| 2003/0221687 A1 | 12/2003 | Kaigler |
| 2003/0229518 A1 | 12/2003 | Abraham-Fuchs |
| 2003/0233071 A1 | 12/2003 | Gillespie, Jr. et al. |
| 2004/0006492 A1 | 1/2004 | Watanabe |
| 2004/0019464 A1 | 1/2004 | Martucci et al. |
| 2004/0039255 A1 | 2/2004 | Simonsen et al. |
| 2004/0054338 A1 | 3/2004 | Bybordi et al. |
| 2004/0054775 A1 | 3/2004 | Poliac et al. |
| 2004/0059284 A1 | 3/2004 | Nash et al. |
| 2004/0064132 A1 | 4/2004 | Boehringer et al. |
| 2004/0078223 A1 | 4/2004 | Sacco et al. |
| 2004/0102743 A1 | 5/2004 | Walker |
| 2004/0120825 A1 | 6/2004 | Bouton et al. |
| 2004/0143458 A1 | 7/2004 | Pulkkinen et al. |
| 2004/0158193 A1 | 8/2004 | Bui et al. |
| 2004/0167802 A1 | 8/2004 | Takada et al. |
| 2004/0167804 A1 | 8/2004 | Simpson et al. |
| 2004/0171982 A1 | 9/2004 | Danchin |
| 2004/0172301 A1 | 9/2004 | Mihai et al. |
| 2004/0176983 A1 | 9/2004 | Birkett et al. |
| 2004/0181314 A1 | 9/2004 | Zaleski |
| 2004/0181433 A1 | 9/2004 | Blair |
| 2004/0193449 A1 | 9/2004 | Wildman et al. |
| 2004/0204962 A1 | 10/2004 | Howser et al. |
| 2004/0227737 A1 | 11/2004 | Novak et al. |
| 2004/0249673 A1 | 12/2004 | Smith |
| 2005/0011282 A1 | 1/2005 | Voege et al. |
| 2005/0022274 A1 | 1/2005 | Campbell et al. |
| 2005/0033124 A1 | 2/2005 | Kelly et al. |
| 2005/0055225 A1 | 3/2005 | Mehl |
| 2005/0055242 A1 | 3/2005 | Bello et al. |
| 2005/0055244 A1 | 3/2005 | Mullan et al. |
| 2005/0060211 A1 | 3/2005 | Xiao et al. |
| 2005/0065471 A1 | 3/2005 | Kuntz |
| 2005/0065817 A1 | 3/2005 | Mihai et al. |
| 2005/0097200 A1 | 5/2005 | Denning, Jr. et al. |
| 2005/0102167 A1 | 5/2005 | Kapoor |
| 2005/0108046 A1 | 5/2005 | Craft |
| 2005/0108057 A1 | 5/2005 | Cohen et al. |
| 2005/0114176 A1 | 5/2005 | Dominick et al. |
| 2005/0116126 A1 | 6/2005 | Ugent et al. |
| 2005/0119914 A1 | 6/2005 | Batch |
| 2005/0124966 A1 | 6/2005 | Karpowicz et al. |
| 2005/0187528 A1 | 8/2005 | Berg |
| 2005/0201345 A1 | 9/2005 | Williamson |
| 2005/0209560 A1 | 9/2005 | Boukhny et al. |
| 2005/0222873 A1 | 10/2005 | Nephin et al. |
| 2005/0230575 A1 | 10/2005 | Zelenski |
| 2005/0240111 A1 | 10/2005 | Chung |
| 2005/0256447 A1 | 11/2005 | Richardson et al. |
| 2005/0261805 A1 | 11/2005 | Mori et al. |
| 2005/0283382 A1 | 12/2005 | Donoghue et al. |
| 2006/0004604 A1 | 1/2006 | White |
| 2006/0029675 A1 | 2/2006 | Ginther |
| 2006/0064323 A1 | 3/2006 | Alleckson et al. |
| 2006/0064491 A1 | 3/2006 | Ebert et al. |
| 2006/0085393 A1 | 4/2006 | Modesitt |
| 2006/0089539 A1 | 4/2006 | Miodownik et al. |
| 2006/0089544 A1 | 4/2006 | Williams, Jr. et al. |
| 2006/0095853 A1 | 5/2006 | Amyot et al. |
| 2006/0132283 A1 | 6/2006 | Eberhart et al. |
| 2006/0144440 A1 | 7/2006 | Merkle |
| 2006/0149171 A1 | 7/2006 | Vogel et al. |
| 2006/0155584 A1 | 7/2006 | Aggarwal |
| 2006/0161460 A1 | 7/2006 | Smitherman et al. |
| 2006/0190130 A1 | 8/2006 | Fedor et al. |
| 2006/0195843 A1 | 8/2006 | Hall |
| 2006/0224051 A1 | 10/2006 | Teller et al. |
| 2006/0229557 A1 | 10/2006 | Fathallah et al. |
| 2006/0246922 A1 | 11/2006 | Gasbarro et al. |
| 2006/0255935 A1 | 11/2006 | Scalisi et al. |
| 2007/0005029 A1 | 1/2007 | Hopkins et al. |
| 2007/0016152 A1 | 1/2007 | Karpowicz et al. |
| 2007/0021697 A1 | 1/2007 | Ginther et al. |
| 2007/0032741 A1 | 2/2007 | Hibner et al. |
| 2007/0032762 A1 | 2/2007 | Vogel |
| 2007/0032763 A1 | 2/2007 | Vogel |
| 2007/0038172 A1 | 2/2007 | Zamierowski |
| 2007/0052683 A1 | 3/2007 | Knott et al. |
| 2007/0055209 A1 | 3/2007 | Patel et al. |
| 2007/0078444 A1 | 4/2007 | Larsson |
| 2007/0118096 A1 | 5/2007 | Smith et al. |
| 2007/0136099 A1 | 6/2007 | Neligh et al. |
| 2007/0138069 A1 | 6/2007 | Roncadi et al. |
| 2007/0156456 A1 | 7/2007 | Mcgillin et al. |
| 2007/0167927 A1 | 7/2007 | Hunt et al. |
| 2007/0179460 A1 | 8/2007 | Adahan |
| 2007/0180904 A1 | 8/2007 | Gao |

(56) References Cited

U.S. PATENT DOCUMENTS

| | | |
|---|---|---|
| 2007/0197881 A1 | 8/2007 | Wolf et al. |
| 2007/0218101 A1 | 9/2007 | Johnson et al. |
| 2007/0219480 A1 | 9/2007 | Kamen et al. |
| 2007/0219826 A1 | 9/2007 | Brodsky et al. |
| 2007/0227360 A1 | 10/2007 | Atlas et al. |
| 2007/0227537 A1 | 10/2007 | Bemister et al. |
| 2007/0233022 A1 | 10/2007 | Henley et al. |
| 2007/0239139 A1 | 10/2007 | Weston |
| 2007/0250009 A1 | 10/2007 | Barak |
| 2007/0255114 A1 | 11/2007 | Ackerman et al. |
| 2007/0255116 A1 | 11/2007 | Mehta et al. |
| 2007/0260226 A1 | 11/2007 | Jaeb et al. |
| 2007/0271298 A1 | 11/2007 | Juang et al. |
| 2007/0276309 A1 | 11/2007 | Xu et al. |
| 2007/0282249 A1 | 12/2007 | Quisenberry et al. |
| 2008/0004818 A1 | 1/2008 | Zaleski |
| 2008/0005000 A1 | 1/2008 | Radl et al. |
| 2008/0009681 A1 | 1/2008 | Hussiny |
| 2008/0015526 A1 | 1/2008 | Reiner et al. |
| 2008/0030345 A1 | 2/2008 | Austin et al. |
| 2008/0039761 A1 | 2/2008 | Heaton et al. |
| 2008/0041401 A1 | 2/2008 | Casola et al. |
| 2008/0051708 A1 | 2/2008 | Kumar et al. |
| 2008/0071209 A1 | 3/2008 | Moubayed et al. |
| 2008/0071216 A1 | 3/2008 | Locke et al. |
| 2008/0071234 A1 | 3/2008 | Kelch et al. |
| 2008/0071235 A1 | 3/2008 | Locke et al. |
| 2008/0077091 A1 | 3/2008 | Mulligan |
| 2008/0082040 A1 | 4/2008 | Kubler et al. |
| 2008/0082077 A1 | 4/2008 | Williams |
| 2008/0086357 A1 | 4/2008 | Choubey et al. |
| 2008/0091175 A1 | 4/2008 | Frikart et al. |
| 2008/0091659 A1 | 4/2008 | McFaul |
| 2008/0119705 A1 | 5/2008 | Patel et al. |
| 2008/0125697 A1 | 5/2008 | Gao |
| 2008/0125698 A1 | 5/2008 | Gerg et al. |
| 2008/0126126 A1 | 5/2008 | Ballai |
| 2008/0132821 A1 | 6/2008 | Propp et al. |
| 2008/0140160 A1 | 6/2008 | Goetz et al. |
| 2008/0167534 A1 | 7/2008 | Young et al. |
| 2008/0177224 A1 | 7/2008 | Kelly et al. |
| 2008/0177579 A1 | 7/2008 | Dehaan |
| 2008/0180268 A1 | 7/2008 | Nissels et al. |
| 2008/0200868 A1 | 8/2008 | Alberti et al. |
| 2008/0200905 A1 | 8/2008 | Heaton |
| 2008/0200906 A1 | 8/2008 | Sanders et al. |
| 2008/0208147 A1 | 8/2008 | Argenta et al. |
| 2008/0209357 A1 | 8/2008 | Vasta et al. |
| 2008/0221396 A1 | 9/2008 | Garces et al. |
| 2008/0228526 A1 | 9/2008 | Locke et al. |
| 2008/0234641 A1 | 9/2008 | Locke et al. |
| 2008/0242945 A1 | 10/2008 | Gugliotti et al. |
| 2008/0243096 A1 | 10/2008 | Svedman |
| 2008/0249377 A1 | 10/2008 | Molducci et al. |
| 2008/0272254 A1 | 11/2008 | Harr et al. |
| 2008/0300572 A1 | 12/2008 | Rankers et al. |
| 2008/0307353 A1 | 12/2008 | Molducci et al. |
| 2008/0312953 A1 | 12/2008 | Claus |
| 2009/0005746 A1 | 1/2009 | Nielsen et al. |
| 2009/0037216 A1 | 2/2009 | Bluemler et al. |
| 2009/0037220 A1 | 2/2009 | Chambers et al. |
| 2009/0043268 A1 | 2/2009 | Eddy et al. |
| 2009/0048492 A1 | 2/2009 | Rantala et al. |
| 2009/0048865 A1 | 2/2009 | Breazeale, Jr. |
| 2009/0082741 A1 | 3/2009 | Hu |
| 2009/0097623 A1 | 4/2009 | Bharadwaj |
| 2009/0099866 A1 | 4/2009 | Newman |
| 2009/0099867 A1 | 4/2009 | Newman |
| 2009/0101219 A1 | 4/2009 | Martini et al. |
| 2009/0115663 A1 | 5/2009 | Brown et al. |
| 2009/0118591 A1 | 5/2009 | Kim et al. |
| 2009/0125055 A1 | 5/2009 | Larkin et al. |
| 2009/0125331 A1 | 5/2009 | Pamsgaard et al. |
| 2009/0136909 A1 | 5/2009 | Asukai et al. |
| 2009/0144091 A1 | 6/2009 | Rago |
| 2009/0157429 A1 | 6/2009 | Lee et al. |
| 2009/0163774 A1 | 6/2009 | Thatha et al. |
| 2009/0171166 A1 | 7/2009 | Amundson et al. |
| 2009/0171288 A1 | 7/2009 | Wheeler |
| 2009/0171289 A1 | 7/2009 | Davis et al. |
| 2009/0177495 A1 | 7/2009 | Abousy et al. |
| 2009/0182266 A1 | 7/2009 | Gordon et al. |
| 2009/0182594 A1 | 7/2009 | Choubey |
| 2009/0187424 A1 | 7/2009 | Grabowski |
| 2009/0204434 A1 | 8/2009 | Breazeale |
| 2009/0204435 A1 | 8/2009 | Gale |
| 2009/0205042 A1 | 8/2009 | Zhou et al. |
| 2009/0206017 A1 | 8/2009 | Rohde et al. |
| 2009/0224889 A1 | 9/2009 | Aggarwal et al. |
| 2009/0227969 A1 | 9/2009 | Jaeb et al. |
| 2009/0254362 A1 | 10/2009 | Choubey et al. |
| 2009/0270833 A1 | 10/2009 | DeBelser et al. |
| 2009/0281822 A1 | 11/2009 | Warner et al. |
| 2009/0281830 A1 | 11/2009 | Mcnames et al. |
| 2009/0281867 A1 | 11/2009 | Sievenpiper et al. |
| 2009/0292264 A1 | 11/2009 | Hudspeth et al. |
| 2009/0299306 A1 | 12/2009 | Buan |
| 2009/0326339 A1 | 12/2009 | Horvitz |
| 2009/0326488 A1 | 12/2009 | Budig et al. |
| 2009/0327102 A1 | 12/2009 | Maniar et al. |
| 2010/0001838 A1 | 1/2010 | Miodownik et al. |
| 2010/0010646 A1 | 1/2010 | Drew et al. |
| 2010/0017471 A1 | 1/2010 | Brown et al. |
| 2010/0020021 A1 | 1/2010 | Mills et al. |
| 2010/0022848 A1 | 1/2010 | Lee et al. |
| 2010/0022990 A1 | 1/2010 | Karpowicz et al. |
| 2010/0030132 A1 | 2/2010 | Niezgoda et al. |
| 2010/0030302 A1 | 2/2010 | Blowers et al. |
| 2010/0036333 A1 | 2/2010 | Schenk, III et al. |
| 2010/0042021 A1 | 2/2010 | Hu et al. |
| 2010/0042059 A1 | 2/2010 | Pratt et al. |
| 2010/0049150 A1 | 2/2010 | Braga et al. |
| 2010/0056875 A1 | 3/2010 | Schoenberg et al. |
| 2010/0063483 A1 | 3/2010 | Adahan |
| 2010/0069829 A1 | 3/2010 | Hutchinson et al. |
| 2010/0090004 A1 | 4/2010 | Sands et al. |
| 2010/0106528 A1 | 4/2010 | Brackett et al. |
| 2010/0113908 A1 | 5/2010 | Vargas et al. |
| 2010/0114026 A1 | 5/2010 | Karratt et al. |
| 2010/0121257 A1 | 5/2010 | King |
| 2010/0126268 A1 | 5/2010 | Baily et al. |
| 2010/0137775 A1 | 6/2010 | Hu et al. |
| 2010/0145161 A1 | 6/2010 | Niyato et al. |
| 2010/0145289 A1 | 6/2010 | Line et al. |
| 2010/0150991 A1 | 6/2010 | Bernstein |
| 2010/0168687 A1 | 7/2010 | Yu |
| 2010/0191178 A1 | 7/2010 | Ross et al. |
| 2010/0191199 A1 | 7/2010 | Evans et al. |
| 2010/0200486 A1 | 8/2010 | Gunther et al. |
| 2010/0204663 A1 | 8/2010 | Wudyka |
| 2010/0207768 A1 | 8/2010 | Pidgeon et al. |
| 2010/0211030 A1 | 8/2010 | Turner et al. |
| 2010/0222645 A1 | 9/2010 | Nadler et al. |
| 2010/0228205 A1 | 9/2010 | Hu et al. |
| 2010/0234708 A1 | 9/2010 | Buck et al. |
| 2010/0251114 A1 | 9/2010 | Wehba et al. |
| 2010/0255876 A1 | 10/2010 | Jordan et al. |
| 2010/0268179 A1 | 10/2010 | Kelch et al. |
| 2010/0274177 A1 | 10/2010 | Rybski et al. |
| 2010/0280435 A1 | 11/2010 | Raney et al. |
| 2010/0280536 A1 | 11/2010 | Hartwell |
| 2010/0282834 A1 | 11/2010 | Devergne et al. |
| 2010/0305490 A1 | 12/2010 | Coulthard et al. |
| 2010/0305523 A1 | 12/2010 | Vess |
| 2010/0313958 A1 | 12/2010 | Patel et al. |
| 2010/0314517 A1 | 12/2010 | Patzer |
| 2010/0317933 A1 | 12/2010 | Colman et al. |
| 2010/0318043 A1 | 12/2010 | Malhi et al. |
| 2010/0318071 A1 | 12/2010 | Wudyka |
| 2011/0003610 A1 | 1/2011 | Key et al. |
| 2011/0004188 A1 | 1/2011 | Shekalim |
| 2011/0006876 A1 | 1/2011 | Moberg et al. |
| 2011/0009824 A1 | 1/2011 | Yodfat et al. |
| 2011/0015585 A1 | 1/2011 | Svedman et al. |

(56) References Cited

U.S. PATENT DOCUMENTS

| | | |
|---|---|---|
| 2011/0015587 A1 | 1/2011 | Tumey et al. |
| 2011/0015590 A1 | 1/2011 | Svedman et al. |
| 2011/0028881 A1 | 2/2011 | Basaglia |
| 2011/0028882 A1 | 2/2011 | Basaglia |
| 2011/0028921 A1 | 2/2011 | Hartwell et al. |
| 2011/0034861 A1 | 2/2011 | Schaefer |
| 2011/0038741 A1 | 2/2011 | Lissner et al. |
| 2011/0040268 A1 | 2/2011 | Eckstein et al. |
| 2011/0040288 A1 | 2/2011 | Eckstein et al. |
| 2011/0054810 A1 | 3/2011 | Turner |
| 2011/0060204 A1 | 3/2011 | Weston |
| 2011/0063117 A1 | 3/2011 | Turner |
| 2011/0066096 A1 | 3/2011 | Svedman |
| 2011/0066110 A1 | 3/2011 | Fathallah et al. |
| 2011/0066123 A1 | 3/2011 | Tout et al. |
| 2011/0071415 A1 | 3/2011 | Karwoski et al. |
| 2011/0071844 A1 | 3/2011 | Cannon et al. |
| 2011/0073107 A1 | 3/2011 | Rodman et al. |
| 2011/0077605 A1 | 3/2011 | Karpowicz et al. |
| 2011/0092927 A1 | 4/2011 | Wilkes et al. |
| 2011/0092958 A1 | 4/2011 | Jacobs |
| 2011/0106028 A1 | 5/2011 | Giezendanner et al. |
| 2011/0106561 A1 | 5/2011 | Eaton, Jr. et al. |
| 2011/0107251 A1 | 5/2011 | Guaitoli et al. |
| 2011/0112492 A1 | 5/2011 | Bharti et al. |
| 2011/0112857 A1 | 5/2011 | Yurko et al. |
| 2011/0130712 A1 | 6/2011 | Topaz |
| 2011/0137759 A1 | 6/2011 | Wellington et al. |
| 2011/0145018 A1 | 6/2011 | Fotsch et al. |
| 2011/0152739 A1 | 6/2011 | Roncadi et al. |
| 2011/0173028 A1 | 7/2011 | Bond |
| 2011/0184754 A1 | 7/2011 | Park et al. |
| 2011/0190703 A1 | 8/2011 | Pratt et al. |
| 2011/0196321 A1 | 8/2011 | Wudyka |
| 2011/0225008 A1 | 9/2011 | Elkouh et al. |
| 2011/0245682 A1 | 10/2011 | Robinson et al. |
| 2011/0246219 A1 | 10/2011 | Smith et al. |
| 2011/0251569 A1 | 10/2011 | Turner et al. |
| 2011/0257572 A1 | 10/2011 | Locke et al. |
| 2011/0275353 A1 | 11/2011 | Liu |
| 2011/0288511 A1 | 11/2011 | Locke et al. |
| 2011/0288602 A1 | 11/2011 | Nachum et al. |
| 2011/0288878 A1 | 11/2011 | Blair |
| 2011/0290979 A1 | 12/2011 | Henault et al. |
| 2011/0313789 A1 | 12/2011 | Kamen et al. |
| 2011/0319813 A1 | 12/2011 | Kamen et al. |
| 2012/0001762 A1 | 1/2012 | Turner et al. |
| 2012/0029312 A1 | 2/2012 | Beaudry et al. |
| 2012/0029313 A1 | 2/2012 | Burdett et al. |
| 2012/0032819 A1 | 2/2012 | Chae et al. |
| 2012/0035427 A1 | 2/2012 | Friedman et al. |
| 2012/0035560 A1 | 2/2012 | Eddy et al. |
| 2012/0035561 A1 | 2/2012 | Locke et al. |
| 2012/0046624 A1 | 2/2012 | Locke et al. |
| 2012/0046625 A1 | 2/2012 | Johannison |
| 2012/0071845 A1 | 3/2012 | Hu et al. |
| 2012/0077605 A1 | 3/2012 | Nakagaito et al. |
| 2012/0081225 A1 | 4/2012 | Waugh et al. |
| 2012/0089369 A1 | 4/2012 | Abuzeni et al. |
| 2012/0123323 A1 | 5/2012 | Kagan et al. |
| 2012/0123358 A1 | 5/2012 | Hall et al. |
| 2012/0123796 A1 | 5/2012 | Mcfaul |
| 2012/0157889 A1 | 6/2012 | Tanis et al. |
| 2012/0157941 A1 | 6/2012 | Luckemeyer et al. |
| 2012/0176394 A1 | 7/2012 | Vik et al. |
| 2012/0181405 A1 | 7/2012 | Zlatic et al. |
| 2012/0182143 A1 | 7/2012 | Gaines et al. |
| 2012/0184930 A1 | 7/2012 | Johannison |
| 2012/0184932 A1 | 7/2012 | Giezendanner et al. |
| 2012/0191475 A1 | 7/2012 | Pandey |
| 2012/0197196 A1 | 8/2012 | Halbert et al. |
| 2012/0197580 A1 | 8/2012 | Vij et al. |
| 2012/0209228 A1 | 8/2012 | Croizat et al. |
| 2012/0212434 A1 | 8/2012 | Bluemler et al. |
| 2012/0212455 A1 | 8/2012 | Kloeffel |
| 2012/0215455 A1 | 8/2012 | Patil et al. |
| 2012/0220960 A1 | 8/2012 | Ruland |
| 2012/0226247 A1 | 9/2012 | Danei et al. |
| 2012/0226768 A1 | 9/2012 | Gaines et al. |
| 2012/0259283 A1 | 10/2012 | Haase |
| 2012/0259651 A1 | 10/2012 | Mallon et al. |
| 2012/0271256 A1 | 10/2012 | Locke et al. |
| 2012/0289895 A1 | 11/2012 | Tsoukalis |
| 2012/0289913 A1 | 11/2012 | Eckstein et al. |
| 2012/0289914 A1 | 11/2012 | Eckstein et al. |
| 2012/0290217 A1 | 11/2012 | Shoval et al. |
| 2012/0293322 A1 | 11/2012 | Ray et al. |
| 2012/0295566 A1 | 11/2012 | Collins et al. |
| 2012/0302976 A1 | 11/2012 | Locke et al. |
| 2012/0302977 A1 | 11/2012 | Buan et al. |
| 2012/0302978 A1 | 11/2012 | Buan et al. |
| 2012/0310205 A1 | 12/2012 | Lee et al. |
| 2013/0018355 A1 | 1/2013 | Brand et al. |
| 2013/0019744 A1 | 1/2013 | Hu |
| 2013/0023719 A1 | 1/2013 | Bennett |
| 2013/0028788 A1 | 1/2013 | Gronau et al. |
| 2013/0030394 A1 | 1/2013 | Locke et al. |
| 2013/0035615 A1 | 2/2013 | Hsieh |
| 2013/0045764 A1 | 2/2013 | Vik et al. |
| 2013/0053692 A1 | 2/2013 | Barron et al. |
| 2013/0062265 A1 | 3/2013 | Balschat et al. |
| 2013/0066285 A1 | 3/2013 | Locke et al. |
| 2013/0066301 A1 | 3/2013 | Locke et al. |
| 2013/0073303 A1 | 3/2013 | Hsu |
| 2013/0076528 A1 | 3/2013 | Boettner et al. |
| 2013/0087609 A1 | 4/2013 | Nichol et al. |
| 2013/0088452 A1 | 4/2013 | Glaser-Seidnitzer et al. |
| 2013/0090613 A1 | 4/2013 | Kelch et al. |
| 2013/0090949 A1 | 4/2013 | Tibebu |
| 2013/0102836 A1 | 4/2013 | Millman |
| 2013/0103419 A1 | 4/2013 | Beaudry |
| 2013/0110057 A1 | 5/2013 | Croteau et al. |
| 2013/0110058 A1 | 5/2013 | Adie et al. |
| 2013/0123755 A1 | 5/2013 | Locke et al. |
| 2013/0124227 A1 | 5/2013 | Ellis |
| 2013/0132855 A1 | 5/2013 | Manicka et al. |
| 2013/0133036 A1 | 5/2013 | Wang et al. |
| 2013/0144227 A1 | 6/2013 | Locke et al. |
| 2013/0144230 A1 | 6/2013 | Wu et al. |
| 2013/0150686 A1 | 6/2013 | Fronterhouse et al. |
| 2013/0150698 A1 | 6/2013 | Hsu et al. |
| 2013/0150813 A1 | 6/2013 | Gordon et al. |
| 2013/0151274 A1 | 6/2013 | Bage et al. |
| 2013/0157571 A1 | 6/2013 | Wondka et al. |
| 2013/0159456 A1 | 6/2013 | Daoud et al. |
| 2013/0160082 A1 | 6/2013 | Miller |
| 2013/0165821 A1 | 6/2013 | Freedman et al. |
| 2013/0165854 A1 | 6/2013 | Sandhu et al. |
| 2013/0165877 A1 | 6/2013 | Leeson et al. |
| 2013/0169432 A1 | 7/2013 | Ozgul et al. |
| 2013/0176230 A1 | 7/2013 | Georgiev et al. |
| 2013/0186405 A1 | 7/2013 | Krzyzanowski et al. |
| 2013/0190717 A1 | 7/2013 | Dollar et al. |
| 2013/0190903 A1 | 7/2013 | Balakrishnan et al. |
| 2013/0191513 A1 | 7/2013 | Kamen et al. |
| 2013/0196703 A1 | 8/2013 | Masoud et al. |
| 2013/0198685 A1 | 8/2013 | Bernini et al. |
| 2013/0204106 A1 | 8/2013 | Bennett |
| 2013/0204210 A1 | 8/2013 | Pratt et al. |
| 2013/0211206 A1 | 8/2013 | Sands et al. |
| 2013/0211854 A1 | 8/2013 | Wagstaff |
| 2013/0212168 A1 | 8/2013 | Bonasera et al. |
| 2013/0214925 A1 | 8/2013 | Weiss |
| 2013/0218053 A1 | 8/2013 | Kaiser et al. |
| 2013/0223979 A1 | 8/2013 | Locke et al. |
| 2013/0226607 A1 | 8/2013 | Woody et al. |
| 2013/0227128 A1 | 8/2013 | Wagstaff |
| 2013/0231596 A1 | 9/2013 | Hornback et al. |
| 2013/0245387 A1 | 9/2013 | Patel |
| 2013/0245580 A1 | 9/2013 | Locke et al. |
| 2013/0253952 A1 | 9/2013 | Burke et al. |
| 2013/0254717 A1 | 9/2013 | Al-Ali et al. |
| 2013/0255681 A1 | 10/2013 | Batch et al. |
| 2013/0262730 A1 | 10/2013 | Al-Ali et al. |

(56) References Cited

U.S. PATENT DOCUMENTS

| | | |
|---|---|---|
| 2013/0267917 A1 | 10/2013 | Pan et al. |
| 2013/0267918 A1 | 10/2013 | Pan et al. |
| 2013/0267919 A1 | 10/2013 | Caso et al. |
| 2013/0268283 A1 | 10/2013 | Vann et al. |
| 2013/0271556 A1 | 10/2013 | Ross et al. |
| 2013/0275145 A1 | 10/2013 | Moore et al. |
| 2013/0282395 A1 | 10/2013 | Rustgi et al. |
| 2013/0285837 A1 | 10/2013 | Uchida |
| 2013/0289536 A1 | 10/2013 | Croizat et al. |
| 2013/0293570 A1 | 11/2013 | Dolgos et al. |
| 2013/0297350 A1 | 11/2013 | Gross et al. |
| 2013/0303975 A1 | 11/2013 | Gvodas et al. |
| 2013/0304489 A1 | 11/2013 | Miller |
| 2013/0310631 A1 | 11/2013 | Lee et al. |
| 2013/0310726 A1 | 11/2013 | Miller et al. |
| 2013/0310778 A1 | 11/2013 | Locke et al. |
| 2013/0310781 A1 | 11/2013 | Phillips et al. |
| 2013/0317420 A1 | 11/2013 | Wehmeyer |
| 2013/0317463 A1 | 11/2013 | Yao et al. |
| 2013/0317753 A1 | 11/2013 | Kamen et al. |
| 2013/0325508 A1 | 12/2013 | Johnson et al. |
| 2013/0327326 A1 | 12/2013 | Brennan |
| 2013/0331748 A1 | 12/2013 | Wright et al. |
| 2013/0331822 A1 | 12/2013 | Patel et al. |
| 2013/0332197 A1 | 12/2013 | Hinkel |
| 2013/0335233 A1 | 12/2013 | Kamar et al. |
| 2013/0345524 A1 | 12/2013 | Meyer et al. |
| 2014/0002234 A1 | 1/2014 | Alwan |
| 2014/0028464 A1 | 1/2014 | Garibaldi |
| 2014/0031884 A1 | 1/2014 | Elghazzawi |
| 2014/0032231 A1 | 1/2014 | Semen et al. |
| 2014/0052202 A1 | 2/2014 | Daynes |
| 2014/0055588 A1 | 2/2014 | Bangera et al. |
| 2014/0058344 A1 | 2/2014 | Toth |
| 2014/0058714 A1 | 2/2014 | Boyer |
| 2014/0087762 A1 | 3/2014 | Galvin et al. |
| 2014/0100516 A1 | 4/2014 | Hunt et al. |
| 2014/0108033 A1 | 4/2014 | Akbay et al. |
| 2014/0108034 A1 | 4/2014 | Akbay et al. |
| 2014/0108035 A1 | 4/2014 | Akbay et al. |
| 2014/0114236 A1 | 4/2014 | Gordon |
| 2014/0114237 A1 | 4/2014 | Gordon |
| 2014/0129250 A1 | 5/2014 | Daniel et al. |
| 2014/0136218 A1 | 5/2014 | Bolene et al. |
| 2014/0148138 A1 | 5/2014 | Chou et al. |
| 2014/0163490 A1 | 6/2014 | Locke et al. |
| 2014/0163493 A1 | 6/2014 | Weston et al. |
| 2014/0171753 A1 | 6/2014 | Montejo et al. |
| 2014/0187888 A1 | 7/2014 | Hatziantoniou |
| 2014/0194835 A1 | 7/2014 | Ehlert |
| 2014/0222446 A1 | 8/2014 | Ash et al. |
| 2014/0235975 A1 | 8/2014 | Carnes |
| 2014/0236106 A1 | 8/2014 | Locke et al. |
| 2014/0244285 A1 | 8/2014 | Hinkle et al. |
| 2014/0244301 A1 | 8/2014 | Lee et al. |
| 2014/0244307 A1 | 8/2014 | Shutko et al. |
| 2014/0266713 A1 | 9/2014 | Sehgal et al. |
| 2014/0275876 A1 | 9/2014 | Hansen et al. |
| 2014/0278502 A1 | 9/2014 | Laskin |
| 2014/0280882 A1 | 9/2014 | Lacerte et al. |
| 2014/0297299 A1 | 10/2014 | Lester, IV |
| 2014/0303551 A1 | 10/2014 | Germain et al. |
| 2014/0316819 A1 | 10/2014 | Dunsirn et al. |
| 2014/0323906 A1 | 10/2014 | Peatfield et al. |
| 2014/0350966 A1 | 11/2014 | Khatana et al. |
| 2014/0366878 A1 | 12/2014 | Baron |
| 2014/0372147 A1 | 12/2014 | White |
| 2014/0372522 A1 | 12/2014 | Orona et al. |
| 2014/0375470 A1 | 12/2014 | Malveaux |
| 2014/0378895 A1 | 12/2014 | Barack |
| 2015/0012290 A1 | 1/2015 | Inciardi et al. |
| 2015/0019237 A1 | 1/2015 | Doyle et al. |
| 2015/0019257 A1 | 1/2015 | Doyle et al. |
| 2015/0025482 A1 | 1/2015 | Begin et al. |
| 2015/0025486 A1 | 1/2015 | Hu et al. |
| 2015/0046137 A1 | 2/2015 | Zeilinger |
| 2015/0066531 A1 | 3/2015 | Jacobson et al. |
| 2015/0072613 A1 | 3/2015 | Swanson |
| 2015/0073363 A1 | 3/2015 | Kelch et al. |
| 2015/0094673 A1 | 4/2015 | Pratt et al. |
| 2015/0094674 A1 | 4/2015 | Pratt et al. |
| 2015/0094830 A1 | 4/2015 | Lipoma et al. |
| 2015/0095056 A1 | 4/2015 | Ryan et al. |
| 2015/0095059 A1 | 4/2015 | Yegge et al. |
| 2015/0095066 A1 | 4/2015 | Ryan et al. |
| 2015/0095068 A1 | 4/2015 | Ryan et al. |
| 2015/0100340 A1 | 4/2015 | Folsom et al. |
| 2015/0112707 A1 | 4/2015 | Manice et al. |
| 2015/0118662 A1 | 4/2015 | Ellison et al. |
| 2015/0119652 A1 | 4/2015 | Hyde et al. |
| 2015/0120318 A1 | 4/2015 | Toyama |
| 2015/0133829 A1 | 5/2015 | DeBusk et al. |
| 2015/0143300 A1 | 5/2015 | Zhang et al. |
| 2015/0159066 A1 | 6/2015 | Hartwell et al. |
| 2015/0164323 A1 | 6/2015 | Holtzclaw |
| 2015/0164376 A1 | 6/2015 | Huang |
| 2015/0186615 A1 | 7/2015 | Armor et al. |
| 2015/0189001 A1 | 7/2015 | Lee et al. |
| 2015/0227716 A1 | 8/2015 | Ryan et al. |
| 2015/0227717 A1 | 8/2015 | Ryan et al. |
| 2015/0234557 A1 | 8/2015 | Dorn |
| 2015/0234995 A1 | 8/2015 | Casady et al. |
| 2015/0242578 A1 | 8/2015 | Siemon |
| 2015/0242583 A1 | 8/2015 | Edson |
| 2015/0254403 A1 | 9/2015 | Laperna |
| 2015/0261920 A1 | 9/2015 | Blick |
| 2015/0363058 A1 | 12/2015 | Chung et al. |
| 2015/0370984 A1 | 12/2015 | Russell et al. |
| 2016/0018963 A1 | 1/2016 | Robbins et al. |
| 2016/0042154 A1 | 2/2016 | Goldberg et al. |
| 2016/0044141 A1 | 2/2016 | Pfützenreuter et al. |
| 2016/0055310 A1 | 2/2016 | Bentley et al. |
| 2016/0063210 A1 | 3/2016 | Bardi et al. |
| 2016/0066864 A1 | 3/2016 | Frieder et al. |
| 2016/0080365 A1 | 3/2016 | Baker et al. |
| 2016/0110507 A1 | 4/2016 | Abbo |
| 2016/0136339 A1 | 5/2016 | Begin et al. |
| 2016/0151015 A1 | 6/2016 | Condurso et al. |
| 2016/0154936 A1 | 6/2016 | Kalathil |
| 2016/0171866 A1 | 6/2016 | Dupasquier et al. |
| 2016/0196399 A1 | 7/2016 | Bonhomme |
| 2016/0203275 A1 | 7/2016 | Benjamin et al. |
| 2016/0246943 A1 | 8/2016 | Lake et al. |
| 2016/0308969 A1 | 10/2016 | Aihara et al. |
| 2016/0321422 A1 | 11/2016 | Albright |
| 2017/0007748 A1 | 1/2017 | Locke et al. |
| 2017/0017765 A1 | 1/2017 | Yegge et al. |
| 2017/0068781 A1 | 3/2017 | Zasowski et al. |
| 2017/0078396 A1 | 3/2017 | Haas et al. |
| 2017/0150939 A1 | 6/2017 | Shah |
| 2017/0348469 A1 | 8/2017 | Armstrong et al. |
| 2017/0273116 A1 | 9/2017 | Elghazzawi |
| 2018/0139572 A1 | 5/2018 | Hansen |
| 2018/0158545 A1 | 6/2018 | Blomquist |
| 2018/0233016 A1 | 8/2018 | Daniel et al. |
| 2018/0233221 A1 | 8/2018 | Blomquist |
| 2018/0318478 A1 | 11/2018 | Armstrong et al. |
| 2019/0298577 A1 | 10/2019 | Locke et al. |
| 2020/0100945 A1 | 4/2020 | Albert et al. |

FOREIGN PATENT DOCUMENTS

| | | |
|---|---|---|
| CN | 102805894 A | 12/2012 |
| CN | 102961815 | 3/2013 |
| CN | 104721892 A | 6/2015 |
| DE | 10 2010 036 405 | 1/2012 |
| DE | 20 2014 10752 U1 | 6/2014 |
| EP | 0 768 071 | 4/1997 |
| EP | 0 829 228 | 3/1998 |
| EP | 0566381 B1 | 7/2002 |
| EP | 1231965 A2 | 8/2002 |
| EP | 1291802 A2 | 3/2003 |
| EP | 1309960 A1 | 5/2003 |
| EP | 0 904 788 | 11/2003 |

(56) References Cited

FOREIGN PATENT DOCUMENTS

| | | |
|---|---|---|
| EP | 0814864 B1 | 12/2003 |
| EP | 1407624 A2 | 4/2004 |
| EP | 1011420 B1 | 12/2004 |
| EP | 1495713 A1 | 1/2005 |
| EP | 1524619 A2 | 4/2005 |
| EP | 1540557 A2 | 6/2005 |
| EP | 1 565 219 | 8/2005 |
| EP | 1579367 A2 | 9/2005 |
| EP | 1587017 A2 | 10/2005 |
| EP | 1 684 146 | 7/2006 |
| EP | 1 702 649 | 9/2006 |
| EP | 1 788 503 | 5/2007 |
| EP | 1 797 918 | 6/2007 |
| EP | 1839244 A1 | 10/2007 |
| EP | 1839615 A1 | 10/2007 |
| EP | 1 857 950 | 11/2007 |
| EP | 1870068 A1 | 12/2007 |
| EP | 1904964 A1 | 4/2008 |
| EP | 1934852 A1 | 6/2008 |
| EP | 1975828 A2 | 10/2008 |
| EP | 1993435 A2 | 11/2008 |
| EP | 2038786 A2 | 3/2009 |
| EP | 2040604 A2 | 4/2009 |
| EP | 2092470 A2 | 8/2009 |
| EP | 2146297 A1 | 1/2010 |
| EP | 2 172 859 | 4/2010 |
| EP | 2 218 478 | 8/2010 |
| EP | 2214552 A1 | 8/2010 |
| EP | 2 246 079 | 11/2010 |
| EP | 2 248 545 | 11/2010 |
| EP | 1 668 556 | 2/2011 |
| EP | 1404213 B1 | 3/2011 |
| EP | 1247229 B1 | 4/2011 |
| EP | 1406540 B1 | 6/2011 |
| EP | 1812094 B1 | 8/2011 |
| EP | 2 366 721 | 9/2011 |
| EP | 2366721 A1 | 9/2011 |
| EP | 2384472 A1 | 11/2011 |
| EP | 2226002 B1 | 1/2012 |
| EP | 1610494 B1 | 3/2012 |
| EP | 1 248 660 | 4/2012 |
| EP | 2023800 B1 | 4/2012 |
| EP | 2451513 A1 | 5/2012 |
| EP | 1 248 661 | 8/2012 |
| EP | 2488977 A1 | 8/2012 |
| EP | 2 503 478 | 9/2012 |
| EP | 2 529 765 | 12/2012 |
| EP | 2 562 665 | 2/2013 |
| EP | 2 389 961 | 3/2013 |
| EP | 2619723 A2 | 7/2013 |
| EP | 1881784 B1 | 10/2013 |
| EP | 2664194 A2 | 11/2013 |
| EP | 2 674 845 | 12/2013 |
| EP | 2 650 027 | 1/2014 |
| EP | 2743850 A2 | 6/2014 |
| EP | 2745204 A1 | 6/2014 |
| EP | 2795492 A1 | 10/2014 |
| EP | 2841895 A1 | 3/2015 |
| EP | 2850771 A1 | 3/2015 |
| EP | 2 066 365 | 4/2015 |
| EP | 2876567 A1 | 5/2015 |
| EP | 2891999 A2 | 7/2015 |
| EP | 2894581 A1 | 7/2015 |
| EP | 2906101 A2 | 8/2015 |
| EP | 2962266 A1 | 1/2016 |
| EP | 2968829 A1 | 1/2016 |
| EP | 2973089 A1 | 1/2016 |
| EP | 3000082 A1 | 3/2016 |
| EP | 3010398 A1 | 4/2016 |
| EP | 3078010 A1 | 10/2016 |
| EP | 2563437 B1 | 3/2017 |
| EP | 3027242 B1 | 4/2017 |
| EP | 2556650 B1 | 5/2017 |
| EP | 2632407 B1 | 8/2017 |
| EP | 3041571 B1 | 9/2017 |
| EP | 2856767 B1 | 11/2017 |
| EP | 2320971 B1 | 5/2018 |
| EP | 2335173 B1 | 5/2018 |
| EP | 3100188 B1 | 6/2018 |
| EP | 2440112 B1 | 10/2018 |
| EP | 2992500 B1 | 12/2018 |
| EP | 2597584 B1 | 1/2019 |
| EP | 3219340 B1 | 1/2019 |
| EP | 2890456 B1 | 2/2019 |
| EP | 2881875 B1 | 5/2019 |
| EP | 2836269 B1 | 8/2019 |
| EP | 2866851 B1 | 9/2019 |
| GB | 2235877 | 3/1991 |
| GB | 2279784 | 1/1995 |
| GB | 2409951 | 7/2005 |
| GB | 2436160 A | 9/2007 |
| GB | 2449400 A | 11/2008 |
| GB | 2456708 A | 7/2009 |
| GB | 2423178 B | 5/2010 |
| GB | 2475091 | 5/2011 |
| GB | 2488904 | 9/2012 |
| GB | 2446923 B | 5/2013 |
| GB | 2499986 A | 9/2013 |
| GB | 2491946 B | 8/2014 |
| WO | WO 1996/019335 | 6/1996 |
| WO | WO 96/27163 A1 | 9/1996 |
| WO | WO 97/44745 A1 | 11/1997 |
| WO | WO 99/24927 A1 | 5/1999 |
| WO | WO 99/63886 A1 | 12/1999 |
| WO | WO 00/60522 A2 | 10/2000 |
| WO | WO 2001/014048 | 3/2001 |
| WO | WO 01/33457 A1 | 5/2001 |
| WO | WO 2001/036027 | 5/2001 |
| WO | WO 2001/054743 | 8/2001 |
| WO | WO 01/81829 A1 | 11/2001 |
| WO | WO 02/17075 A2 | 2/2002 |
| WO | WO 02/33577 A1 | 4/2002 |
| WO | WO 02/078594 A2 | 10/2002 |
| WO | WO 02/101713 A1 | 12/2002 |
| WO | WO 03/054668 A2 | 7/2003 |
| WO | WO 2003/055432 | 7/2003 |
| WO | WO 2003/094090 | 11/2003 |
| WO | WO 2003/101508 | 12/2003 |
| WO | WO 2004/057514 A2 | 7/2004 |
| WO | WO 2004/074457 A2 | 9/2004 |
| WO | WO 2005/022349 A2 | 3/2005 |
| WO | WO 2005/031632 A2 | 4/2005 |
| WO | WO 2005/036447 A2 | 4/2005 |
| WO | WO 2005/045461 A1 | 5/2005 |
| WO | WO 2005/053793 A1 | 6/2005 |
| WO | WO 2005/057466 A2 | 6/2005 |
| WO | WO 2005/083619 A2 | 9/2005 |
| WO | WO 2005/101282 A2 | 10/2005 |
| WO | WO 2005/109297 | 11/2005 |
| WO | WO 2005/120097 A2 | 12/2005 |
| WO | WO 2006/021154 A1 | 3/2006 |
| WO | WO 2006/066583 A1 | 6/2006 |
| WO | WO 2006/066585 A2 | 6/2006 |
| WO | WO 2006/071711 A2 | 7/2006 |
| WO | WO 2006/099120 A2 | 9/2006 |
| WO | WO 2006/108858 A1 | 10/2006 |
| WO | WO 2006/111109 A1 | 10/2006 |
| WO | WO 2007/027490 A2 | 3/2007 |
| WO | WO 2007/035646 A2 | 3/2007 |
| WO | WO 2007/127879 A2 | 11/2007 |
| WO | WO 2007/133478 A2 | 11/2007 |
| WO | WO 2007/137869 A2 | 12/2007 |
| WO | WO 2008/010012 A2 | 1/2008 |
| WO | WO 2008/036344 | 3/2008 |
| WO | WO 2008/036360 | 3/2008 |
| WO | WO 2008/036361 | 3/2008 |
| WO | WO 2008/039314 | 4/2008 |
| WO | WO 2008/062382 A2 | 5/2008 |
| WO | WO 2008/104609 | 9/2008 |
| WO | WO 2008/116295 | 10/2008 |
| WO | WO 2008/132215 | 11/2008 |
| WO | WO 2009/021523 | 2/2009 |
| WO | WO-2009023634 A2 | 2/2009 |
| WO | WO 2009/047524 | 4/2009 |

(56) References Cited

FOREIGN PATENT DOCUMENTS

| | | |
|---|---|---|
| WO | WO 2009/089390 | 7/2009 |
| WO | WO 2009/093116 | 7/2009 |
| WO | WO 2009/140669 A2 | 11/2009 |
| WO | WO 2009/151645 | 12/2009 |
| WO | WO 2010/017484 | 2/2010 |
| WO | WO 2010/025166 A1 | 3/2010 |
| WO | WO 2010/025467 A1 | 3/2010 |
| WO | WO 2010/039481 | 4/2010 |
| WO | WO 2010/078558 A1 | 7/2010 |
| WO | WO 2010/085033 | 7/2010 |
| WO | WO 2010/089368 | 8/2010 |
| WO | WO 2010/126668 | 11/2010 |
| WO | WO 2010/132617 A2 | 11/2010 |
| WO | WO 2010/145780 | 12/2010 |
| WO | WO 2011/023275 | 3/2011 |
| WO | WO 2011/023384 A1 | 3/2011 |
| WO | WO 2011/039676 A2 | 4/2011 |
| WO | WO 2011/046860 A2 | 4/2011 |
| WO | WO 2011/047334 A1 | 4/2011 |
| WO | WO 2011/107972 | 9/2011 |
| WO | WO 2011/123933 A1 | 10/2011 |
| WO | WO 2011/124388 | 10/2011 |
| WO | WO 2011/137230 | 11/2011 |
| WO | WO 2012/009869 | 1/2012 |
| WO | WO 2012/027342 | 3/2012 |
| WO | WO 2012/027912 | 3/2012 |
| WO | WO 2012/027913 | 3/2012 |
| WO | WO 2012/027914 | 3/2012 |
| WO | WO 2012/027915 | 3/2012 |
| WO | WO 2012/027916 | 3/2012 |
| WO | WO 2012/051278 | 4/2012 |
| WO | WO 2012/100624 | 8/2012 |
| WO | WO 2012/107430 | 8/2012 |
| WO | WO 2012/127281 | 9/2012 |
| WO | WO 2012/156655 | 11/2012 |
| WO | WO 2012/160164 | 11/2012 |
| WO | WO 2012/172818 | 12/2012 |
| WO | WO 2013/014278 | 1/2013 |
| WO | WO 2013/025815 | 2/2013 |
| WO | WO 2013/026999 A1 | 2/2013 |
| WO | WO 2013/029330 | 3/2013 |
| WO | WO 2013/036853 A2 | 3/2013 |
| WO | WO 2013/054217 | 4/2013 |
| WO | WO 2013/061887 A1 | 5/2013 |
| WO | WO 2013/063848 | 5/2013 |
| WO | WO 2013/066775 | 5/2013 |
| WO | WO 2013/089712 | 6/2013 |
| WO | WO 2013/102855 | 7/2013 |
| WO | WO 2013/109517 | 7/2013 |
| WO | WO 2013/119978 | 8/2013 |
| WO | WO 2013/123022 | 8/2013 |
| WO | WO 2013/126049 | 8/2013 |
| WO | WO 2013/136181 | 9/2013 |
| WO | WO 2013/138182 A1 | 9/2013 |
| WO | WO 2013/140255 | 9/2013 |
| WO | WO 2013/141870 | 9/2013 |
| WO | WO 2013/150025 | 10/2013 |
| WO | WO 2013/155193 A1 | 10/2013 |
| WO | WO 2013/175076 | 11/2013 |
| WO | WO 2013/182218 | 12/2013 |
| WO | WO 2014/012802 | 1/2014 |
| WO | WO 2014/015215 A2 | 1/2014 |
| WO | WO 2014/018786 A2 | 1/2014 |
| WO | WO 2014/075494 A1 | 5/2014 |
| WO | WO 2014/089086 A1 | 6/2014 |
| WO | WO 2014/100036 A1 | 6/2014 |
| WO | WO 2014/100687 A2 | 6/2014 |
| WO | WO 2014/106056 A2 | 7/2014 |
| WO | WO 2014/123846 A1 | 8/2014 |
| WO | WO 2014/133822 A2 | 9/2014 |
| WO | WO 2014/141221 A2 | 9/2014 |
| WO | WO 2014/145496 A1 | 9/2014 |
| WO | WO 2014/150255 A2 | 9/2014 |
| WO | WO 2014/151930 | 9/2014 |
| WO | WO 2014/152963 A1 | 9/2014 |
| WO | WO 2014/189070 A1 | 11/2014 |
| WO | WO 2014/009876 | 12/2014 |
| WO | WO 2015/019273 A2 | 2/2015 |
| WO | WO 2015/023515 | 2/2015 |
| WO | WO 2015/025482 A1 | 2/2015 |
| WO | WO 2015/026387 A1 | 2/2015 |
| WO | WO 2015/050816 A1 | 4/2015 |
| WO | WO 2015/078112 A1 | 6/2015 |
| WO | WO 2015/085249 A1 | 6/2015 |
| WO | WO 2015/091070 | 6/2015 |
| WO | WO 2015/124670 A1 | 8/2015 |
| WO | WO 2015/132528 A1 | 9/2015 |

OTHER PUBLICATIONS

International Search Report and Written Opinion, re PCT Application No. PCT/GB2014/050786, mailed Jun. 12, 2014.
Cinterion PHS8-p. 3G Hspa+, 2012. URL: http://www.cinterion.com/tl_files/cinterion/downloads/cinterion_datasheet_PHS8_web.pdf.
Huntleigh Healthcare, "Negative Pressure Positive Outcomes" WoundASSIST TNP Console and Canister Brochure, 2007, in 6 pages.
International Search Report and Written Opinion, re PCT Application No. PCT/US2014/026692, mailed Mar. 2, 2015.
Invitation to Pay Additional Fees and Search Report, re PCT Application No. PCT/US2014/026692, mailed Sep. 26, 2014.
International Search Report and Written Opinion, re PCT Application No. PCT/US2014/050233, mailed Jan. 7, 2015.
International Search Report and Written Opinion, re PCT Application No. PCT/US2014/066441, mailed Jun. 25, 2015.
International Search Report and Written Opinion, re PCT Application No. PCT/US2014/065680, mailed May 14, 2015.
"Vivano—Product application description", Hartmann Vivano, accessed Feb. 28, 2013, in 3 pages. URL: http://www.vivanosystem.info/20809.php.

* cited by examiner

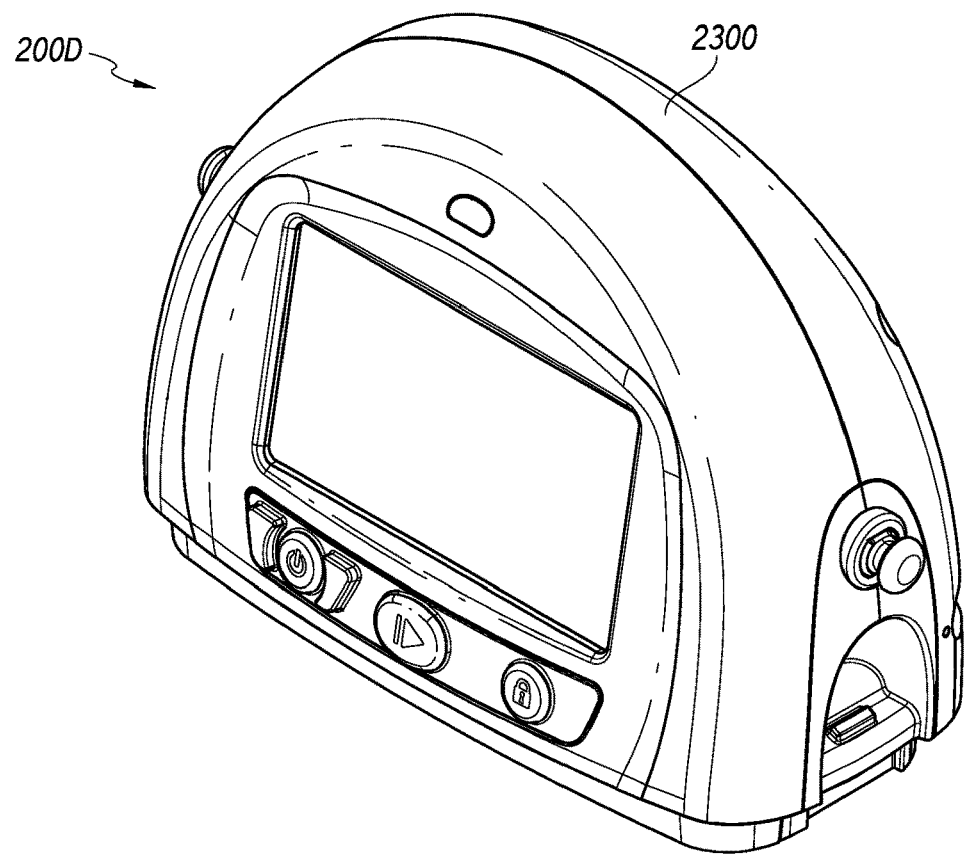
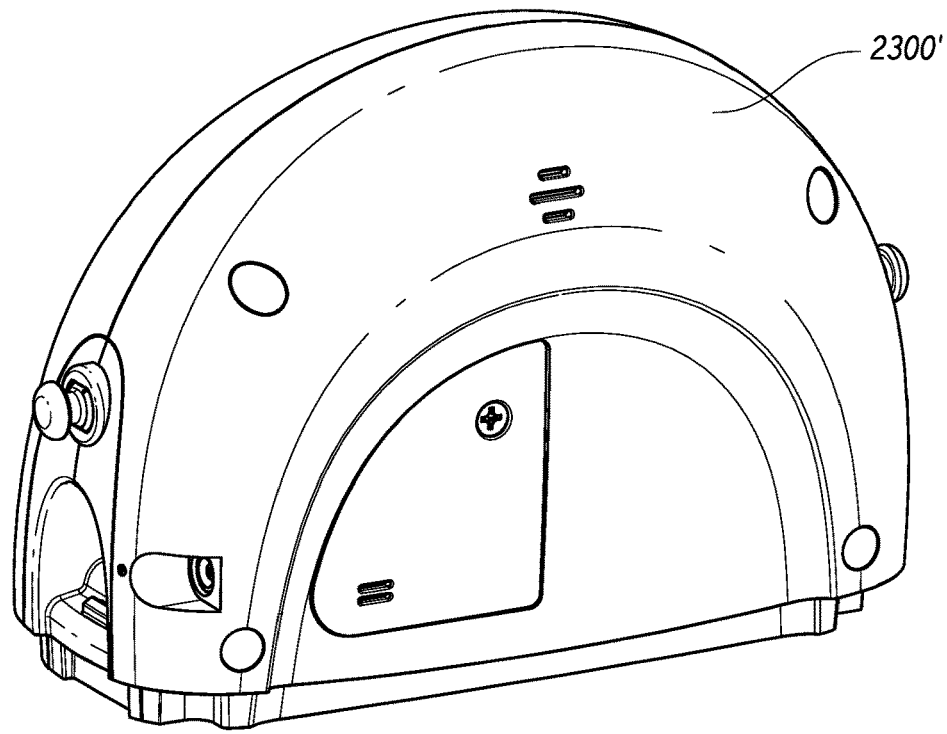
FIG. 2D

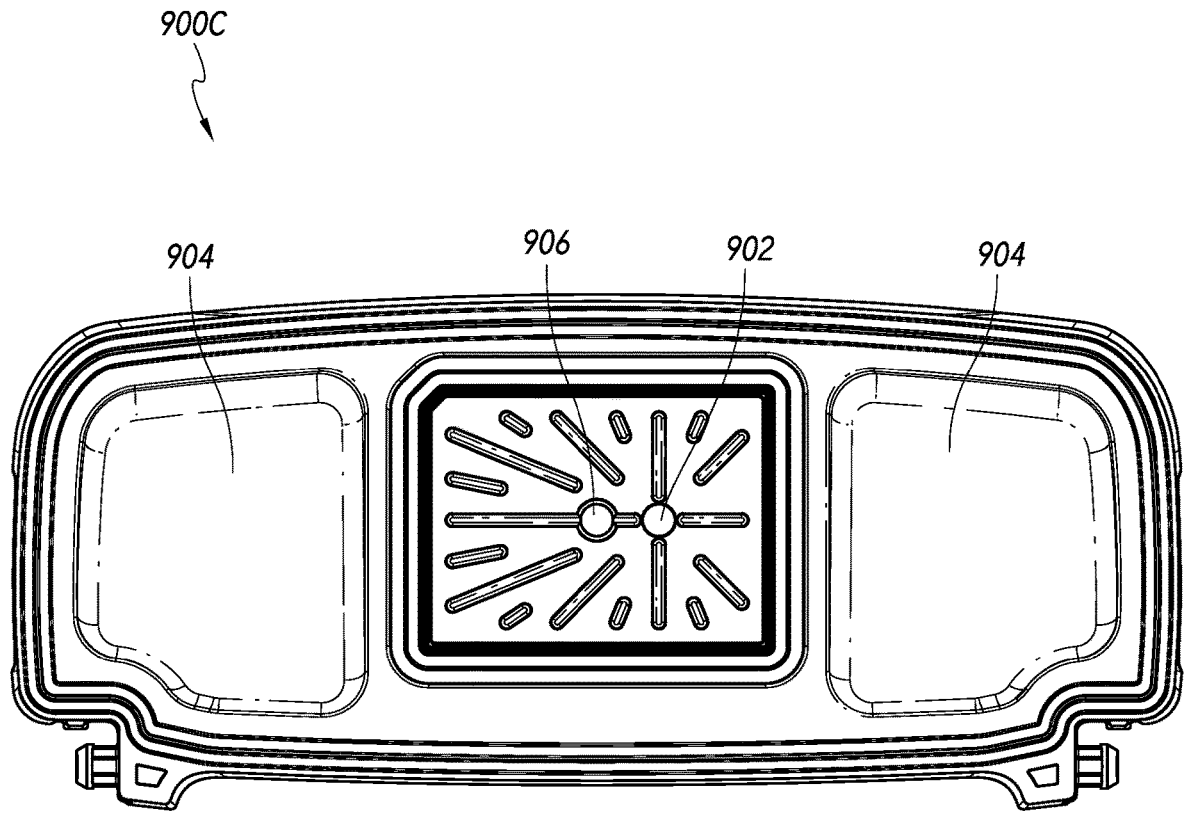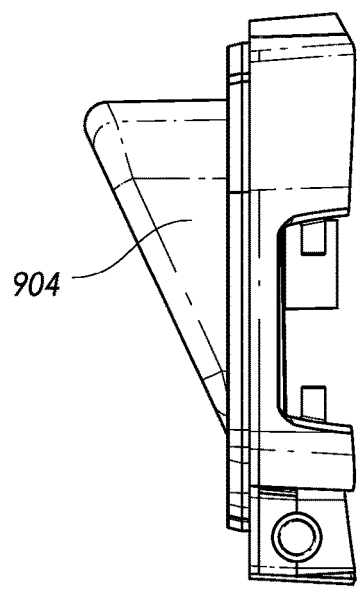
FIG. 9C

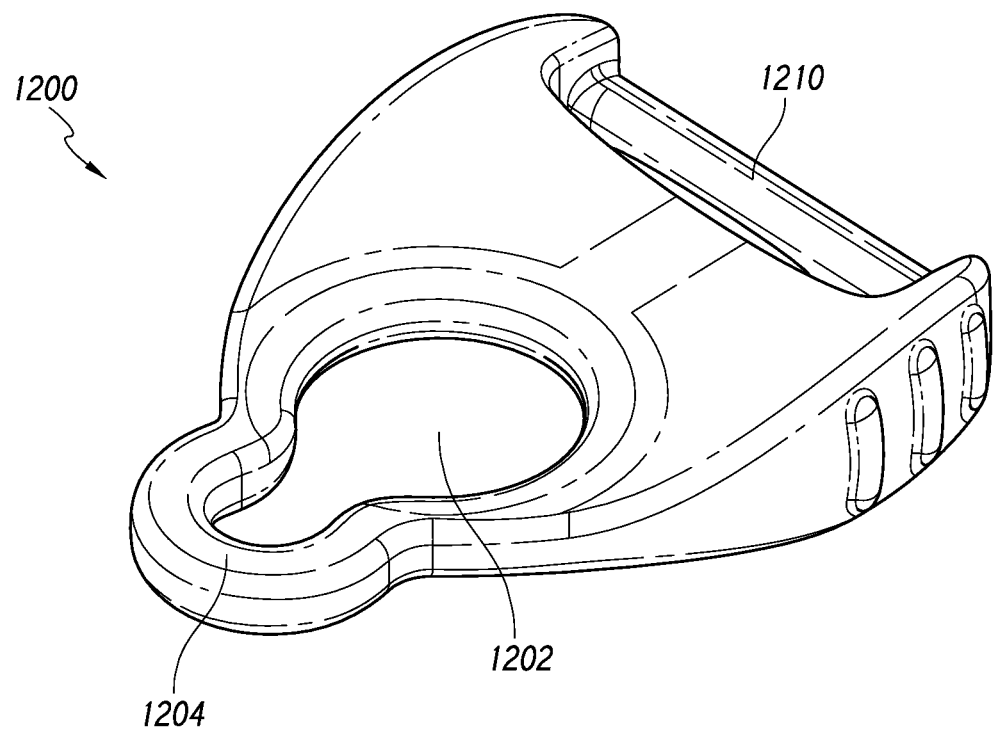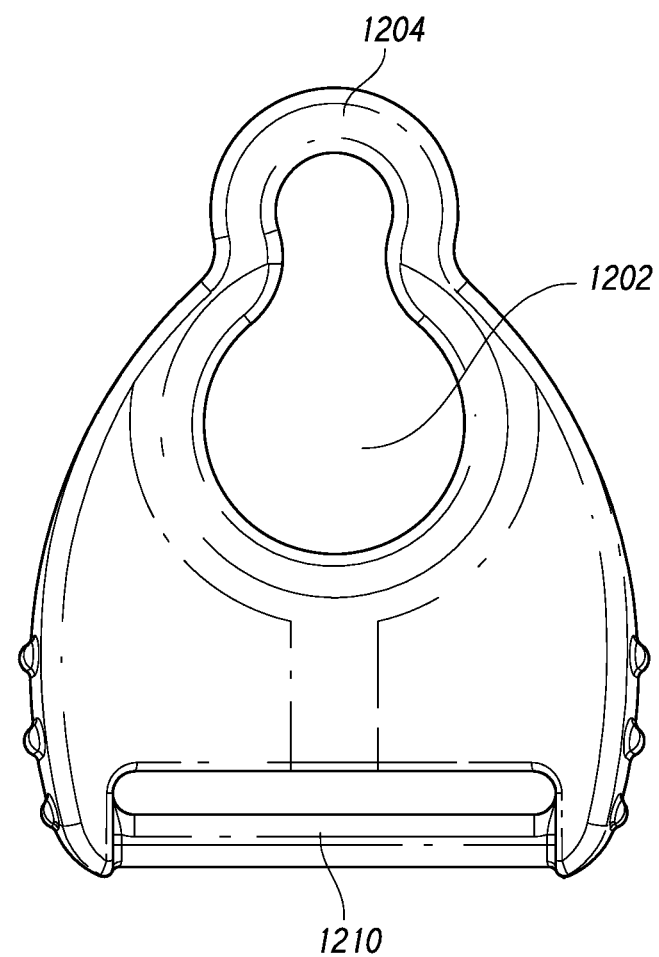
FIG. 12

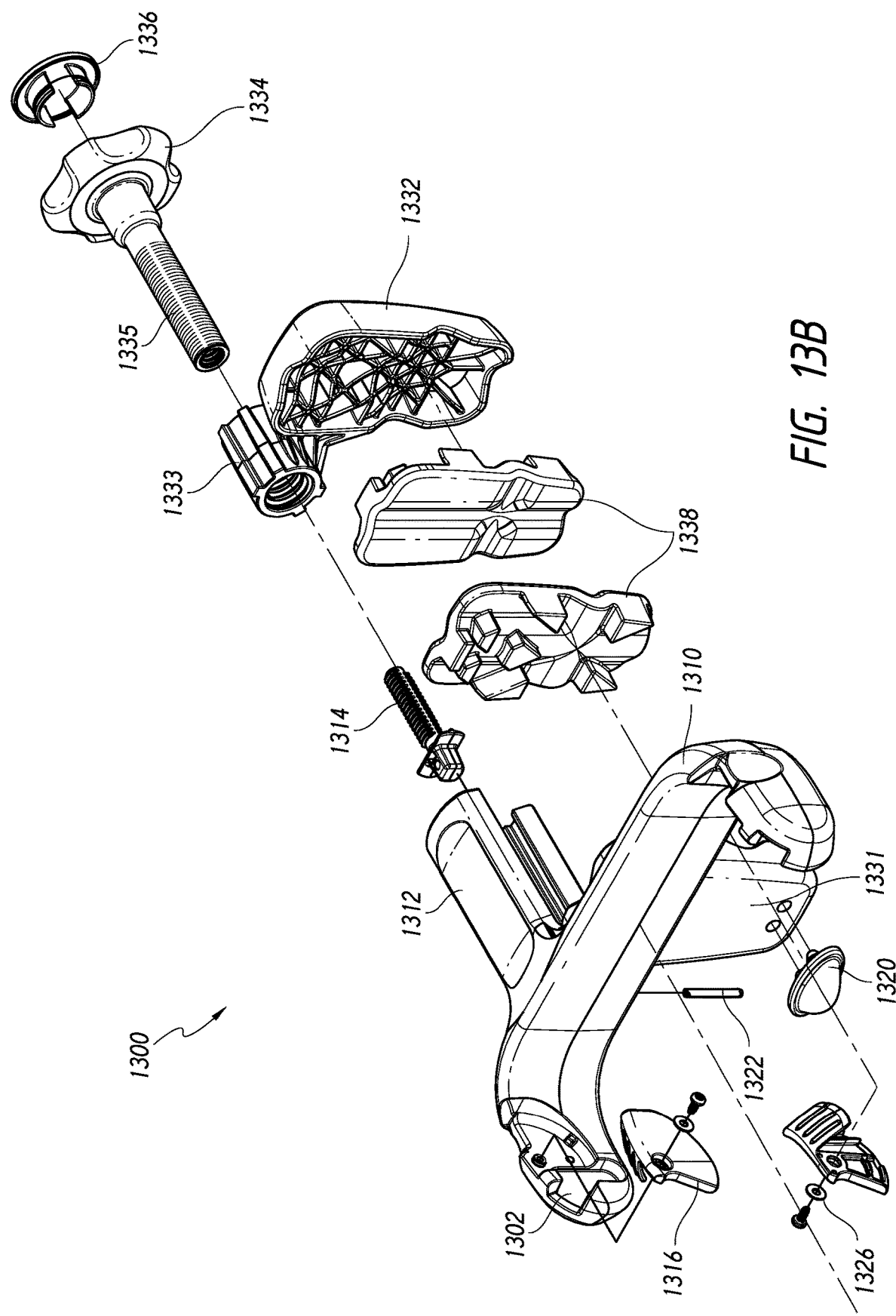

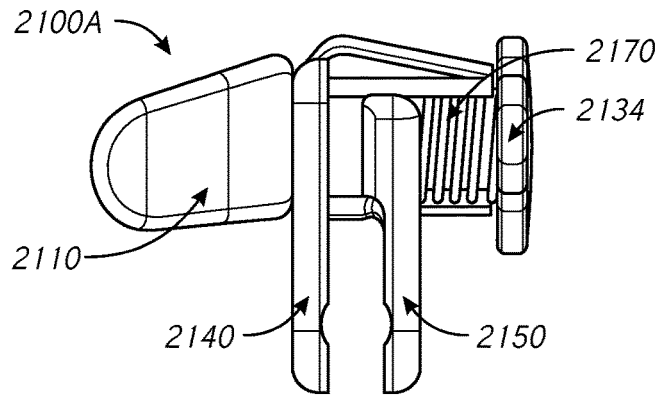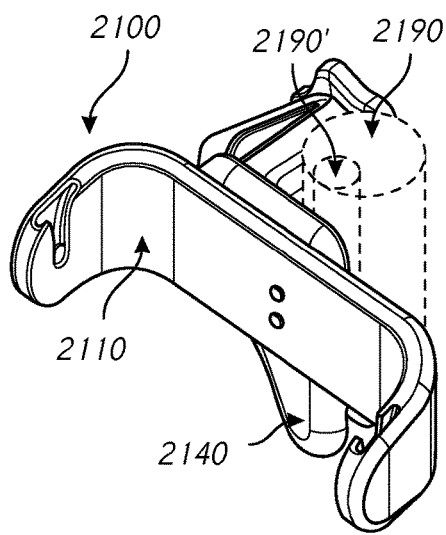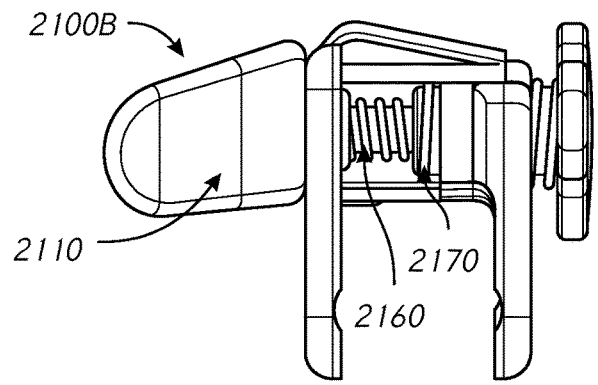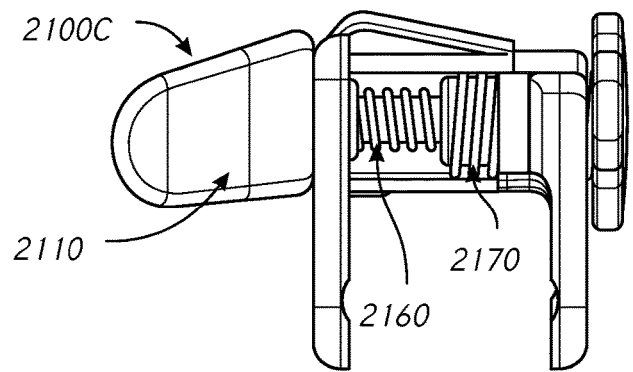
FIG. 13C

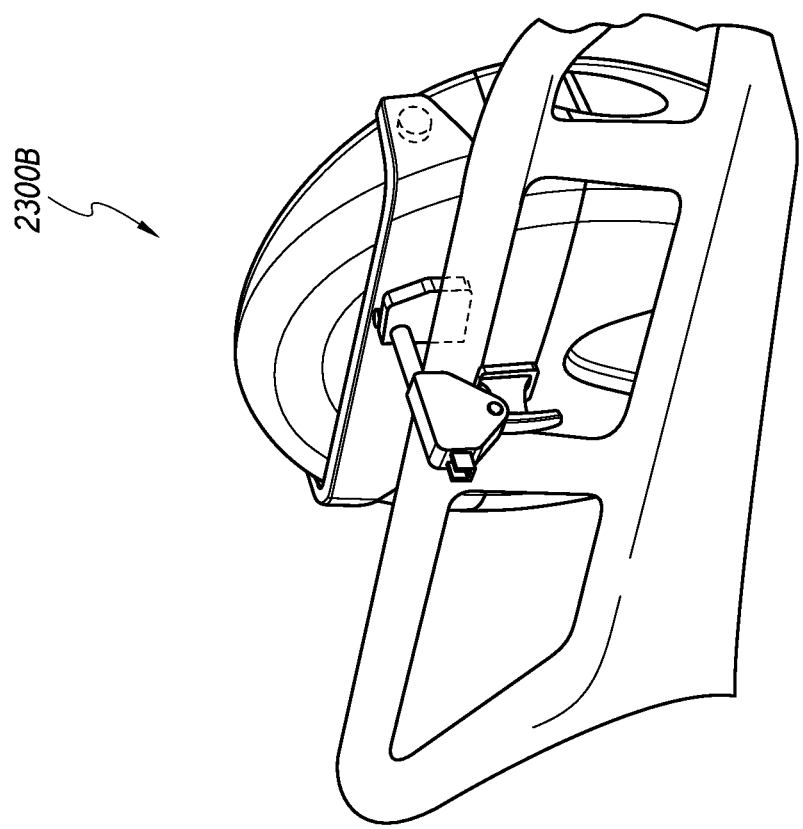
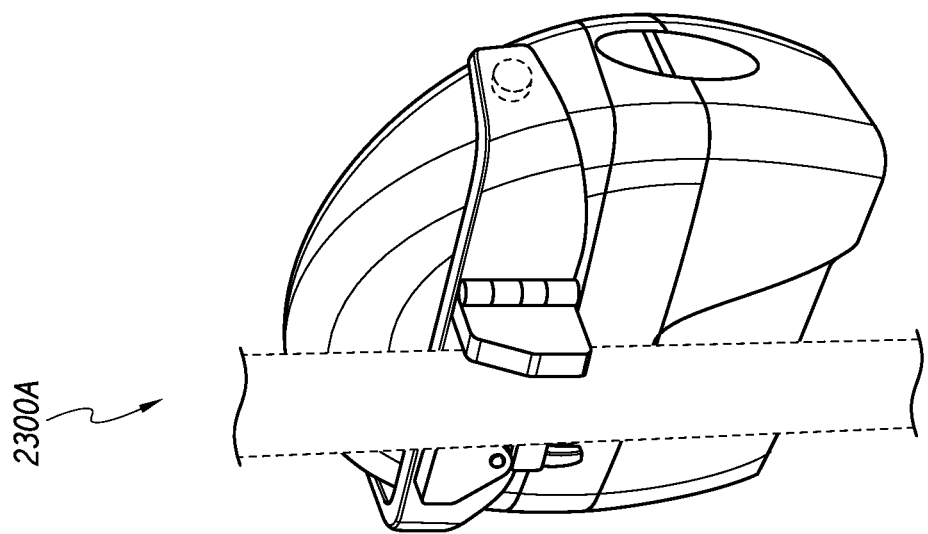
FIG. 13K smith&nephew

| Home | Device Records | Fleet Status | Contact Us |

Device 92581574 - Summary    Select a device    🔍 Enter device number    [Logout]

✏️ Edit Device Properties    📄 Generate Data Report

- Search
- Summary
- Therapy
- Alarms
- Software Updates
- Error Log
- Location Tracking

Device Properties — 1605

| Manufacturing Date | 10-1-2012 |
|---|---|
| Distributor | UHS-[branch] |
| Battery life | 19.2 Ah |
| Battery Charge | 75% |
| Software Version | v. 2.45 |
| Lifetime Therapy | 234:12:43 |
| Device Placement (dd:hh:mm) | 31:23:45 |
| Total Patient Therapy (dd:hh:mm) | 23:12:53 |

Last Reported Address — 1606

| Aquisition Time | Sunday, March 12, 2013 |
|---|---|
| Reported Location | (38.804420, 77.043283) |
| Nearby Address | 520 King St. Alexandria VA, 22324 |

1622

1606a

Trademark of Smith & Nephew    Availability    Terms of Use    Copyright & Disclaimer

*FIG. 16D*

*FIG. 16I* smith&nephew

| Home | Device Records | Fleet Status | Contact Us |

Select one or multiple devices from your current fleet to view

Show [10 ▼] Entries

Select By [All ▼]     🔍 Enter Search Items

🔍 Enter device number    [Logout]

| | Device ˄˅ | Country ˄˅ | State ˄˅ | Zip ˄˅ | Distributor ˄˅ | Facility ˄˅ |
|---|---|---|---|---|---|---|
| ☐ | 2054052 | United States | Virginia | 22314 | LHS (branch) | (Hospital Name) |
| ☑ | 5488263 | United States | Indiana | 46104 | Apna (branch) | (Hospital Name) |
| ☐ | 70267512 | United States | Indiana | 46140 | LHS (branch) | (Hospital Name) |
| ☑ | 67380952 | United States | Virginia | 22305 | Apna (branch) | (Hospital Name) |
| ☐ | 92501574 | United States | Virginia | 22314 | LHS (branch) | (Hospital Name) |
| ☐ | 2054052 | United States | Indiana | 46104 | Apna (branch) | (Hospital Name) |
| ☑ | 5488263 | United States | Indiana | 46143 | LHS (branch) | (Hospital Name) |
| ☐ | 70267512 | United States | Virginia | 22314 | Apna (branch) | (Hospital Name) |
| ☐ | 67380952 | United States | Virginia | 22305 | LHS (branch) | (Hospital Name) |
| ☐ | 92501574 | | | | | |

|◀ ◀ Page [1] of 3 ▶ ▶|

Search
Properties
Therapy
Battery
Software Version
Location

Availability    [Display Data]

Trademark of Smith & Nephew    Terms of Use    Copyright & Disclaimer

FIG. 16M

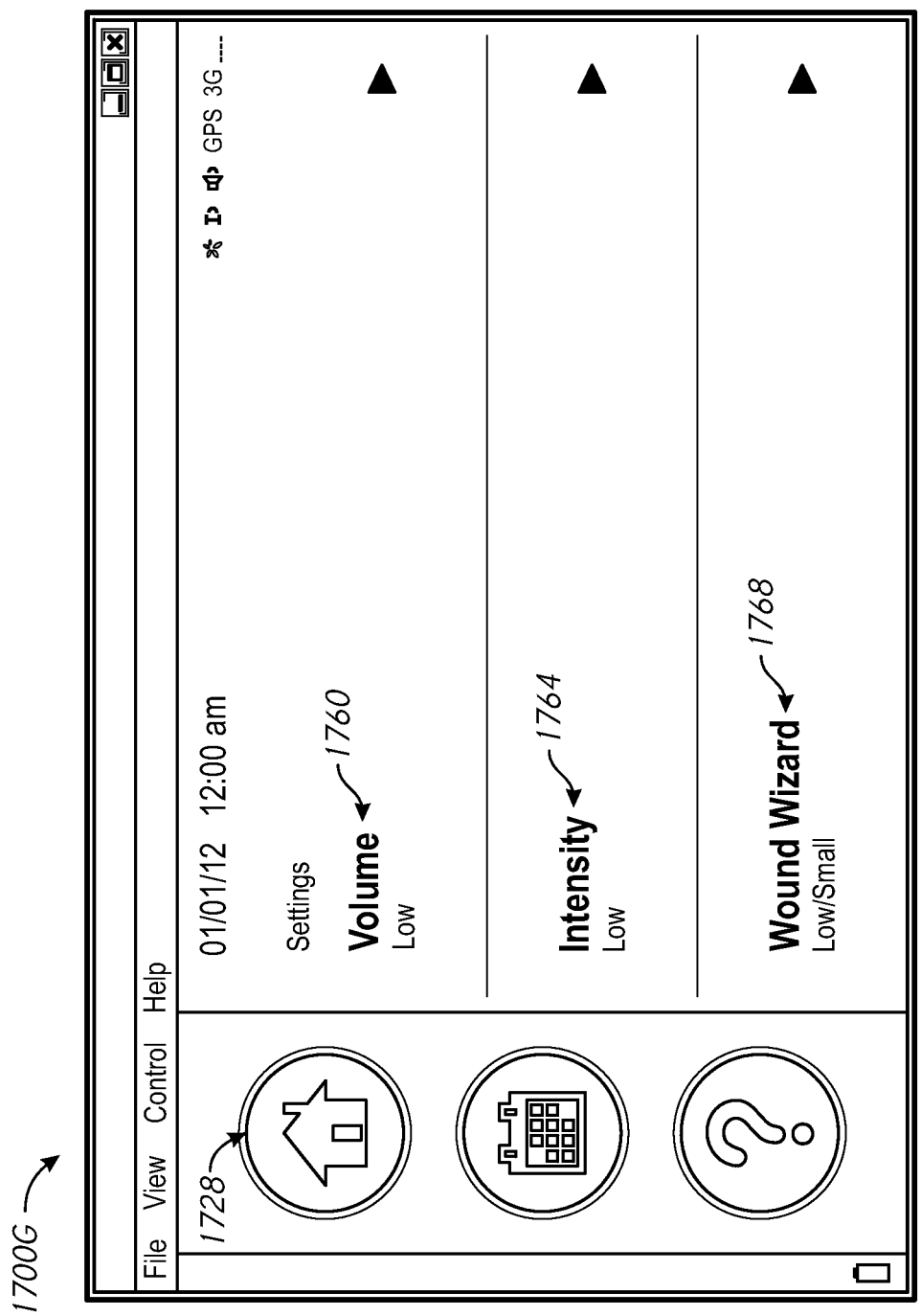

ATTACHMENT SYSTEM FOR MOUNTING APPARATUS

CROSS-REFERENCE TO RELATED APPLICATIONS

This application is a continuation of U.S. patent application Ser. No. 14/775,339, filed Sep. 11, 2015, which is a national stage application of International Patent Application No. PCT/US2014/026692, filed Mar. 13, 2014, which claims the benefit of U.S. Provisional Application No. 61/785,384, filed Mar. 14, 2013, and U.S. Provisional Application No. 61/860,809, filed Jul. 31, 2013, the disclosures of which are hereby incorporated by reference in their entireties.

BACKGROUND

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and method of using TNP systems. In addition, embodiments disclosed herein relate to attachment mechanisms or systems for negative pressure therapy devices.

SUMMARY

In some embodiments, an apparatus for applying negative pressure therapy to a wound includes a source of negative pressure configured to be coupled to a dressing, a first controller configured to perform a first set of tasks, and a second controller in communication with the first controller, the second controller configured to perform a second set of tasks. The first set of tasks can be associated with a first risk level and a second set of tasks can be associated with a second risk level different from the first risk level. The first set of tasks performed by the first controller can include processing input received from a user and providing data to be output to the user, wherein input received from the user can include negative pressure therapy parameters. The second set of tasks performed by the second controller can include operating the source of negative pressure in accordance with the negative pressure therapy parameters. Processing input received from the user can be associated with a first level of responsiveness and operating the source of negative pressure can be associated with a second level of responsiveness, the second level of responsiveness exceeding the first level of responsiveness.

The apparatus of the preceding paragraph may also include any combination of the following features described in this paragraph, among others described herein. The apparatus can include a third controller in communication with the first controller, the third controller configured to perform a third set of tasks associated with a third risk level different from the first and second risk levels. The third set of tasks performed by the third controller can include communicating data to a remote computing device and communicating data to the remote computing device can be associated with a third level of responsiveness, the third level of responsiveness being different from the first and second levels of responsiveness. The apparatus can include a dressing configured to be placed over the wound and to create a substantially fluid impermeable seal over the wound.

In certain embodiments, an apparatus for applying negative pressure therapy to a wound includes a source of negative pressure configured to be coupled to a dressing, the source of negative pressure configured to aspirate fluid from the wound, a canister configured to collect fluid aspirated from the wound, a fluid flow path configured to fluidically connect the dressing, canister, and source of negative pressure, and a flow restrictor configured to be placed in the fluid flow path. The apparatus can also include first and second pressure sensors configured to measure pressure downstream of the flow restrictor, the second pressure sensor configured to operate as a backup pressure sensor to the first pressure sensor, a third pressure sensor configured to measure pressure upstream of the flow restrictor, and a controller configured to indicate, based at least in part on the pressure measurements received from the first, second, and third pressure sensors, at least one of a leakage, blockage, and overpressure in the fluid flow path.

In various embodiments, an apparatus for applying negative pressure therapy to a wound, includes a source of negative pressure configured to be fluidically connected to a dressing configured to be placed over a wound, the source of negative pressure configured to deliver negative pressure wound therapy to the wound in accordance with a plurality negative pressure therapy parameters. The apparatus can also include a controller configured to provide a graphical user interface (GUI) configured to permit adjustment of at least some of the plurality of negative pressure therapy parameters, receive, via the GUI, a first adjustment of a first negative pressure therapy parameter, adjust or cause adjustment of operation of the source of negative pressure based at least in part on the first adjustment of the first negative pressure therapy parameter, record a plurality of historical data parameters associated with the plurality of negative pressure therapy parameters, wherein at least one historical data parameter is associated with first and second settings of a negative therapy pressure therapy parameter, the first and second settings assigned to the negative pressure therapy parameter at different times, and transmit or cause transmission over a communication interface at least some of the plurality of historical data parameters to a remote computer.

The apparatus of any of preceding paragraphs may also include any combination of the following features described in this paragraph, among others described herein. At least some of the plurality of historical data parameters transmitted to the remote computer can include one or more of apparatus identification data, apparatus location data, therapy history data, and alarm data. The controller can also be configured to record or cause recording of apparatus location data corresponding to a geographical location of the apparatus. The controller can also be configured to record or cause recording of apparatus location data based on at least one of global positioning data (GPS) and cellular network data. The controller can also be configured to periodically transmit or cause periodic transmission over the communication interface of the at least some of the plurality of historical data parameters to the remote computer. The controller can also be configured to receive, via the GUI, a request to transmit the at least some of the plurality of historical data parameters to the remote computer and transmit or cause transmission of the at least some of plurality of historical data parameters to the remote computer. The controller can also be configured to determine or cause determination of a flow rate in a fluid flow path, the fluid flow path including the source of negative pressure and the dressing and provide, via the GUI, an indication of the determined flow rate. The indication of the flow rate can include a gauge.

The apparatus of any of preceding paragraphs may also include any combination of the following features described in this paragraph, among others described herein. The apparatus can include a pressure sensor configured to measure pressure in at least a portion of the fluid flow path, and the controller can also be configured to determine or cause determination of the flow rate in the fluid flow path based at least in part on pressure measured by the pressure sensor. The source of negative pressure can a vacuum pump and the controller is can also be configured to determine or cause determination of the flow rate in the fluid flow path based at least in part on a measured speed of the vacuum pump. The controller can also be configured to deactivate or cause deactivation of the source of negative pressure in response to determining that the flow rate satisfies a high flow threshold and provide, via the GUI, a high flow indication. The provided high flow indication can also include information for resolving the high flow condition.

The apparatus of any of preceding paragraphs may also include any combination of the following features described in this paragraph, among others described herein. The controller can also be configured to chronologically display, via the GUI, at least some of the historical data parameters associated with the plurality of negative pressure therapy parameters. At least some of the historical data parameters can include one or more errors associated with delivery of negative pressure wound therapy. The controller can also be configured to provide, via the GUI, a log including total negative pressure wound therapy time delivered over a plurality of time periods and one or more errors can be included in the log. The controller can also be configured to in response to transmitting or causing transmission of the at least some of the plurality of historical data parameters, receive or cause receiving from the remote computer of a second adjustment of a second negative pressure therapy parameter and adjust or cause adjustment of operation of the source of negative pressure based at least in part on the received second adjustment of the second negative pressure therapy parameter. The controller can also be configured to permit, via the GUI, adjustment of the second negative pressure therapy parameter.

The apparatus of any of preceding paragraphs may also include any combination of the following features described in this paragraph, among others described herein. The apparatus can include a touch screen display configured to display the GUI and permit adjustment of at least some of the plurality of negative pressure therapy parameters. The apparatus can be configured to treat two wounds with negative pressure wound therapy and the processor can also be configured to, via the GUI, permit activation of treatment of two wounds. The GUI can be configured to include a plurality of screens and a plurality of icons grouped into a menu and the menu can be configured to be displayed in the same portion of each screen.

In some embodiments, a negative pressure wound therapy apparatus includes a source of negative pressure configured to be fluidically connected to a dressing configured to be placed over a wound and a controller. The controller can be configured to detect or cause detection of presence of at least one temporary blockage in a fluid flow path including the source of negative pressure, a canister configured to store fluid aspirated from the wound, and the dressing, the at least one temporary blockage caused by fluid aspirated from the wound being aspirated into the canister. The controller can also be configured to clear or cause clearance of the at least one temporary blockage by increasing a level of negative pressure provided by the source of negative pressure.

The apparatus of any of preceding paragraphs may also include any combination of the following features described in this paragraph, among others described herein. The controller can also be configured to detect or cause detection of presence of the at least one temporary blockage in the fluid flow path by deactivating or causing deactivation of the source of negative pressure and detecting or causing detection of a substantially discontinuous decay of negative pressure in the fluid flow path while the source of negative pressure is deactivated. The apparatus can also include a pressure sensor configured to measure pressure at a canister inlet and the controller can also be configured to detect or cause detection of presence of the at least one temporary blockage by detecting an increase in pressure measured by the pressure sensor, the increase in pressure caused by the at least one temporary blockage.

In certain embodiments, a computer system includes at least one processor configured to receive, over a communication interface, a plurality of operational parameters from a plurality of negative pressure wound therapy devices, each negative pressure wound therapy device configured to provide negative pressure wound therapy, group at least some of the plurality of negative pressure wound therapy devices into a fleet, and provide at least some of the plurality of received operational parameters for at least some of the devices in the fleet based on a common ownership or common leasing status.

The computer system of the preceding paragraph may also include any combination of the following features described in this paragraph, among others described herein. The processer can also be configured to provide at least one of geographical location data, battery charge data, and battery life data for at least some of the devices in the fleet. The processor can also be configured to receive an adjustment of at least one operational parameter associated with at least one device in the fleet and transmit the received adjustment thereby causing the at least one device to modify delivery of negative pressure wound therapy in accordance with the adjustment.

In various embodiments, an attachment system for mounting an apparatus includes a cradle configured to be removably attached to the apparatus, a first arm attached to the cradle and a second arm, the second arm configured to be moved between a clamped position and an unclamped position, wherein the first and second arms are configured to be substantially securely attached to a structure in the clamped position, and wherein the first and second arms are configured to not be substantially securely attached to the structure in the unclamped position. The attachment system also includes a first screw, a second screw attached to the second arm, the first screw engaged with the second screw, and a knob attached to the second screw, the knob configured to move the second arm between the clamped and unclamped positions.

The attachment system of the preceding paragraph may also include any combination of the following features described in this paragraph, among others described herein. The first and second screws can be power screws. The first screw can include a first thread and the second screw can include a second thread, wherein the first and second threads can be Acme threads. The first screw includes a substantially hollow portion and at least a part of the second screw is configured to be positioned in the interior portion of the first screw in the clamped position. The interior portion of the first screw can include an interior thread configured to engage with the second thread of the second screw. The first screw can include a first thread oriented in a first direction and the second screw can include a second thread oriented in a second direction opposite from the first direction. Rotation of the handle can cause the second arm to move a distance proportional to an aggregate of a first lead of the first screw and a second lead of the second screw. The second arm can also be configured to be moved between a fully open and a fully closed position, the first and second arms being in contact in the fully closed position, and the first and second arms being separated by a distance in the fully open position, whereby about four rotations of the knob cause the second arm to move between the fully closed and fully open positions.

The attachment system of any of preceding paragraphs may also include any combination of the following features described in this paragraph, among others described herein. The structure can be at least one of a pole and a bedrail. The negative pressure source can be configured to be fluidically connected to a dressing configured to be placed over a wound and to create a substantially fluid impermeable seal over the wound. The apparatus can include a pump. The pump can be a negative pressure wound therapy (NPWT) apparatus. In certain embodiments, the attachment system of any of preceding paragraphs can be used in a method of attaching a negative pressure wound therapy (NPWT) apparatus to a structure.

In some embodiments, an attachment system for mounting an apparatus includes a cradle configured to be removably attached to the apparatus, a first clamp arm attached to the cradle and a second clamp arm, the second clamp arm configured to be moved between a clamped position and an unclamped position, wherein the first and second clamp arms are configured to be substantially securely attached to a structure in the clamped position, a first screw engaged with a second screw, the first screw including a first thread oriented in an opposite direction from a second thread of the second screw, and the second screw configured to move the second arm between the clamped and unclamped positions.

The attachment system of any of preceding paragraphs may also include any combination of the following features described in this paragraph, among others described herein. The apparatus can be a pump. The pump can be a negative pressure wound therapy (NPWT) apparatus. In certain embodiments, the attachment system of any of preceding paragraphs can be used in a method of attaching a negative pressure wound therapy (NPWT) apparatus to a structure.

In certain embodiments, an attachment system for mounting an apparatus includes a cradle having a first arm, a housing, and a plurality of latches configured to be removably attached to the apparatus. The attachment system also includes a second arm configured to be moved between a clamped position and an unclamped position, wherein the first and second arms are configured to be substantially securely attached to a structure in the clamped position, and wherein the first and second arms are configured to not be substantially securely attached to the structure in the unclamped position. The attachments system also includes a first screw positioned at least partly within the housing of the cradle, the first screw including a first thread oriented in a first direction and a second screw including a second thread oriented in a second direction, the second screw positioned at least partly within the housing of the cradle, the second screw attached to the second arm via an opening in the second arm, the opening including a first interior thread configured to engage with the second thread of the second screw. The second screw includes a substantially hollow interior portion having a second interior thread configured to engage with the first thread of the first screw so that at least a part of the first screw is configured to be positioned in the interior of the second screw in the clamped position. The attachment system also includes a knob attached to the second screw, the knob configured to move the second arm between the clamped and unclamped positions.

The attachment system of any of preceding paragraphs may also include any combination of the following features described in this paragraph, among others described herein. The apparatus can be a pump. The pump can be a negative pressure wound therapy (NPWT) apparatus. In certain embodiments, the attachment system of any of preceding paragraphs can be used in a method of attaching a negative pressure wound therapy (NPWT) apparatus to a structure.

In various embodiments, a method of operating a negative pressure wound therapy apparatus includes operating a source of negative pressure configured to be fluidically connected to a dressing configured to be placed over a wound, the source of negative pressure configured to deliver negative pressure wound therapy to the wound in accordance with a plurality negative pressure therapy parameters. The method also includes operating a graphical user interface (GUI) configured to permit adjustment of at least some of the plurality of negative pressure therapy parameters and providing, via the GUI, a first adjustment of a first negative pressure therapy parameter thereby causing adjustment of operation of the source of negative pressure based at least in part on the first adjustment of the first negative pressure therapy parameter. The apparatus is configured to record a plurality of historical data parameters associated with the plurality of negative pressure therapy parameters and is further configured to transmit over a communication interface at least some of the plurality of historical data parameters to a remote computer. At least one historical data parameter is associated with first and second settings of a negative therapy pressure therapy parameter, the first and second settings assigned to the negative pressure therapy parameter at different times.

The method of the preceding paragraph may also include any combination of the following features described in this paragraph, among others described herein. At least some of the plurality of historical data parameters transmitted to the remote computer can include one or more of apparatus identification data, apparatus location data, therapy history data, and alarm data. The apparatus can also be configured to record apparatus location data corresponding to a geographical location of the apparatus. The apparatus can also be configured to record apparatus location data based on at least one of global positioning data (GPS) and cellular network data. The apparatus can also be configured to periodically transmit over the communication interface of the at least some of the plurality of historical data parameters to the remote computer. The method can also include providing, via the GUI, a request to transmit the at least some of the plurality of historical data parameters to the remote computer thereby causing transmission of the at least some of plurality of historical data parameters to the remote computer. The apparatus can also be configured to determine a flow rate in a fluid flow path, the fluid flow path comprising the source of negative pressure and the dressing and provide, via the GUI, an indication of the determined flow rate. The indication of the flow rate can include a gauge. The apparatus can also include a pressure sensor configured to measure pressure in at least a portion of the fluid flow path and the apparatus can also be configured to determine the flow rate in the fluid flow path based at least in part on pressure measured by the pressure sensor.

The method of any of preceding paragraphs may also include any combination of the following features described in this paragraph, among others described herein. The source of negative pressure can include a vacuum pump and the apparatus can be also configured to determine the flow rate in the fluid flow path based at least in part on a measured speed of the vacuum pump. The apparatus can also be configured to deactivate the source of negative pressure in response to determining that the flow rate satisfies a high flow threshold and provide, via the GUI, a high flow indication. The provided high flow indication can include information for resolving the high flow condition. The GUI can be configured to chronologically display at least some of the historical data parameters associated with the plurality of negative pressure therapy parameters. At least some of the historical data parameters can include one or more errors associated with delivery of negative pressure wound therapy. The GUI can be configured to display a log comprising total negative pressure wound therapy time delivered over a plurality of time periods and one or more errors can be included in the log.

The method of any of preceding paragraphs may also include any combination of the following features described in this paragraph, among others described herein. The apparatus can also be configured to in response to transmitting the at least some of the plurality of historical data parameters, receive from the remote computer a second adjustment of a second negative pressure therapy parameter and adjust operation of the source of negative pressure based at least in part on the received second adjustment of the second negative pressure therapy parameter. The GUI can be configured to permit adjustment of the second negative pressure therapy parameter. The apparatus can include a touch screen display configured to display the GUI. The apparatus can be configured to treat two wounds with negative pressure wound therapy and the GUI can be configured to permit activation of treatment of two wounds. The GUI can be configured to include a plurality of screens and a plurality of icons grouped into a menu and the menu can be configured to be displayed in the same portion of each screen.

In certain embodiments, a method of operating a negative pressure wound therapy apparatus includes operating a source of negative pressure configured to be fluidically connected to a dressing configured to be placed over a wound, the source of negative pressure configured to deliver negative pressure wound therapy to the wound. The apparatus is configured to detect presence of at least one temporary blockage in a fluid flow path comprising the source of negative pressure, a canister configured to store fluid aspirated from the wound, and the dressing, the at least one temporary blockage caused by fluid aspirated from the wound being aspirated into the canister and clear the at least one temporary blockage by increasing a level of negative pressure provided by the source of negative pressure.

The method of any of preceding paragraphs may also include any combination of the following features described in this paragraph, among others described herein. The apparatus can also be configured to detect presence of the at least one temporary blockage in the fluid flow path by deactivating the source of negative pressure and detecting substantially discontinuous decay of negative pressure in the fluid flow path while the source of negative pressure is deactivated. The apparatus can also include a pressure sensor configured to measure pressure at a canister inlet and the apparatus can also be configured to detect presence of the at least one temporary blockage by detecting an increase in pressure measured by the pressure sensor, the increase in pressure caused by the at least one temporary blockage.

In some embodiments, a method of managing a plurality of negative pressure wound therapy devices includes receiving, over a communication interface, a plurality of operational parameters from the plurality of negative pressure wound therapy devices, each negative pressure wound therapy device configured to provide negative pressure wound therapy, grouping at least some of the plurality of negative pressure wound therapy devices into a fleet and providing at least some of the plurality of received operational parameters for at least some of the devices in the fleet based on a common ownership or common leasing status. The method can be performed by a processor.

The method of any of preceding paragraphs may also include any combination of the following features described in this paragraph, among others described herein. The method can also include providing at least one of geographical location data, battery charge data, and battery life data for at least some of the devices in the fleet. The method can also include receiving an adjustment of at least one operational parameter associated with at least one device in the fleet and transmitting the received adjustment thereby causing the at least one device to modify delivery of negative pressure wound therapy in accordance with the adjustment.

In various embodiments, a negative pressure wound therapy device includes a housing having a protrusion formed in an exterior of the housing and a mount configured to be attached to the protrusion, the mount including a first portion and a second portion. The first portion includes a first circular opening, the first opening having a diameter larger than a diameter of the protrusion, and a second elongated opening extending from the first opening, the second opening having a width that is substantially same as the diameter of the protrusion. The second portion includes a rod configured to permit attachment of a carry strap. The mount is configured to be attached to the device by coupling the mount to the protrusion in a region of the second elongated opening.

BRIEF DESCRIPTION OF THE DRAWINGS

Embodiments of the present invention will now be described hereinafter, by way of example only, with reference to the accompanying drawings in which:

FIGS. 2A-2F illustrate a pump assembly and canister according to some embodiments.

FIGS. 9A-9C illustrate a canister bulkhead according to some embodiments.

FIG. 12 illustrates a strap mount attachment according to some embodiments.

FIGS. 13A-13B illustrate an attachment according to some embodiments.

FIG. 13C illustrates an attachment system according to some embodiments.

FIG. 13K illustrates attachment systems in operation according to some embodiments.

DETAILED DESCRIPTION OF SOME EMBODIMENTS

Overview

Figure 1:
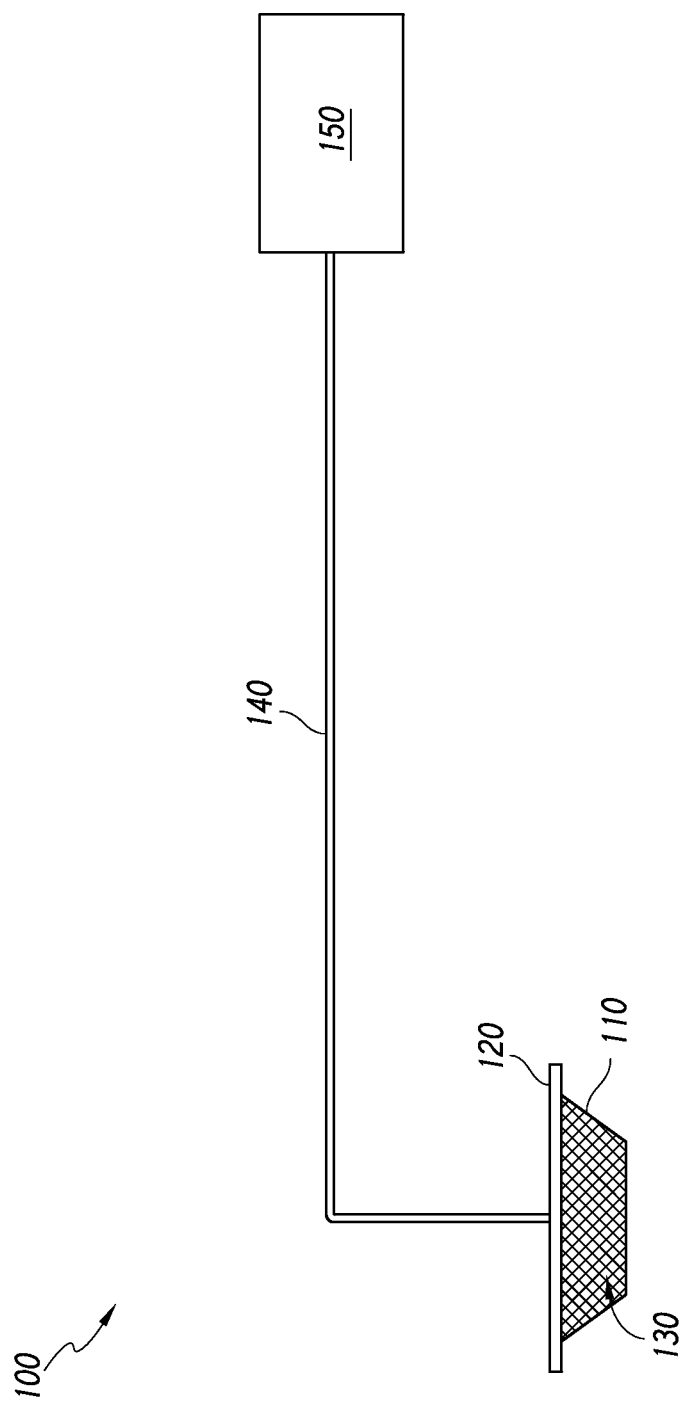
FIG. 1 illustrates a reduced pressure wound therapy system according to some embodiments.

Embodiments disclosed herein relate to systems and methods of treating a wound with reduced pressure. As is used herein, reduced or negative pressure levels, such as X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present invention are generally applicable to use in topical negative pressure ("TNP") or reduced or negative pressure therapy systems. Briefly, negative pressure wound therapy assists in the closure and healing of many forms of "hard to heal" wounds by reducing tissue oedema, encouraging blood flow and granular tissue formation, and/or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

In some embodiments, the pump assembly can include one or more processors or controllers responsible for various system functions associated with various levels of responsiveness, such as interfacing with a user (e.g., patient, physician, nurse, etc.), controlling a negative pressure pump, providing network connectivity, and the like. In some embodiments, levels of responsiveness can correspond to or be associated with levels of risk. For example, controlling a source of negative pressure may be classified as a high risk activity, as delivery of therapy is important for patient safety, healing, etc. Accordingly, controlling the source of negative pressure can be associated with a high level of responsiveness. The pump assembly can also include one or more input/output devices for receiving and providing data. These devices can include screens, touchscreens, buttons, knobs, ports, and the like. The pump assembly can be configured to present graphical user interface (GUI) screens for controlling and monitoring the operation of the TNP system.

In some embodiments, the TNP system can be configured to determine and monitor flow of fluid in the system. This can be accomplished by using one or more pressure transducers or sensors that measure pressure in a fluid flow path and provide feedback to a controller. In various embodiments, determining of fluid flow can be accomplished by utilizing one or more of the following techniques: monitoring the speed of a pump motor, monitoring flow of fluid in a portion of a fluid flow path by placing a calibrated fluid flow restrictor, and monitoring one or more characteristics, such as amplitude, frequency, or slope of detected pressure pulses. Calculated flow rate can be used to determine whether desired therapy is delivered to a patient, whether there are one or more leaks present in the system, and the like.

In some embodiments, the system can be configured to provide indication, alarms, etc. reflecting operating conditions to a user. The system can include visual, audible, tactile, and other types of indicators and/or alarms configured to signal to the user various operating conditions. Such conditions include system on/off, standby, pause, normal operation, dressing problem, leak, error, and the like. The indicators and/or alarms can include speakers, displays, light sources, etc., and/or combinations thereof. In various embodiments, indications, alarms, etc. are guided by one or more applicable standards.

In certain embodiments, a pump assembly can include one or more communications processors for providing external connectivity. Such connectivity can be used for various activities, such as location tracking of the pump assembly, compliance monitoring, tracking of operational parameters, remote selection and adjustment of therapy settings, and the like. Connectivity can include Global Positioning System (GPS) technology, cellular connectivity (e.g., 2G, 3G, LTE, 4G), WiFi connectivity, Internet connectivity, and the like. In some embodiments, wired connectivity can be utilized. In various embodiments, the pump assembly can communicate data to a cloud and receive data from the cloud. The data can include location data, compliance monitoring data, operational parameters, data for remote selection and adjustment of therapy settings, and the like.

Embodiments of the present invention relate to attachment systems for mounting an apparatus or device, including but not limited to a negative pressure wound therapy ("NPWT") apparatus. In some embodiments, an attachment system includes a cradle configured to be removably attached to the apparatus. The attachment system includes a first clamp arm attached to the cradle and a second clamp arm. The second clamp arm can be configured to be moved between an unclamped position and a clamped position in which the first and second clamp arms are configured to be substantially securely attached to a structure. In the unclamped position, the first and second arms can be configured to not be attached to the structure. The structure can include any suitable structure for mounting the apparatus (e.g., medical apparatus), such as an IV pole, bedrail, and the like. The attachment system also includes a first screw engaged with a second screw which can be configured to move the second arm between the clamped and unclamped positions. The second screw can be attached to a handle. The threads of the first and second screws can be opposite pitch such that a single handle rotation provides double or substantially double linear motion as compared to using one screw. For example, in one embodiment approximately four rotations of the handle are needed to move the second clamp arm between a fully closed position in which the first and second clamp arms are not separated or substantially not separated (e.g., are in contact) and a fully open position in which the first and second clamp arms are separated by a maximum distance from each other. As a result, the attachment system can be used to efficiently and securely attach the apparatus to structures of varying thickness.

Negative Pressure System

FIG. 1 illustrates an embodiment of a negative or reduced pressure wound treatment (or TNP or NPWT) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly or NPWT apparatus 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. In some embodiments, the wound cover 120 has a top side and a bottom side, and the bottom side adhesively (or in any other suitable manner) seals with wound cavity 110. The conduit 140 or any other conduit disclosed herein can be formed from polyurethane, PVC, nylon, polyethylene, silicone, or any other suitable material.

Some embodiments of the wound cover 120 can have a port (not shown) configured to receive an end of the conduit 140. In some embodiments, the conduit 140 can otherwise pass through and/or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. In some embodiments, though not required, the pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. In some embodiments, the components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively a pressure range of over approximately −100 mmHg, or even −150 mmHg, can be supplied by the pump assembly 150.

In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure set points. Low set point can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High set point can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low set point can be delivered for a first time duration, and upon expiration of the first time duration, negative pressure at high set point can be delivered for a second time duration. Upon expiration of the second time duration, negative pressure at low set point can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high set points and vice versa can be performed according to a step waveform, square waveform, sinusoidal waveform, and the like.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Further description of such wound dressings and other components of a negative pressure wound therapy system that may be used with the pump assembly and other embodiments of the present application are found in U.S. Patent Publication Nos. 2012/0116334, 2011/0213287, 2011/0282309, 2012/0136325 and 2013/0110058, which are incorporated by reference in their entirety. In other embodiments, other suitable wound dressings can be utilized.

Pump Assembly and Canister

Figure 2A:
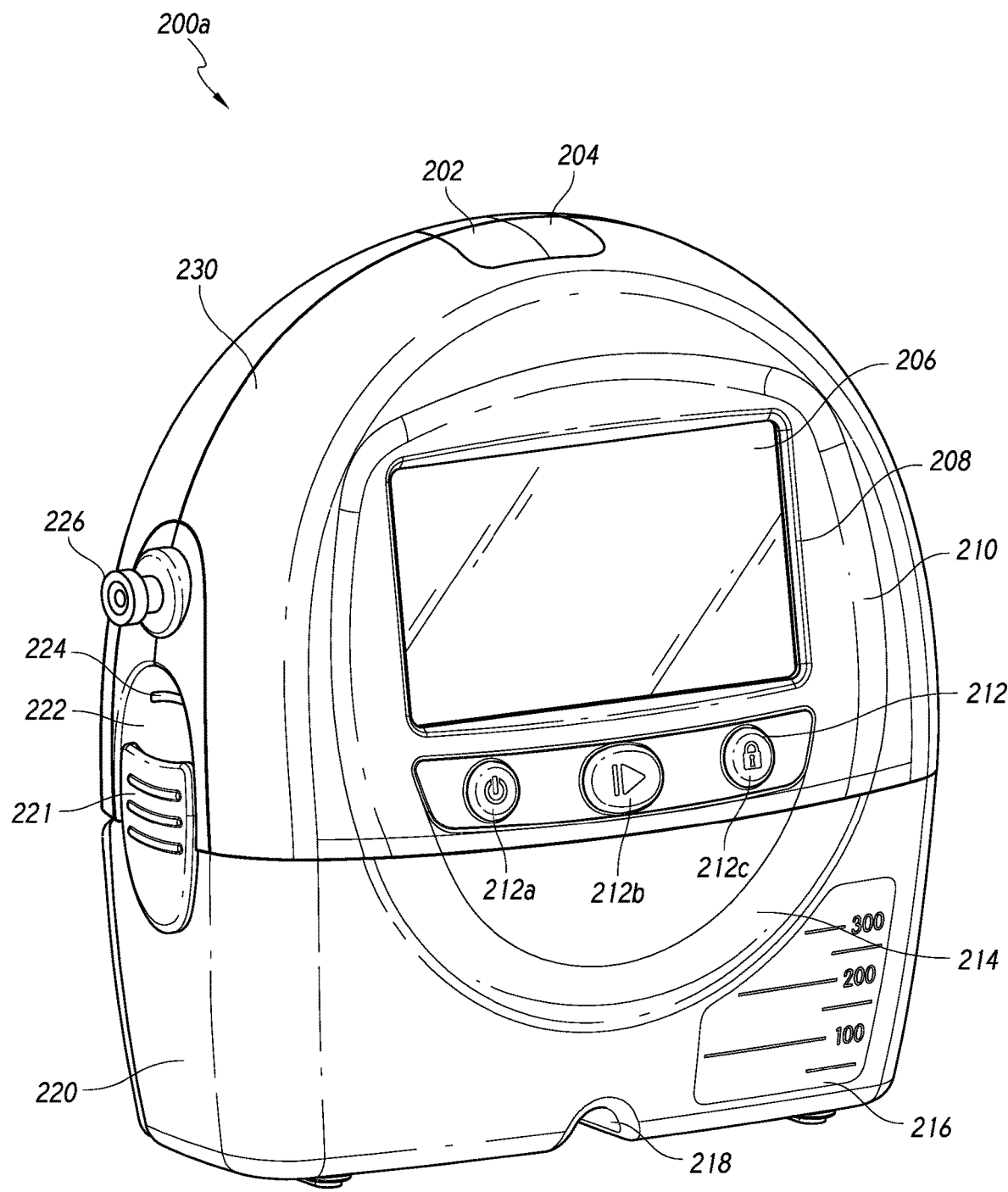

FIG. 2A illustrates a front view 200A of a pump assembly 230 and canister 220 according to some embodiments. As is illustrated, the pump assembly 230 and the canister are connected, thereby forming a device (or NPWT apparatus). The pump assembly 230 comprises one or more indicators, such as visual indicator 202 configured to indicate alarms and visual indicator 204 configured to indicate status of the TNP system. The indicators 202 and 204 can be configured to alert a user to a variety of operating and/or failure conditions of the system, including alerting the user to normal or proper operating conditions, pump failure, power supplied to the pump or power failure, detection of a leak within the wound cover or flow pathway, suction blockage, or any other similar or suitable conditions or combinations thereof. In some embodiments, the pump assembly 230 can comprise additional indicators. In some embodiments, a single indicator is used. In other embodiments, multiple indicators are used. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 comprises a display or screen 206 mounted in a recess 208 formed in a case of the pump assembly. In some embodiments, the display 206 can be a touch screen display. In some embodiments, the display 206 can support playback of audiovisual (AV) content, such as instructional videos. As explained below, the display 206 can be configured to render a number of screens or graphical user interfaces (GUIs) for configuring, controlling, and monitoring the operation of the TNP system. The pump assembly 230 comprises a gripping portion 210 formed in the case of the pump assembly. The gripping portion 210 can be configured to assist the user to hold the pump assembly 230, such as during removal of the canister 220. In some embodiments, the canister 220 can be replaced with another canister, such as when the canister 220 has been filled with fluid.

The pump assembly 230 comprises one or more keys or buttons 212 configured to allow the user to operate and monitor the operation of the TNP system. As is illustrated, in some embodiments, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 and/or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. In some embodiments, multiple key presses and/or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 comprises an air outlet 224 for allowing air removed from the wound cavity 110 to escape. Air entering the pump assembly can be passed through one or more suitable filters (described below, such as in FIG. 10), such as antibacterial filters. This can maintain reusability of the pump assembly. The pump assembly 230 includes one or more mounts 226 for connecting a carry strap to the pump assembly 230 or for attaching a cradle. In the illustrated embodiment, two mounts 226 can be formed on the sides of the pump assembly 230. In some embodiments, various of these features are omitted and/or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 comprises two latches 221 on the sides of the canister. The exterior of the canister 220 can formed from frosted plastic so that the canister is substantially opaque and the contents of the canister and substantially hidden from plain view. The canister 220 comprises a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. The canister 220 comprises a tubing channel 218 for connecting to the conduit 140. In some embodiments, various of these features, such as the gripping portion 214, are omitted and/or various additional features are added to the canister 220.

Figure 2B:
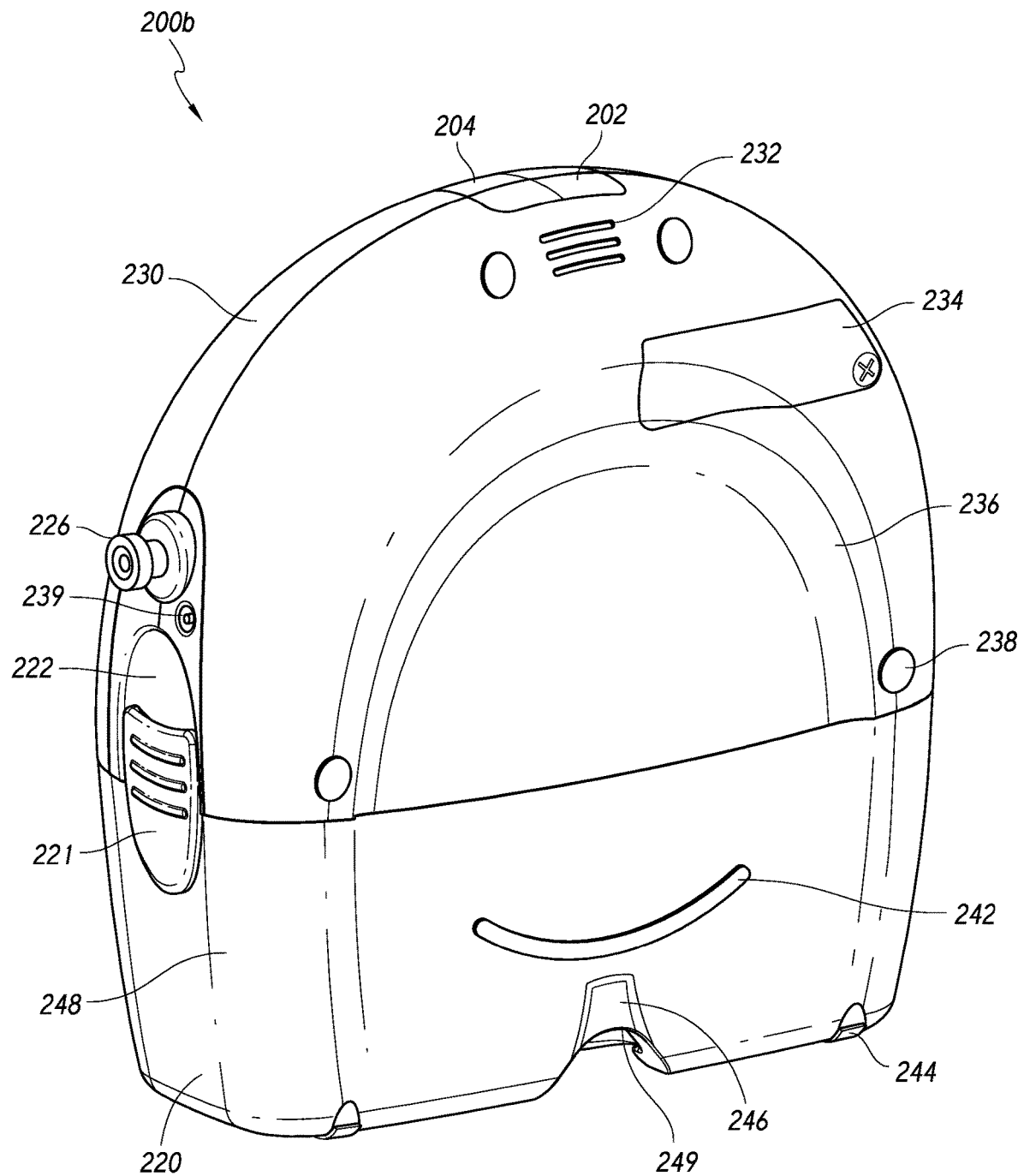

FIG. 2B illustrates a rear view 200B of the pump assembly 230 and canister 220 according to some embodiments. The pump assembly 230 comprises a speaker port 232 for producing and/or radiating sound. The pump assembly 230 includes a filter access door 234 for accessing and replacing one or more filters, such as odor filter, antibacterial filters, etc. In one embodiment, the access door 234 can be used to access a chamber (such as a plenum chamber) in which noise suppressing or sound absorbing material is placed. The chamber and sound absorbing material can be part of a silencing system that is used to suppress or absorb noise generated by the source of negative pressure. Sound absorbing material can serve to break up sound waves as travel (or reverberate) through the chamber. Sound absorbing material can further function as an odor suppressant. In one embodiment, for example, sound absorbing material can be impregnated with activated charcoal for odor suppression. The access door 234 can further include a seal (such as a sealing gasket) for tight closure of the chamber. Additional details of the silencing system are described in U.S. Patent Publication No. 2010/0185165, which is incorporated by reference in its entirety.

The pump assembly 230 comprises a gripping portion 236 formed in the case of the pump assembly. As is illustrated, the gripping portion 236 is a recess formed in the outer casing of the pump assembly 230. In some embodiments, the gripping portion 236 may include rubber, silicone, etc. coating. The gripping portion 236 can be configured (e.g., positioned and dimensioned) to allow the user to firmly hold the pump assembly 230, such as during removal of the canister 220. The pump assembly 230 includes one or more covers 238 configured as screw covers and/or feet or protectors for placing the pump assembly 230 on a surface. The covers 230 can be formed out of rubber, silicone, or any other suitable material. The pump assembly 230 comprises a power jack 239 for charging and recharging an internal battery of the pump assembly. In some embodiments, the power jack 239 is a direct current (DC) jack. In some embodiments, the pump assembly can comprise a disposable power source, such as batteries, so that no power jack is needed.

The canister 220 includes one or more feet 244 for placing the canister on a surface. The feet 244 can be formed out of rubber, silicone, or any other suitable material and can be angled at a suitable angle so that the canister 220 remains stable when placed on the surface. The canister 220 comprises a tube mount relief 246 configured to allow one or more tubes to exit to the front of the device. The canister 220 includes a stand or kickstand 248 for supporting the canister when it is placed on a surface. As explained below, the kickstand 248 can pivot between an opened and closed position. In closed position, the kickstand 248 can be latched to the canister 220. In some embodiments, the kickstand 248 can be made out of opaque material, such as plastic. In other embodiments, the kickstand 248 can be made out of transparent material. The kickstand 248 includes a gripping portion 242 formed in the kickstand. The gripping portion 242 can be configured to allow the user to place the kickstand 248 in the closed position. The kickstand 248 comprises a hole 249 to allow the user to place the kickstand in the open position. The hole 249 can be sized to allow the user to extend the kickstand using a finger.

Figure 2C:
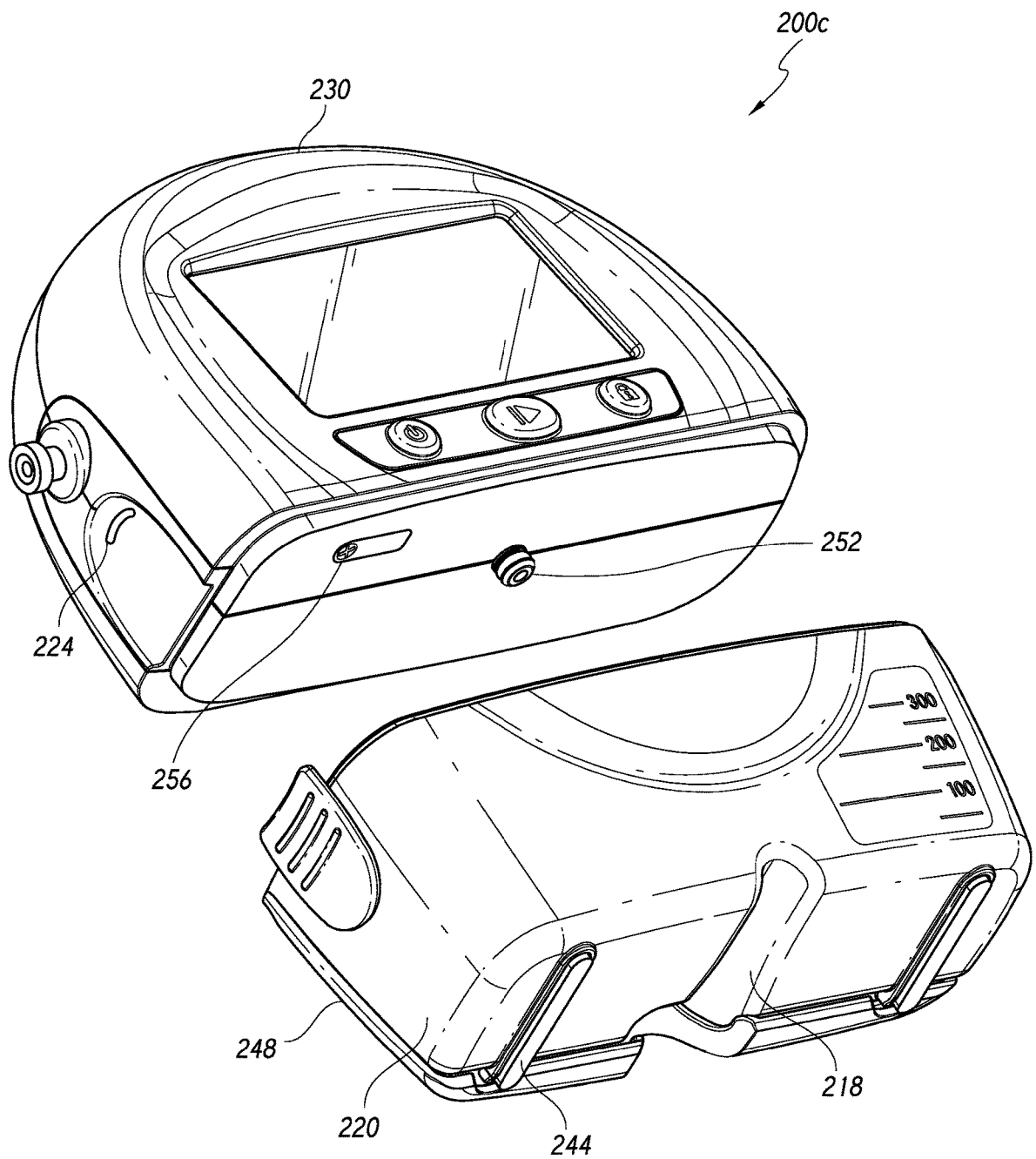

FIG. 2C illustrates a view 200C of the pump assembly 230 separated from the canister 220 according to some embodiments. The pump assembly 230 includes a vacuum attachment or connector 252 through which a vacuum pump communicates negative pressure to the canister 220. The pump assembly 230 comprises a USB access door 256 configured to allow access to one or more USB ports. In some embodiments, the USB access door is omitted and USB ports are accessed through the door 234. The pump assembly 230 can include additional access doors configured to allow access to additional serial, parallel, and/or hybrid data transfer interfaces, such as SD, Compact Disc (CD), DVD, FireWire, Thunderbolt, PCI Express, and the like. In other embodiments, one or more of these additional ports are accessed through the door 234.

FIG. 2D illustrates a schematic front view 230D and rear view 230D' of a pump assembly 200D according to some embodiments.

Figure 2E:
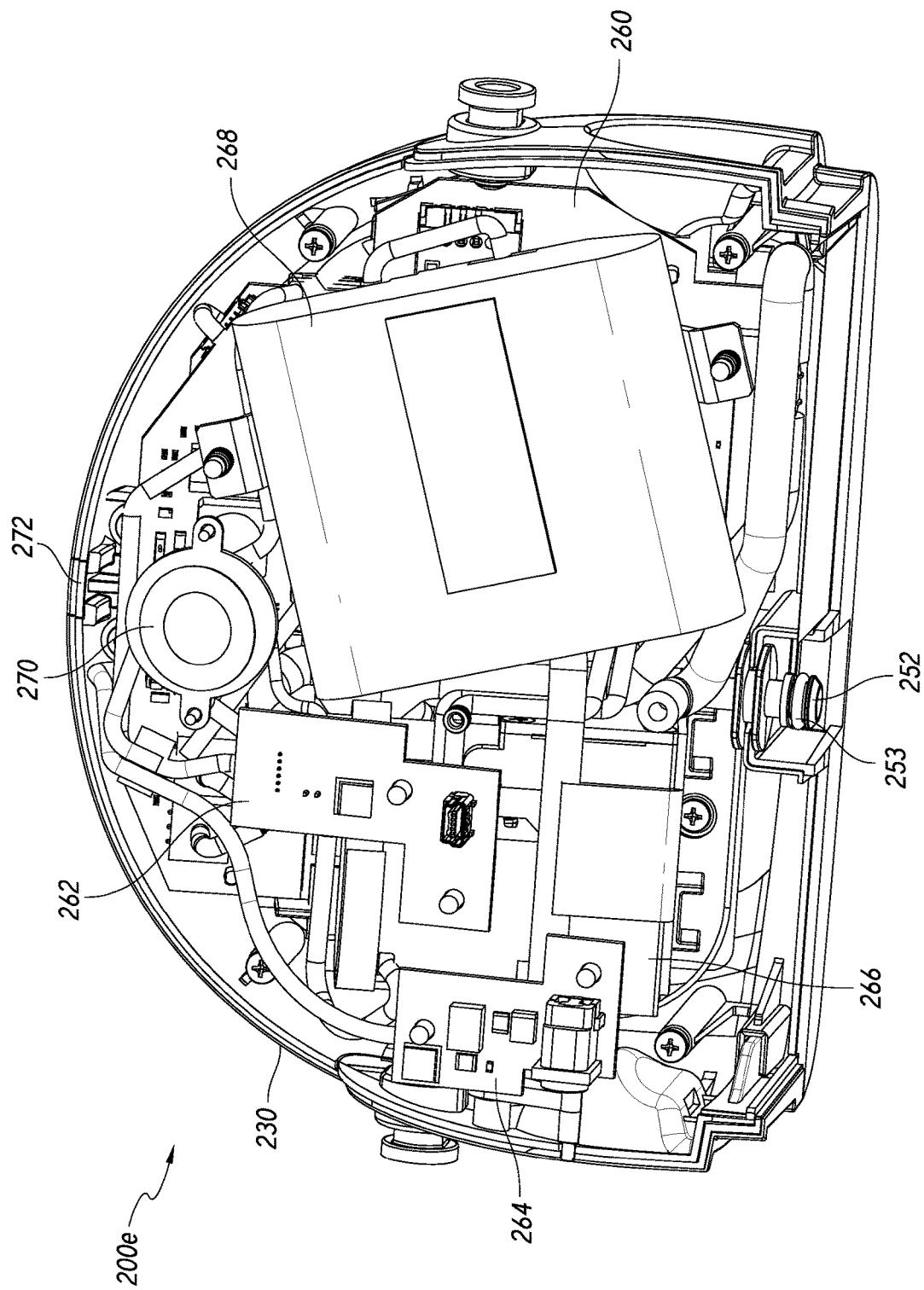

FIG. 2E illustrates a view 200E of the interior components of the pump assembly 230 according to some embodiments. The pump assembly 230 can include various components, such as a canister connector 252 which includes a sealing ring 253, control printed circuit board (PCB) 260, peripherals PCB 262 (e.g., for USB connectivity), power supply PCB 264, vacuum pump 266, power supply 268 (e.g., rechargeable battery), speaker 270, and light guide or pipe 272 (e.g., for status indication using guided light emitted by one or more LEDs). Further details of status indication are provided in U.S. Pat. No. 8,294,586, which is assigned to the assignee of the present application and is incorporated by reference in its entirety. Other components can be included, such as electrical cables, connectors, tubing, valves, filters, fasteners, screws, holders, and so on. In some embodiments, the pump assembly 230 can comprise alternative or additional components.

Figure 2F:
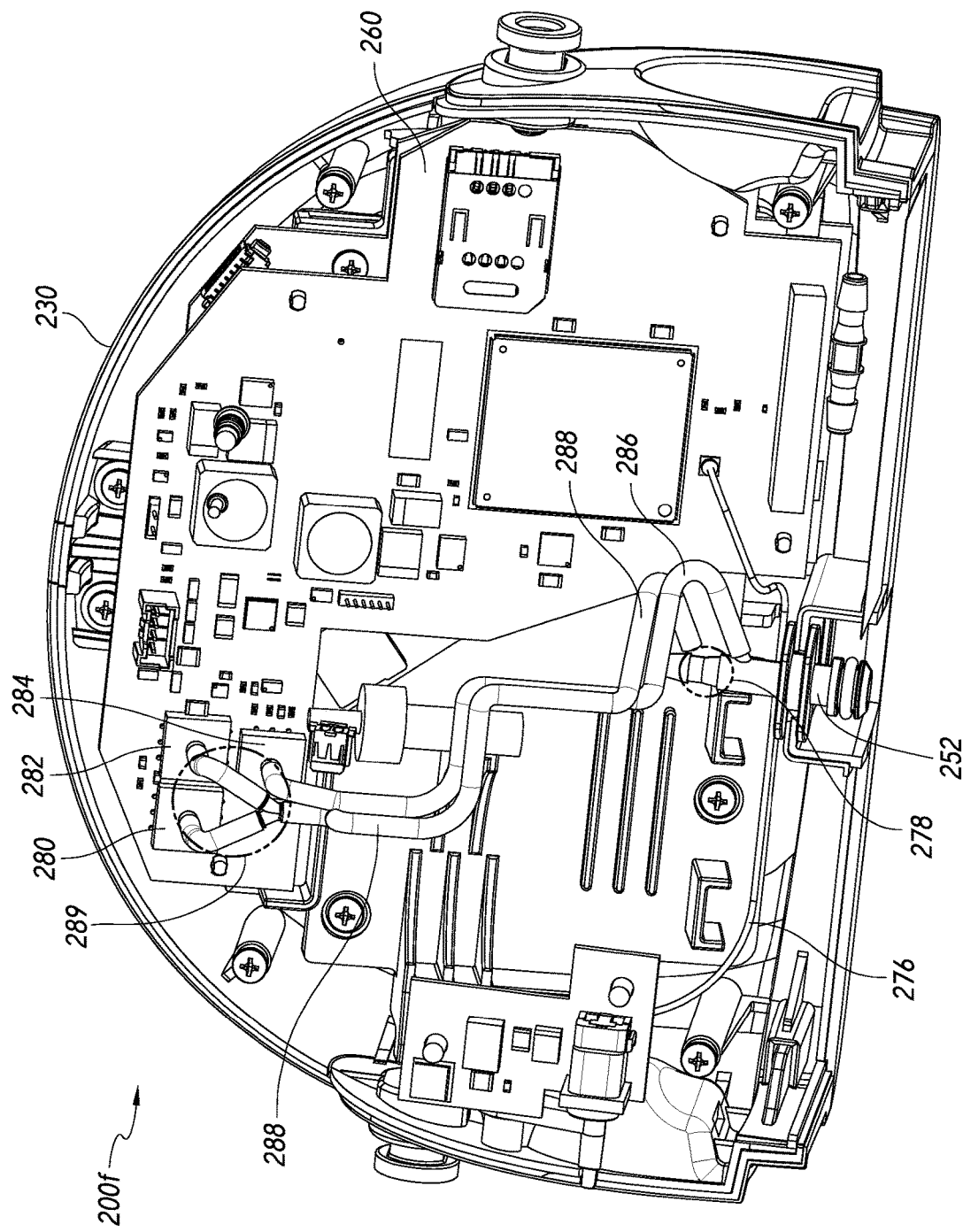

FIG. 2F illustrates another view 200F of the interior components of the pump assembly 230 according to some embodiments. As is explained below, the pump assembly 230 includes an antenna 276. The connector 252 between the vacuum pump 266 and the canister 220 includes a flow restrictor 278. As is explained below, the flow restrictor 278 can be a calibrated flow restrictor used for measuring flow in the fluid flow path and for determining various operating conditions, such as leaks, blockages, high pressure (overvacuum), and the like. In some embodiments, flow across the restrictor 278 can be determined by measuring a pressure differential (or pressure drop) across the flow restrictor. In various embodiments, flow across the restrictor 278 can be characterized as high flow (e.g., due to a leak), low flow (e.g., due to a blockage or canister being full), normal flow, etc. As is illustrated, pressure sensor 284 measures pressure upstream (or on the canister side) of the flow restrictor 278. Pressure sensor 284 can be an electronic pressure sensor mounted on the control PCB 264. Conduit or lumen 286 can connect the upstream side of the flow restrictor 278 with the pressure sensor 284. Pressure sensors 280 and 282 measure pressure downstream (or on the vacuum pump side) of the flow restrictor 278. Pressure sensors 280 and 282 can be electronic pressure sensors mounted on the control PCB 264. Conduit or lumen 288 can connect the downstream side of the flow restrictor 278 with the pressure sensors 280 and 284 via a Y-connector 289.

In some embodiments, one of pressure sensors 280 and 282 can be designated as a primary pressure sensor and the other as a backup pressure sensor in case the primary pressure sensor becomes defective or inoperative. For example, pressure sensor 280 can be the primary pressure sensor and pressure sensor 282 can be the backup pressure sensor. Pressure drop across the flow restrictor 278 can be determined by subtracting pressure measured by sensor 280 and sensor 284. If pressure sensor 280 fails, pressure drop across the flow restrictor can be determined by subtracting pressure measured by sensor 282 and sensor 284. In certain embodiments, the backup pressure sensor can be used for monitoring and indicating high pressure conditions, that is when the pressure in the flow path exceeds a maximum pressure threshold. In some embodiments, one or more differential pressure sensors can be used. For example, a differential pressure sensor connected to the upstream and downstream sides of the flow restrictor 278 can measure the pressure drop across the flow restrictor. In some embodiments, one or more of these components, such as the flow restrictor 278, are omitted and/or additional components, such as one or more flow meters, are used.

Figure 3A:
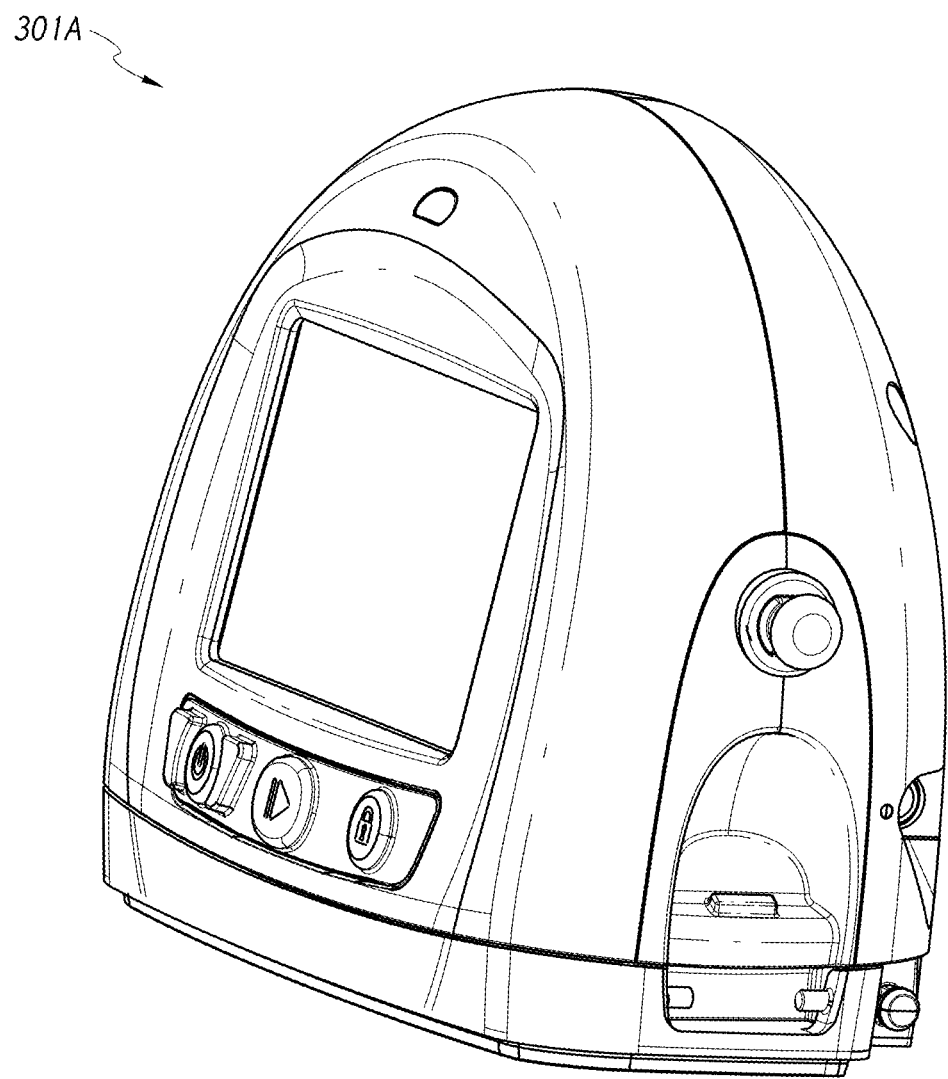
FIGS. 3A-3H illustrate a pump assembly according to some embodiments.
Figure 3B:
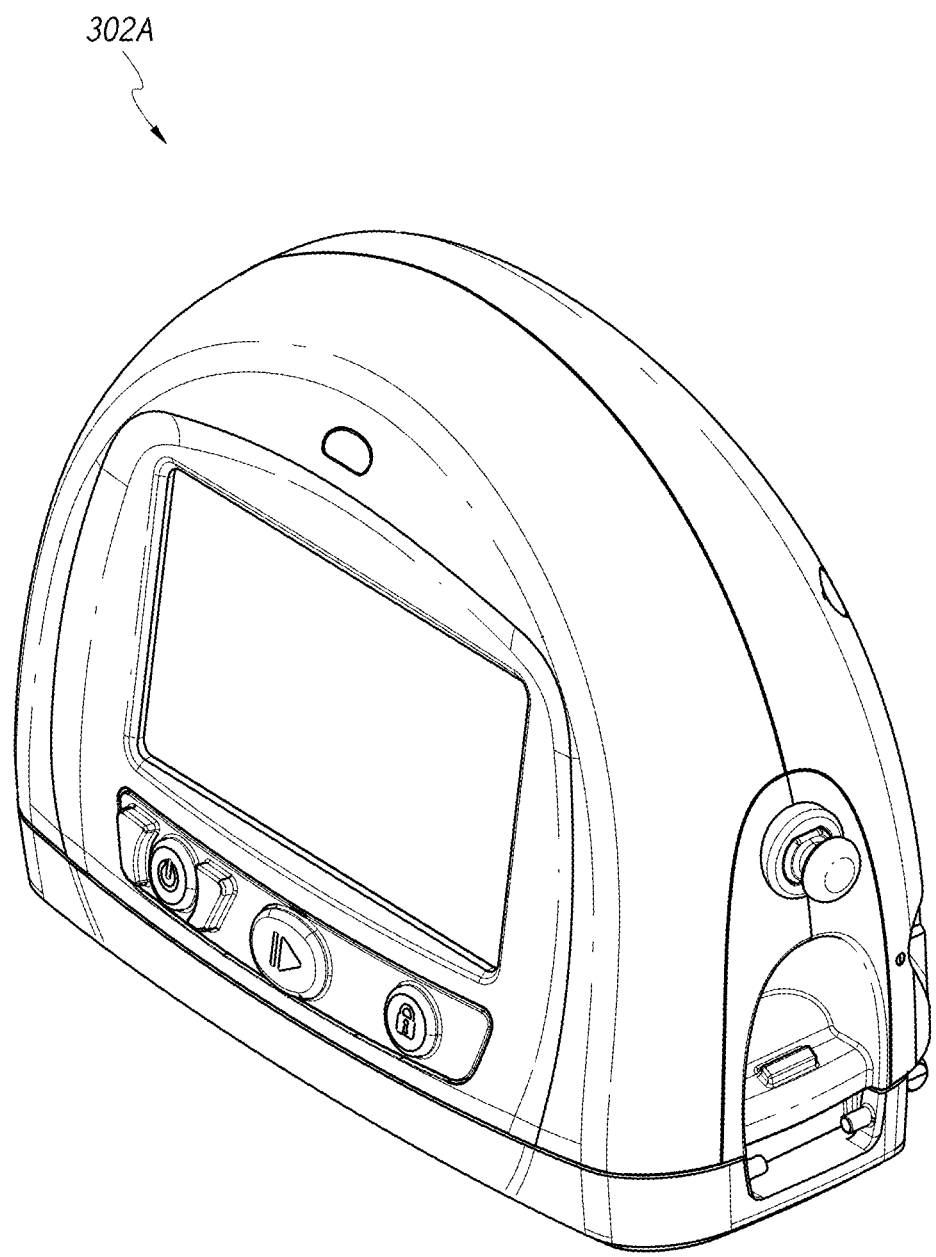
Figure 3C:
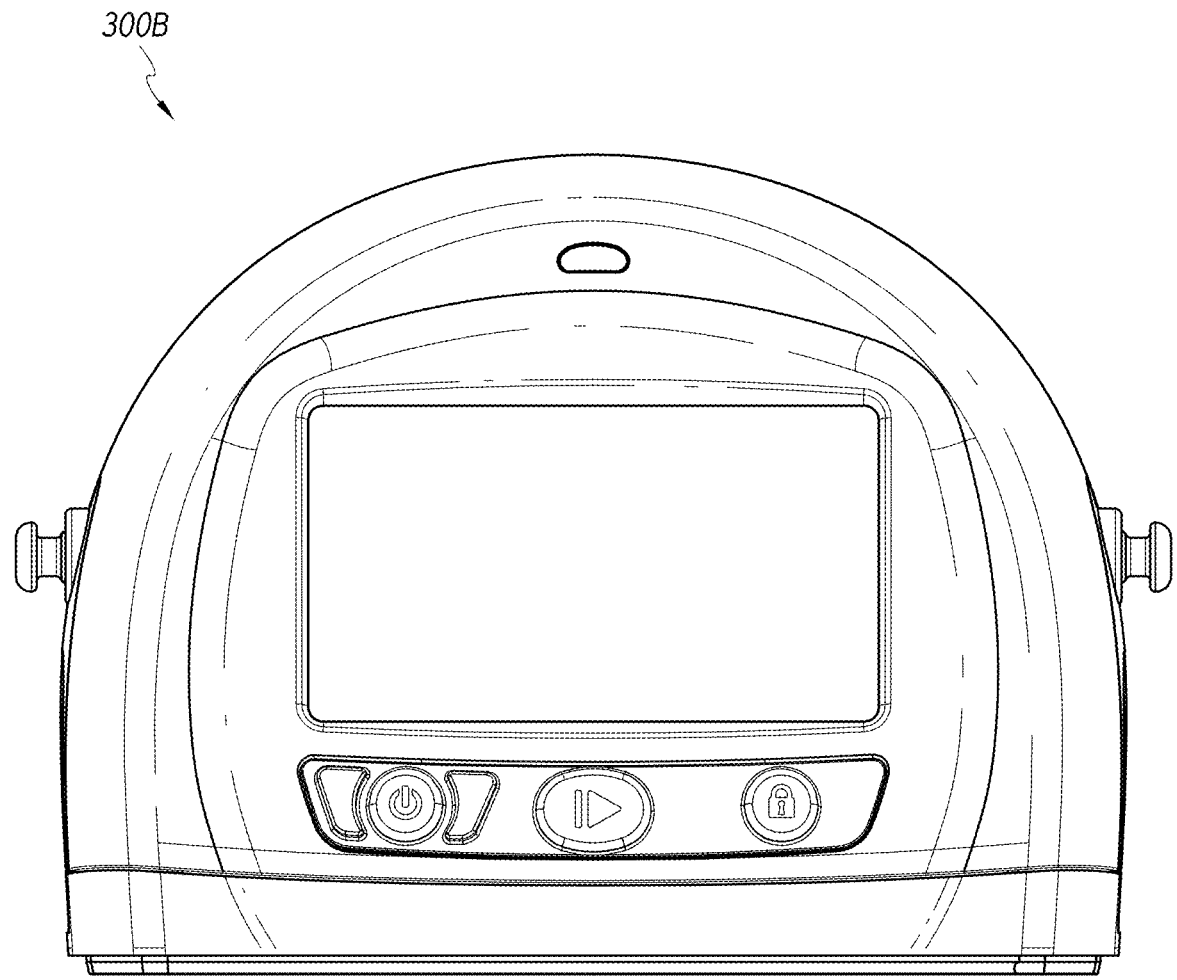
Figure 3D:
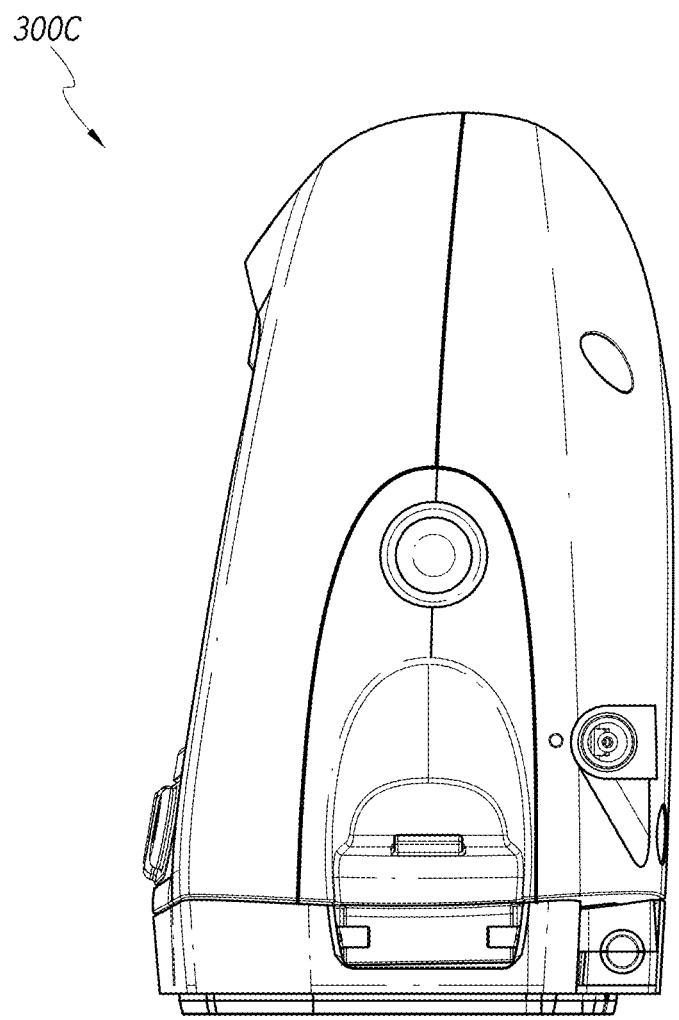
Figure 3E:
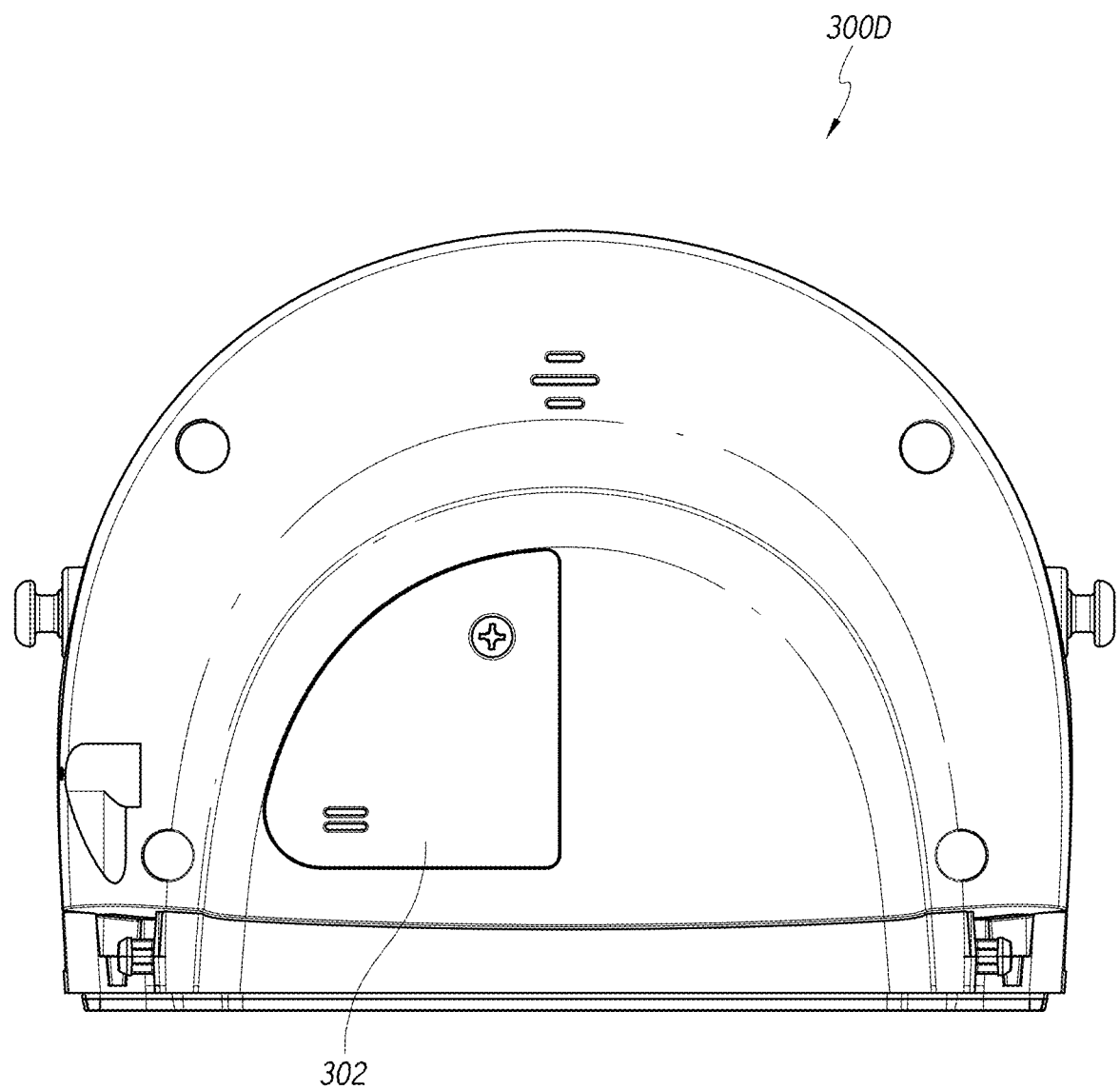
Figure 3F:
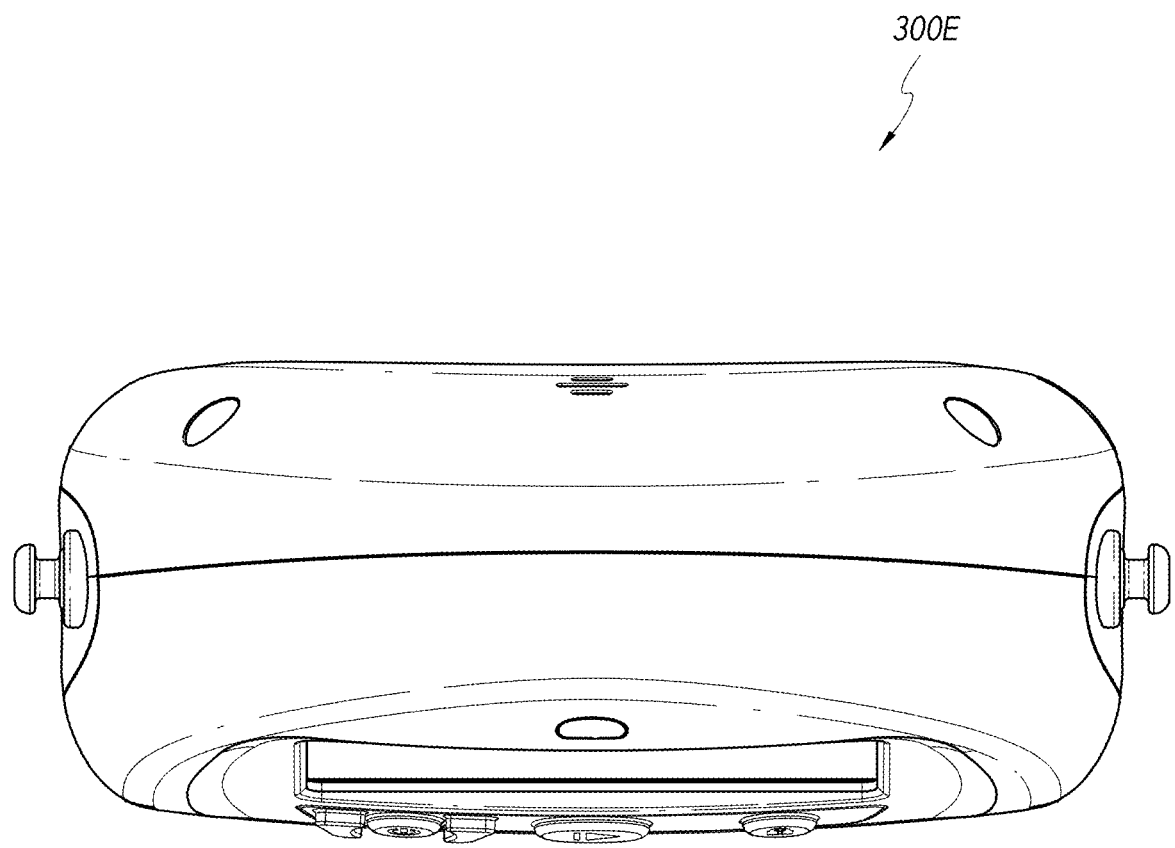
Figure 3G:
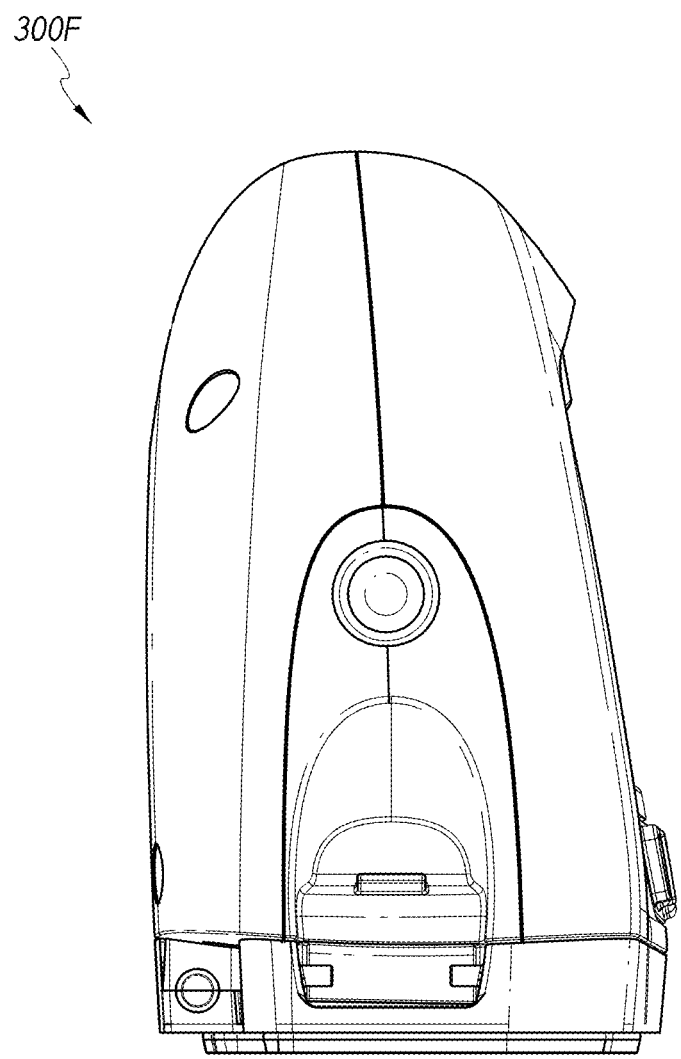
Figure 3H:
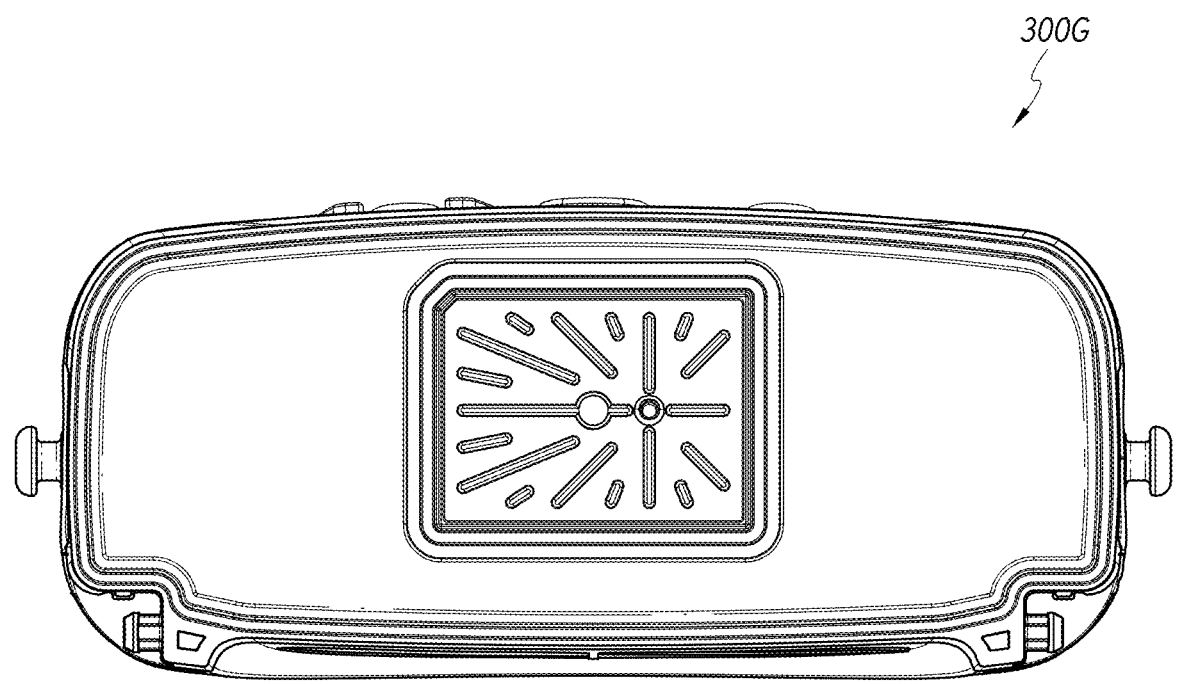
Figure 10:
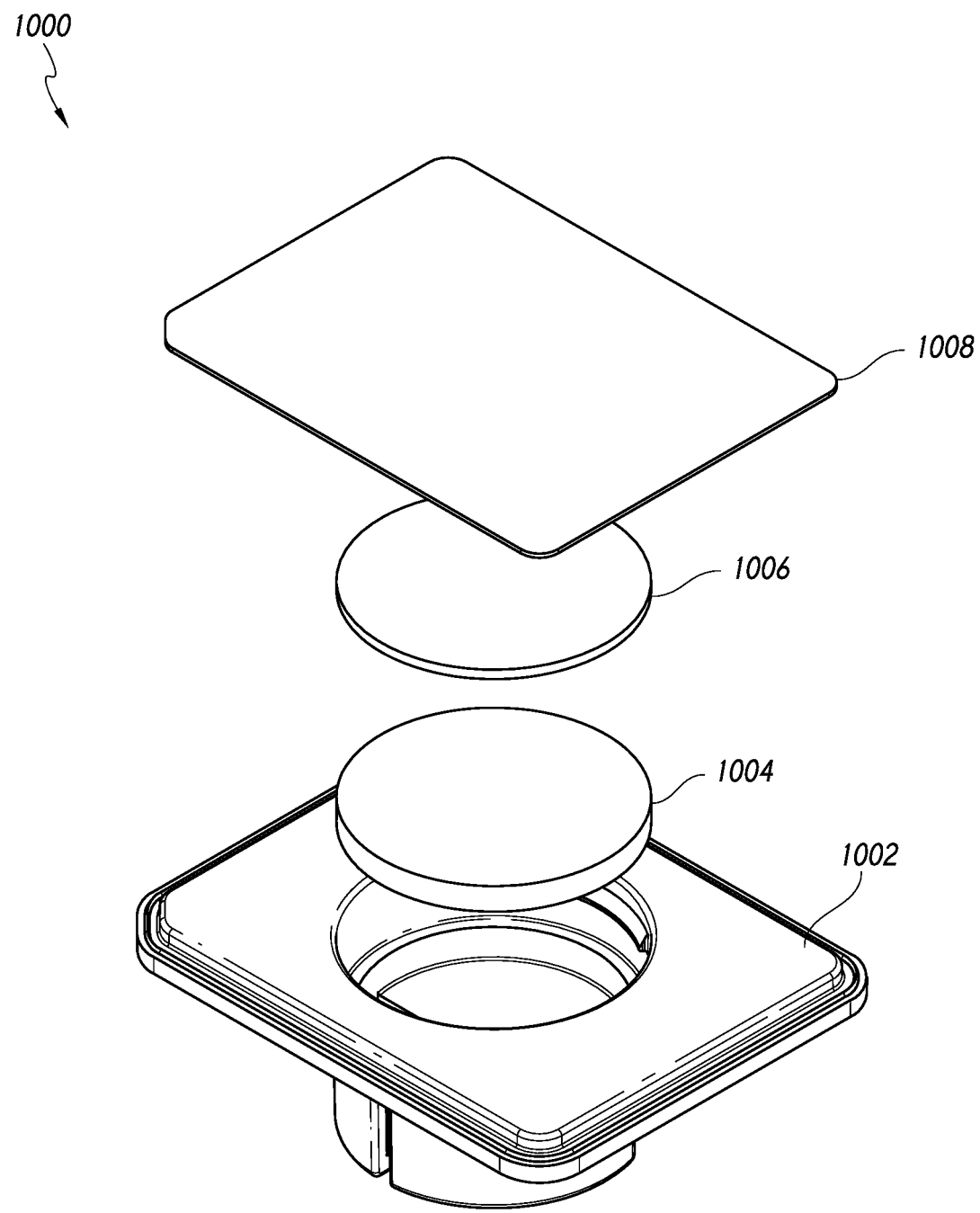
FIG. 10 illustrates a canister filter stack according to some embodiments.

FIGS. 3A-3H illustrate a pump assembly according to some embodiments. FIG. 3A illustrates a perspective view 301A of the pump assembly. FIG. 3B illustrates another perspective view 302A of the pump assembly. FIG. 3C illustrates a front view 300B of the pump assembly. FIG. 3D illustrates a right side view 300C of the pump assembly. FIG. 3E illustrates a rear view 300D of the pump assembly. As is illustrated, the pump assembly includes a filter enclosure 302, which can comprise a removable cover for accessing one or more filters (as illustrated in FIG. 10 and described below). FIG. 3F illustrates a top view 300E of the pump assembly. FIG. 3G illustrates a left side view 300F of the pump assembly. FIG. 3H illustrates a bottom view 300G of the pump assembly.

Figure 4A:
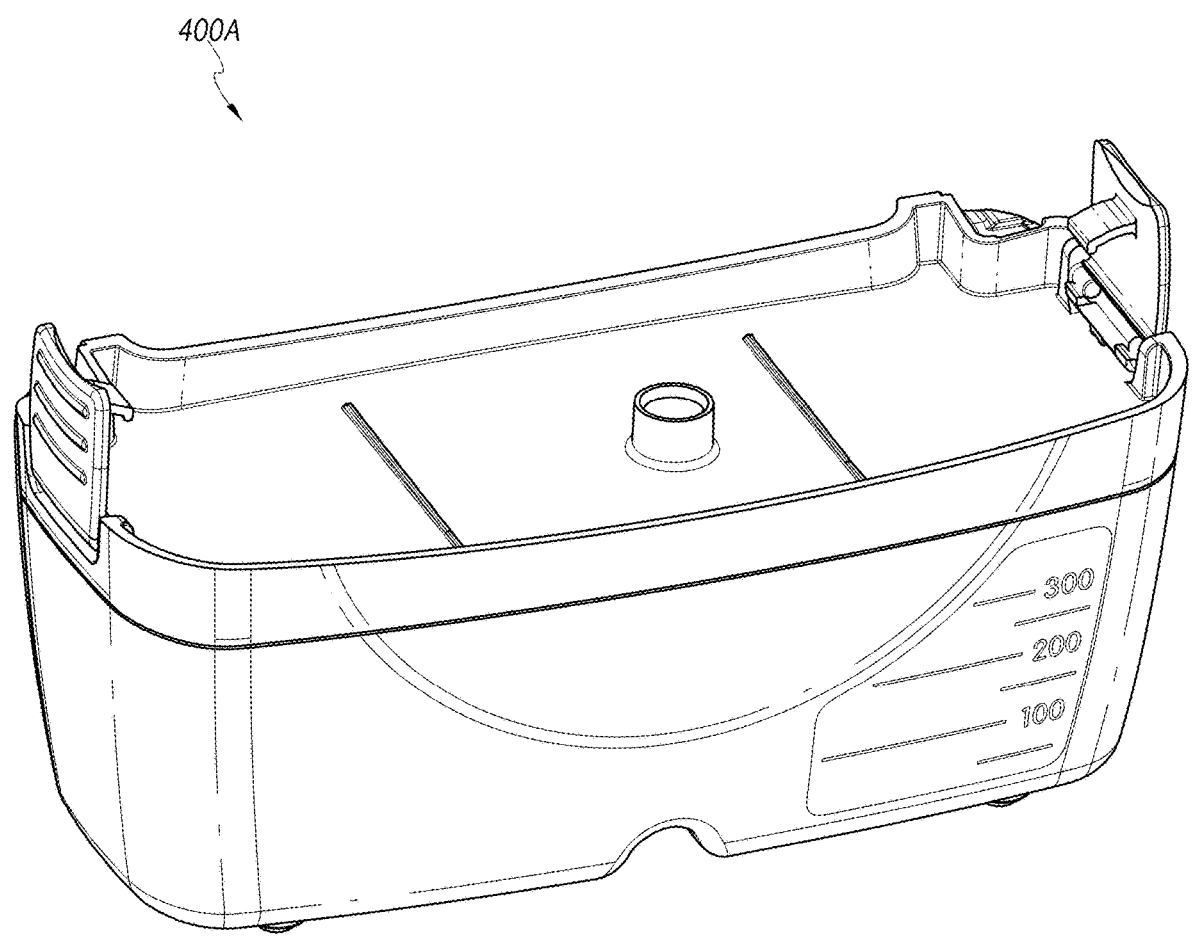
FIGS. 4A-4H illustrate a canister according to some embodiments.
Figure 4B:
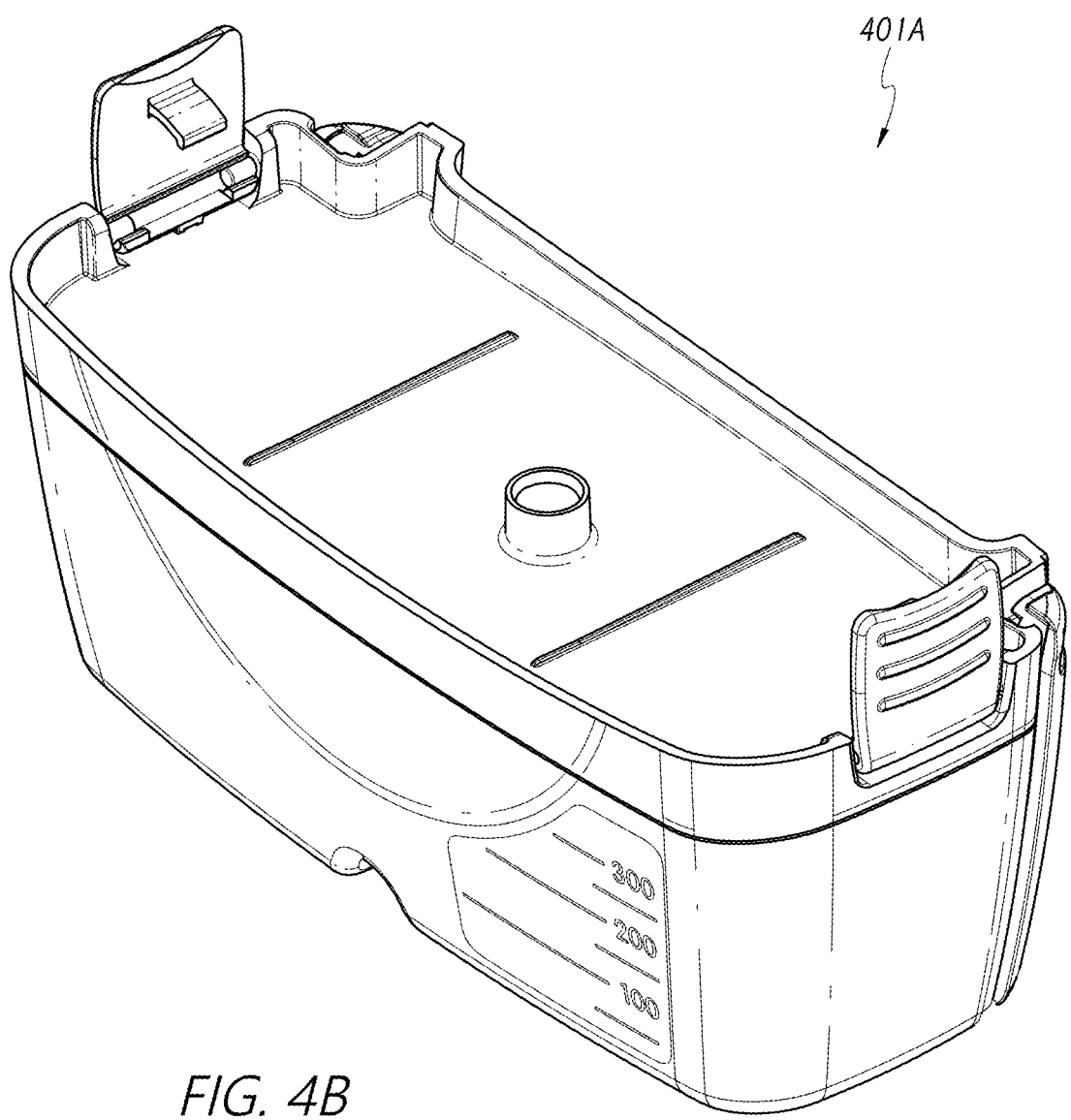
Figure 4C:
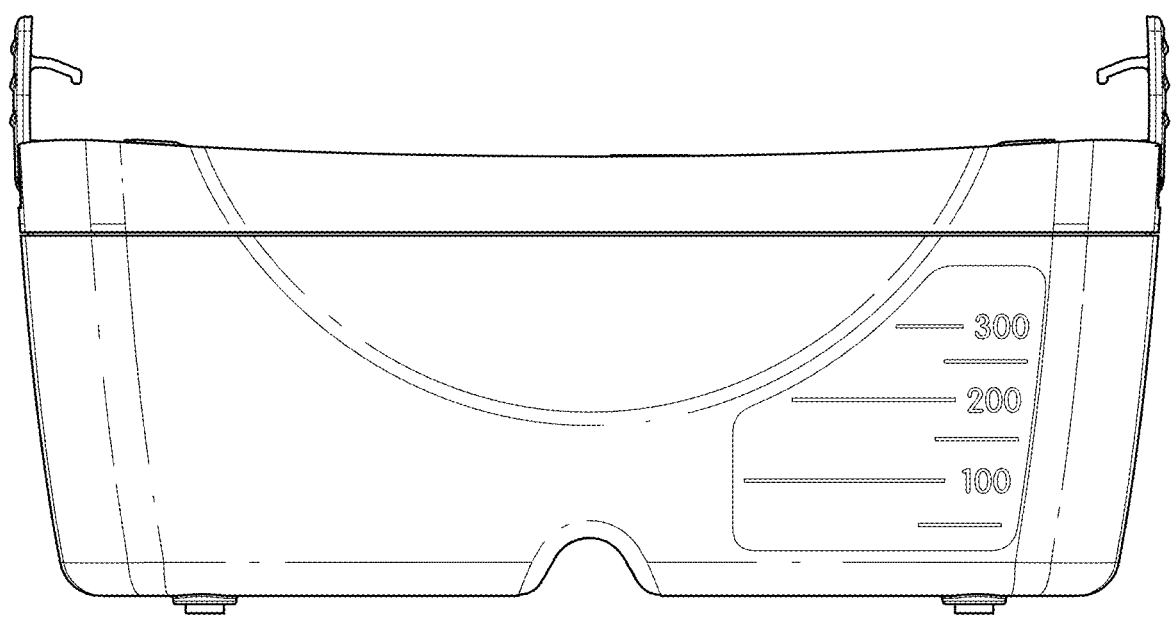
Figure 4D:
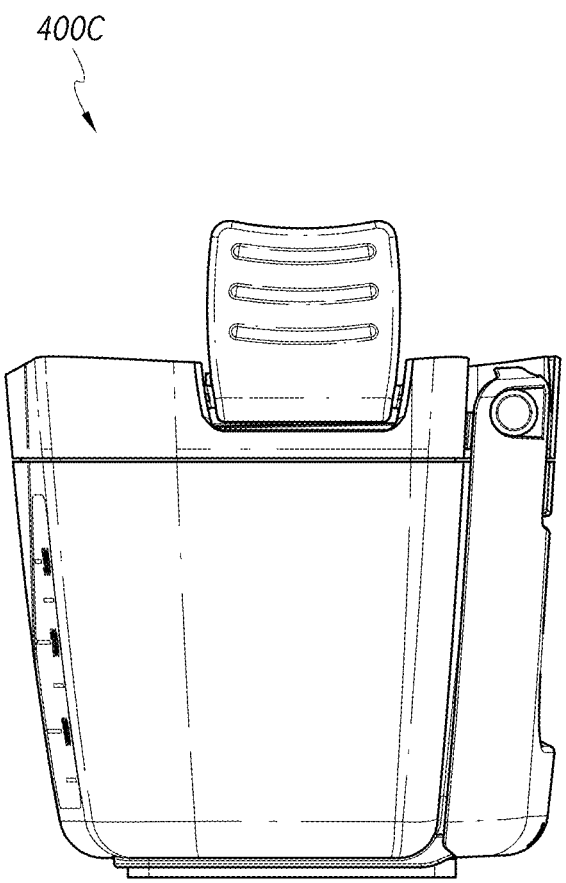
Figure 4E:
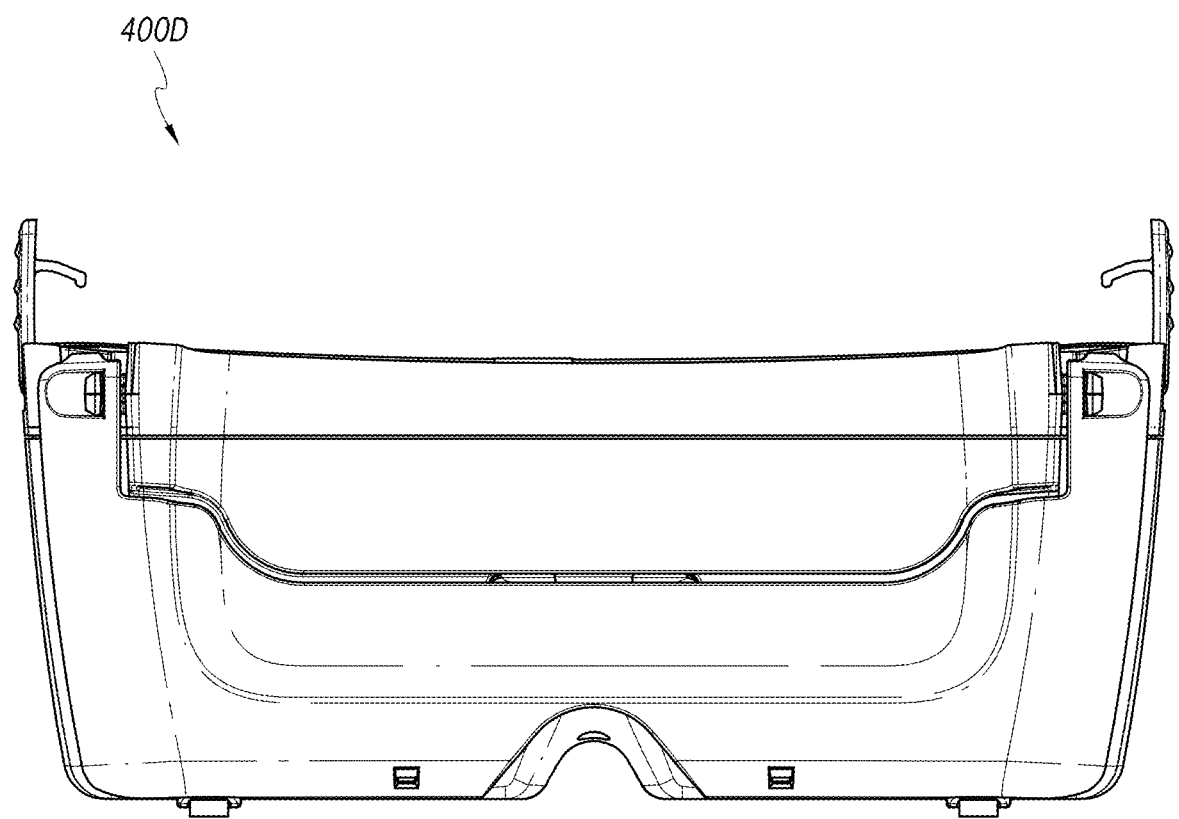
Figure 4F:
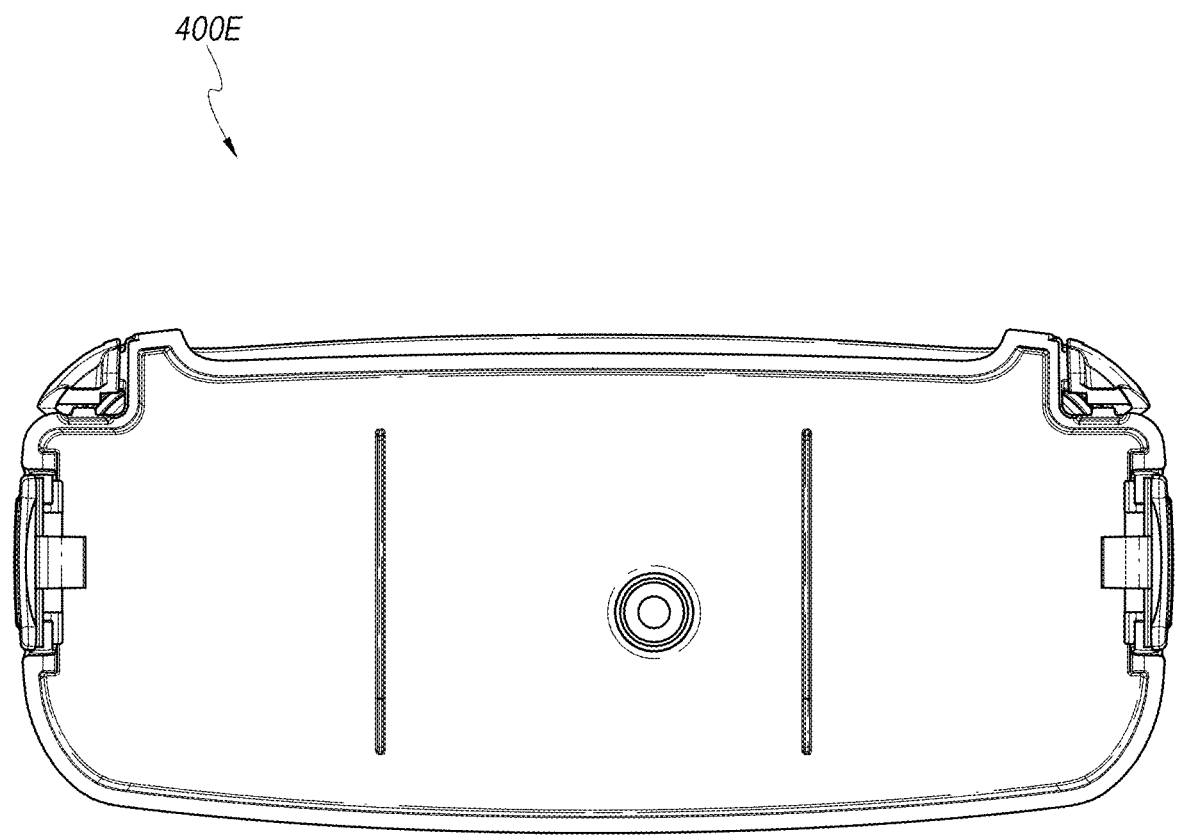
Figure 4G:
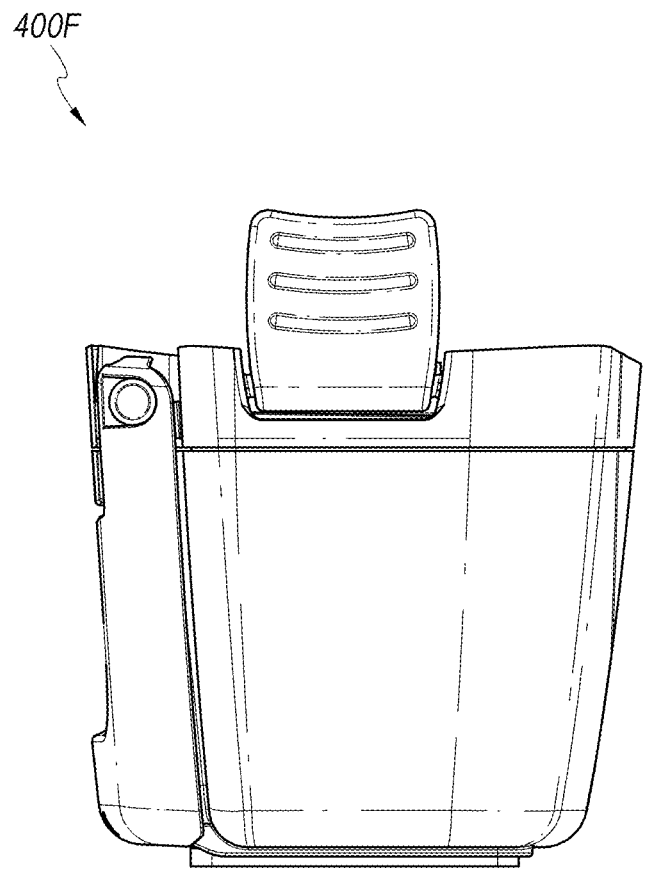
Figure 4H:
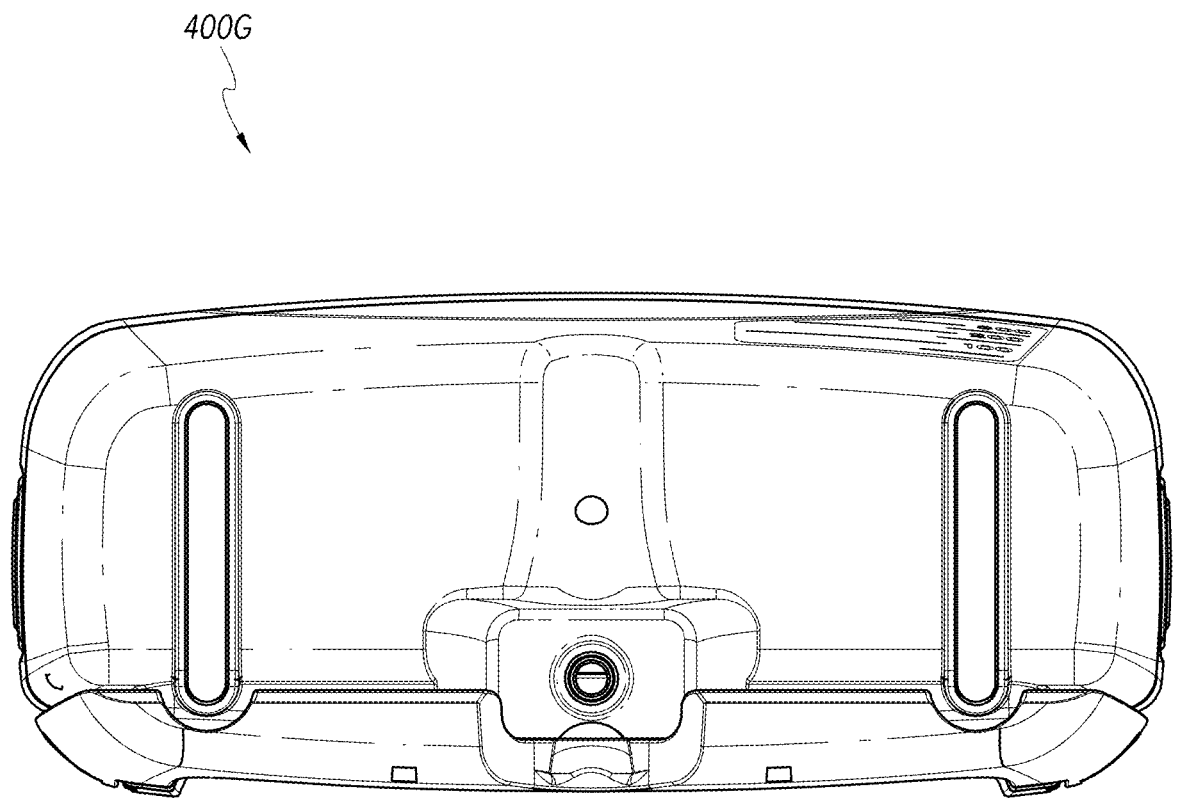

FIGS. 4A-4H illustrate a canister, such as 300 mL canister, according to some embodiments. FIG. 4A illustrates a perspective view 400A of the canister. FIG. 4B illustrates another perspective view 401A of the canister. FIG. 4C illustrates a front view 400B of the canister. FIG. 4D illustrates a right side view 400C of the canister. FIG. 4E illustrates a rear view 400D of the canister. FIG. 4F illustrates a top view 400E of the canister. FIG. 4G illustrates a left side view 400F of the canister. FIG. 4H illustrates a bottom view 400G of the canister.

Figure 5A:
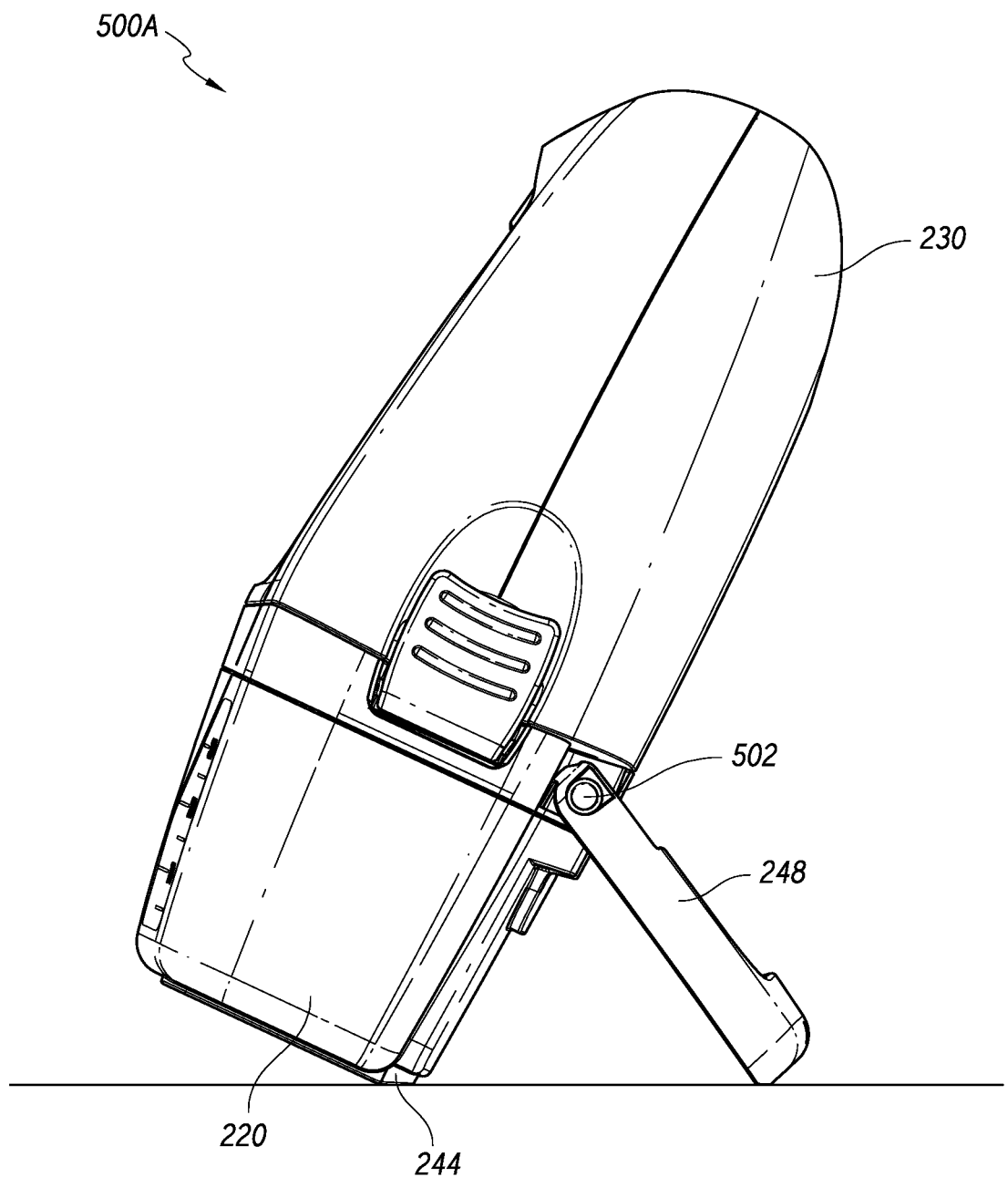
FIGS. 5A-5C illustrate a kickstand in operation according to some embodiments.
Figure 5B:
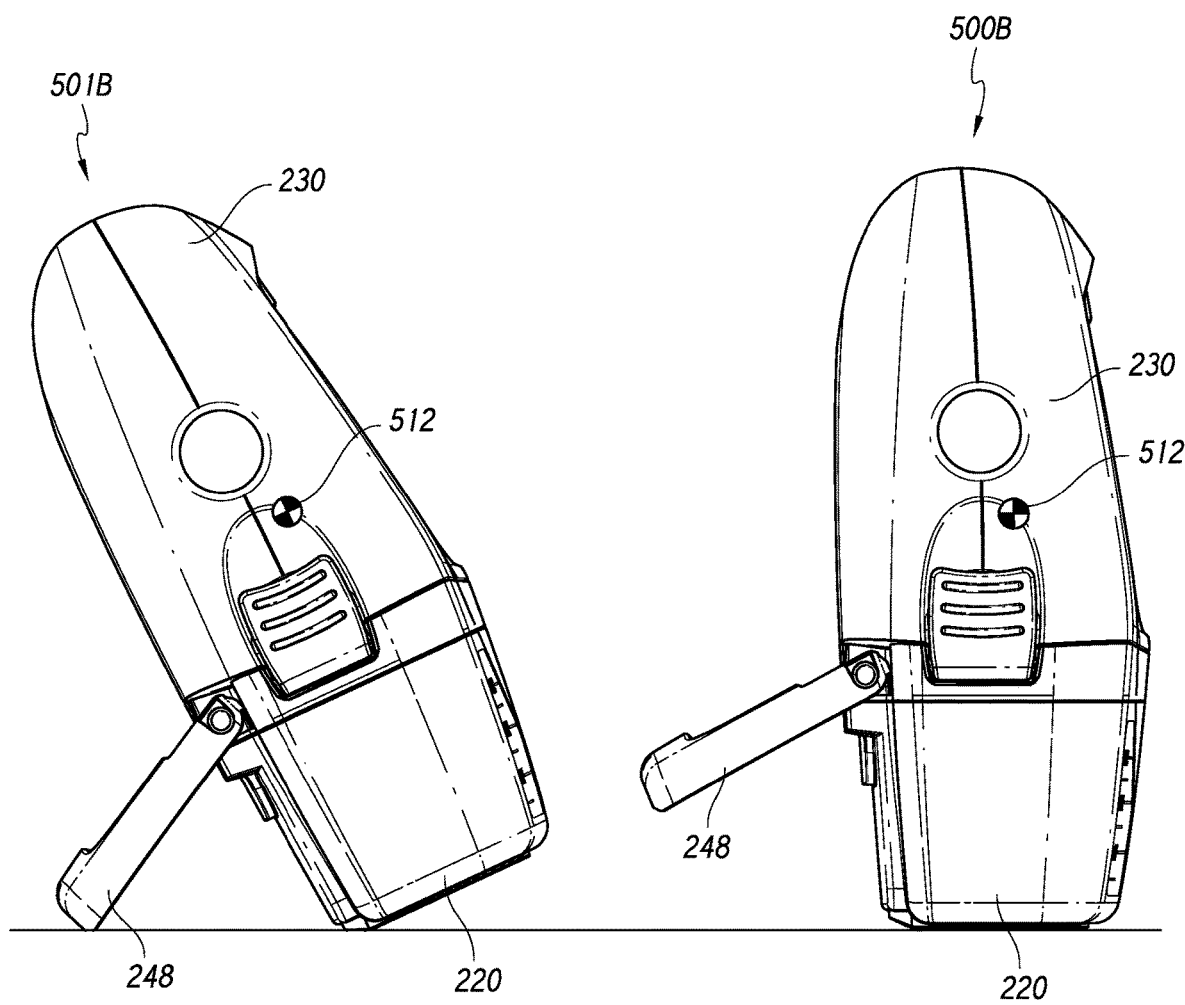
Figure 5C:
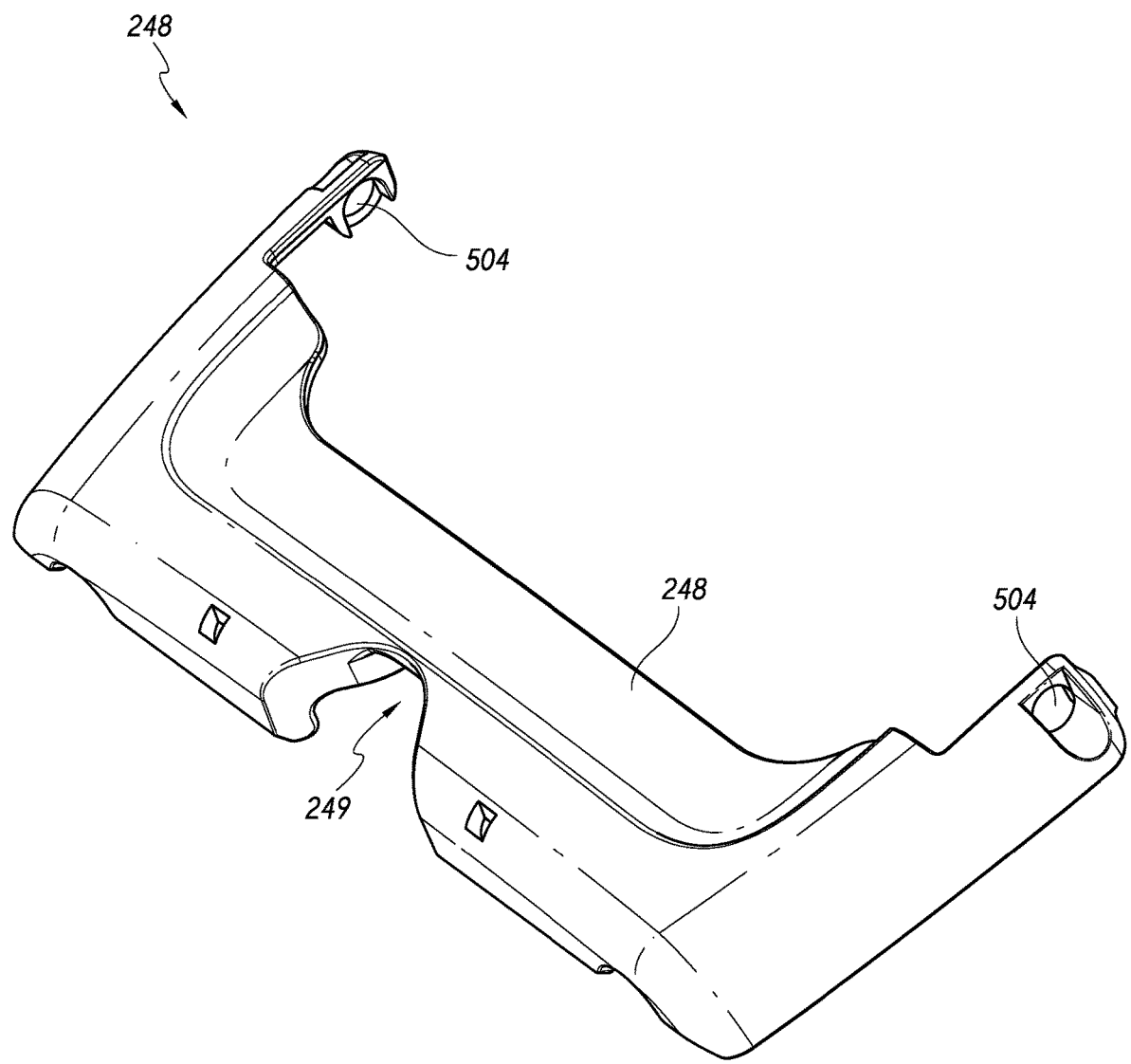

FIGS. 5A-5C illustrate a kickstand in operation according to some embodiments. FIG. 5A illustrates the kickstand 248 is an extended (or opened) position. As is illustrated, the pump assembly 230 and the canister 220 are connected or assembled together, such as by using the latches 221. The device 500A is supported on a surface by the kickstand 248 and feet 244. In the illustrated embodiment, the kickstand 248 is extended by operating one or more pivots 502. FIG. 5B illustrates positioning the device on the surface. As is illustrated in 500B, the kickstand 248 is extended and the device is placed substantially vertically on the surface and/or improve visibility of the screen 206 (e.g., by reducing glare). In 501B, the device is tilted so that it rests on the surface in a stable manner. The tilt of the device in 501B relative to 501A is illustrated by an indicator 512. In some embodiments, the tilt can be less than 30 degrees, about 30 degrees, or greater than 30 degrees. FIG. 5C illustrates the kickstand 248 that includes the hole 249 and two pivot holes 504. In some embodiments, the tilt of the device is adjustable to accommodate the needs of a user. For example, the kickstand 248 can utilize a ratchet mechanism.

Figure 6A:
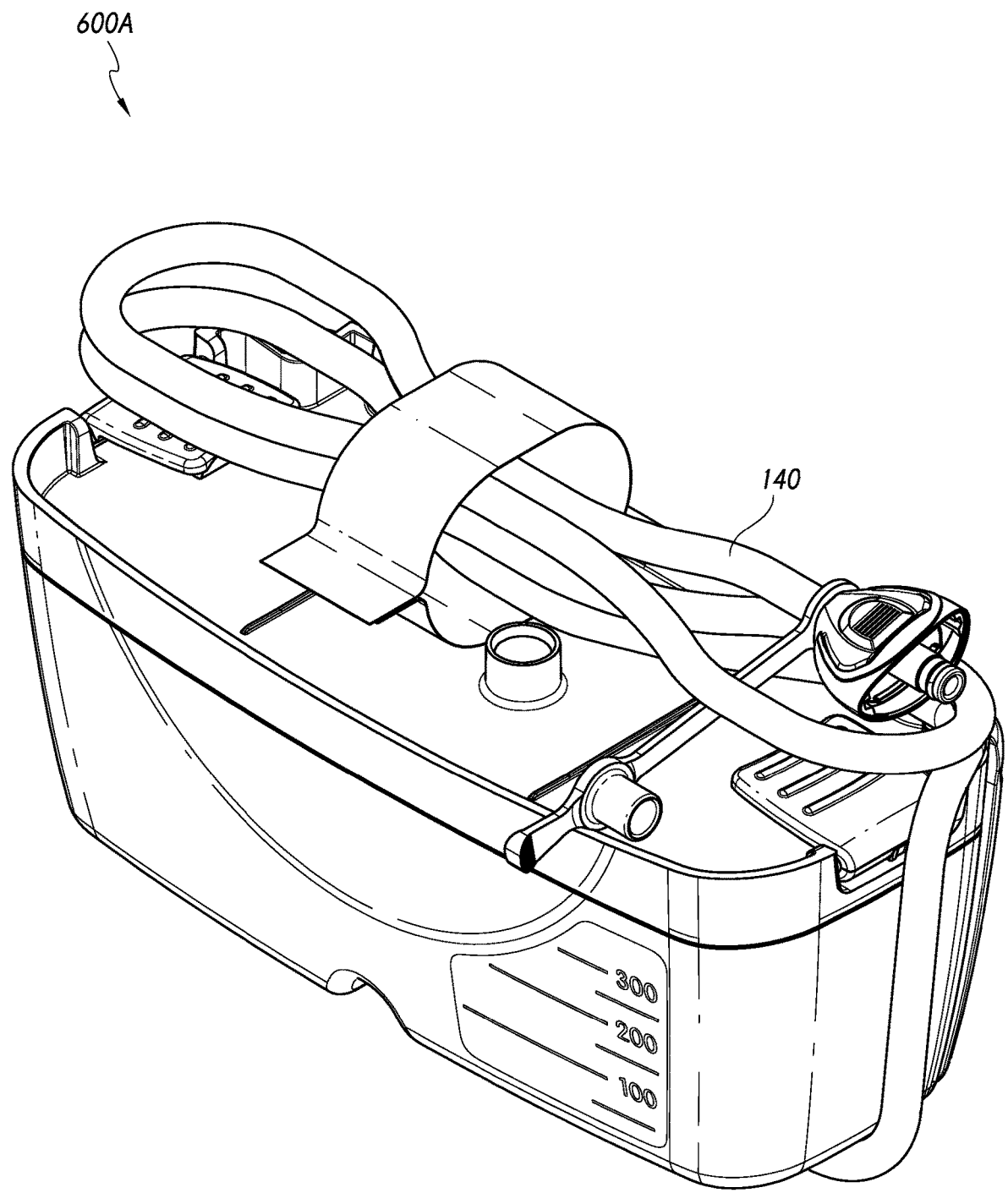
FIGS. 6A-6F illustrate a canister according to some embodiments.
Figure 6B:
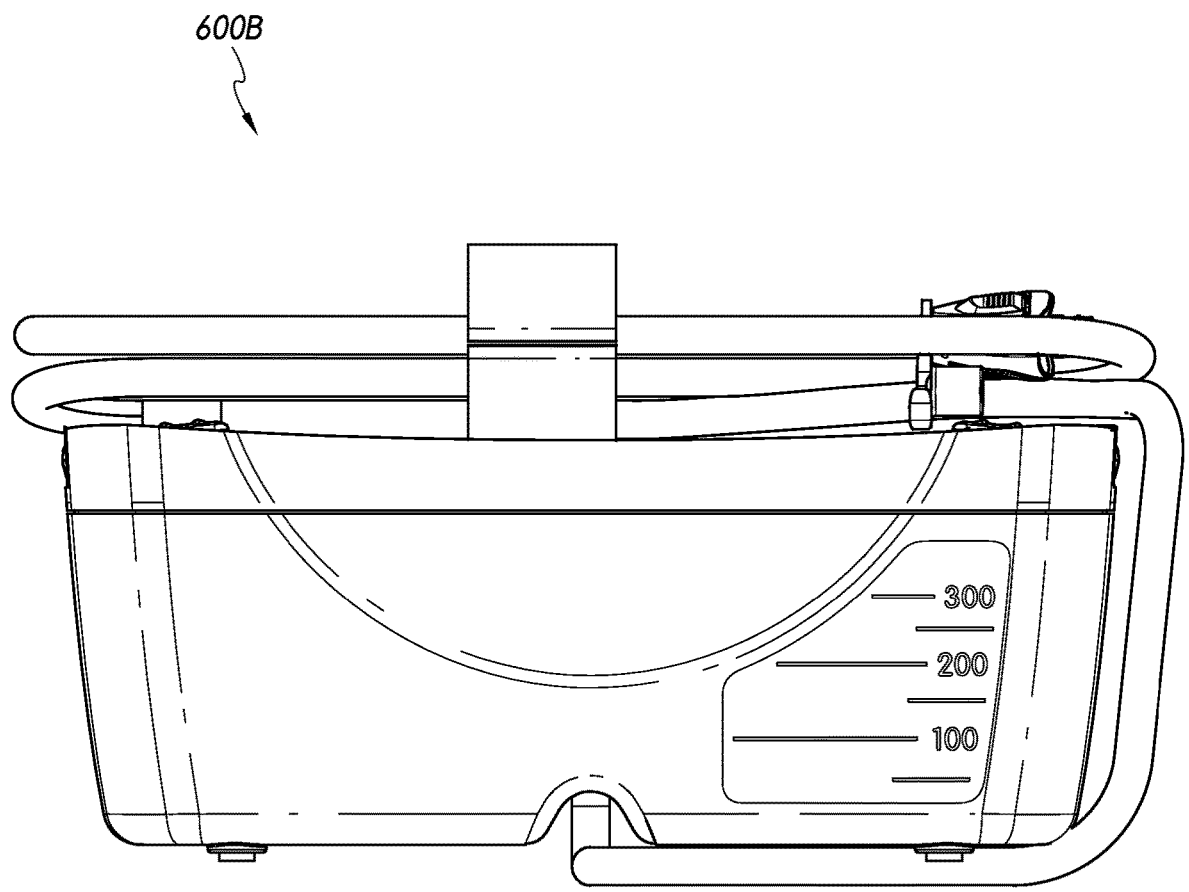
Figure 6C:
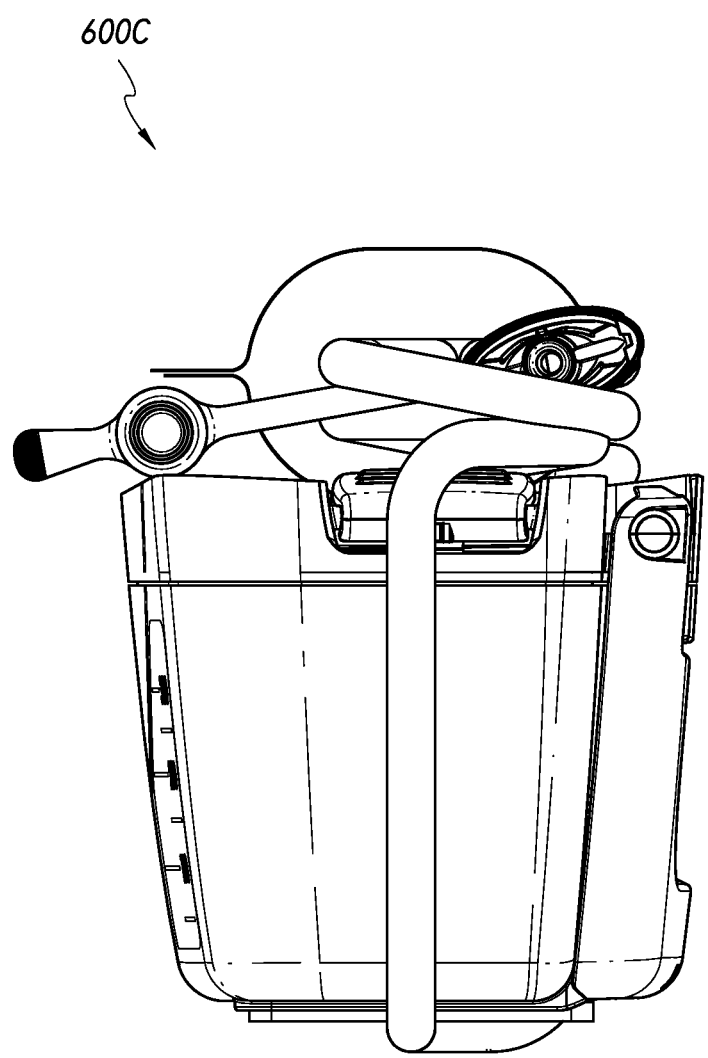
Figure 6D:
Figure 6E:
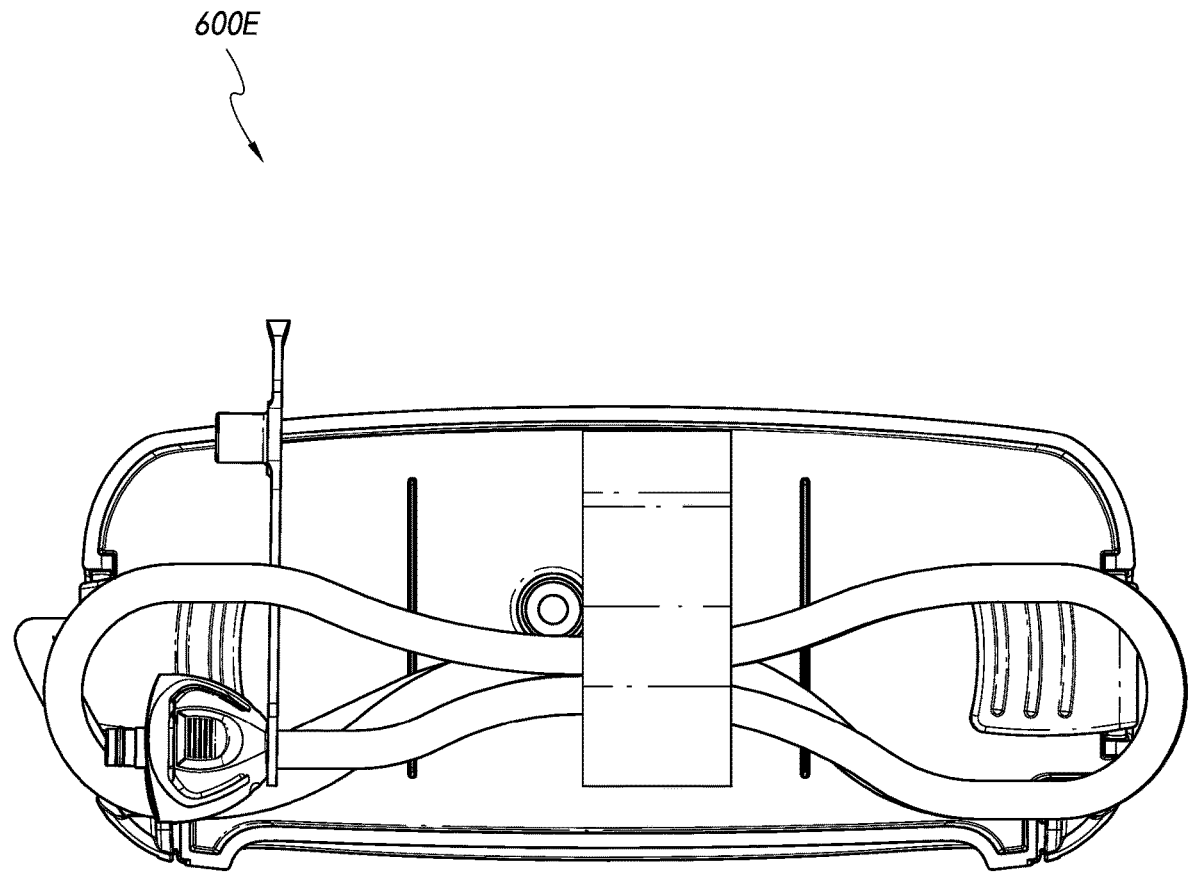
Figure 6F:
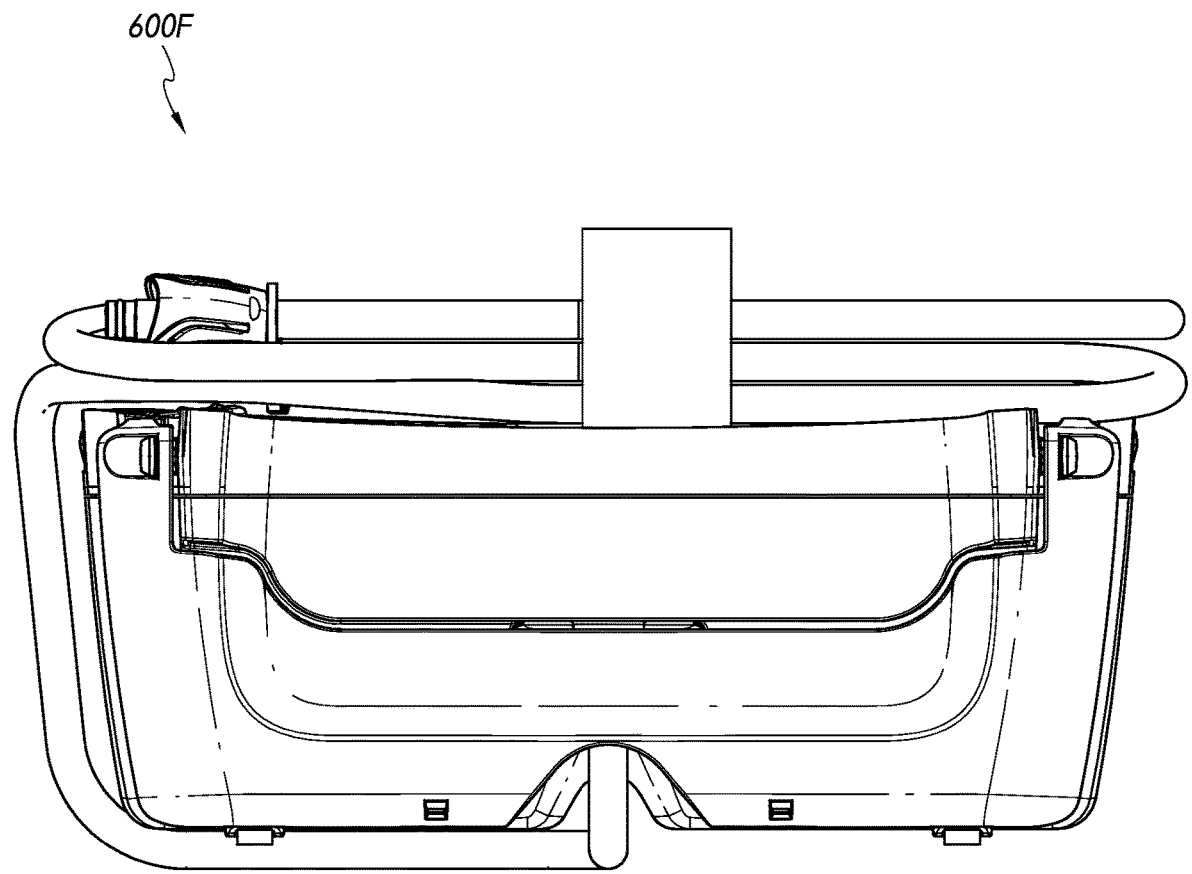

FIGS. 6A-6F illustrate a canister, such as a 300 mL canister, according to some embodiments. FIG. 6A illustrates a perspective view 600A of the canister. The canister comprises a tube 140 configured to connect the canister to the wound cover 120. FIG. 6B illustrates a front view 600B of the canister. FIG. 6C illustrates a side view 600C of the canister. FIG. 6D illustrates another side view 600D of the canister. As is illustrated, the kickstand 248 is in an open position supporting the tilted canister on a surface. FIG. 6E illustrates a top view 600E of the canister. FIG. 6F illustrates a rear view 600F of the canister.

Figure 7A:
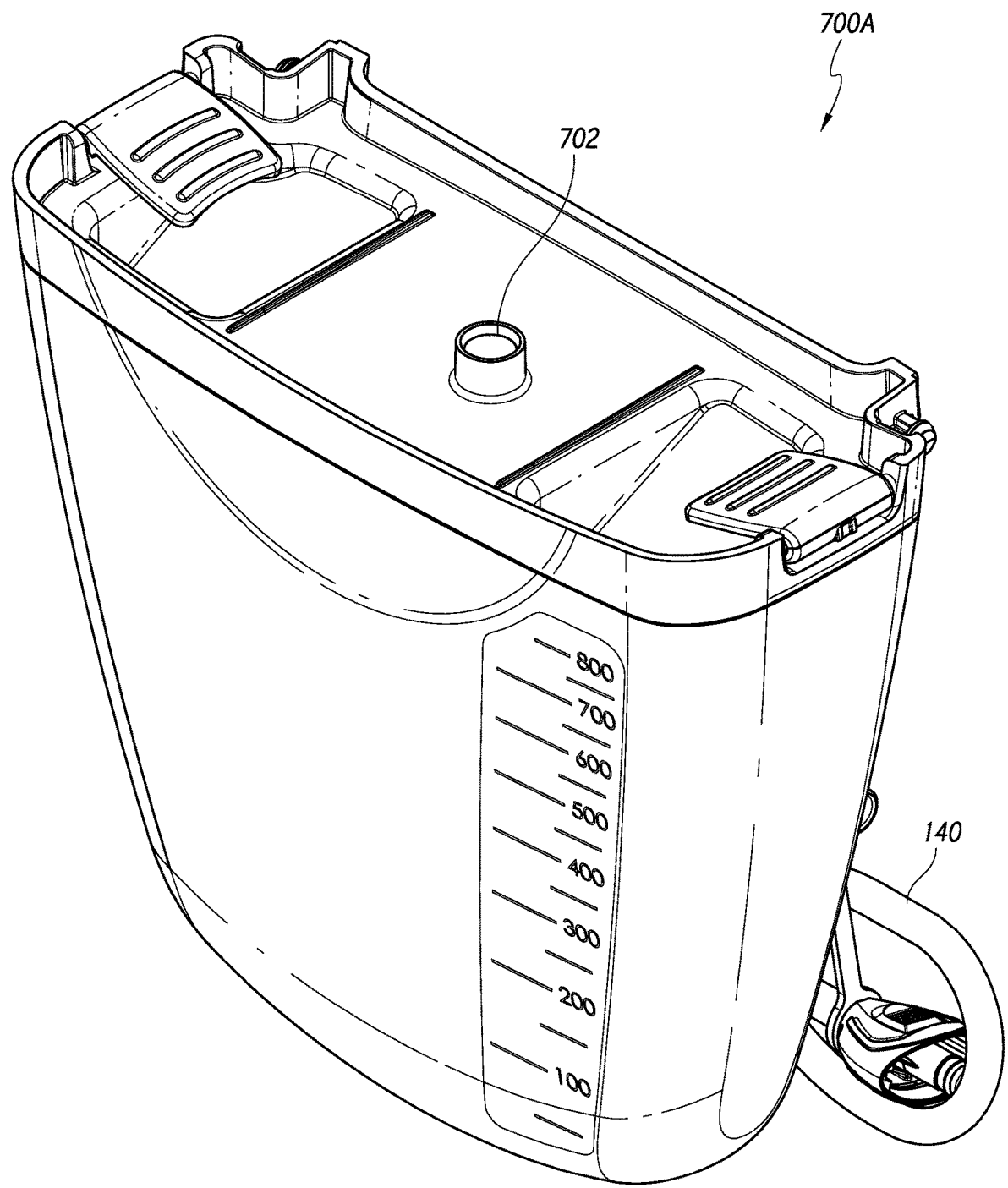
FIGS. 7A-7E illustrate a canister according to various embodiments.
Figure 7B:
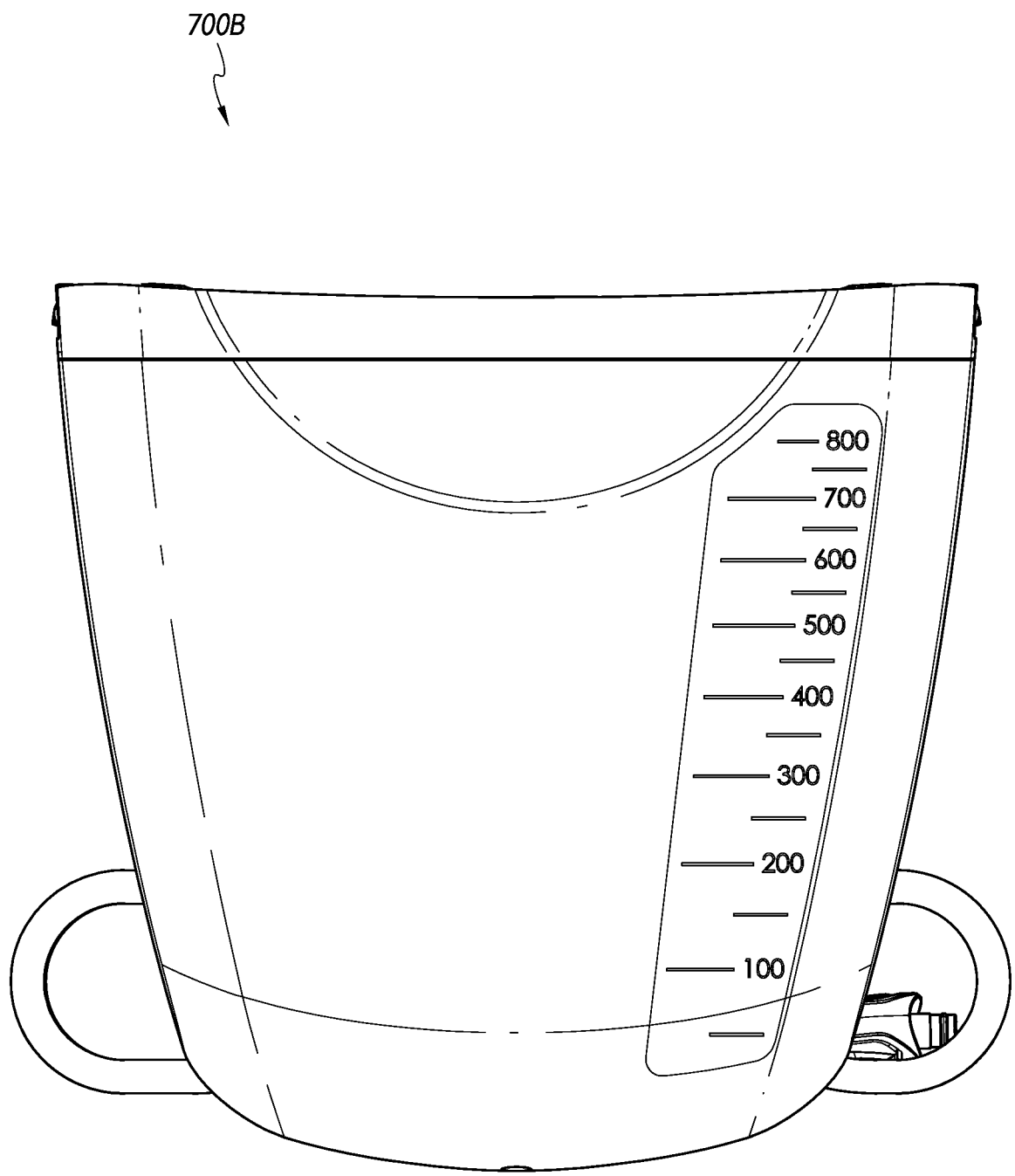
Figure 7C:
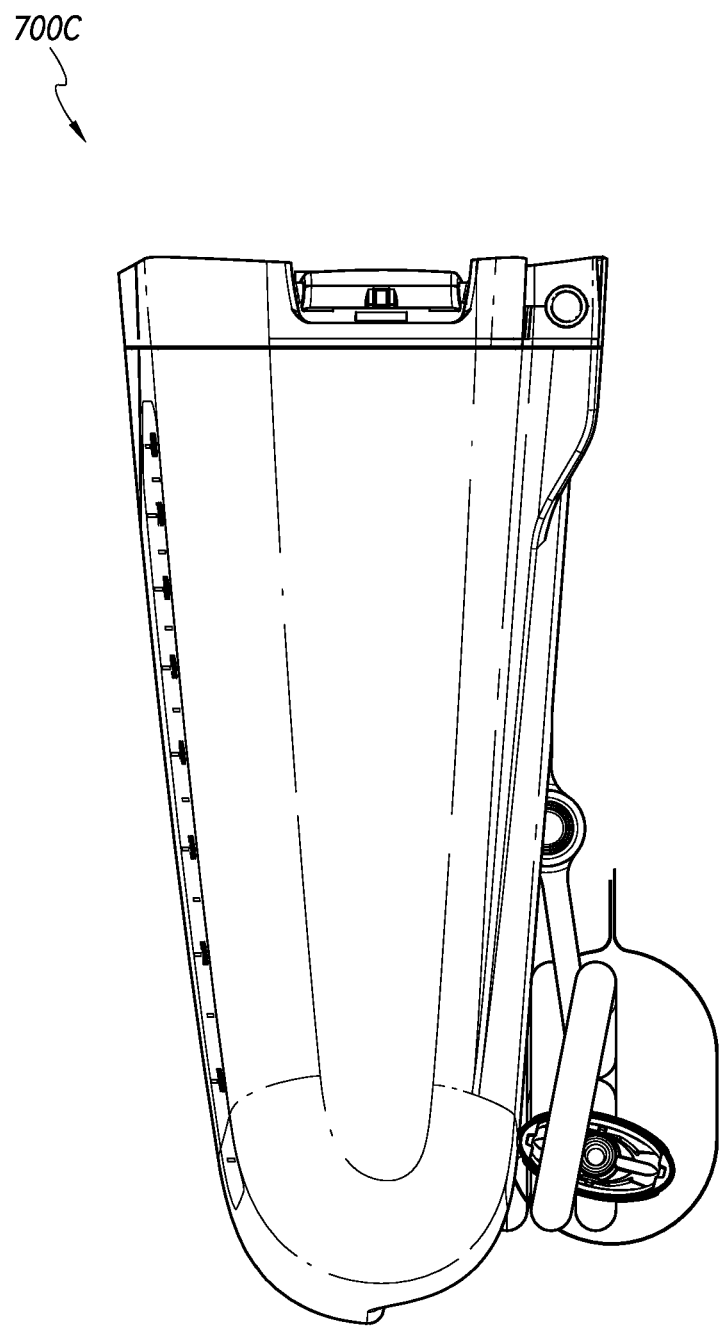
Figure 7D:
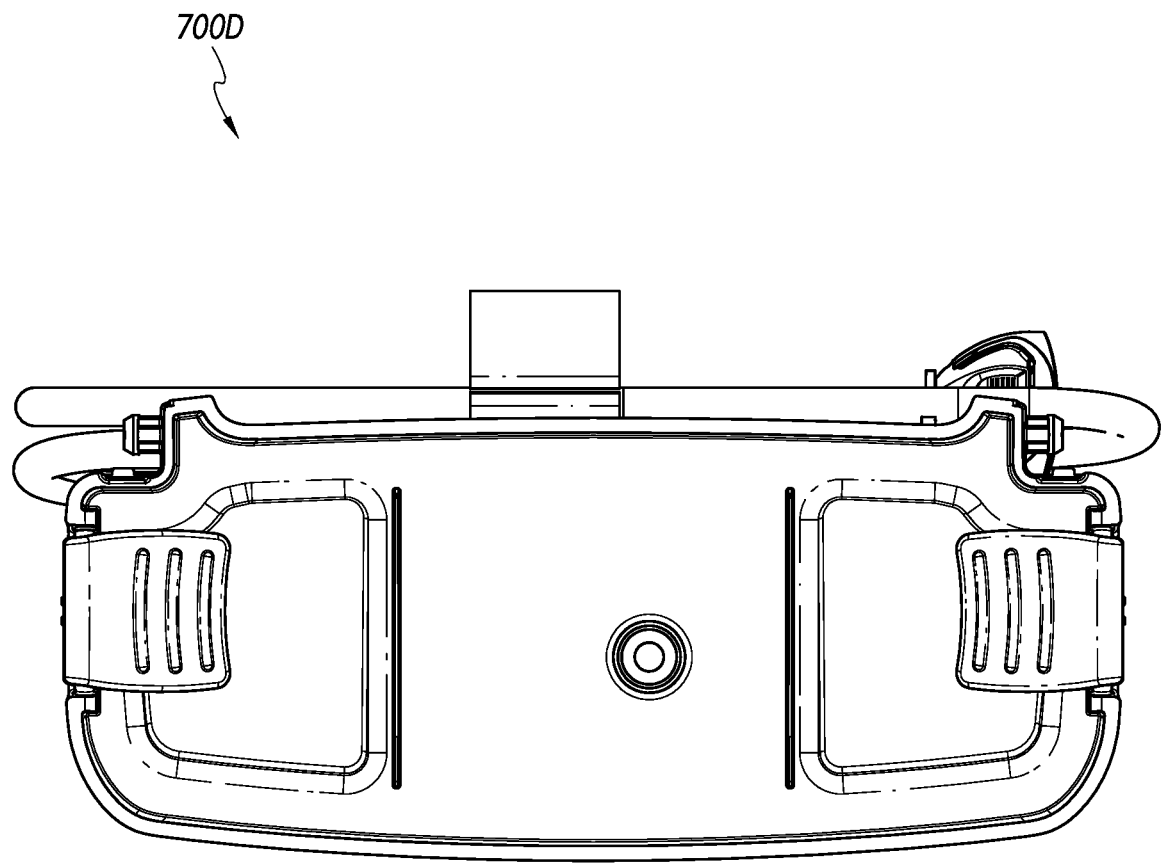
Figure 7E:
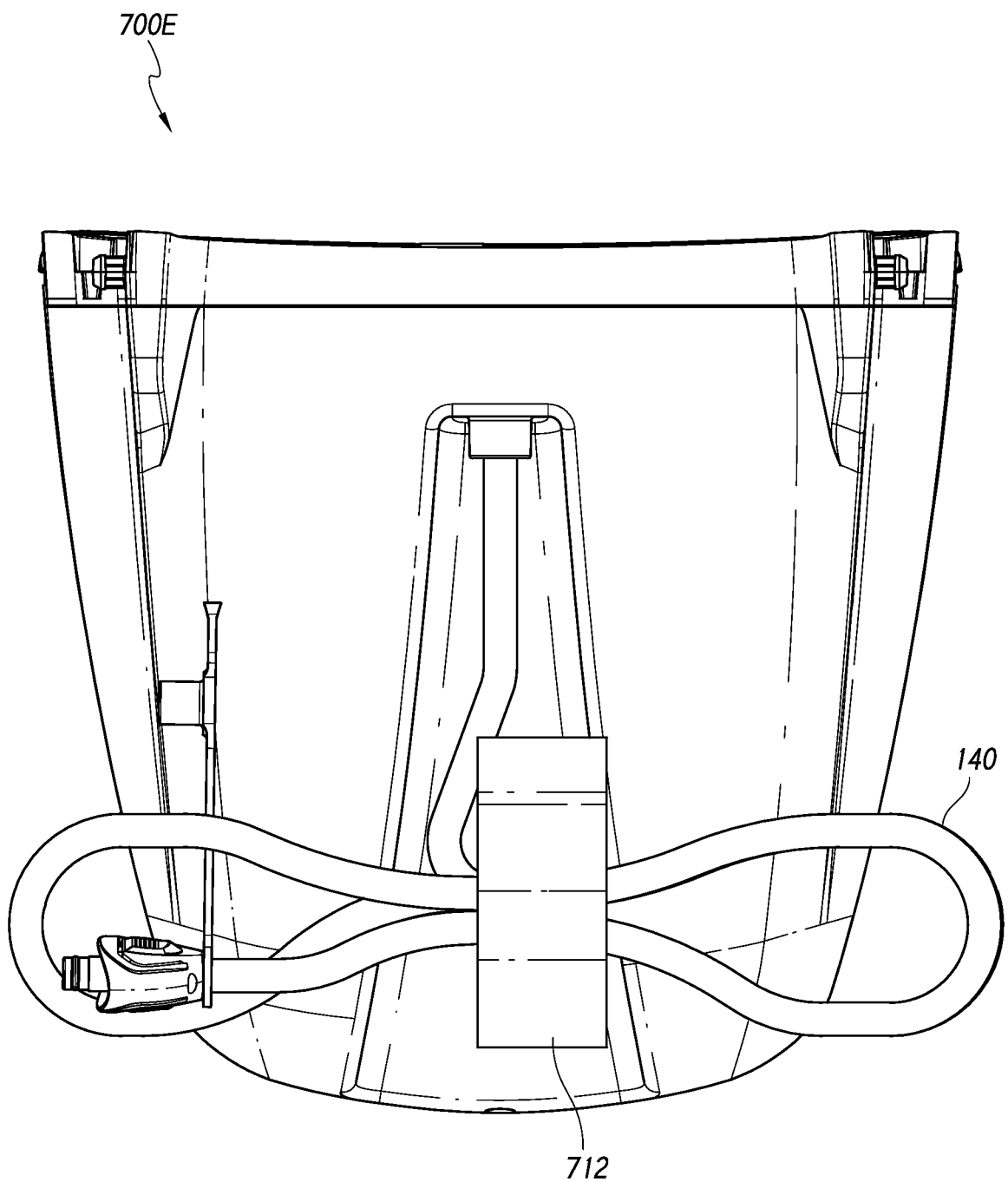

FIGS. 7A-7E illustrate a canister, such as a 800 mL canister, according to various embodiments. FIG. 7A illustrates a perspective view 700A of the canister. The canister comprises a tube 140 configured to connect the canister to the wound cover 120. The canister includes a vacuum attachment or connector 702 through which the canister receives vacuum communicated by the pump assembly 230. In some embodiments, the connector 702 is configured to be connected to or mated with the connector 252 of the pump assembly 230. FIG. 7B illustrates a front view 700B of the canister. FIG. 7C illustrates a side view 700C of the canister. FIG. 7D illustrates a top view 700D of the canister. FIG. 7E illustrates a rear view 700E of the canister. The canister comprises a clip 712 for holding the tube 140.

Figure 8A:
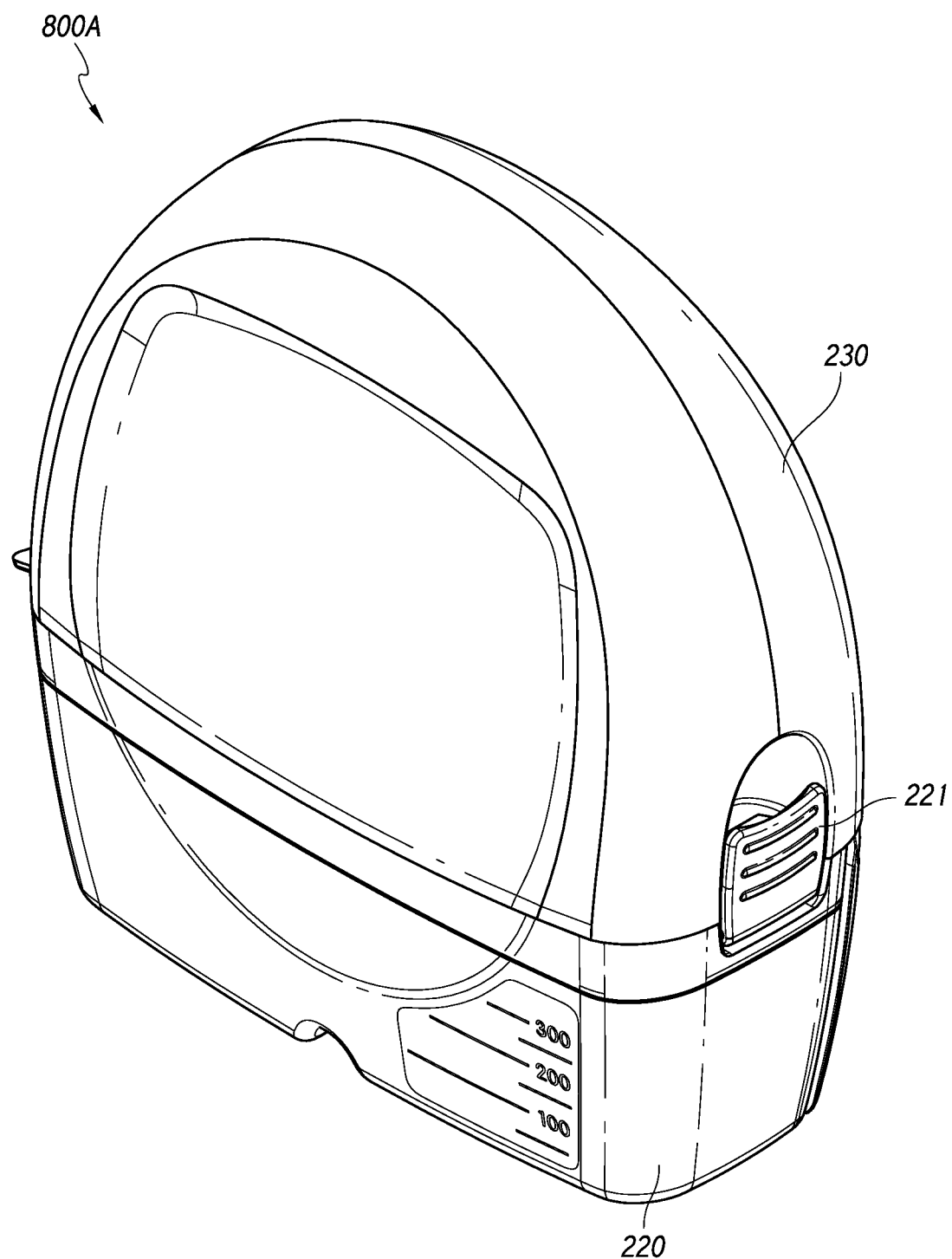
FIGS. 8A-8G illustrate a pump assembly and canister according to certain embodiments.
Figure 8B:
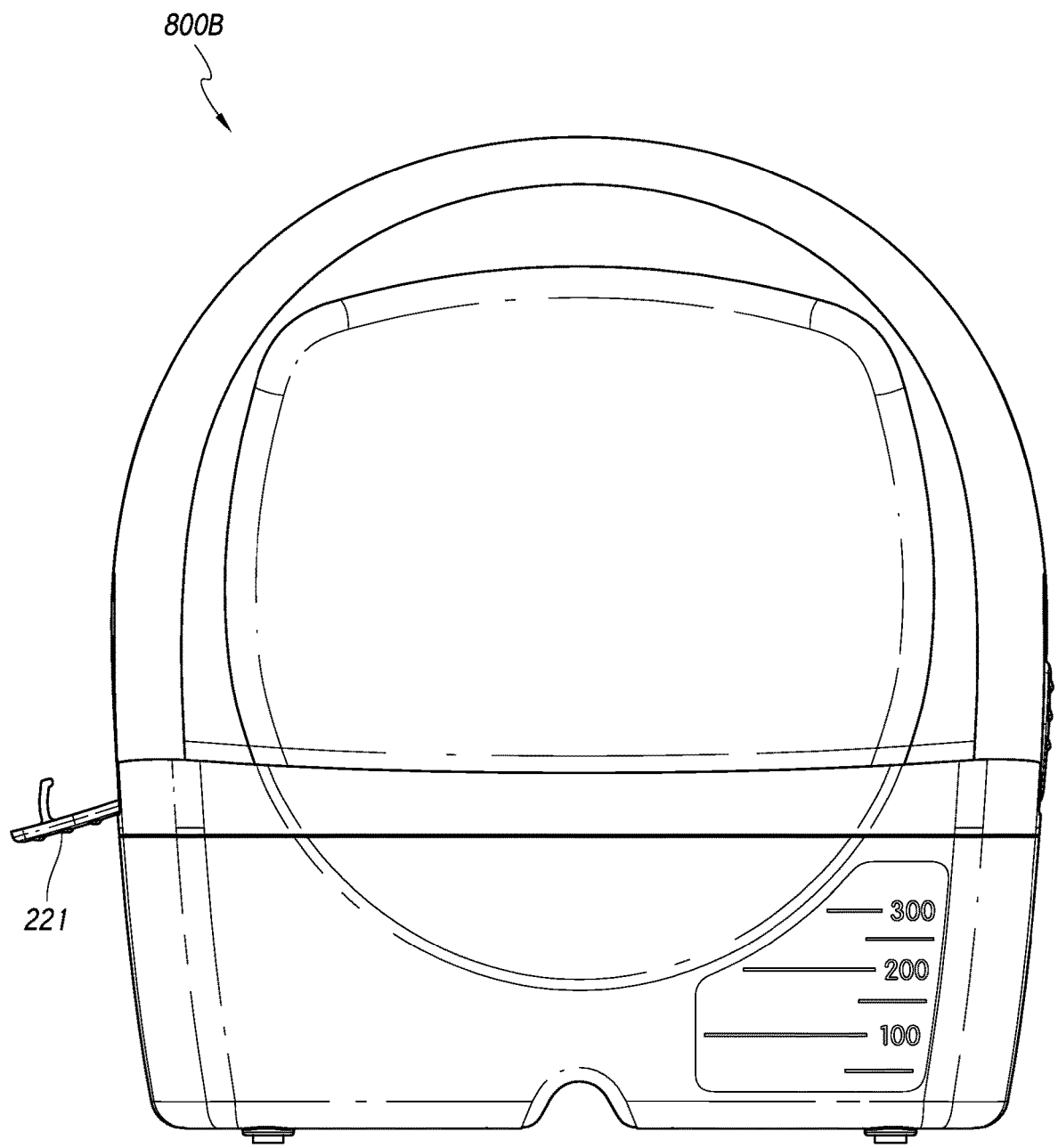
Figure 8C:
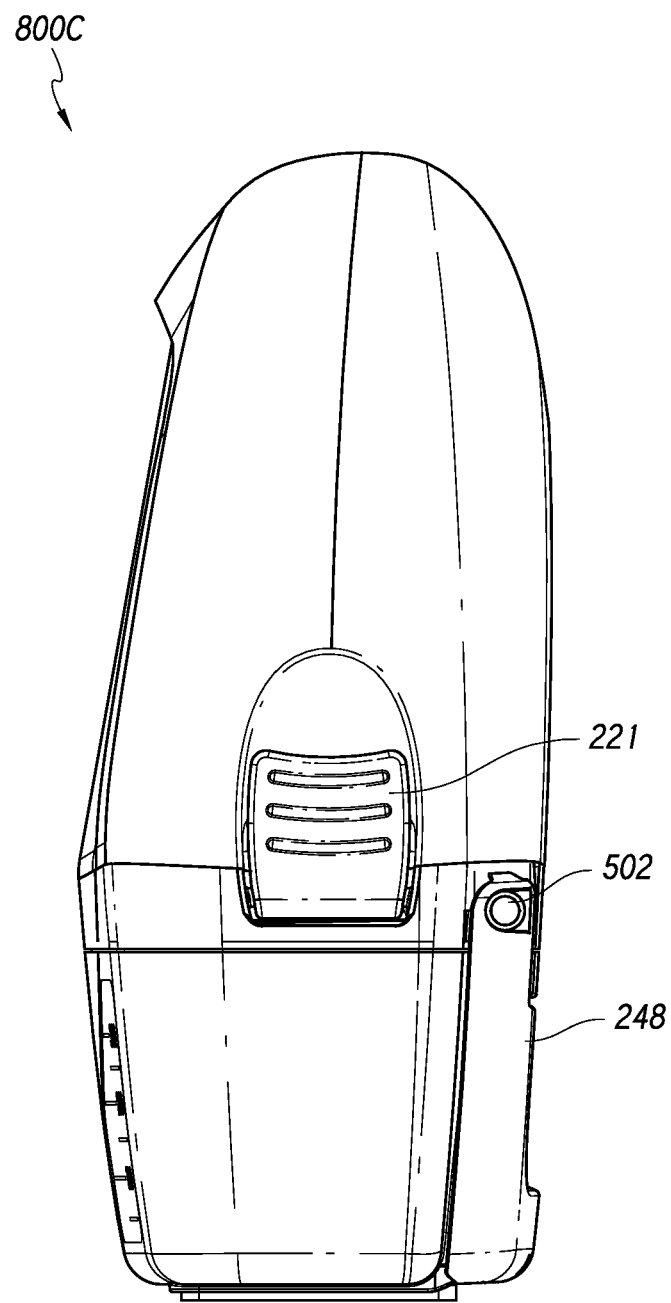
Figure 8D:
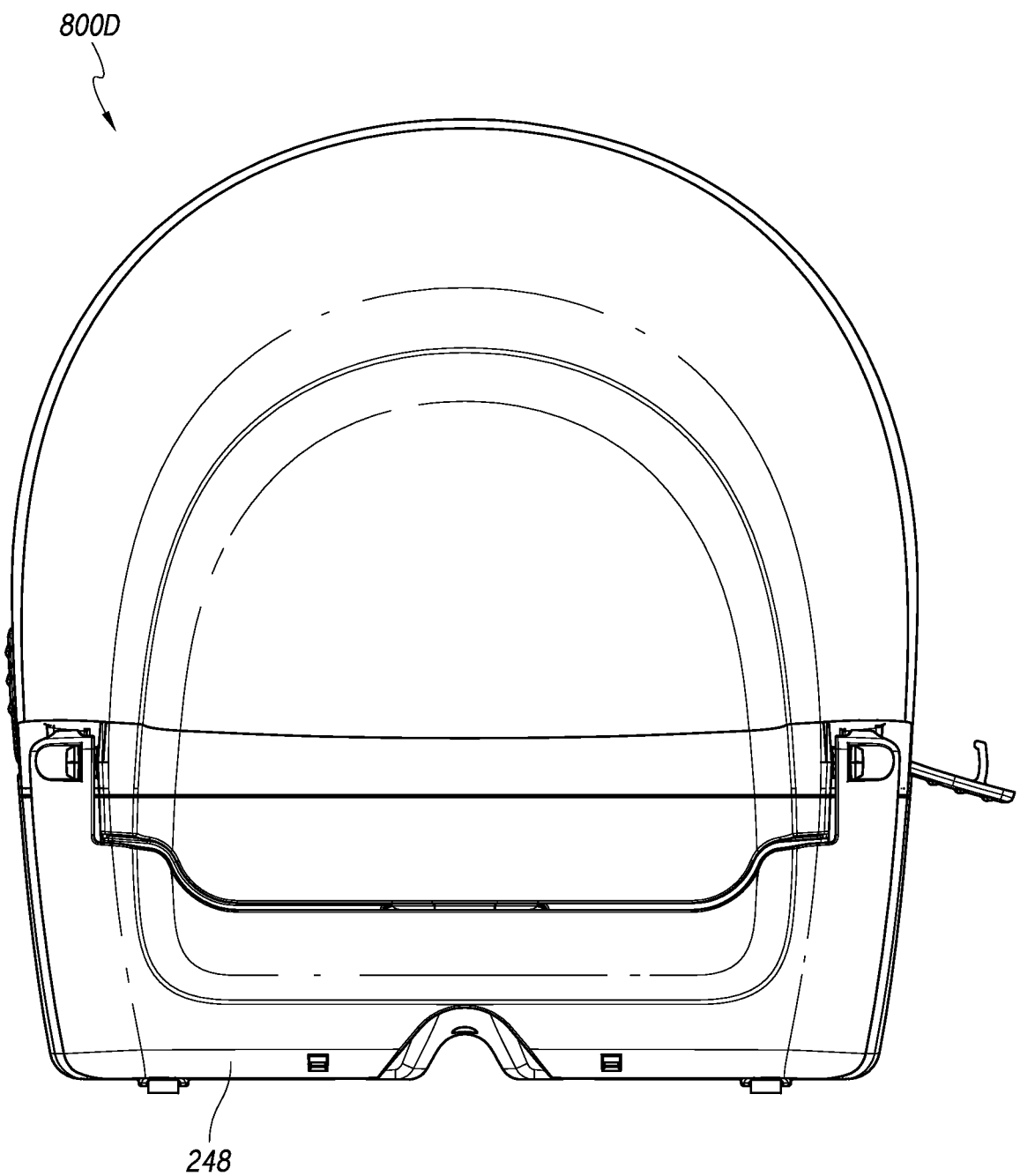
Figure 8E:
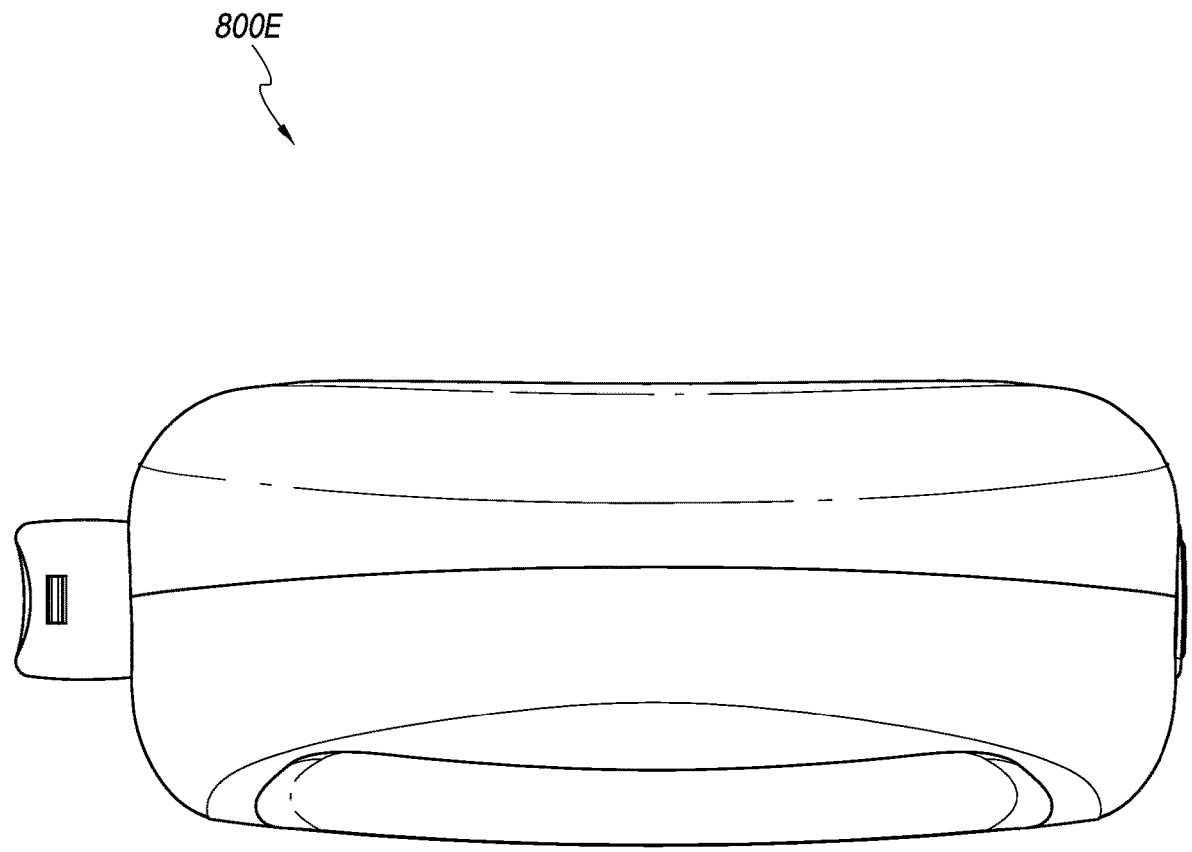
Figure 8F:
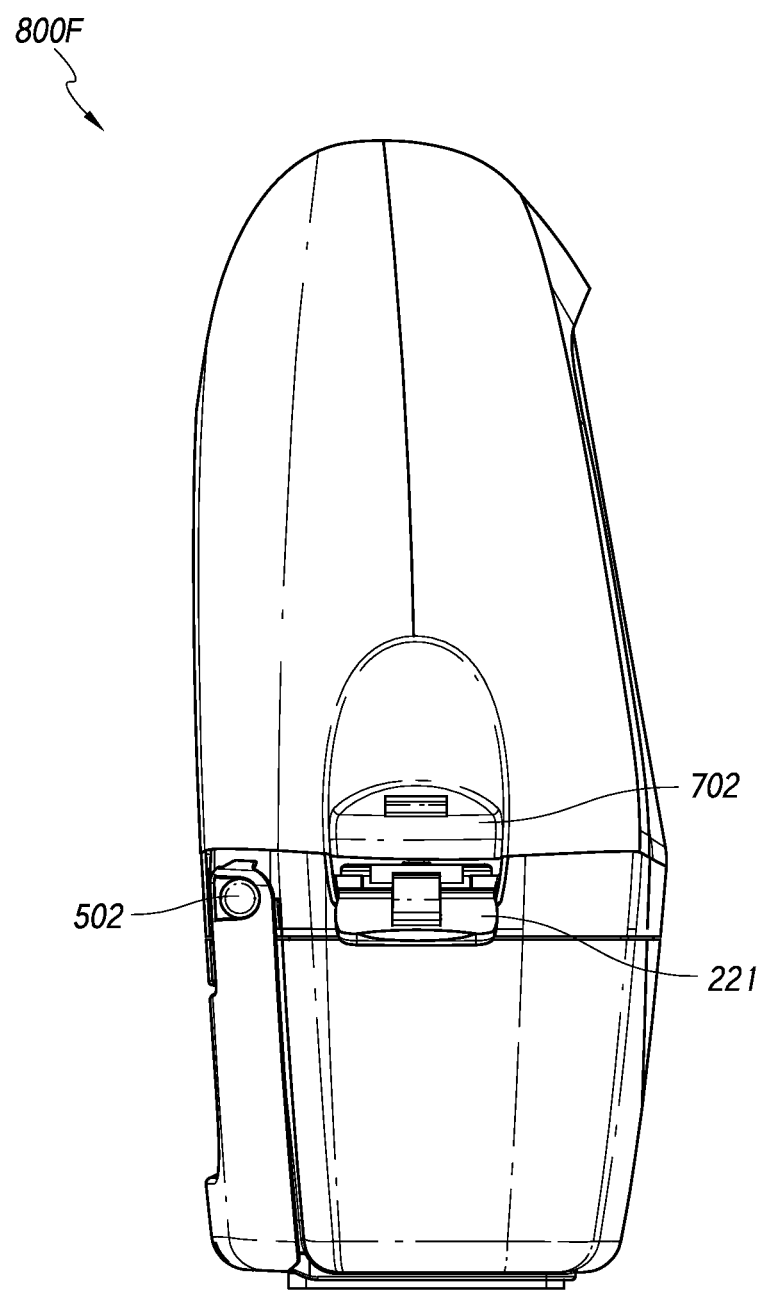
Figure 8G:
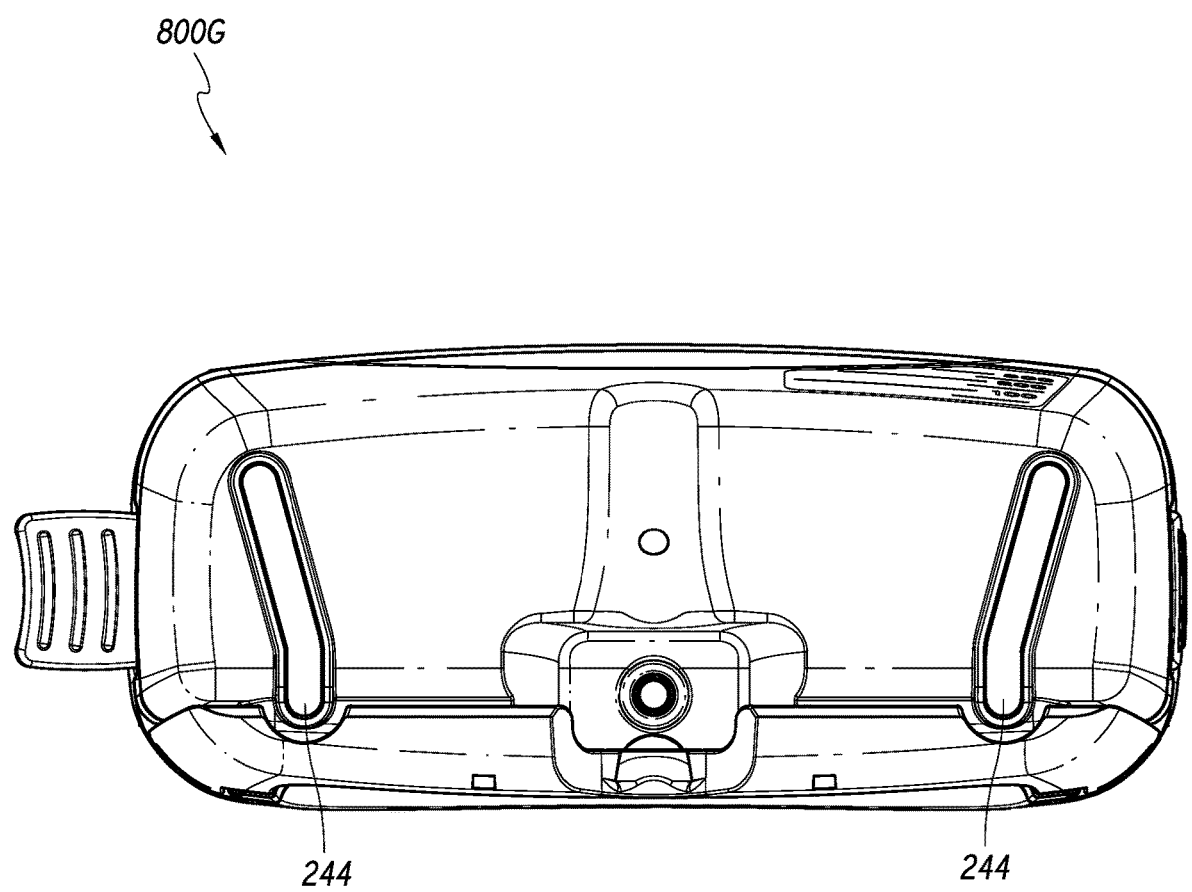

FIGS. 8A-8G illustrate a device according to certain embodiments. FIG. 8A illustrates a perspective view 800A of the device, which includes a pump assembly 230 and canister 220. The canister 220 can be connected to the pump assembly 230 using one or more latches 221, such as two latches 221 on the sides of the canister 220. FIG. 8B illustrates a front view 800B of the device. FIG. 8C illustrates a right side view 800C of the device. The device comprises a kickstand 248 that is configured to be opened or close via one or more pivots 502. FIG. 8D illustrates a rear view 800D of the device. FIG. 8E illustrates a top view 800E of the device. FIG. 8F illustrates a left side view 800F of the device. The latch 221 can be configured to connect to the recess 702 formed on the pump assembly 230 in order to connect the canister 220 to the pump assembly 230. FIG. 8G illustrates a bottom view 800G of the device. The canister 220 includes feet 244.

Figure 9A:
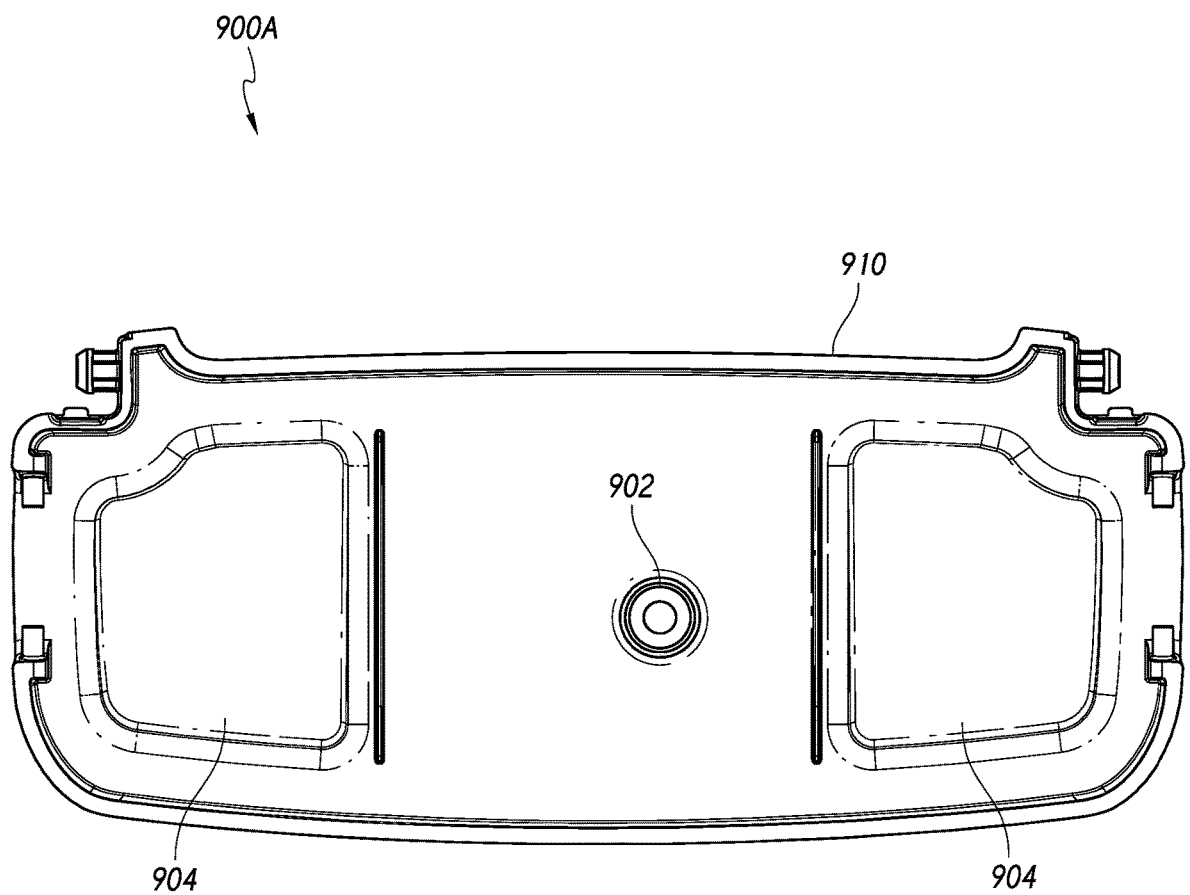
Figure 9B:
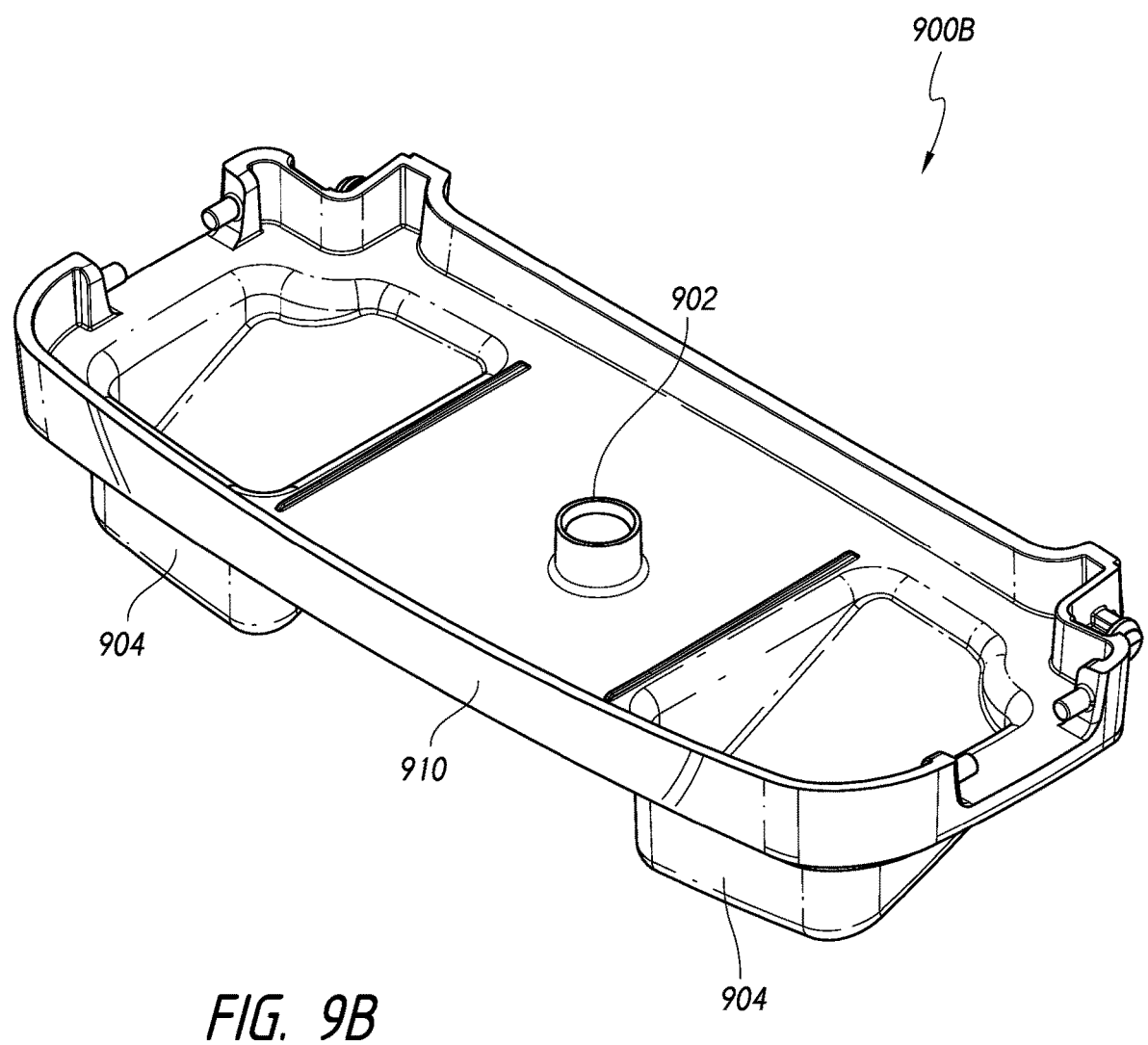

FIGS. 9A-9C illustrate a canister bulkhead 910 according to some embodiments. FIG. 9A illustrates a top view 900A of the canister bulkhead 910. FIG. 9B illustrates a perspective view 900B of the canister bulkhead 910. FIG. 9C illustrates a bottom view 900C of the canister bulkhead 910. The canister bulkhead can be configured to connect the canister 220 to a negative pressure source of the pump assembly 230, such as via a pump assembly bulkhead. To facilitate this function, the canister bulkhead 910 comprises a connector or port 902 which attaches to the vacuum connector 252 of the pump assembly 230. The canister bulkhead 910 also includes a gate mark or gate 906 to facilitate connecting the canister 220 to the pump assembly 230. The canister bulkhead 910 includes one or more regions or protrusions 904 configured to limit the capacity of the canister 220 as it fills up or when it becomes full so that the device (and the canister) can be oriented vertically, horizontally, and/or vertically tilted (e.g., when the kickstand 248 is extended). As is shown in FIGS. 9B and 9C, the volume of fluid held by the canister 220 is reduced or limited by the one or more protrusions 904. In some embodiments, the device bulkhead is flat. In other embodiments, the device bulkhead can mate with the features of the canister bulkhead 910.

FIG. 10 illustrates a canister filter stack 1000 according to some embodiments. The canister filter stack 1000 comprises a filter carrier 1002, shutoff 1004, odor filter 1006, and antibacterial filter 1008. The shutoff 1004 operates to stop suction when the canister 220 becomes full such that canister overfill is prevented. The shutoff can be formed out of hydrophilic material. The odor filter 1006 can comprise material that absorbs, reduces or eliminates odor. For example, such material can be active carbon, activated charcoal, or the like. The material can be hydrophobic. The antibacterial filter 1008 can inhibit or eliminate the growth of microorganisms. In some embodiments, the components of the filter stack 1000 can be arranged in any suitable order. For example, the odor filter 1006 can be integrated into the shutoff 1004 as an additive to the material of the shutoff 1004 or as a layer formed on the material of the shutoff 1004. In some embodiments, the filter stack 1000 is placed in the canister. In some embodiments, the filter stack 1000 is placed in the connector between the canister in the pump assembly. In some embodiments, the filter stack 1000 is placed in the pump assembly.

Figure 11:
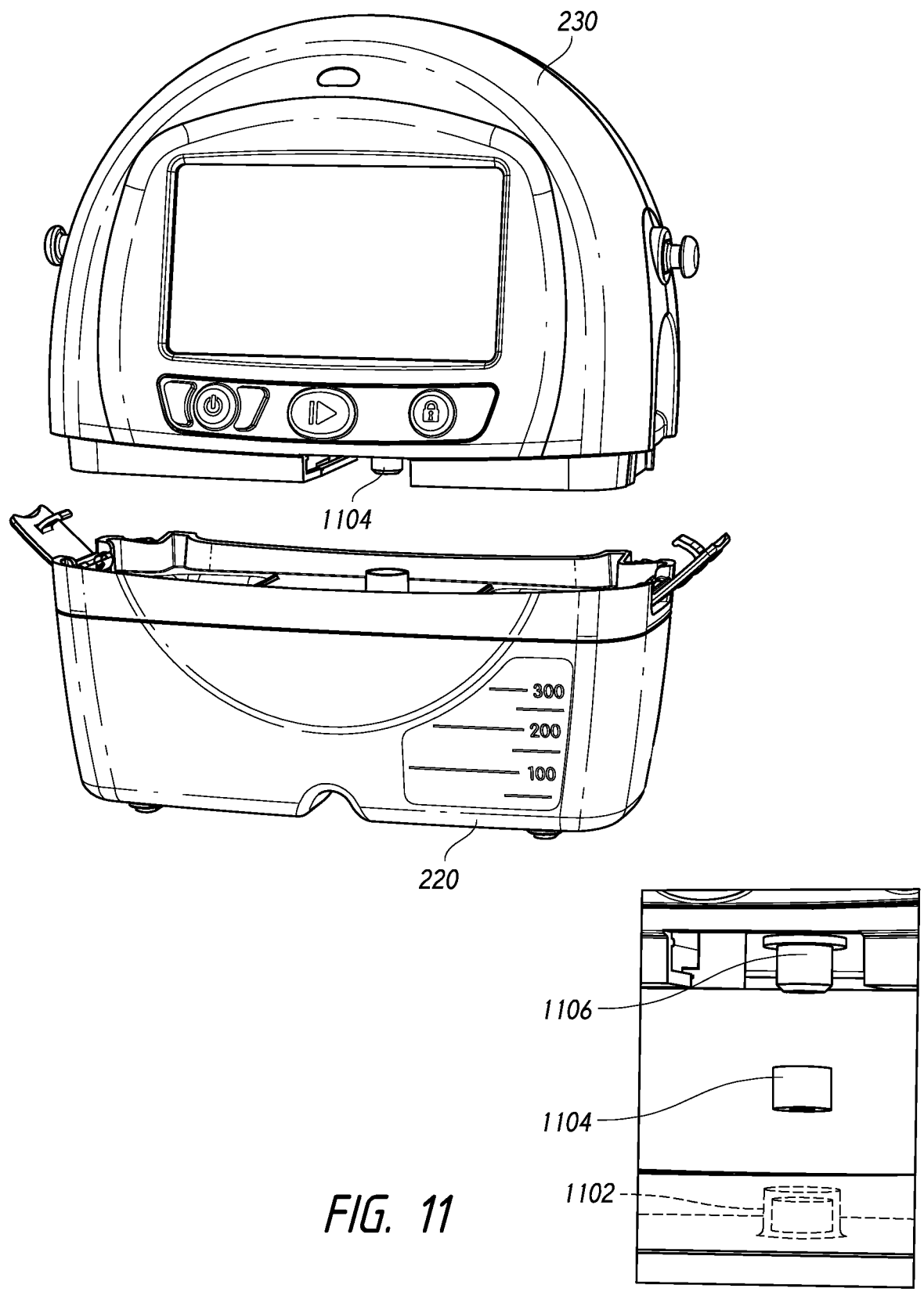
FIG. 11 illustrates a connection between a canister and pump assembly according to some embodiments.

FIG. 11 illustrates a connection 1104 between the canister 220 and pump assembly 230 according to some embodiments. As is illustrated, the connection 1104 is placed between the vacuum attachment 1106 of the pump assembly 230 and the attachment or port 1102 of the canister 220. The connection 1104 can be a washer, ring, or the like which ensures a substantially leak-free seal between the canister 220 and the pump assembly 230.

Strap

In some embodiments, a strap can be attached to the pump assembly 230 for carrying the device of the shoulder, waist, etc. The strap can be adjustable in length. FIG. 12 illustrates a strap mount attachment 1200 according to some embodiments. The attachment 1200 can be detachably clipped onto mounts 226 (FIG. 2B) of the pump assembly 230. In operation, a hole 1202 of the attachment 1200 can be aligned with the mount 226, and a portion 1204 can be attached to the mount 226. The inner diameter of the portion 1204 can be selected so that there is a substantially tight fit with the mount 226. A strap (not shown) can be attached to a rod 1210. In some embodiments, two attachments 1200 are clipped onto two mounts 226 located on the opposing sides of the pump assembly 230.

In some embodiments, the device can be placed into a carrying case or carrying bag. The carrying case can be configured for accommodating the pump assembly 230 connected to the canister 220. The carrying case can include a pouch configured to enclose the device, the pouch comprising an upper portion and a lower portion. A lower opening in the lower portion of the pouch can be configured to permit insertion of the device. The lower opening can include a closure configured to close the lower opening and to prevent the apparatus from being displaced from the pouch. The lower opening can also include an aperture (e.g., for the tube 140) that remains open between an interior and exterior of the pouch after the closure closes the lower opening. The lower opening can comprise a flap that can be lifted to permit viewing of the canister 220. The upper portion can also include a flap that can be lifted to permit access to the display 206 and/or buttons 212. Additional details of the carrying bag are provided in U.S. Pat. No. 8,240,470, which is assigned to the assignee of the present application and is incorporated by reference in its entirety. In some embodiments, the pump assembly 230 and/or canister 220 includes a clip for attaching the pump assembly to a patient's belt, pocket, etc.

Attachment System

Figure 13A:
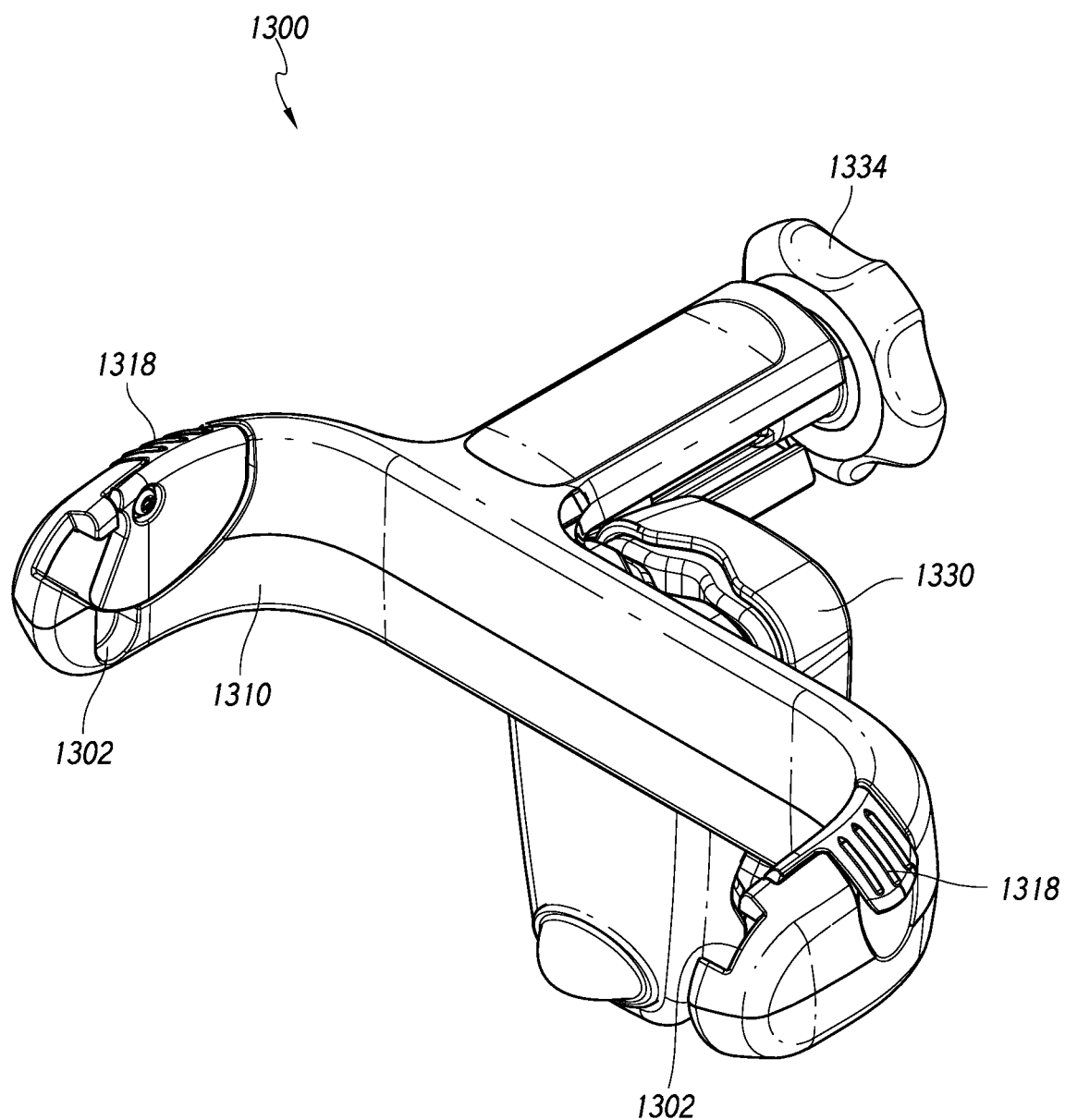

FIGS. 13A-13B illustrate an attachment system 1300 according to some embodiments. In operation, the attachment system 1300 is used to mount a device or apparatus to any suitable structure, such as an IV pole (e.g., an IV pole having a diameter between 0.75 inches and 2.0 inches), a bedrail (e.g., a bedrail having a width between 0.75 inches and 3 inches), and the like. The attachment system 1300 can be used to mount to the structure any suitable device, such as a medical treatment device, including but not limited to NPWT apparatus or device. The attachment system 1300 can be configured to be adjustable so that a secure connection can be made efficiently. As is illustrated in FIG. 13A, the attachment system 1300 includes a cradle 1310, which attaches to the device, and a clamp 1330. The clamp 1330 is adjustable for secure attachment to various structures. In the illustrated embodiment, the width of the clamp 1330 is adjusted by turning a knob 1334. In some embodiments, the cradle 1310 attaches to the device by placing a mount 226 (see FIGS. 2A-2B) into a recess 1302 and activating a closure 1318. The closure 1318 can be a latch, lock, or any other suitable mechanism for attaching the device to the cradle 1310. The cradle 1310 can include one or more closures 1318, such as two closures on each side of the cradle.

The attachment system 1300 attaches to a structure, such as a pole, rail, or the like by turning the knob 1334 so that a portion of the structure is secured in the space between the first and second clamp arms as described below. The device can be removed from the cradle 1310 by deactivating the one or more closures 1318. For example, the one or more closures 1318 can be released or unlocked (e.g., by pressing) to allow detachment of the device from the cradle 1310. The attachment system 1300 is configured to be attached to structures of various thickness. For example, the attachment system 1300 can be attached to a thin pole or tube as well as to a thick bedrail.

FIG. 13B illustrates an exploded view of the attachment system 1300 according to some embodiments. As is illustrated in FIG. 13B, the cradle 1310 includes a cradle housing 1312 and first lead screw 1314. The screw 1314 can be positioned insider the cradle housing 1312 and can be allowed to freely rotate inside the housing 1312. The cradle 1310 also comprises a left closure 1316 and right closure 1318 for attaching the cradle to the device (e.g., NPWT apparatus 230). The cradle 1310 further includes non the device-facing side a bumper 1320, which can be made out of rubber. The cradle 1310 also includes a pin 1322, which can be a coiled spring, screws 1324, and washers 1326 for attaching the closures 1316 and 1318 to the cradle. The clamp 1330 includes a first clamp arm 1331, second clamp arm 1332, a second screw 1335 to which a handle 1334 is attached, and a cap 1336 configured to be attached to the handle 1334. Pads 1338, such as a rubber pads, are configured to be attached to the first and second clamp arms 1331 and 1332. The second clamp arm 1332 includes an opening 1333 for placing the second screw 1335. The opening 1333 can include interior threading configured to engage with the threading of the second screw 1335. The second screw 1335 can include a hollow interior tunnel portion for engaging with the first screw 1314. The interior portion of the second screw 1335 can include threading configured to engage with the threading of the first screw 1314. In other embodiments, the second screw 1335 is attached to the second clamp arm 1332 using any other suitable attachment.

In some embodiments, in operation the cradle 1310 is attached to the device (e.g., apparatus 230). Rear of the device 230 can rest against the bumper 1320 when the cradle 1310 is attached. In some embodiments, recess(es) 1302 and/or closure(s) 1318 can be configured such that the cradle 1310 can be attached to the device only in a configuration in which the rear of the device rests against the bumper 1320. Attaching the device incorrectly, such as backwards so that the front of the deice rests against the bumper 1320, is not be allowed. The attachment system 1300 attaches to a structure, such as pole, rail, or the like, by turning the knob 1334 so that a portion of the structure is placed in between the first and second clamp arms 1331 and 1332. This is accomplished by action of the first and second screws 1314 and 1335 moving the second clamp arm 1332 to a desired distance from the first clamp arm 1331 (which is stationary). The knob 1334 is then turned to securely mount the device onto the structure. Dismounting is performed by turning to knob 1334 to remove the device from the structure. The cradle can be disconnected from the device by unlatching or unlocking the closure(s) 1318.

FIG. 13C illustrates an attachment system 2100 according to some embodiments. The attachment system 2100 can be used to mount to a structure any suitable device, such as a medical treatment device, including but not limited to NPWT apparatus or device 230. The attachment system 210 includes a cradle 2110, first clamp arm 2140, and second clamp arm 2150. The first clamp arm 2140 is attached or connected to the cradle 2110, and thereby remains stationary when the attachment is in operation. The second clamp arm 2150 moves with respect to the first clamp arm 2140, which varies the gap between the first and second cradle arms. Structure is secured between the first and second cradle arms 2140 and 2150. The structure can be thin, such as pole 2190', or thick, such as pole or rail 2190.

The attachment system 2100 includes first and second screws 2160 and 2170. Second screw 2170 is connected to a knob 2134. In operation, turning the knob 2170 causes the first and second screws 2160 and 2170 to cause the second clamp arm 2150 to move linearly in smooth and uniform manner with respect to the first clamp arm 2140. The second clamp arm 2150 moves from a clamped position in which the device is mounted to the structure and an unclamped position in which the device is not mounted to the structure. The second clamp arm 2150 also moves between a fully closed position in which the first and second clamp arms 2140 and 2150 are not separated or substantially not separated (e.g., are in contact with each other) and a fully open position in which the first and second clamp arms 2140 and 2150 are separated by a maximum distance from each other. This maximum distance places an upper limit on the maximum thickness of the structure to which the device can be attached using the attachment system 2100. Movement of the second clamp arm 2150 is illustrated in views 2100A, 2100B, and 2100C. In view 2100A, the first and second clamp arms 2140 and 2150 are located close to each other. In views 2100B and 2100C, the gap between the first and second clamp arms 2140 and 2150 widens. That is, the second clamp arm 2150 is moved farther away from the first clamp arm 2140, such as by turning the knob 2134.

The first screw 2160 can be located within or substantially within a housing of the cradle, and the first screw 2160 can be allowed to freely rotate inside the housing. The first screw 2160 has a thread with a lead (distance along the screw's axis that is covered by ne complete rotation of the screw) and a pitch (distance from the crest of one thread to the next). In one embodiment, the lead and pitch of the first screw are the same. The second screw 2170 has a thread with a lead and a pitch, which may be the same in one embodiment. The threads of the first and second screws 2160 and 2170 can be square, Acme, buttress, and the like. In some embodiments, the first and second screws 2160 and 2170 have threads of the same type, such as Acme threads. In some embodiments, the first and second screws 2160 and 2170 have threads of different type. The second screw 2170 can be connected or attached to the second clamp arm 2150, such as via an opening 1333 illustrated in FIG. 13B.

In some embodiments, the thread of the first screw 2160 and the thread of the second screw 2170 can be oriented in opposite directions (or opposite pitch). For example, the thread of the first screw 2160 can be right-handed while the thread of the second screw 2170 can be left-handed and vice versa. When first and second screws 2160 and 2170 with threads oriented in opposite directions are engaged with one another, a single rotation of the handle 2134 provides double or substantially double linear movement as opposed to using a single screw. The first and second screws 2160 and 2170 can be engaged by the second screw 2170 having a hollow opening configured to receive at least a portion of the first screw 2160. As is illustrated in FIG. 13B, the hollow opening can have interior thread configured to be engaged with the thread of the first screw 2160. In some embodiments, the first screw 2160 can include a hollow opening configured to receive at least a part of the second screw 2170. In other embodiments, first and second screws 2160 and 2170 are engaged in any suitable way, such as via using a nut.

In some embodiments, such dual-screw arrangement allows for quick mounting to structures of various thickness and while maintaining good control over the tightness (or security) of the attachment to the structure. For example, between about 4 and 10 rotations of the handle are needed to change the configuration of first and second clamp arms 2140 and 2150 from fully closed position to fully open position and vice versa. In some embodiments, a nominal clamping force of the attachment to the structure is approximately 20-30 pound force (lbf) is achieved. The maximum clamping force before part failure can be approximately 100 lbf. Torque required to achieve nominal clamping can be less than about 20 inch pound force (inlb). In other embodiments, other suitable clamping forces, maximum clamping forces, and nominal clamping torques can be used. The dual-screw arrangement can be more durable and cheaper than alternative arrangements, such as using a single screw with steep pitch thread, using a single screw with multi-start threads, and the like.

In some embodiments, the first and second screws 2160 and 2170 are power screws configured to transform rotary motion into linear motion. Power screws are described in a document titled "Power Screws," which is accessible at http://www.roymech.co.uk/Useful_Tables/Cams_Springs/Power_Screws.html. Efficiency of power screws is described in a document titled "Power Screw Equations," which is accessible at http://www.roymech.co.uk/Useful_Tables/Cams_Springs/Power_Screws_1.html. Power screw strength analysis is provided in a document titled "Strength Considerations for Power Screws," which is accessible at http://www.roymech.co.uk/Useful_Tables/Cams_Springs/Power_Screws_2.html. Each of these documents is incorporated by reference in their entirety.

In some embodiments, the cradle 2110, first and second clamp arms 2140 and 2150, and knob 2134 are made out of plastic material, thereby making the attachment system 2100 lightweight. In some embodiments, one or more of other attachment parts described herein is also made of plastic material. In some embodiments, the first clamp arm is not configured to be stationary while the second clamp arm is configured to be stationary. In some embodiments, the first and second clamp arms are non-stationary. In some embodiments, handle is not used.

Figure 13D:
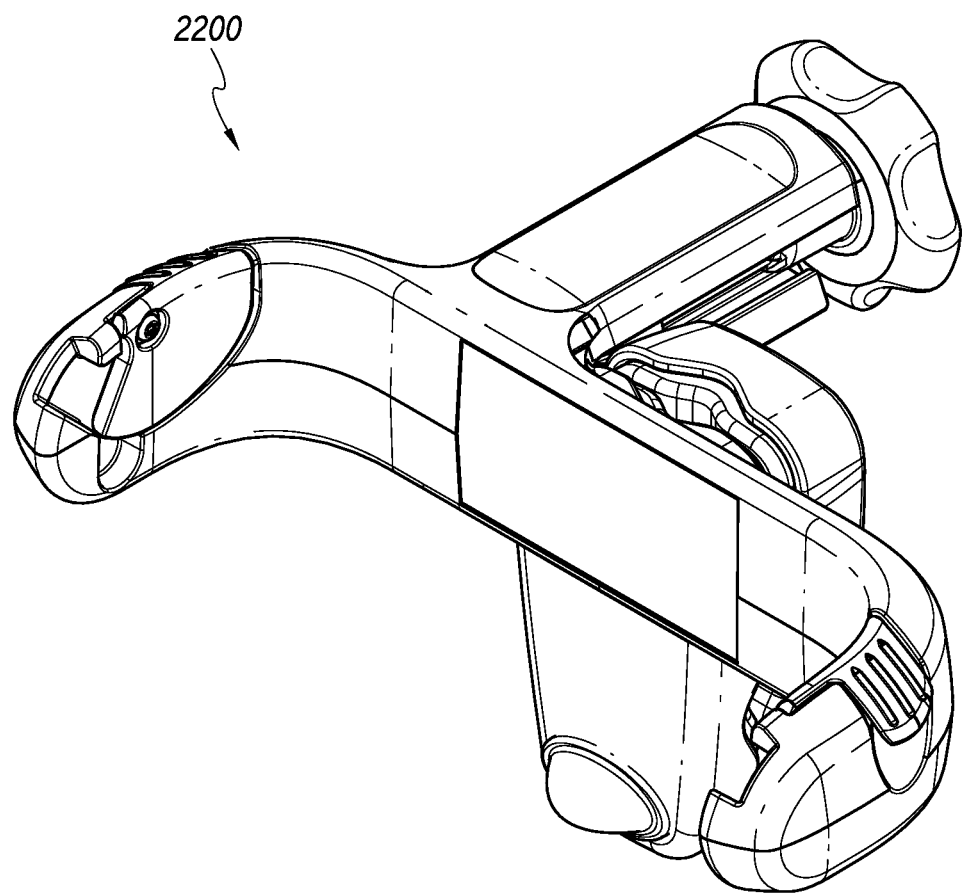
FIGS. 13D-13J illustrate an attachment system according to some embodiments.
Figure 13E:
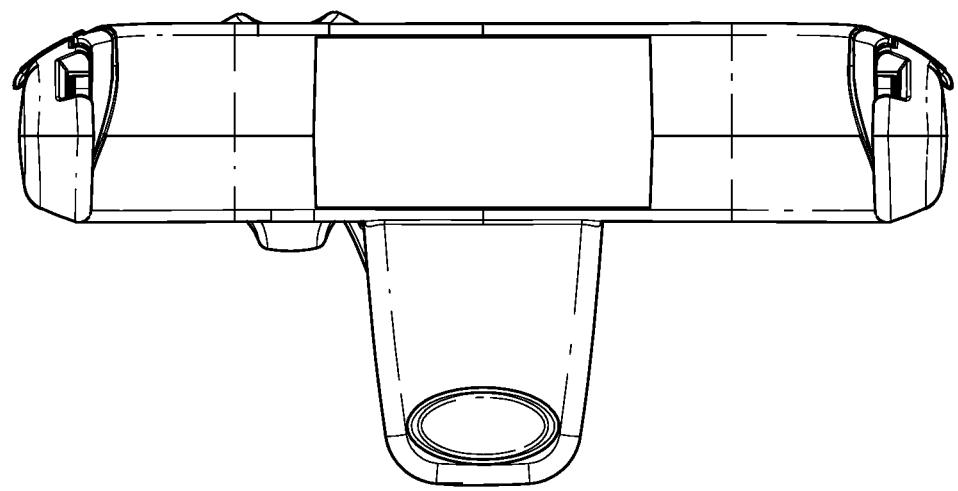
Figure 13F:
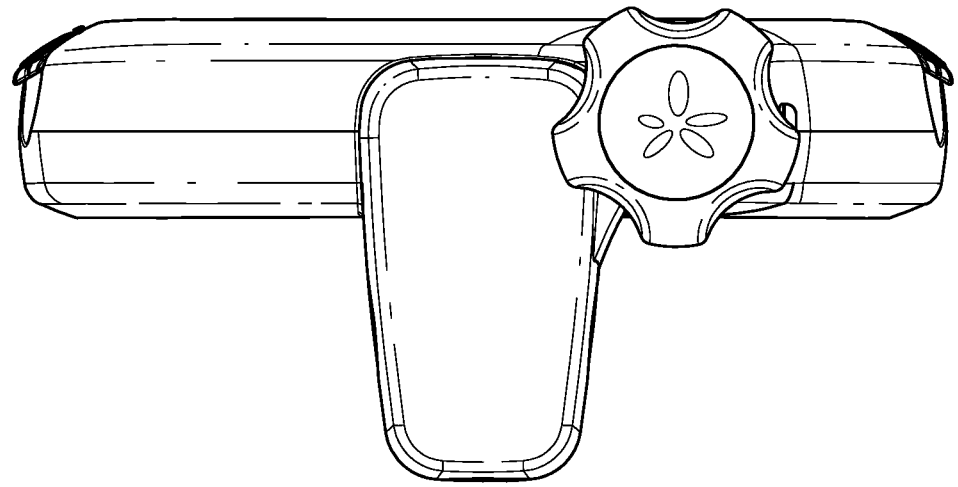
Figure 13G:
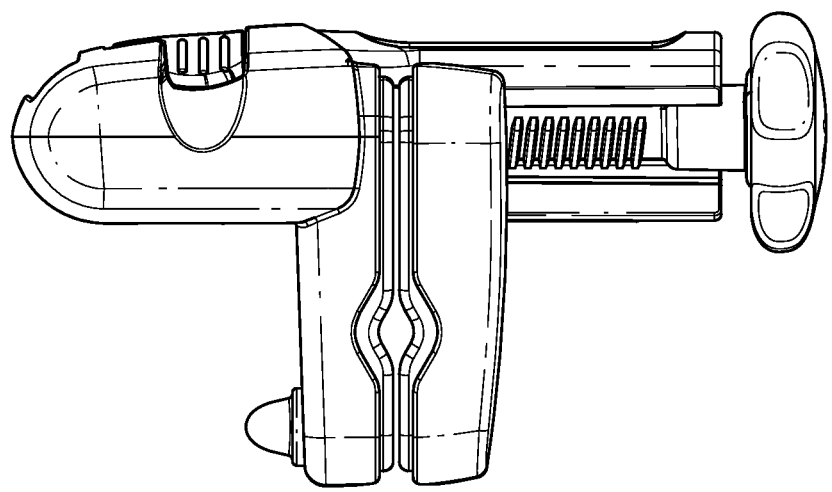
Figure 13H:
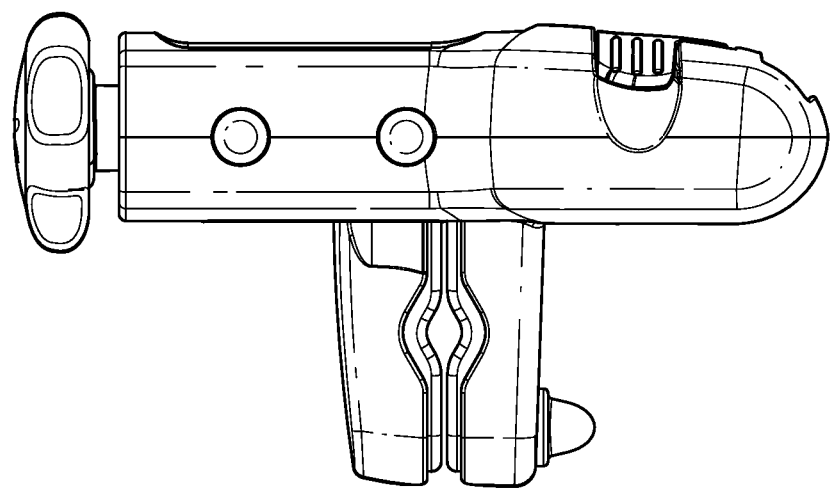
Figure 13I:
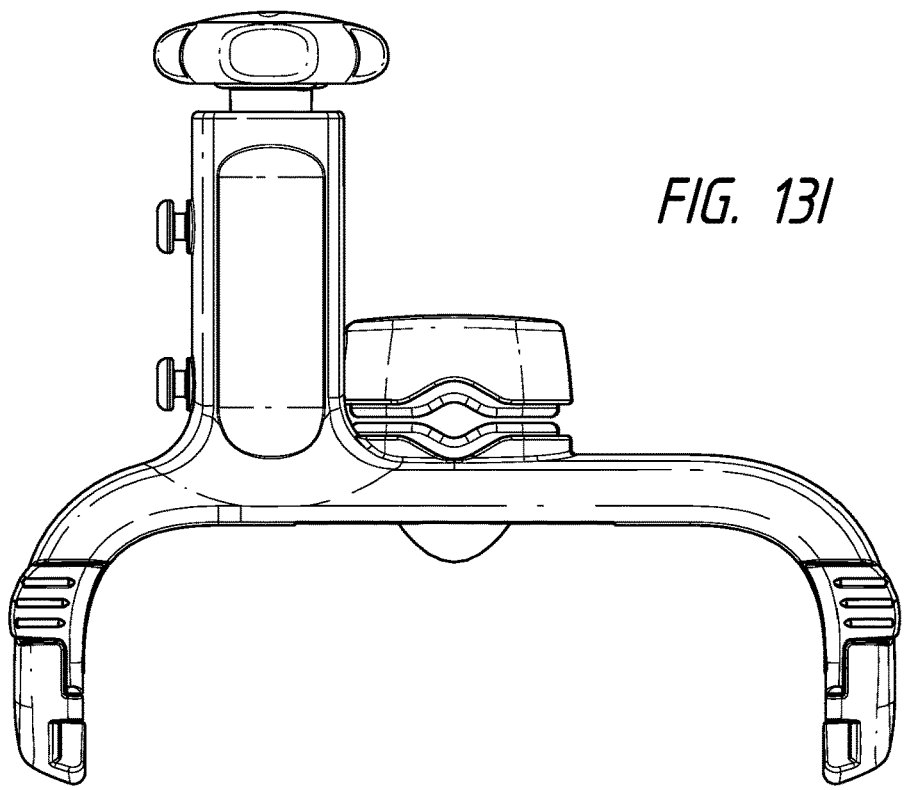
Figure 13J:
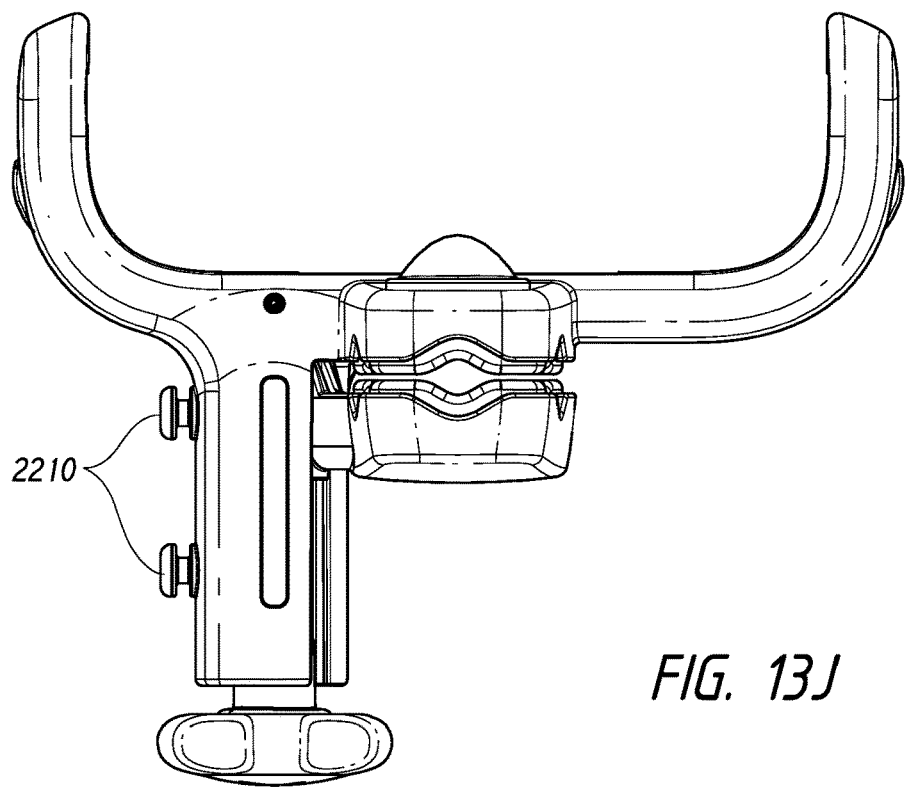

FIGS. 13D-13J illustrate an attachment system according to some embodiments. The attachment system 2200 can be used to mount to a structure any suitable device, such as a medical treatment device, including but not limited to NPWT apparatus or device. FIG. 13D illustrates a perspective view of the attachment system in a closed or almost closed position. FIG. 13E illustrates a front view of the attachment system illustrated in FIG. 13D. FIG. 13F illustrates a rear view of the attachment system illustrated in FIG. 13D. FIG. 13G illustrates a right side view of the attachment system illustrated in FIG. 13D. FIG. 13H illustrates a left side view of the attachment system illustrated in FIG. 13D. FIG. 13I illustrates a top view of the attachment system illustrated in FIG. 13D. FIG. 13J illustrates a bottom view of the attachment system illustrated in FIG. 13D. As is illustrated, the attachment system 2200 includes one or more protrusions or projections 2210 which can be used for securing one or more items, such as carry straps, carrying cases or bags, etc.

FIG. 13K illustrates attachment systems in operation according to some embodiments. As is illustrated in 2300A, an apparatus (e.g., NPWT apparatus 230) is mounted to an IV pole using an attachment system according to some embodiments. As is illustrated in 2300B, the apparatus is mounted to a bed rail using an attachment system according to some embodiments. Attachment systems illustrated in FIG. 13K may be selected from any one of attachment systems 1300, 2100, or 2200.

Electronics and Software

Figure 14:
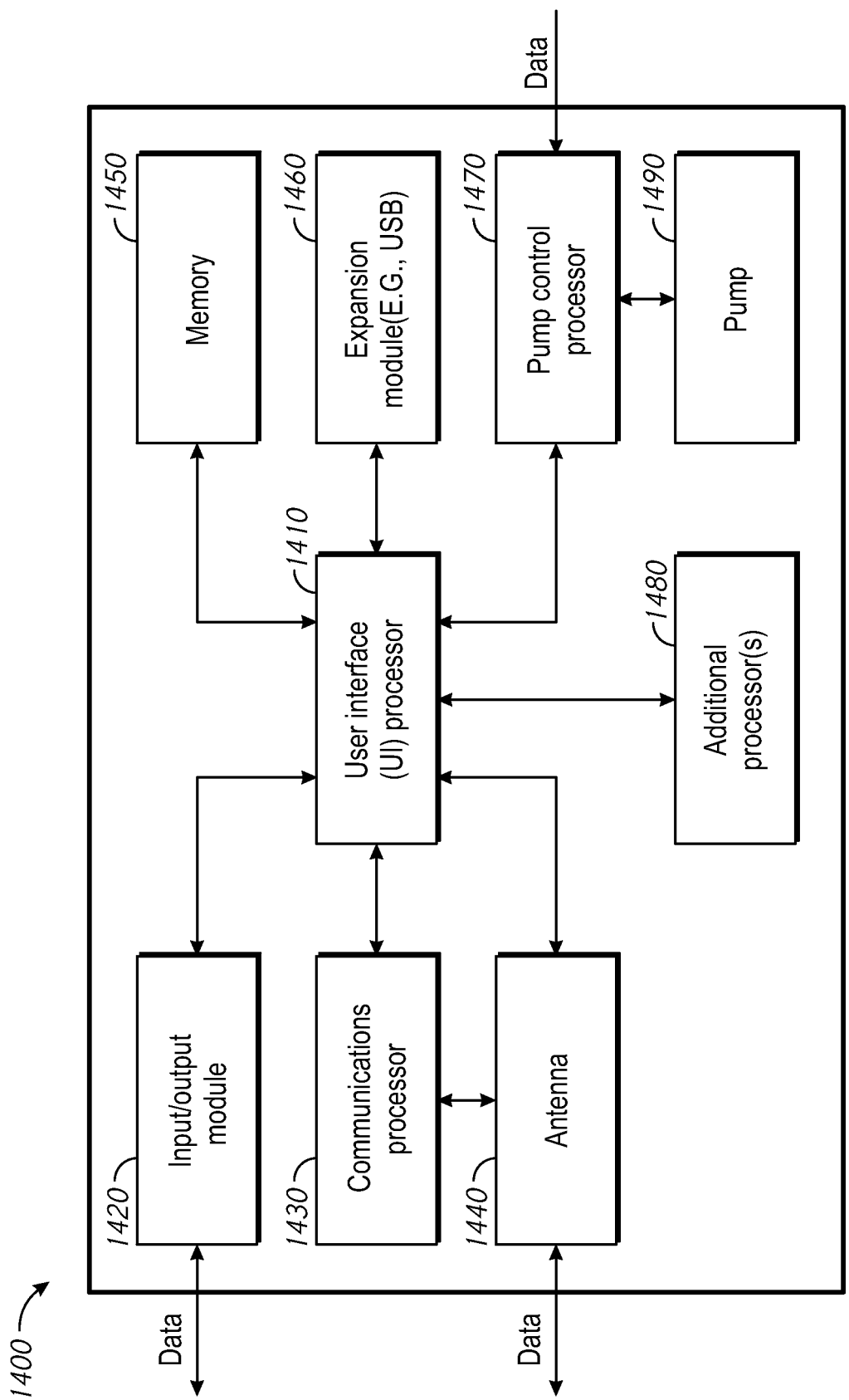
FIG. 14 illustrates an electrical component schematic of a pump assembly according to some embodiments.

FIG. 14 illustrates an electrical component schematic 1400 of a pump assembly according to some embodiments. Electrical components can operate to accept user input, provide output to the user, operate the pump assembly and the TNP system, provide network connectivity, and so on. Electrical components can be mounted on one or more PCBs, such as the control PCB 260, peripherals PCB 262, and/or power supply PCB 264. As is illustrated, the pump assembly 230 can include multiple processors. It may be advantageous to utilize multiple processors in order to allocate or assign various tasks to different processors. In some embodiments, a first processor can be responsible for user activity and a second processor can be responsible for controlling the pump. This way, the activity of controlling the pump, which may necessitate a higher level of responsiveness (corresponding to higher risk level), can be off-loaded to a dedicated processor and, thereby, will not be interrupted by user interface tasks, which may take longer to complete because of interactions with the user.

The pump assembly 230 can comprise a user interface processor or controller 1410 configured to operate one or more components for accepting user input and providing output to the user, such as the display 206, buttons 212, etc. Input to the pump assembly 230 and output from the pump assembly can controlled by an input/output (I/O) module 1420. For example, the I/O module can receive data from one or more ports, such as serial, parallel, hybrid ports, and the like. The processor 1410 also receives data from and provides data to one or more expansion modules 1460, such as one or more USB ports, SD ports, Compact Disc (CD) drives, DVD drives, FireWire ports, Thunderbolt ports, PCI Express ports, and the like. The processor 1410, along with other controllers or processors, stores data in one or more memory modules 1450, which can be internal and/or external to the processor 1410. Any suitable type of memory can be used, including volatile and/or non-volatile memory, such as RAM, ROM, magnetic memory, solid-state memory, Magnetoresistive random-access memory (MRAM), and the like.

In some embodiments, the processor 1410 can be a general purpose controller, such as a low-power processor. In other embodiments, the processor 1410 can be an application specific processor. In some embodiments, the processor 1410 can be configured as a "central" processor in the electronic architecture of the pump assembly 230, and the processor 1410 can coordinate the activity of other processors, such as a pump control processor 1470, communications processor 1430, and one or more additional processors 1480. The processor 1410 can run a suitable operating system, such as a Linux, Windows CE, VxWorks, etc.

The pump control processor 1470 can be configured to control the operation of a negative pressure pump 1490. The pump 1490 can be a suitable pump, such as a diaphragm pump, peristaltic pump, rotary pump, rotary vane pump, scroll pump, screw pump, liquid ring pump, diaphragm pump operated by a piezoelectric transducer, voice coil pump, and the like. In some embodiments, the pump control processor 1470 can measure pressure in a fluid flow path, using data received from one or more pressure sensors, calculate the rate of fluid flow, and control the pump. In some embodiments, the pump control processor 1470 controls the pump motor so that a desired level of negative pressure in achieved in the wound cavity 110. The desired level of negative pressure can be pressure set or selected by the user. In various embodiments, the pump control processor 1470 controls the pump (e.g., pump motor) using pulse-width modulation (PWM). A control signal for driving the pump can be a 0-100% duty cycle PWM signal. The pump control processor 1470 can perform flow rate calculations and detect alarms. The pump control processor 1470 can communicate information to the processor 1410. The pump control processor 1470 can include internal memory and/or can utilize memory 1450. The pump control processor 1470 can be a low-power processor.

A communications processor 1430 can be configured to provide wired and/or wireless connectivity. The communications processor 1430 can utilize one or more antennas 1440 (such as antenna 276) for sending and receiving data. In some embodiments, the communications processor 1430 can provide one or more of the following types of connections: Global Positioning System (GPS) technology, cellular connectivity (e.g., 2G, 3G, LTE, 4G), WiFi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software and/or firmware, and the like. In some embodiments, the communications processor 1430 can provide dual GPS/cellular functionality. Cellular functionality can, for example, be 3G functionality. In such cases, if the GPS module is not be able to establish satellite connection due to various factors including atmospheric conditions, building or terrain interference, satellite geometry, and so on, the device location can be determined using the 3G network connection, such as by using cell identification, triangulation, forward link timing, and the like. In some embodiments, the pump assembly 230 can include a SIM card, and SIM-based positional information can be obtained.

The communications processor 1430 can communicate information to the processor 1410. The communications processor 1430 can include internal memory and/or can utilize memory 1450. The communications processor 1430 can be a low-power processor.

In some embodiments, the pump assembly 230 can store data illustrated in Table 1. This data can be stored, for example, in memory 1450. In various embodiments, different or additional data can be stored by the pump assembly 230. In some embodiments, location information can be acquired by GPS or any other suitable method, such as cellular triangulation, cell identification forward link timing, and the like.

TABLE 1

Example Data Stored by the Pump Assembly

| Category | Item | Type | Source |
|---|---|---|---|
| GPS | Location | Latitude, Longitude, Altitude | Acquired from GPS |
|  | Timestamp Location Acquired | Timestamp |  |
| Therapy | Total time therapy ON since device activation | Minutes | Calculated on device |
|  | Total time therapy ON since last maintenance reset | Minutes | based on user control |
|  | Device Placement; accumulated daily hours starting from first Therapy ON after last maintenance reset, stopping at last Therapy OFF before returning for Maintenance and maintenance reset. (Includes both THERAPY ON and THERAPY OFF hours) | Minutes |  |
| Device | Serial Number | Alphanumeric | Set by Pump Utility |
|  | Controller Firmware Version | Alphanumeric | Unique version identifier, hard coded in firmware |
| Events | Device Event Log (See Table 3 for example) | List of Events (See Table 2) | Generated in response to various user actions and detected events |

In certain embodiments, the pump assembly 230 can track and log therapy and other operational data. Such data can be stored, for example, in the memory 1450. In some embodiments, the pump assembly 230 can store log data illustrated in Table 2. Table 3 illustrates an example event log according to some embodiments. One or more such event logs can be stored by the pump assembly 230. As is illustrated, the event log can include timestamps indicating the time of occurrence. In some embodiments, additional and/or alternative data can be logged.

TABLE 2

Example Data Tracked by the Pump Assembly

| Category | ID | Type | Data Content | Notes |
|---|---|---|---|---|
| Device | 0 | Startup (Created DB) |  | First time, out-of-the-box. |
|  | 1 | Startup (Resumed DB) |  | Subsequent power-ups. |
|  | 2 | Startup (Corrupt DB, Recreated) |  | Corrupt configuration was detected. The database was deleted and recreated, and next run was in out-of-the-box mode. |
|  | 3 | Shutdown (Signaled) |  | Normal shutdown, handled/registered by software. |
|  | 4 | Shutdown (Inferred) |  | Unexpected shutdown; on next power-up, last active time registered as shutdown event. |
| Therapy | 5 | Start Delivery (Continuous) | modes, setpoints | Modes are Y-connect status, and intensity. |
|  | 6 | Start Delivery (Intermittent) | modes, setpoints | Modes are Y-connect status, and intensity. |
|  | 7 | Stop Delivery |  |  |
|  | 8 | Set Therapy Pressure Setpoint | mmHg | This and other therapy adjustment events are only recorded while therapy is being delivered. |
|  | 9 | Set Standby Pressure Setpoint | mmHg |  |
|  | 10 | Set Intermittent Therapy Duration | setting (30 s, 60 s, etc) |  |
|  | 11 | Set Intermittent Standby Duration | setting (30 s, 60 s, etc) |  |
|  | 12 | SetMode | cont/intermittent |  |
|  | 13 | Set Intensity | low/med/high |  |
|  | 14 | Set Y Connect | yes/no |  |
| Alarm | 15 | Over Vacuum | high mmHg |  |
|  | 16 | High Vacuum | high deviation mmHg |  |
|  | 17 | Blocked Full Canister | low airflow lpm |  |
|  | 18 | High Flow Leak | high airflow lpm |  |
|  | 19 | Low Vacuum | low mmHg |  |
|  | 20 | Battery Failure |  |  |
|  | 21 | Critical Battery |  |  |
|  | 22 | Low Battery |  |  |
|  | 23 | Inactivity |  |  |
| Maintenance | 24 | Maintenance Reset |  |  |
|  | 25 | Reset to Defaults |  |  |
|  | 26 | Software/Device Warning | Warning code | Any detected, minor unexpected software behavior will be logged as an event |
|  | 27 | Software/Device Fault | Fault code | Any detected, severe unexpected software behavior will be logged as an event |

TABLE 3

Example Event Log

| Timestamp | Type ID | Type Description | Data |
|---|---|---|---|
| 1:23:45 4/2/2012 (UTC-12) | 0 | Startup (Created DB) | |
| 1:29:23 4/2/2012 (UTC-12) | 15 | Set Intensity | medium |
| 1:29:43 4/2/2012 (UTC-12) | 10 | Set Therapy Pressure Setpoint | 120 mmHg |
| 1:31:02 4/2/2012 (UTC-12) | 7 | Start Delivery (Continuous) | 120 mmHg continuous, medium intensity, no Y connect |
| 1:44:20 4/2/2012 (UTC-12) | 20 | High Flow Leak | 4 lpm |
| 1:44:24 4/2/2012 (UTC-12) | 9 | Stop Delivery | |

In some embodiments, using the connectivity provided by the communications processor 1430, the device can upload any of the data stored, maintained, and/or tracked by the pump assembly 230. In some embodiments, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. In certain embodiments, the device can provide Internet browsing functionality using one or more browser programs, mail programs, application software (e.g., apps), etc. In various embodiments, additional processors 1480, such as processor for controlling the display 206, can be utilized.

Figure 15:
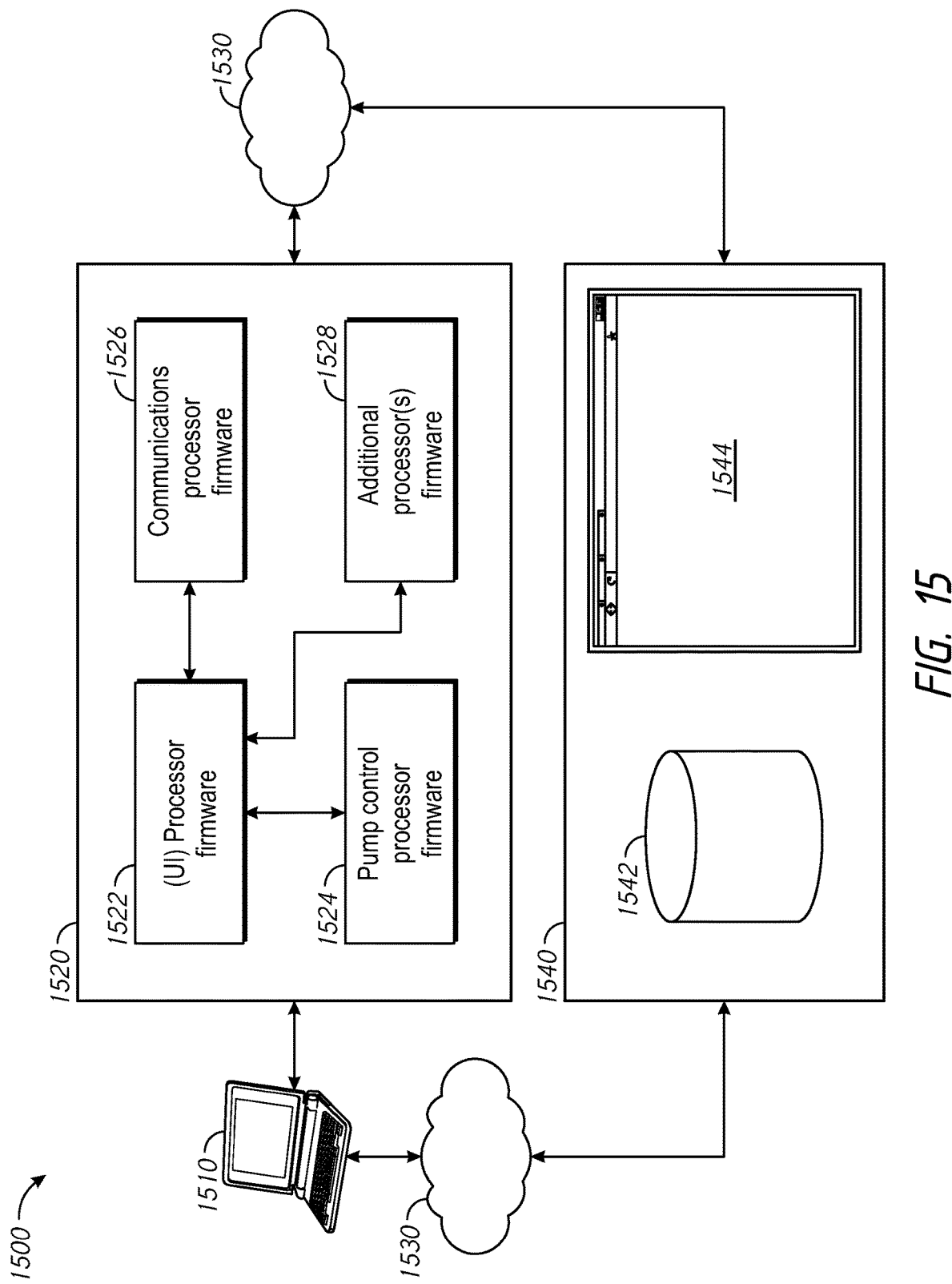
FIG. 15 illustrates a firmware and/or software diagram according to some embodiments.

FIG. 15 illustrates a firmware and/or software diagram 1500 according to some embodiments. A pump assembly 1520 includes a user interface processor firmware and/or software 1522, which can be executed by the user interface processor 1410, pump control processor firmware and/or software, which can be executed by the pump control processor 1470, communications processor firmware and/or software 1526, which can be executed by the communications processor 1430, and additional processor(s) firmware and/or software, which can be executed by one or more additional processors 1480. The pump assembly 1520 can be connected to a computer 1510, which can be a laptop, desktop, tablet, smartphone, and the like. A wired or wireless connection can be utilized to connect the computer 1510 to the pump assembly 1520. In some embodiments, a USB connection is used. The connection between the computer 1510 and the pump assembly 1520 can be used for various activities, such as pump assembly location tracking, asset tracking, compliance monitoring, selection, uploading of logs, alarms, and other operational data, and adjustment of therapy settings, upgrading of software and/or firmware, and the like. The pump assembly 1520 and computer 1510 can communicate with a remote computer or server 1540 via the cloud 1530. The remote computer 1540 can include a data storage module 1542 and a web interface 1544 for accessing the remote computer.

The connection between the computer 1510 and pump assembly 1520 can be utilized to perform one or more of the following: initialization and programming of the pump assembly 1520, firmware and/or software upgrades, maintenance and troubleshooting, selecting and adjusting therapy parameters, and the like. In some embodiments, the computer 1510 can execute an application program for communicating the pump assembly 1520.

The pump assembly 1520 can upload various data to the remote computer 1540 via the cloud 1530. In some embodiments, the pump assembly 1520 can upload data to one or more remote computers 1540. As explained above, upload data can include activity log(s), alarm log(s), therapy duration information, total therapy time, lifetime therapy information, device information, device location information, patient information, etc. In addition, the pump assembly 1520 can receive and process commands received from the cloud 1530.

Remote Interface

Figure 16A:
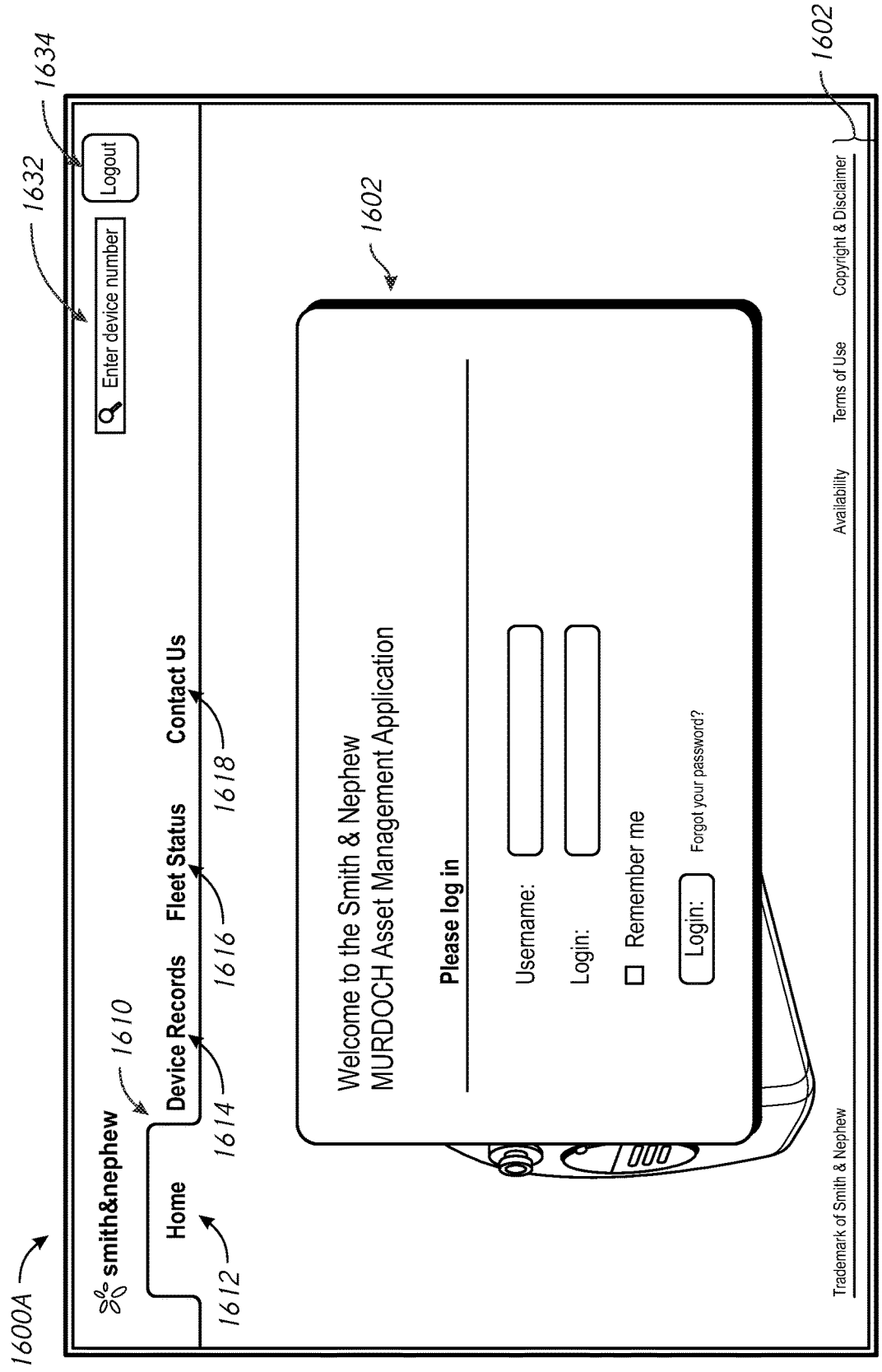
FIGS. 16A-16S illustrate remote interface screens according to some embodiments
Figure 16B:
Figure 16C:
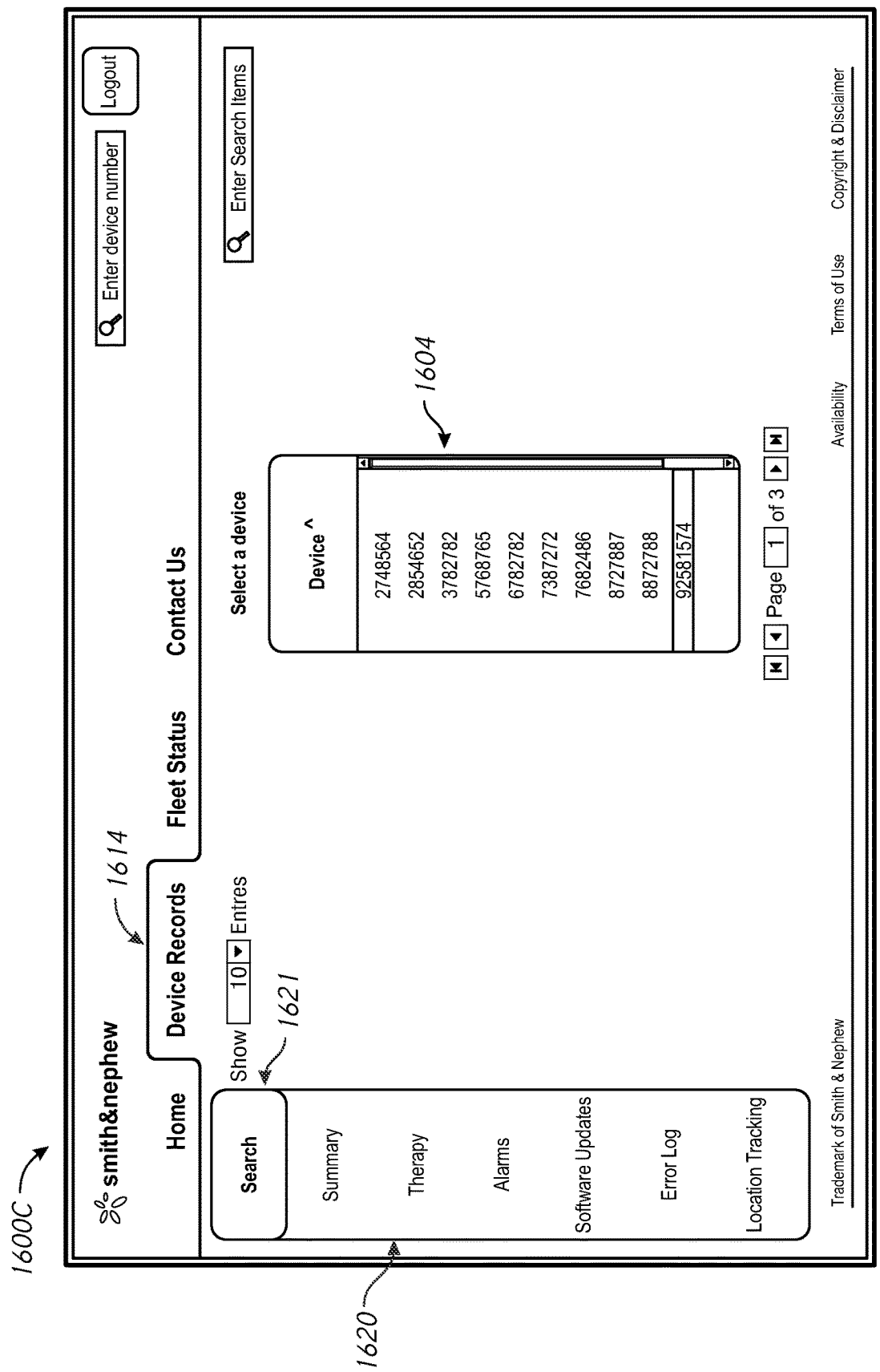
Figure 16E:
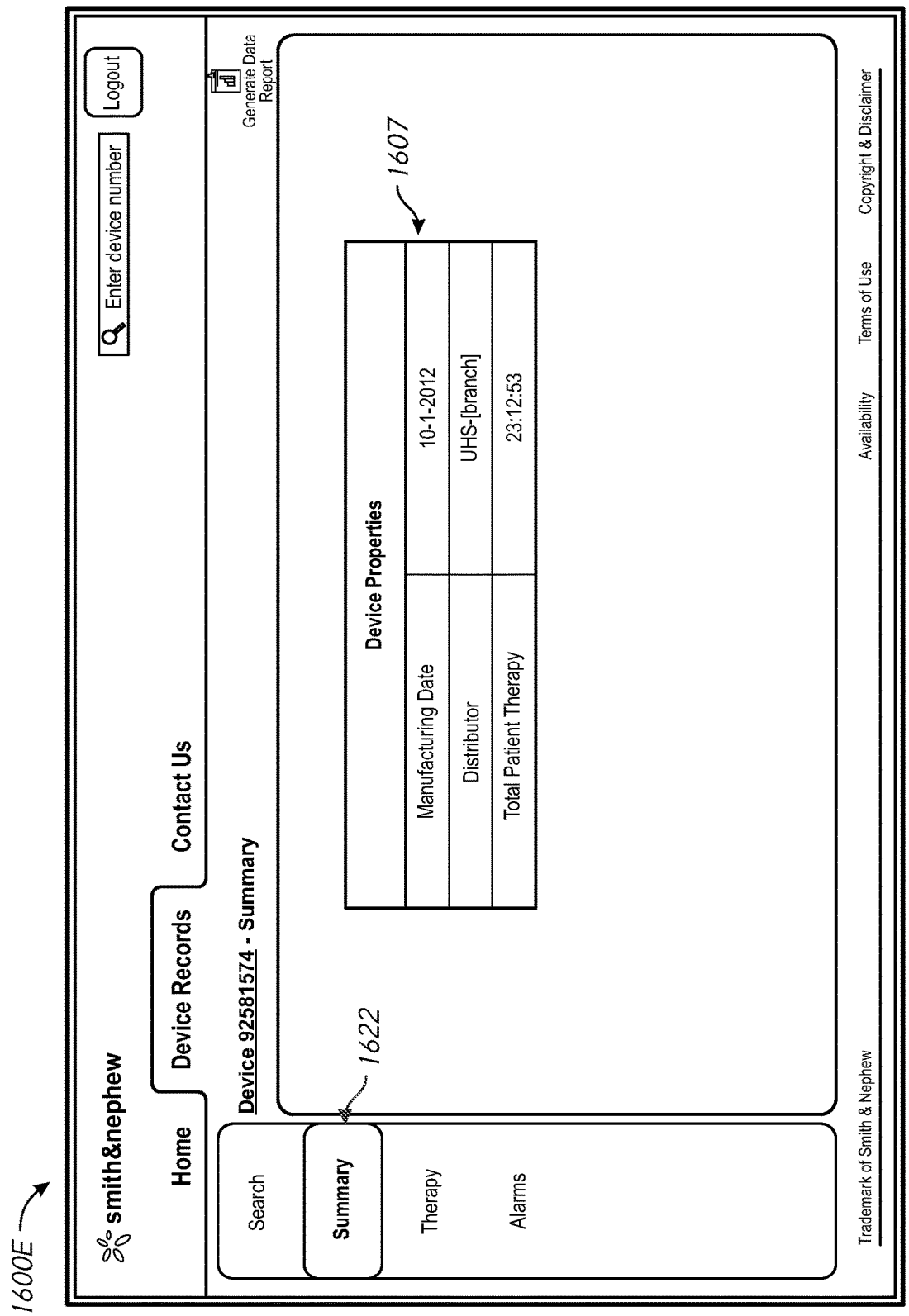
Figure 16F:
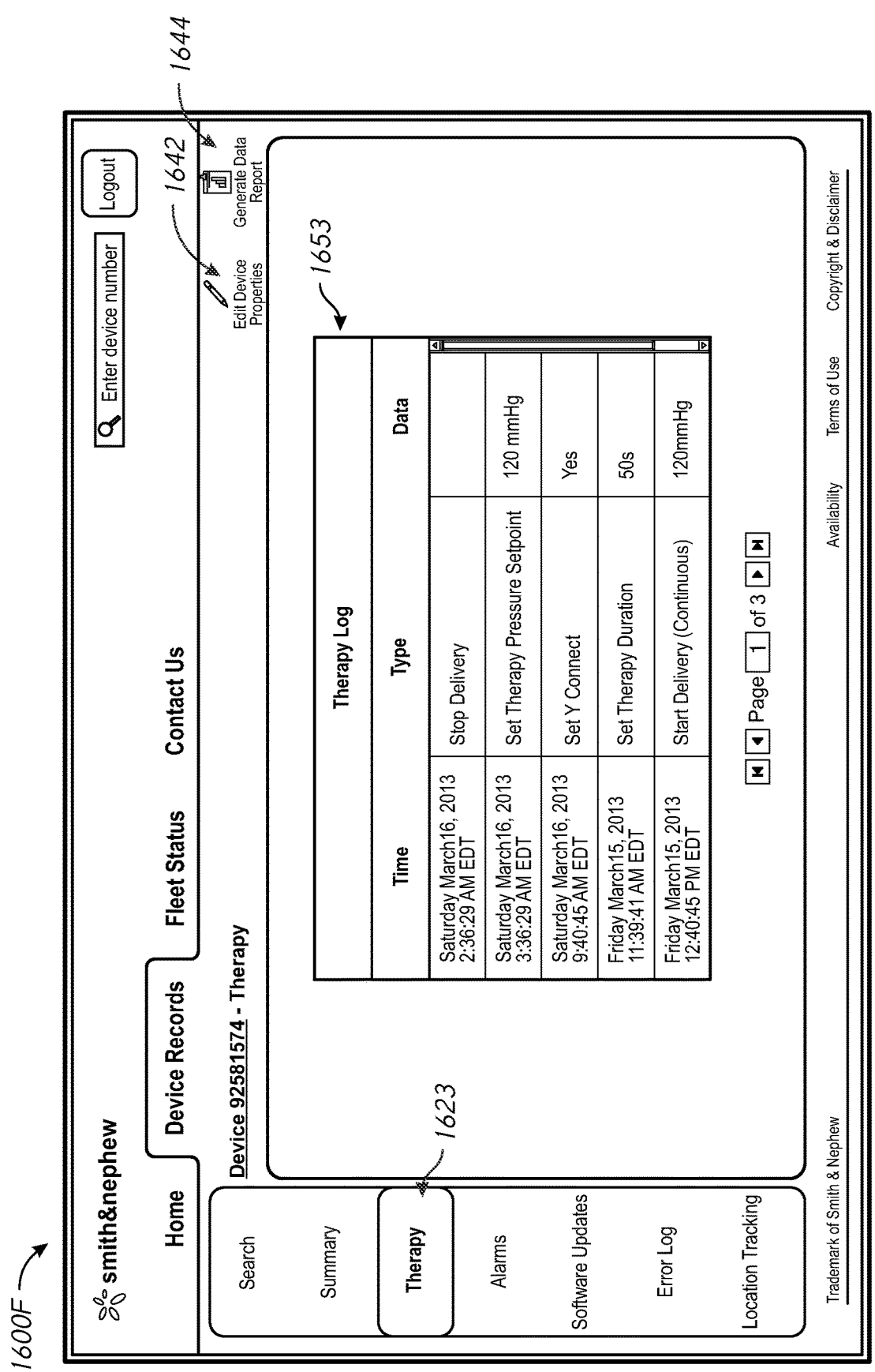
Figure 16G:
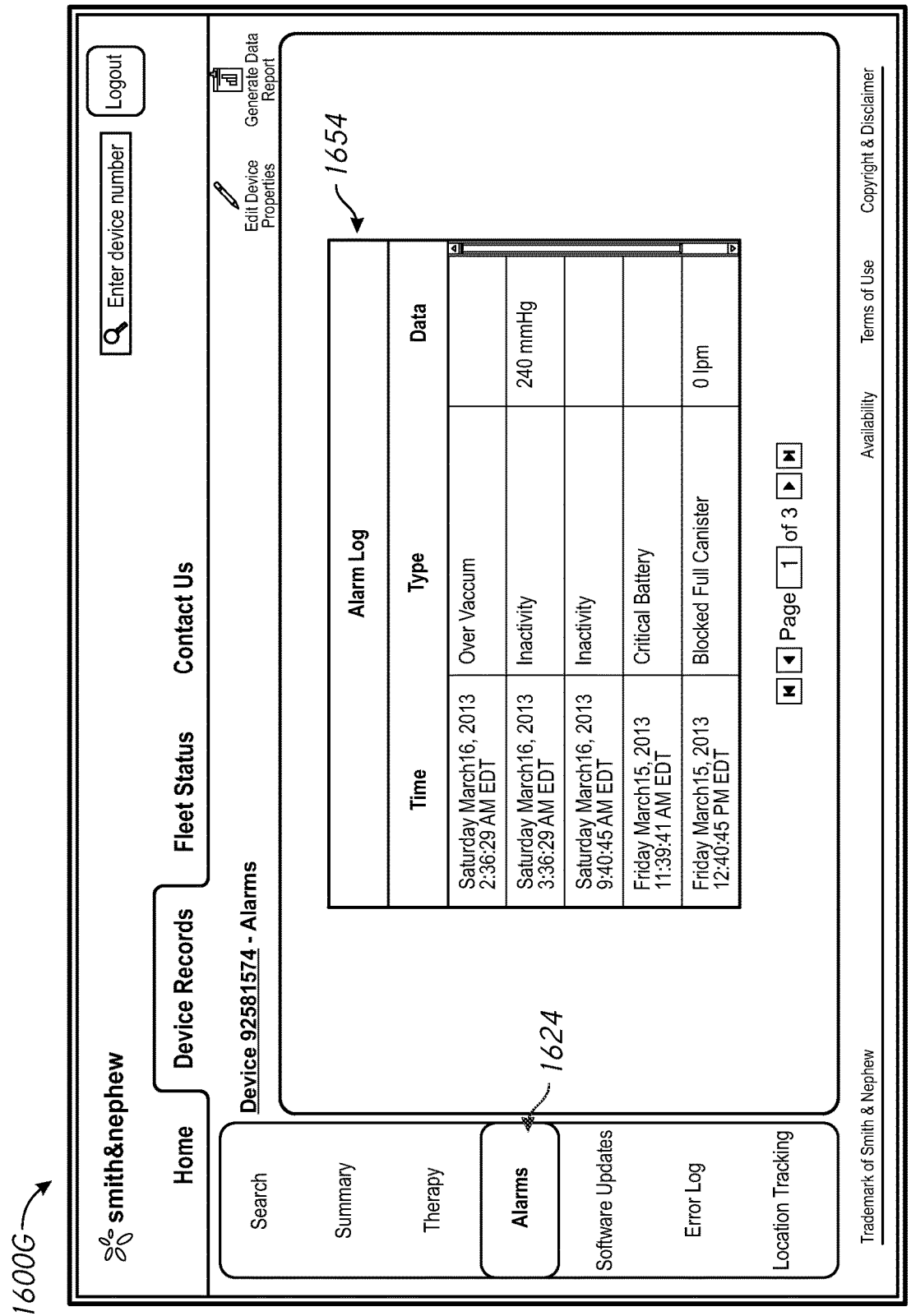
Figure 16H:
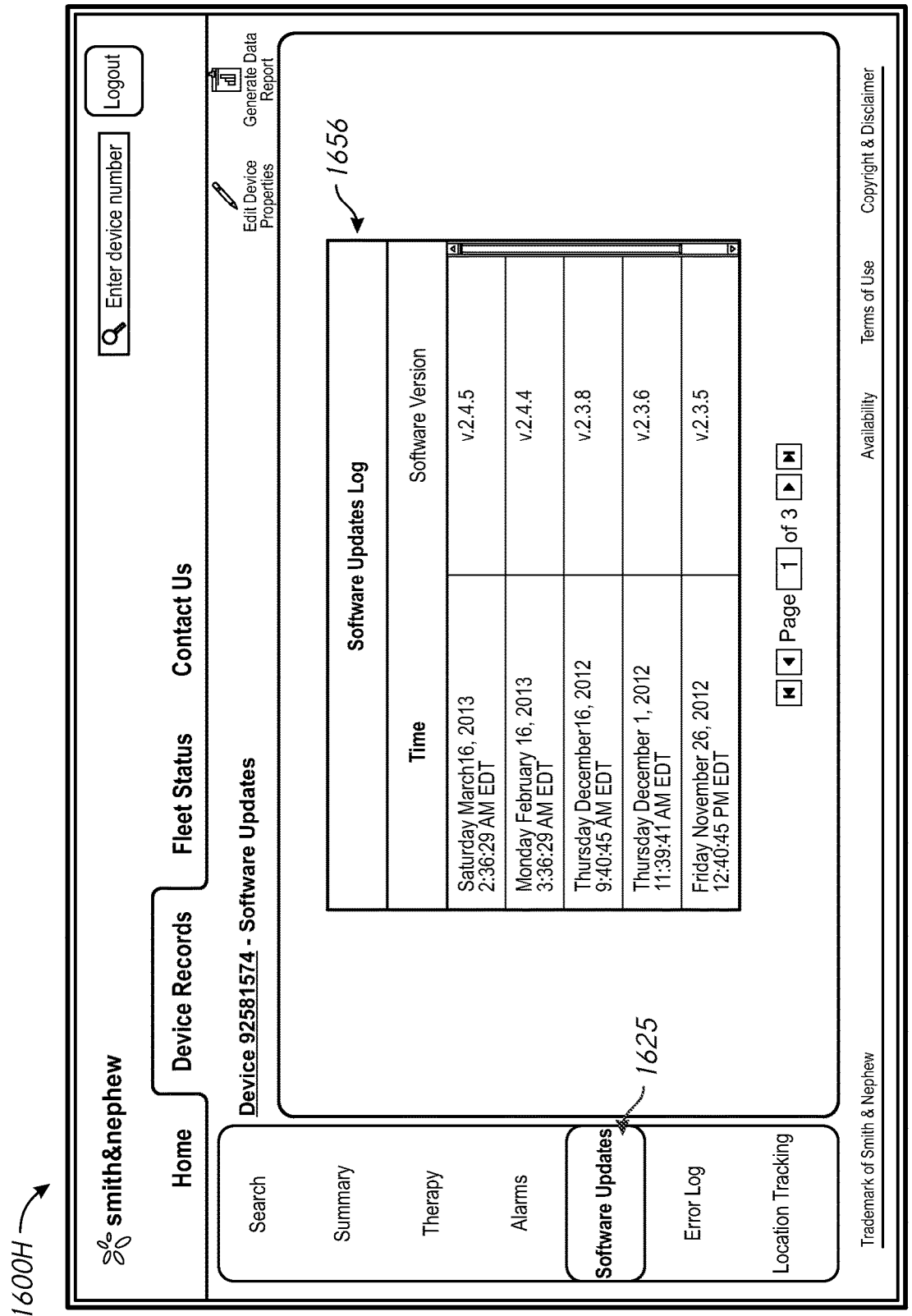
Figure 16I:
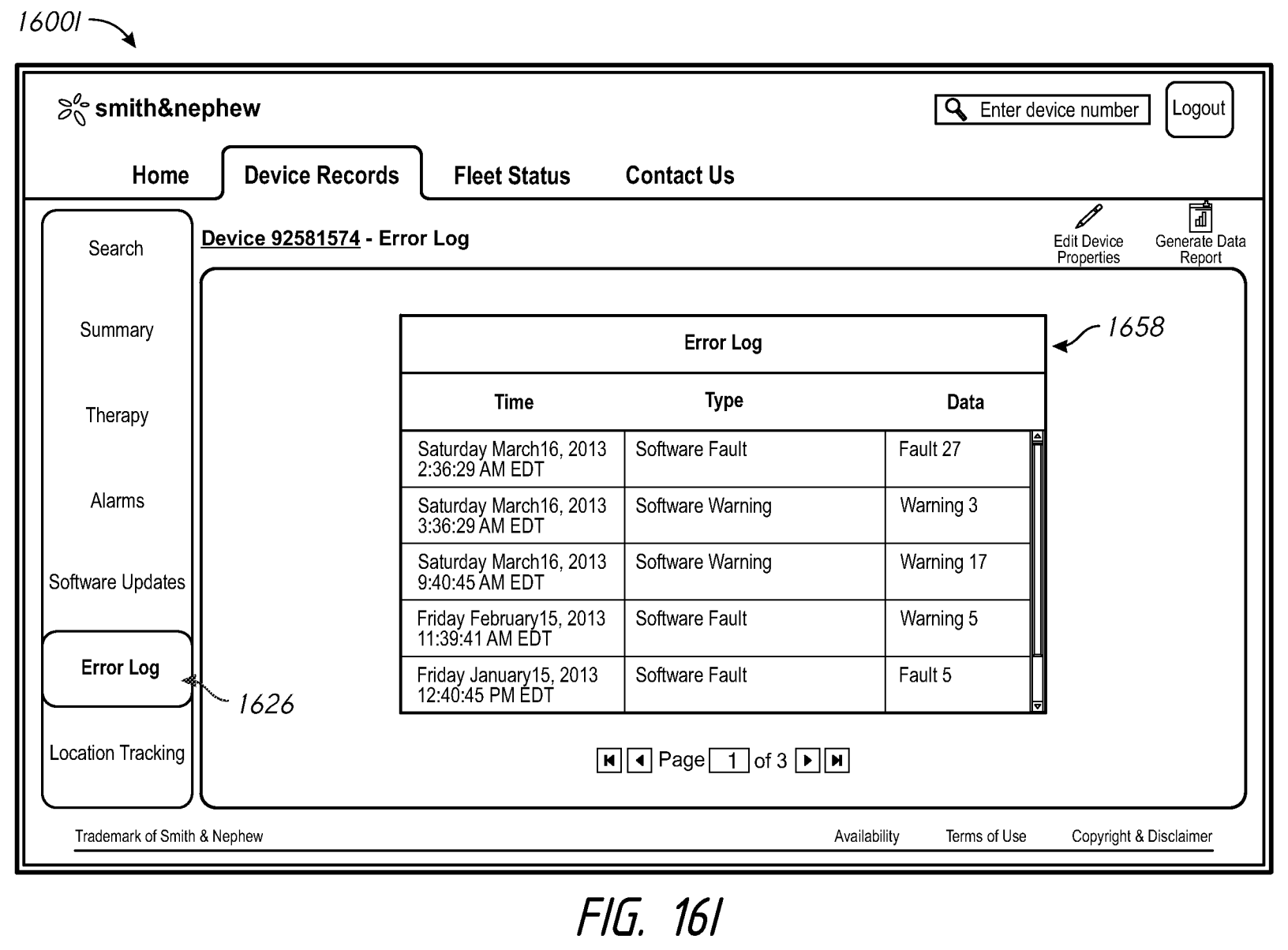
Figure 16J:
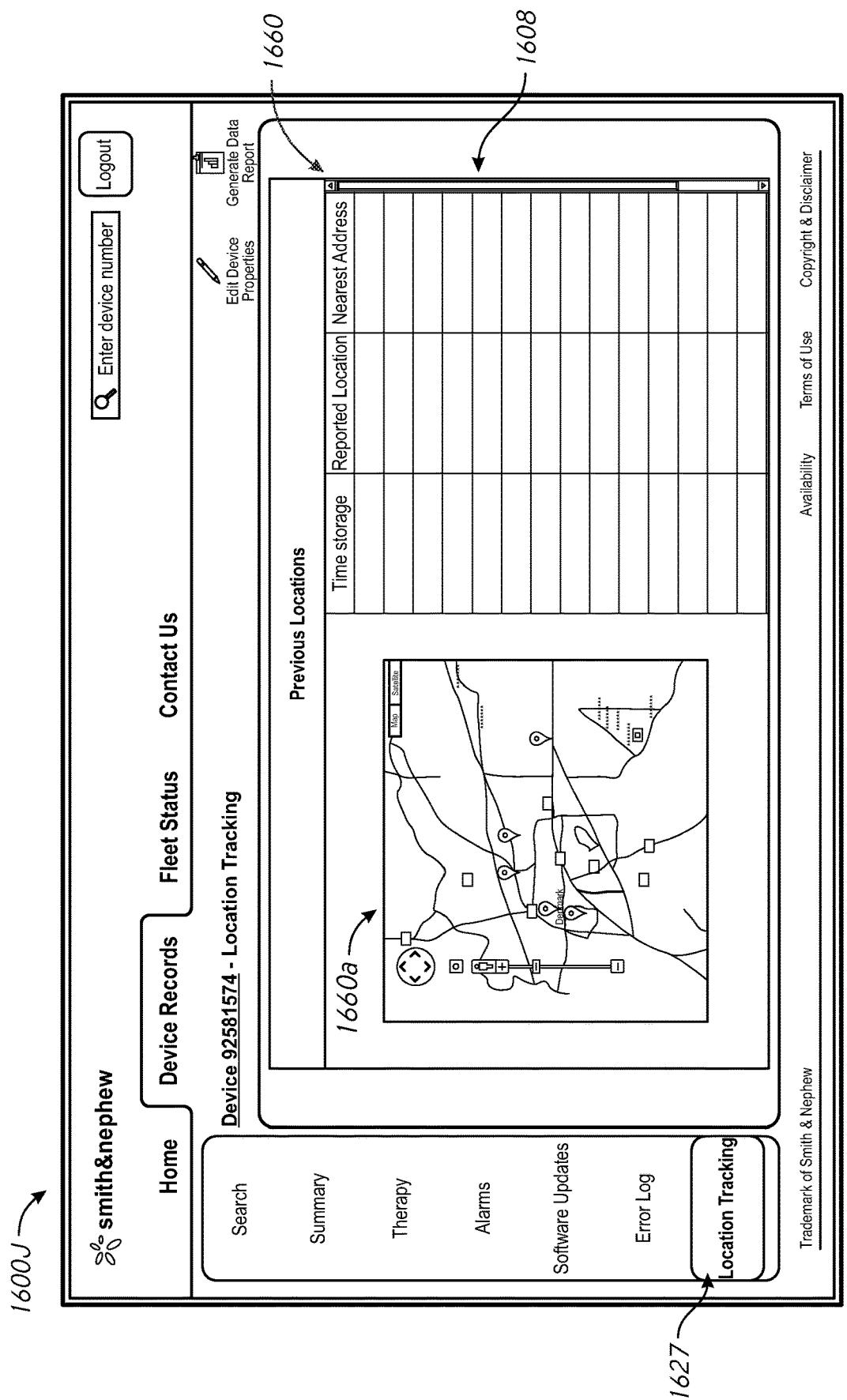
Figure 16K:
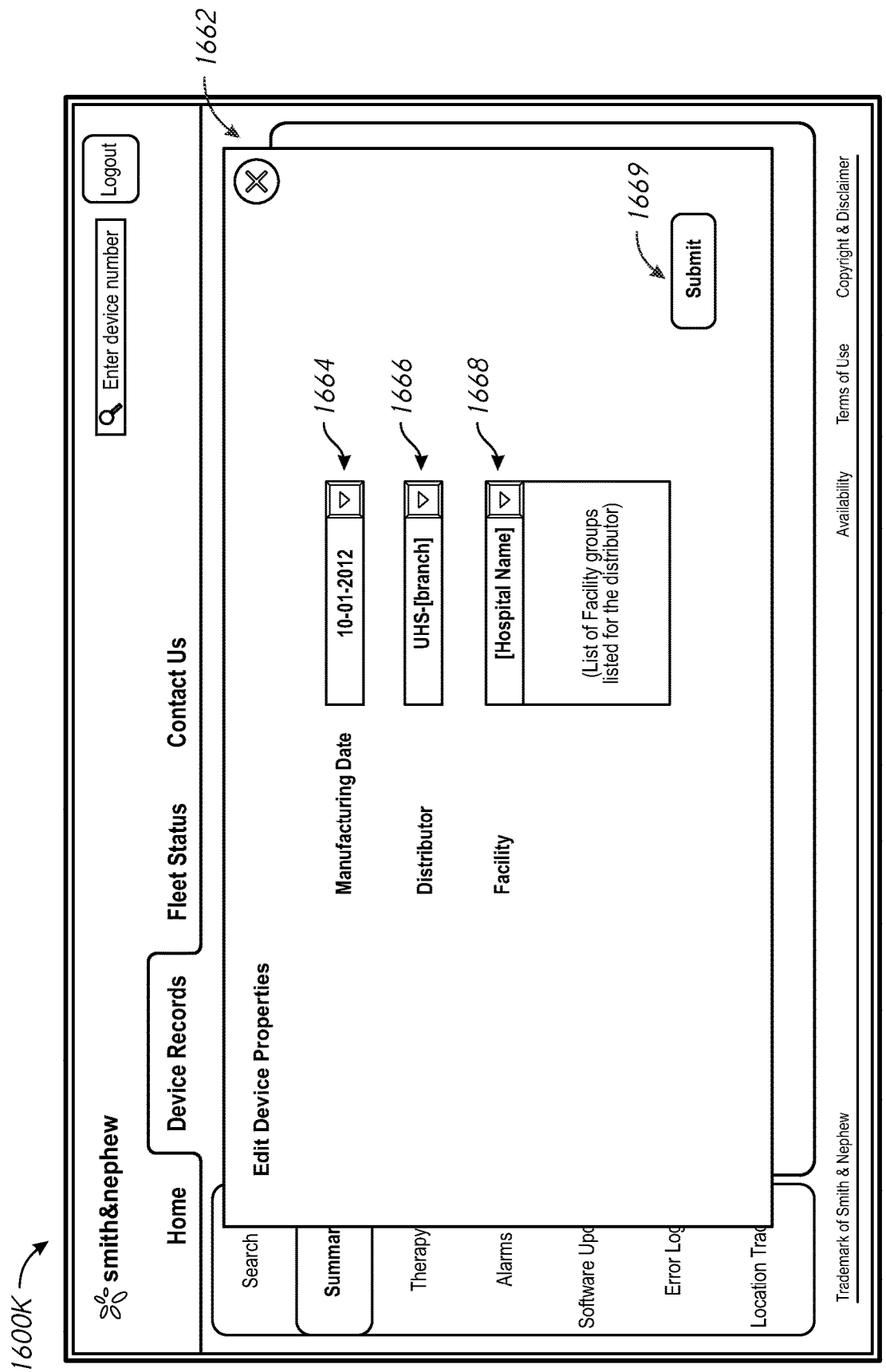
Figure 16L:
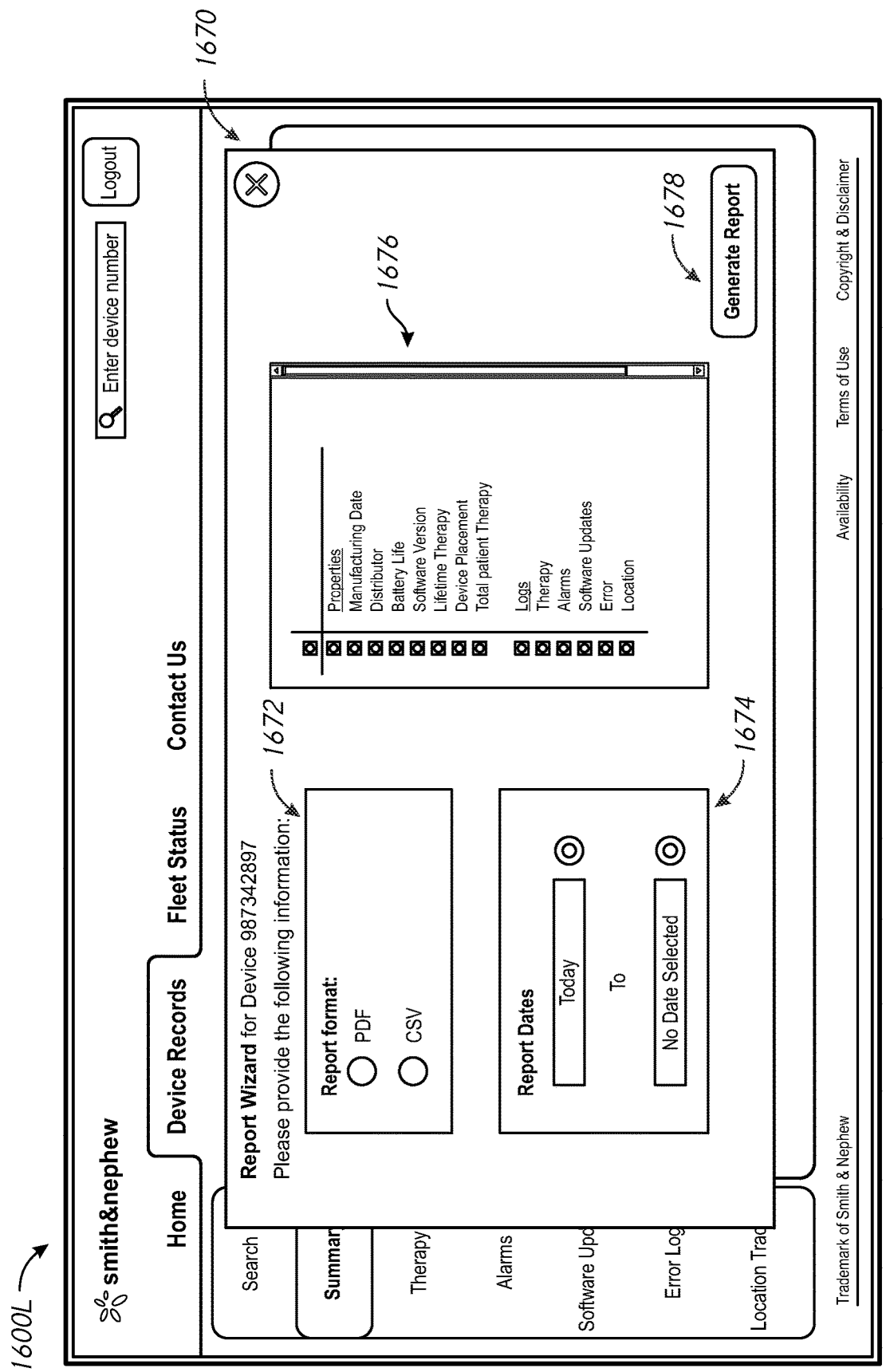
Figure 16N:
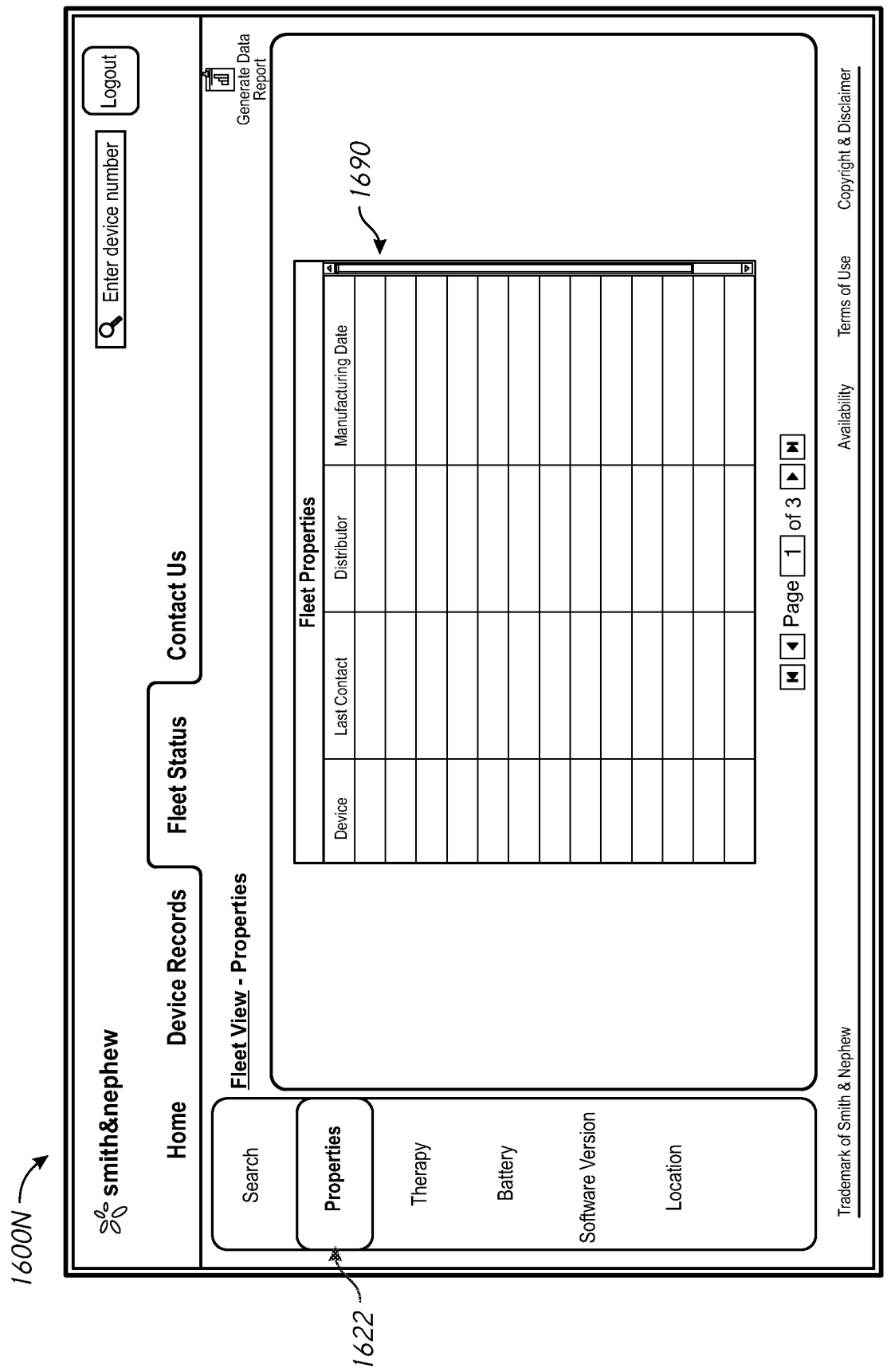
Figure 160:
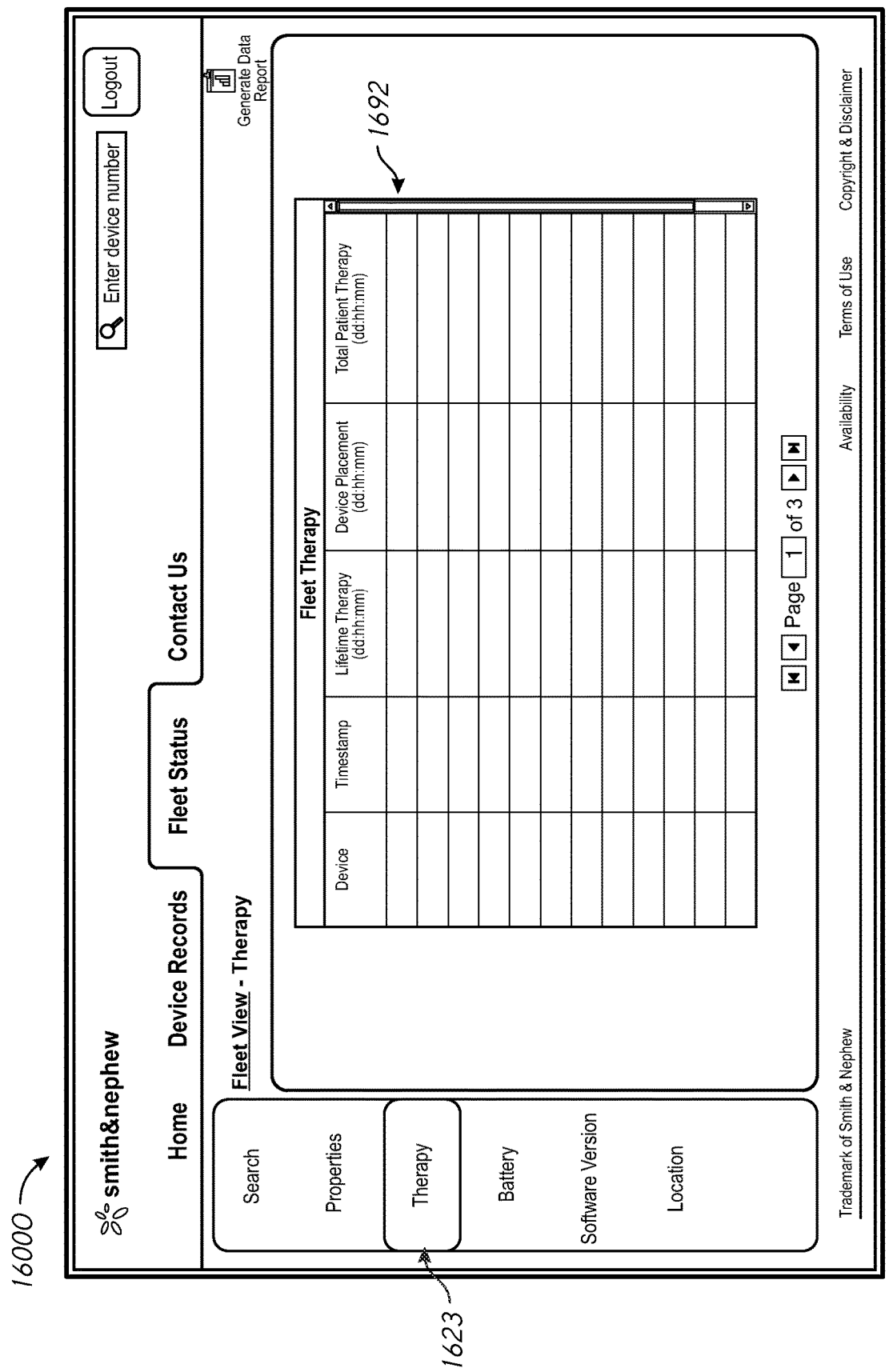
Figure 16P:
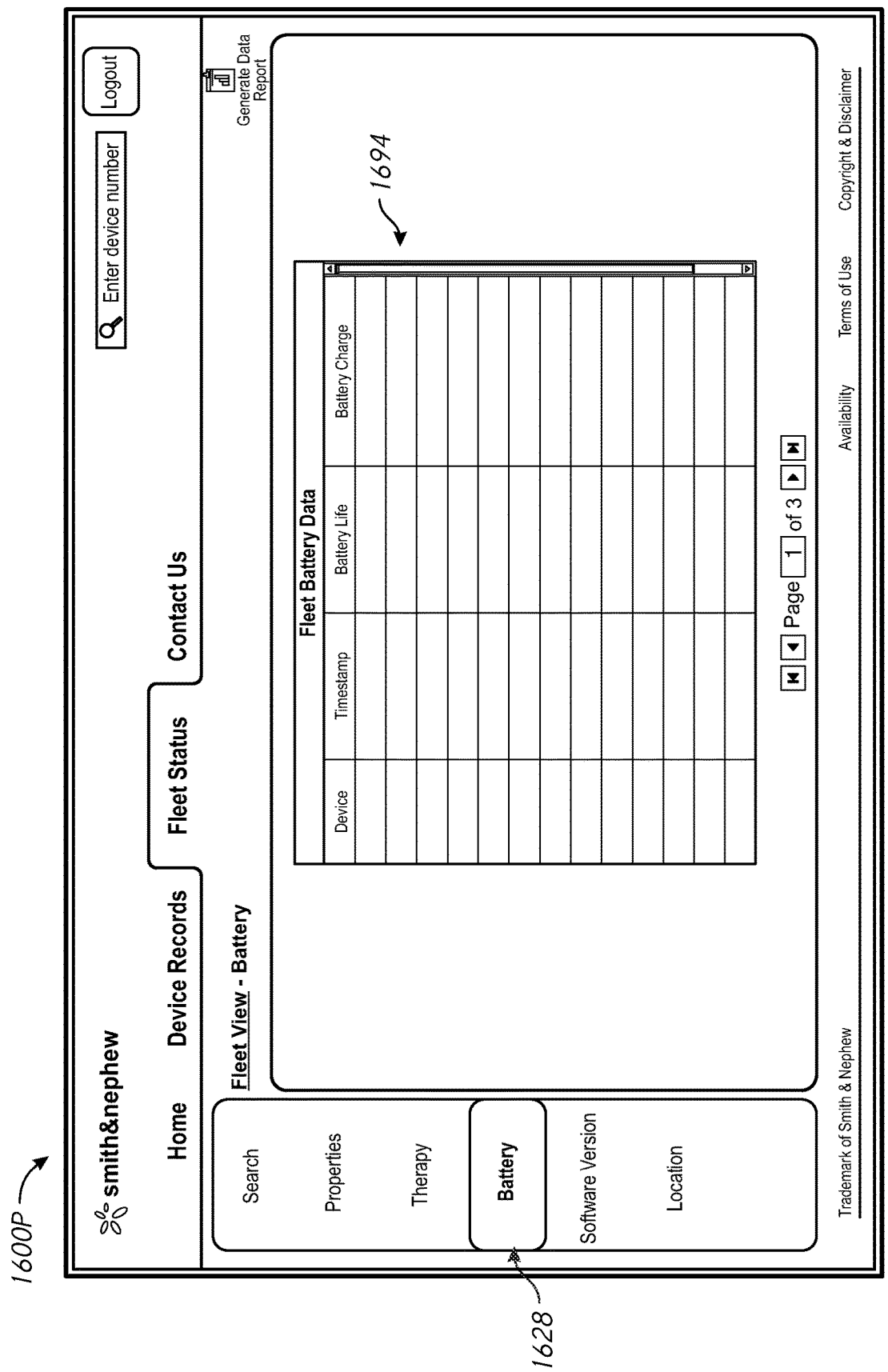
Figure 16Q:
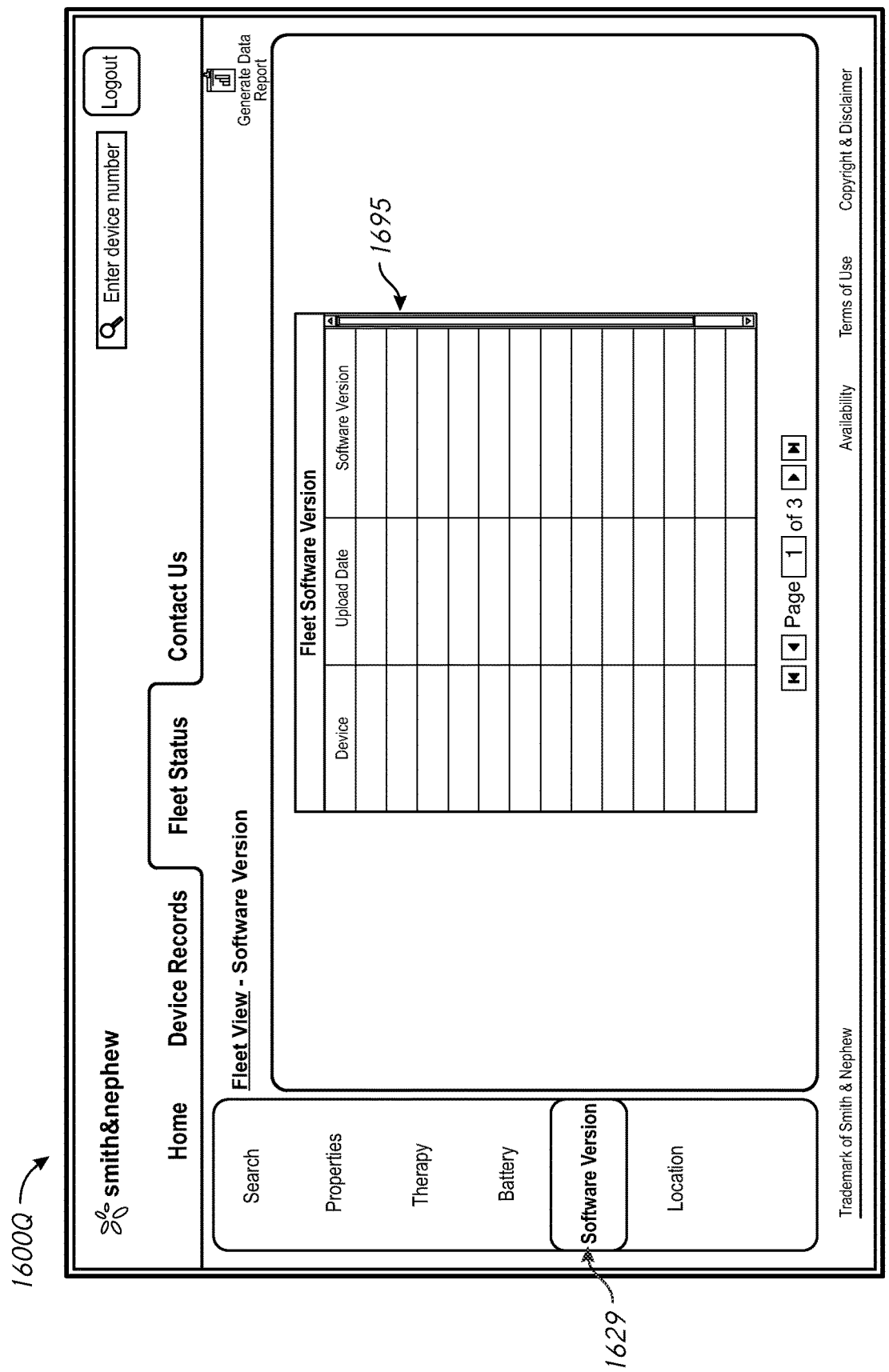
Figure 16R:
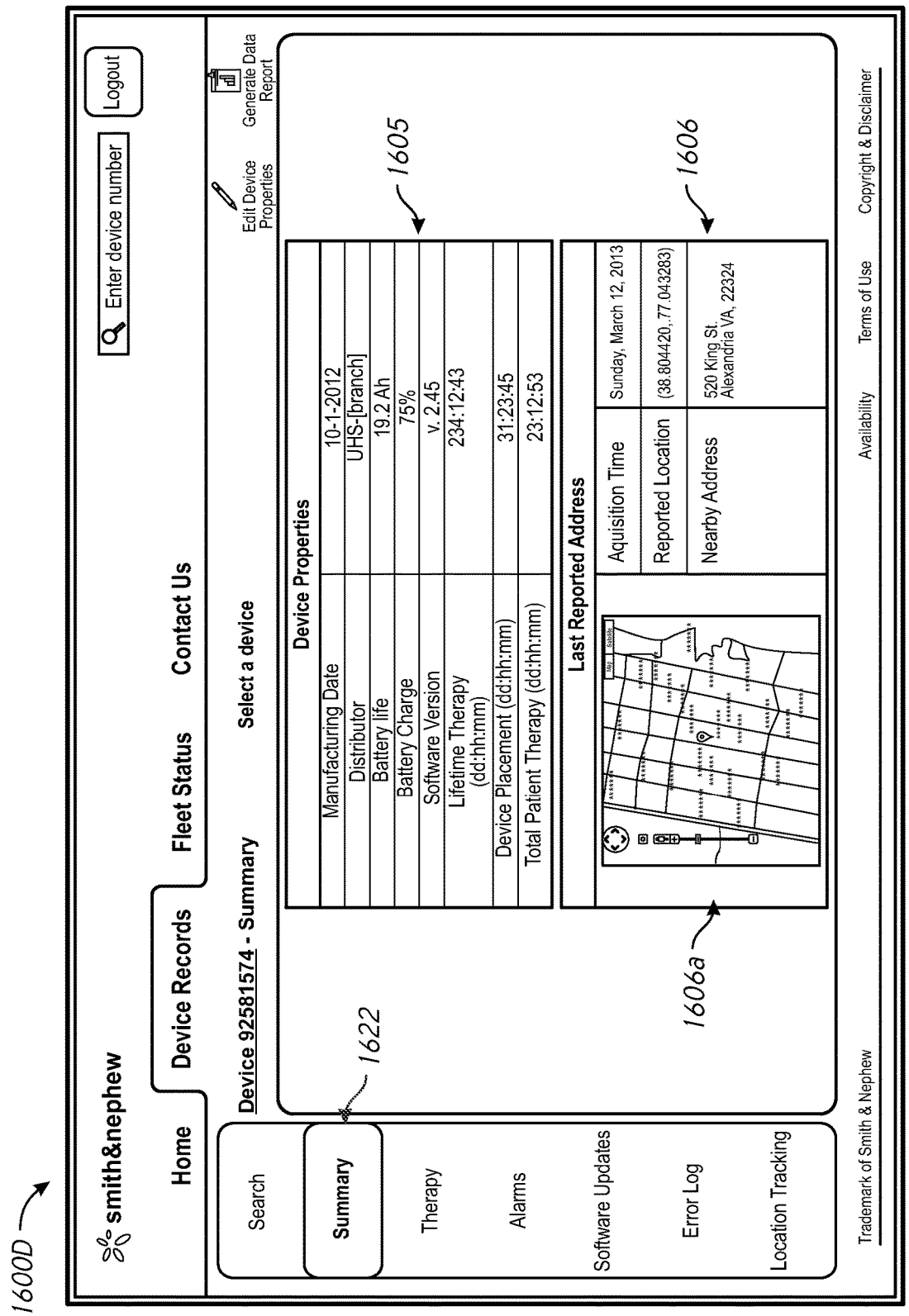
Figure 16S:
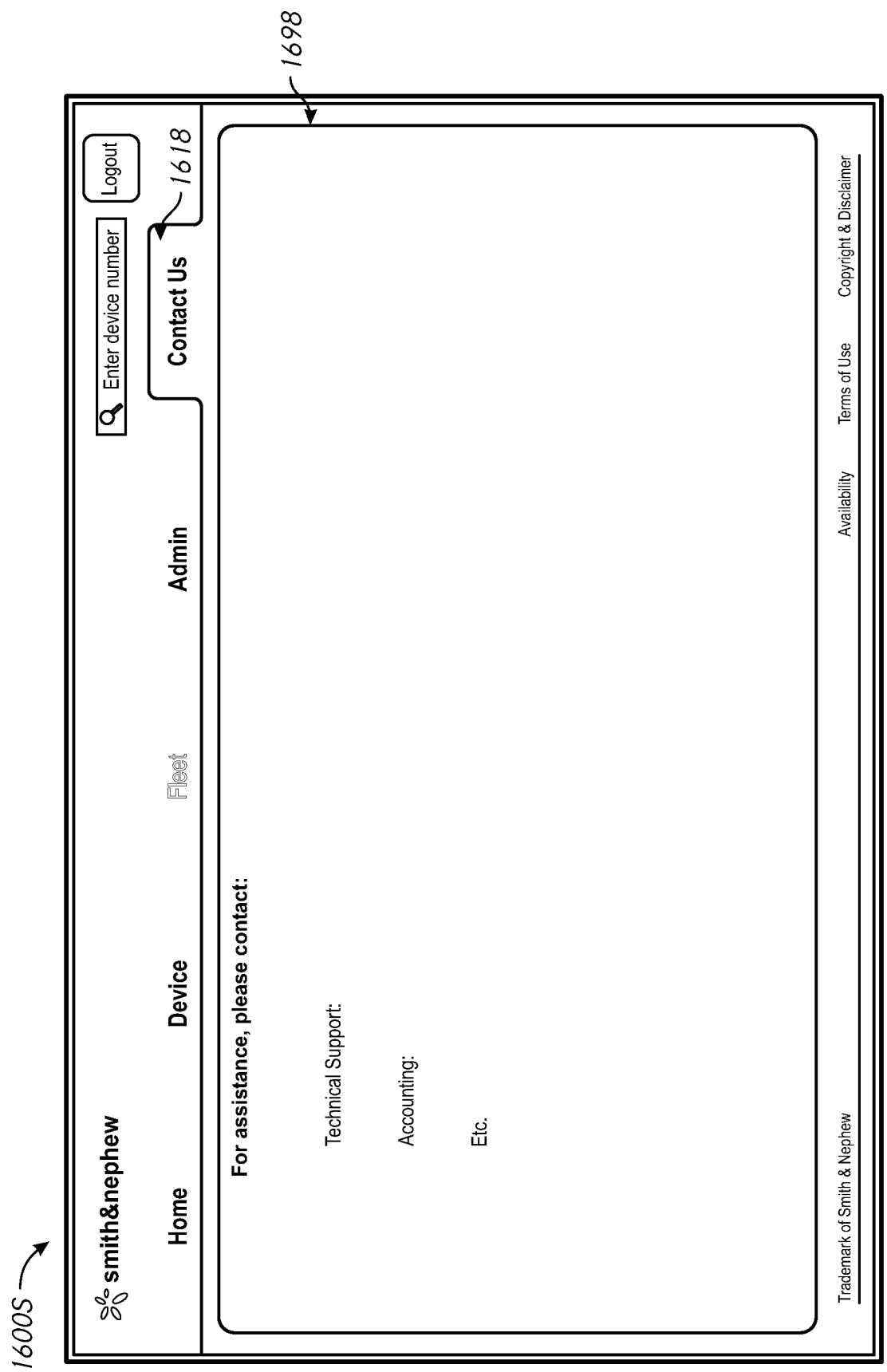

FIGS. 16A-16S illustrate remote interface screens or pages according to some embodiments. These screens can be generated in the web interface 1544 of the remote computer 1540. The remote computer 1540 can be referred to as a cloud platform. FIG. 16A illustrates a login screen 1600A for accessing data uploaded by one or more devices. The login screen 1600A includes a menu 1610, comprising menu item 1612 for accessing a home page, menu item 1614 for accessing device records, menu item 1616 for accessing fleet status, and menu item 1618 for accessing contacts page. The login screen 1600A also includes a search box 1632 for locating device information, a logout button 1634, and additional information menu 1636 for displaying accessibility information, terms of use, patent, trademark, and copyright notices, and disclaimers. Menu items 1612 through 1618 and the search box 1632 can be deactivated until the cloud platform 1540 successfully verifies user's credentials.

The login screen 1600A comprises a login window 1602 where a user enters credential for verification. If the user has forgotten their password, a link can be sent to the user's email account to allow the user to reset the password. After the cloud platform 1540 has verified the submitted login credentials, the application will display a home page 1600B illustrated in FIG. 16B. The home page 1600B displays an image of the device, a welcome message, the menu 1610, in which menu items have been activated, search box 1632 which has been activated, and logout button 1634. From the home screen 1600B, the user can select the device records 1614 menu item or fleet status menu item 1616 depending on whether the user would like to view one or multiple devices. In some embodiments, various groups of users with various privileges can be supported. For example, a treatment facility user group for facilities that own or rent multiple devices, can have administrator privileges allowing one or more users to add and/or remove devices. To accomplish this, the menu 1610 can have additional and/or alternative menu items, such as administrator item.

The user can select device records menu item 1614, which can bring up a device records screen 1600C illustrated in FIG. 16C. The device records screen 1600C includes a menu 1620 comprising menu items for searching devices 1621, device summary information 1622, device therapy information 1623, device alarms information 1624, device software and/or firmware updates 1625, device error log information 1626, and device location tracking 1627. The device records screen 1600C provide a list or table 1604 of all devices available to the user. The results can be split into separate pages to reduce page upload time. The table 1604 can be filtered by the search menu and can be sorted in ascending or descending order. The user can also select how many entries will be displayed per page.

Upon selecting a device in the table 1604, a device summary screen 1600D illustrated in FIG. 16D. In some embodiments, the user's login privileges will determine which data items will be shown on the page and whether the current device location will be reported. Table 4 illustrates which data items are visible on the device summary screen 1600D, according to the user's user group according to certain embodiments. As is illustrated in the table, the following user groups can be supported: administrator, clinician, billing, distributor/purchaser logistics, distributor/purchaser customer service/technical support, maintenance, customer service, hotline, logistics. In Table 4, FIG. 2-5 corresponds to FIG. 16D, FIG. 2-6 corresponds to FIG. 16E, FIG. 2-7 corresponds to FIG. 16F, FIG. 2-8 corresponds to FIG. 16G, FIG. 2-9 corresponds to FIG. 16H, FIG. 2-10 corresponds to FIG. 16I, and FIG. 2-11 corresponds to FIG. 16J.

Device properties can be shown in table 1605 and location information, including a map 1606a, can be shown in table 1606. All values shown in tables 1605 and 1606 can reflect the latest dataset uploaded from the device. In some embodiments, where appropriate, a tooltip feature can be added to tables 1605 and 1606 to provide more detail (e.g., the definition of "Device Placement") when a user hovers a pointing device over a particular table item. As is illustrated in table 1606, map 1606a is used to display the latest reported address. The location coordinates, the time that this location was acquired by GPS (or via cellular network data), and the nearest street address are displayed alongside the map. The closest street address can be determined via reverse geo-coding.

According to some embodiments, the device summary screen 1600D corresponds to a summary screen as viewed by a user having administrator ("Admin") privileges. As shown in Table 4, members of the "Admin" User Group will have access to all data items and navigation choices. All other User Groups will have access to various subsets of this screen, as described in Table 4. For example, FIG. 16E displays the summary screen 1600E as viewed by a user that has been assigned to a "Clinician" user group. Such user can view information listed in table 1607.

TABLE 4

Example Access to Device Information Based on User Credentials

| | | User Interface Accessibility | | | | | | | |
|---|---|---|---|---|---|---|---|---|---|
| | | Summary Screen (FIGS. 2-5, 2-6) | | | | | | | |
| User Group | Members | Edit Device Properties | Serial Number | Total Patient Therapy | Device Placement | Manufacture Date | Software Version | Battery Charge | Battery Life |
| Admin | Website Administrator (S&N) | Y | Y | Y | Y | Y | Y | Y | Y |
| Clinician | Clinician | | Y | Y | | | | | |
| Billing | Customer - Renter (Billing) Distributor/ Purchaser (Billing) Billing (S&N) | | Y | Y | Y | | | | |
| D/P Logistics | Distributor/ Purchaser (Logistics) | | Y | | | | | | |
| D/P CSTS | Distributor/ Purchaser (Cust Serv/ Tech Support) | | Y | Y | | Y | Y | Y | |
| Maintenance | Distributor/ Purchaser (Maintenance) Quality & Complaints (S&N) Service & Repair (S&N) | | Y | Y | | Y | Y | Y | Y |
| Customer Svc | Customer Service (S&N) | | Y | | | | | | |
| Hotline | Clinical/ Technical Hotline (S&N) | | Y | Y | | Y | Y | Y | |
| Logistics | Logistics (S&N) | | Y | | | Y | Y | | Y |

TABLE 4-continued

Example Access to Device Information Based on User Credentials

| User Group | Members | User Interface Accessibility Summary Screen (FIGS. 2-5, 2-6) | | Therapy | Alarms | Software Update | Error | Location |
|---|---|---|---|---|---|---|---|---|
| | | Device Lifetime Therapy | Location | Log Screen (FIG. 2-7) | Log Screen (FIG. 2-8) | Log Screen (FIG. 2-9) | Log Screen (FIG. 2-10) | Tracking Screen (FIG. 2-11) |
| Admin | Website Administrator (S&N) | Y | Y | Y | Y | Y | Y | Y |
| Clinician | Clinician | | | Y | Y | | | |
| Billing | Customer - Renter (Billing) Distributor/ Purchaser (Billing) Billing (S&N) | | | Y | | | | |
| D/P Logistics | Distributor/ Purchaser (Logistics) | | Y | | | | | Y |
| D/P CSTS | Distributor/ Purchaser (Cust Serv/ Tech Support) | | | Y | Y | | | |
| Maintenance | Distributor/ Purchaser (Maintenance) Quality & Complaints (S&N) Service & Repair (S&N) | Y | Y | Y | Y | Y | Y | |
| Customer Svc | Customer Service (S&N) | | Y | | | | | Y |
| Hotline | Clinical/ Technical Hotline (S&N) | | | Y | Y | | | |
| Logistics | Logistics (S&N) | Y | Y | | | Y | | Y |

FIG. 16F illustrates device therapy information screen 1600F. The screen 1600F can be selected via menu item 1623. In some embodiments, events listed in the therapy log 1652 include all therapy ON and OFF events, as well as adjustments to therapy mode and pressure. All past uploaded data can be displayed with each event sorted by its timestamp or in any order selected by the user. Device properties editor 1642 and report generator 1644 can be selected by the user to perform functions explained below.

FIG. 16G illustrates device alarm information screen 1600G. The screen 1600G can be selected via menu item 1624. In some embodiments, alarm logs listed in the table 1654 provide a sequential listing of each alarm event. Each event is described by the alarm type and any relevant data (e.g. over-vacuum high pressure). Different ordering options can be selected by the user. FIG. 16H illustrates device software information screen 1600H. The screen 1600H can be selected via menu item 1625. In some embodiments, the table 1656 lists all past successful (and, optionally, unsuccessful) software updates by their timestamps or in any other order selected by the user.

FIG. 16I illustrates device error information screen 1600I. The screen 1600I can be selected via menu item 1626. In some embodiments, the table 1658 lists each logged error event sequentially in the order selected by the user. The error fault or warning code is provided for each error event. FIG. 16J illustrates device location information screen 1600J. The screen 1600J can be selected via menu item 1627. In some embodiments, the table 1660 lists all past reported locations of the device. A map 1600a illustrates markers at up to N of the most recent reported locations. N can be any suitable integer number. If a row 1660b in the table 1600 is selected, then the corresponding marker on the map 1600a will be highlighted.

FIG. 16K illustrates device properties editor screen 1600K. The screen 1600K can be selected via button 1642. In some embodiments, device properties editor 1662 allows the user to update device data not uploaded by the device, such as, for example, manufacturing date 1664, distributor information 1666, and facility information 1668. The distributor 1666 and facility 1668 fields can be drop down menus that show all distributor device groups stored on the cloud system 1540 and all facilities device groups stored under the selected distributor. Updated information can be saved in the cloud system 1540, such as in the data storage module 1542, by pressing the update button 1669.

FIG. 16L illustrates report generator screen 1600L. The screen 1600L can be selected via button 1644. In some embodiments, report generator 1670 can be used to download reports of past and current device records in CVS, PDF, or any other suitable format. The format of the report can be selected in 1672, report dates can be selected in 1676, properties for including in the report can be selected in 1676, and report can be generated and downloaded by pressing button 1678.

In some embodiments, a user, such as a facility user, can view multiple devices owned and/or leased. These devices can be referred to as a fleet. Fleet management can be selected via menu item 1616, which brings up a set of menus that displays the latest data from multiple devices in the user's current fleet.

In certain embodiments, to access fleet records, the user should first select one or more devices from the fleet search screen 1600M illustrated in FIG. 16M. Screen 1600M can be selected via menu items 1616 and 1621. Screen 1600M includes search menu 1682 and results table 1684. Data associated with one or more devices from the fleet can be displayed by pressing button 1686. Fleet device properties screen 1600N illustrated in FIG. 16N shows a list of summary data for a set of devices selected in the fleet search screen 1600M. Device properties are listed in the table 1690. The properties screen 1600N can be accessed via menu item 1622. Therapy data for the selected devices can be viewed by selecting menu item 1623 to bring up fleet device therapy information screen 1600O illustrated in FIG. 16O. In some embodiments, latest therapy information for all selected devices can be viewed in table 1692.

In various embodiments, fleet device battery information screen 1600P illustrated in FIG. 16P shows the last reported battery life and battery charge for all selected devices. Battery information can be displayed in the table 1694. The fleet battery information screen 1600P can be selected via menu item 1628. Fleet device software information screen 1600Q illustrated in FIG. 16Q shows the current software version, in table 1685, for all selected devices. The fleet device software information screen 1600Q can be selected via menu item 1629. Fleet device location information screen 1600R illustrated in FIG. 16R shows the last reported address for all selected devices. The fleet location information screen 1600Q can be selected via menu item 1629. Device location information can be shown in table 1696 which includes a map 1696a. In some embodiments, the map 1696a includes markers for N past locations of each selected device, where N is a suitable integer number.

Contacts page 1600S illustrated in FIG. 16S can be selected via menu item 16518. Contact information, such as administrative and technical contacts information, can be provided in window 1698.

Graphical User Interface

Figure 17A:
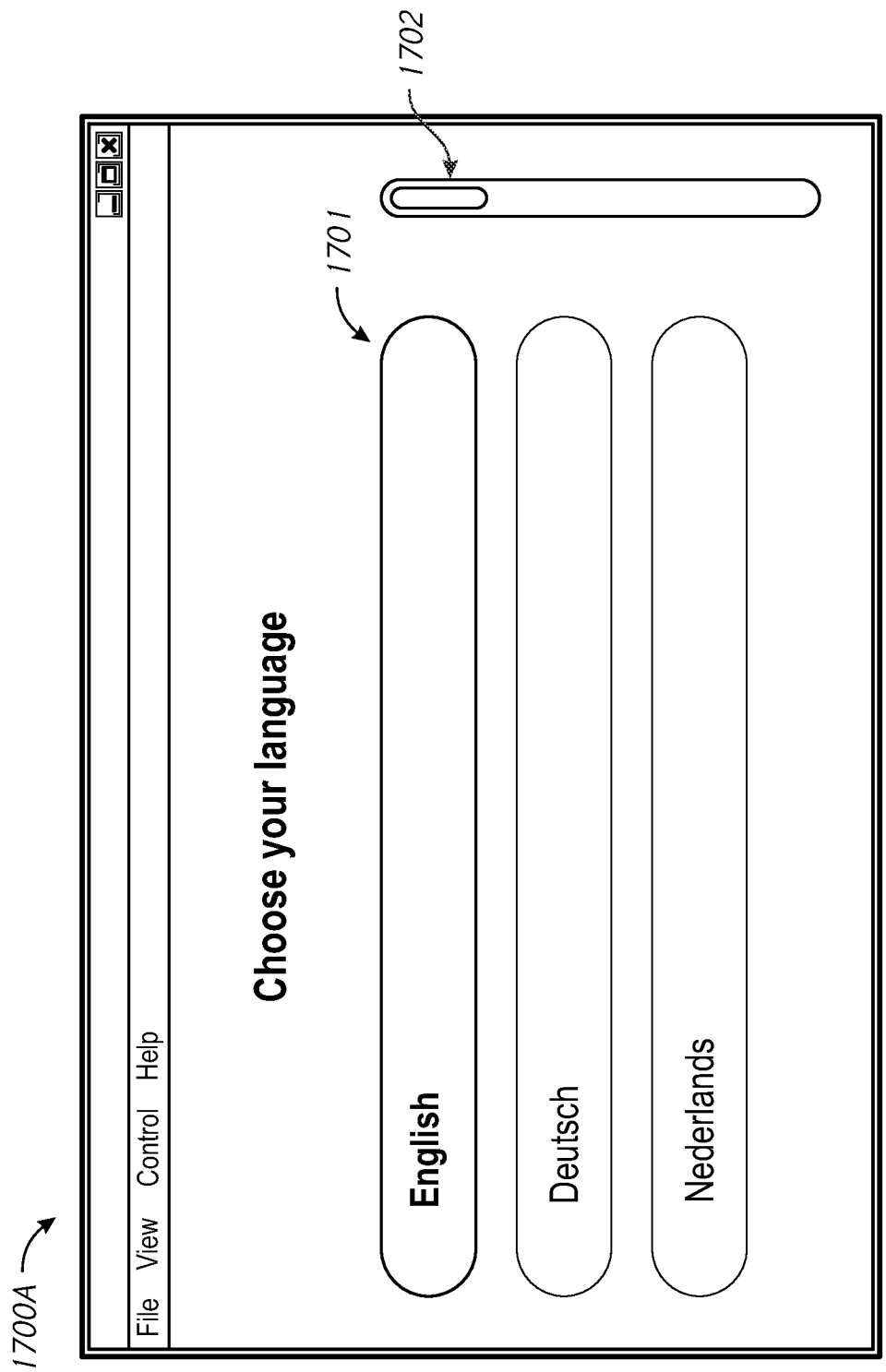
FIGS. 17A-17V illustrate graphical user interface screens according to some embodiments.
Figure 17B:
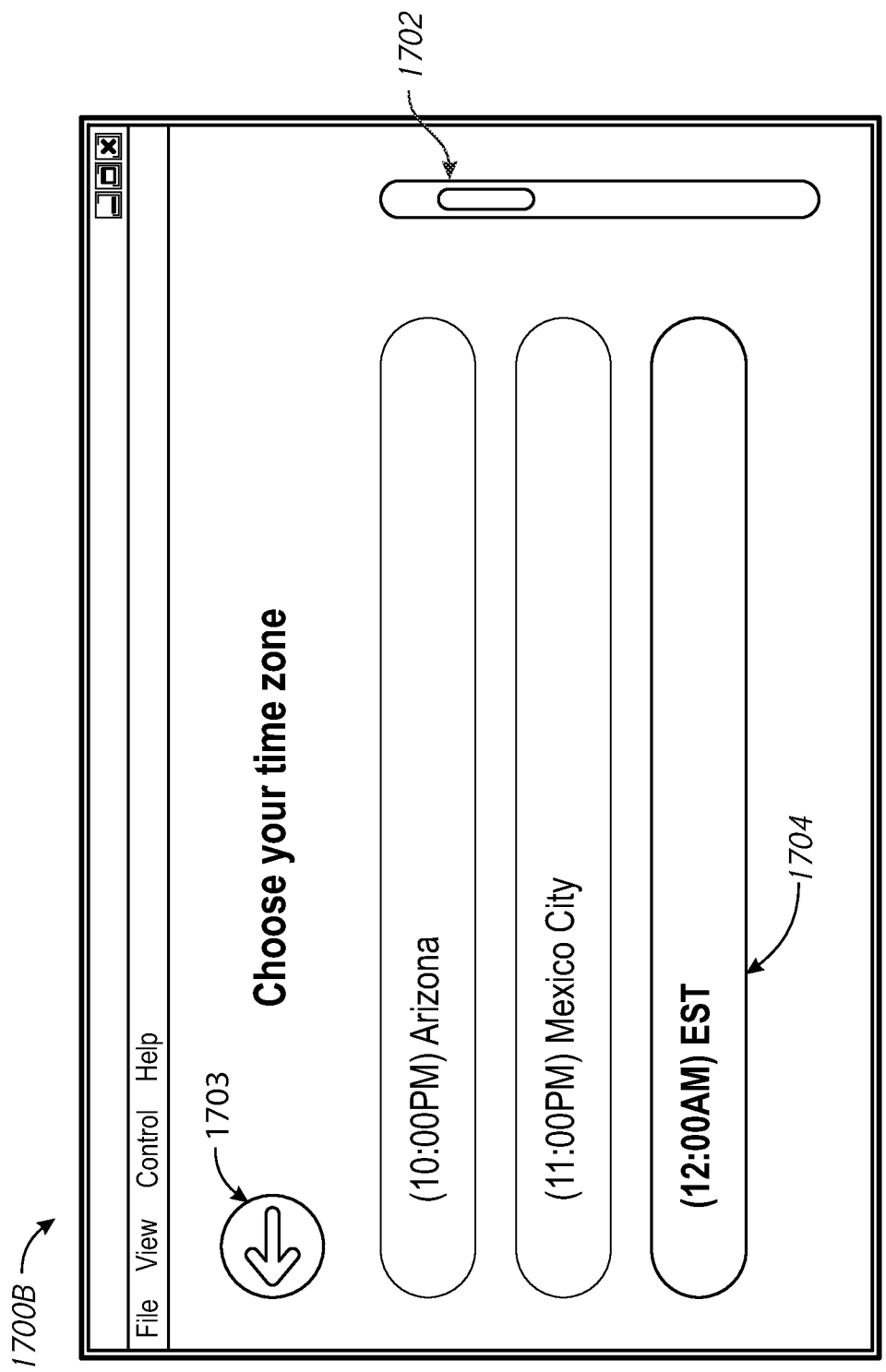
Figure 17C:
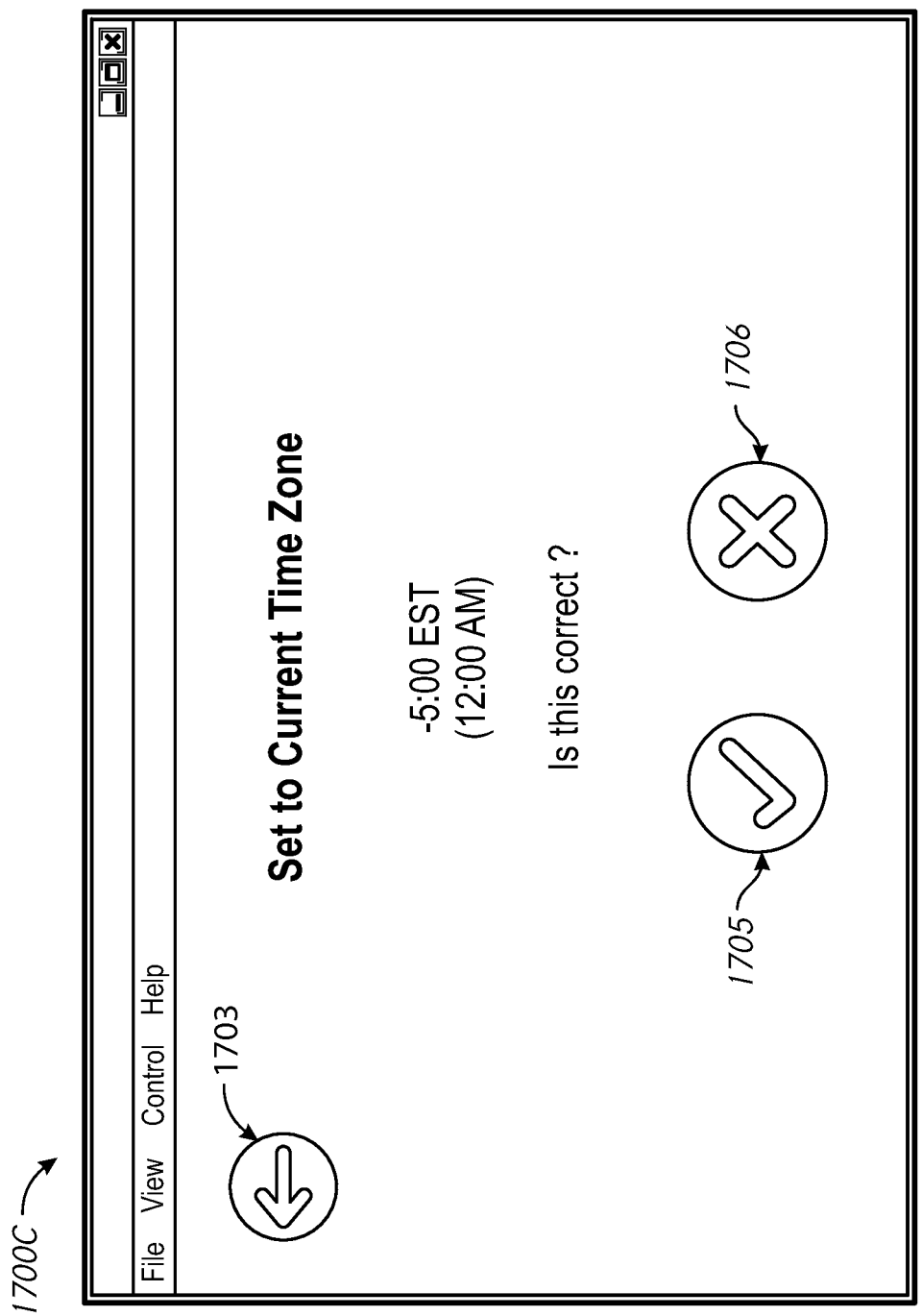
Figure 17D:
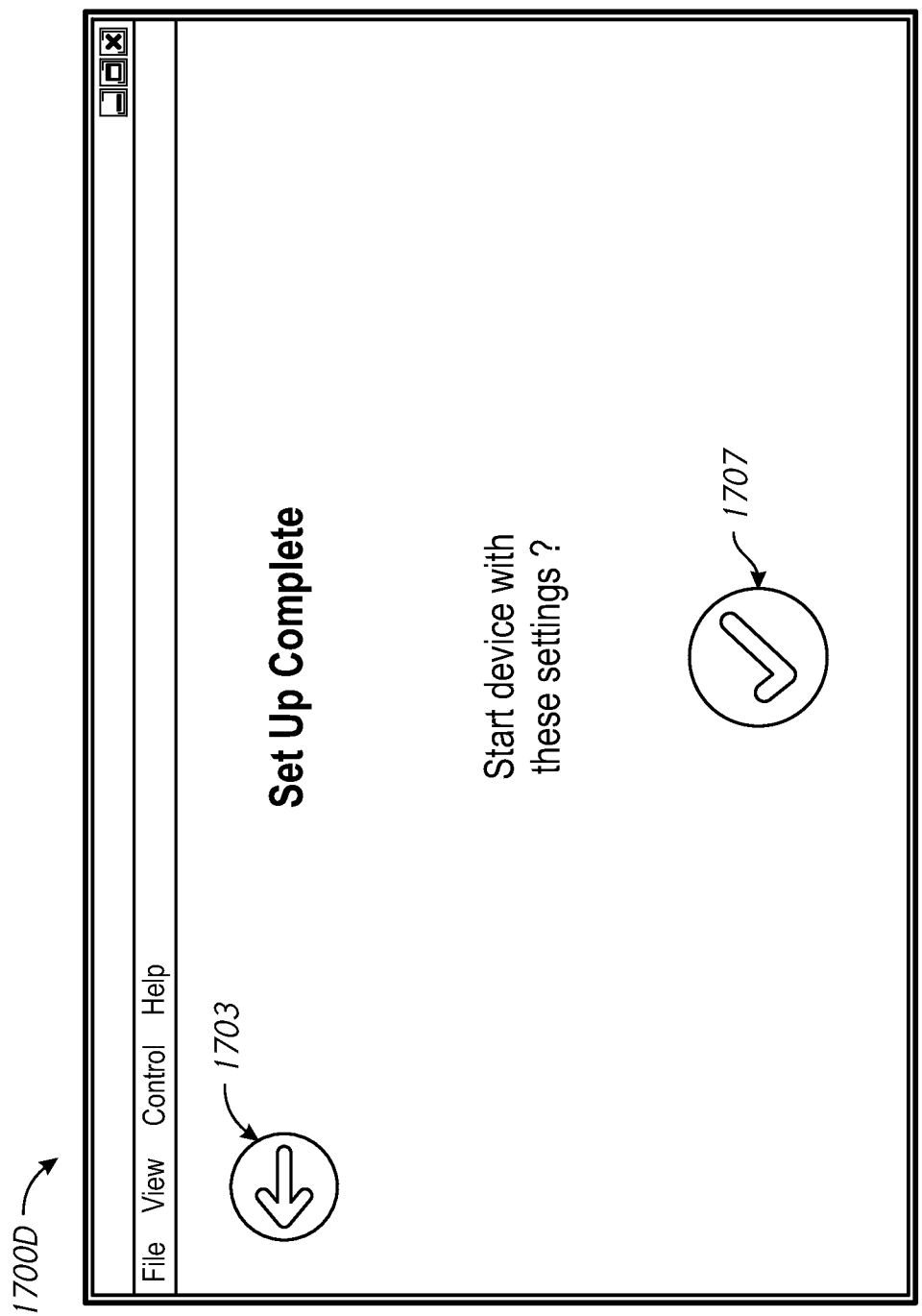
Figure 17E:
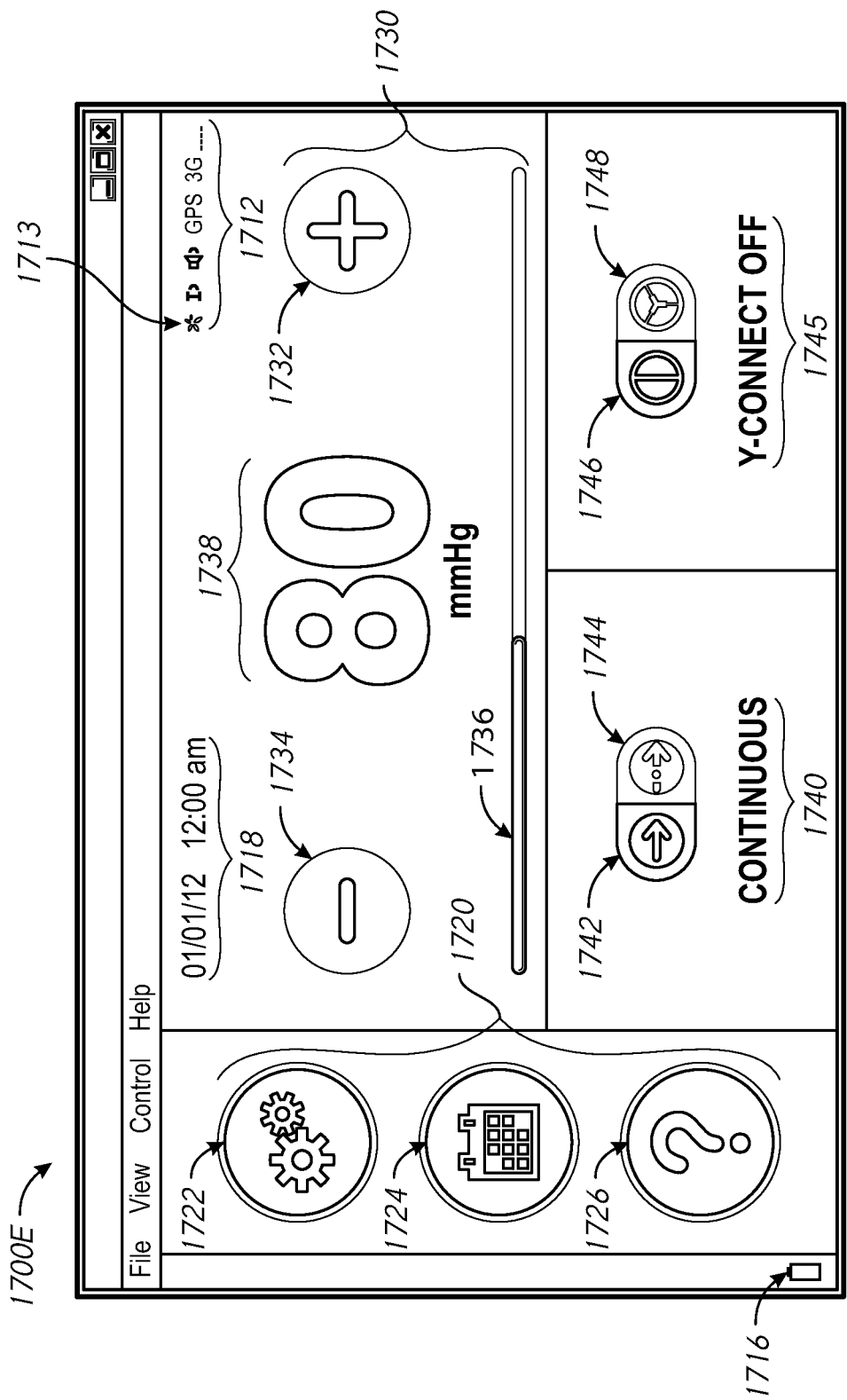
Figure 17F:
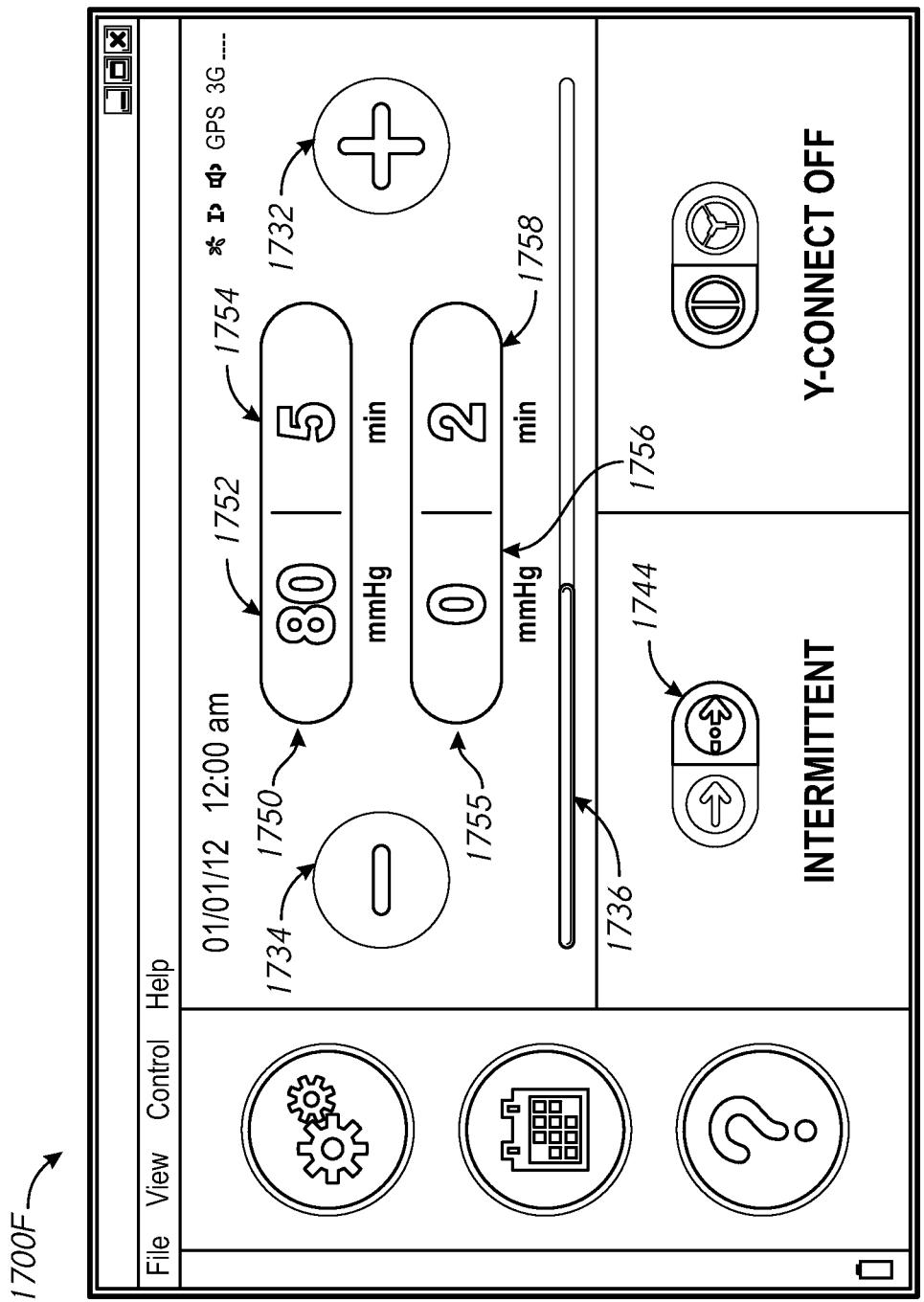
Figure 17H:
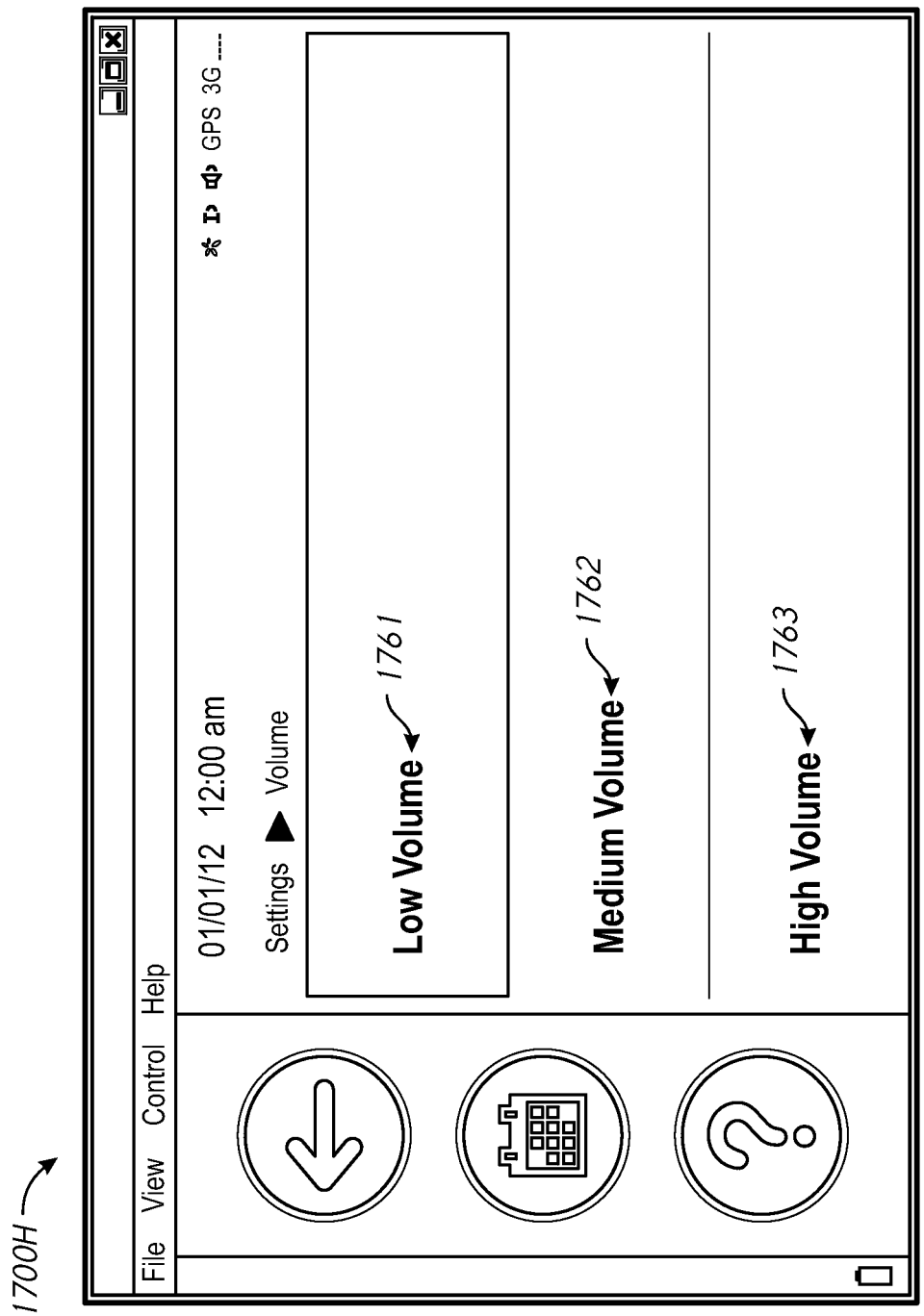
Figure 17I:
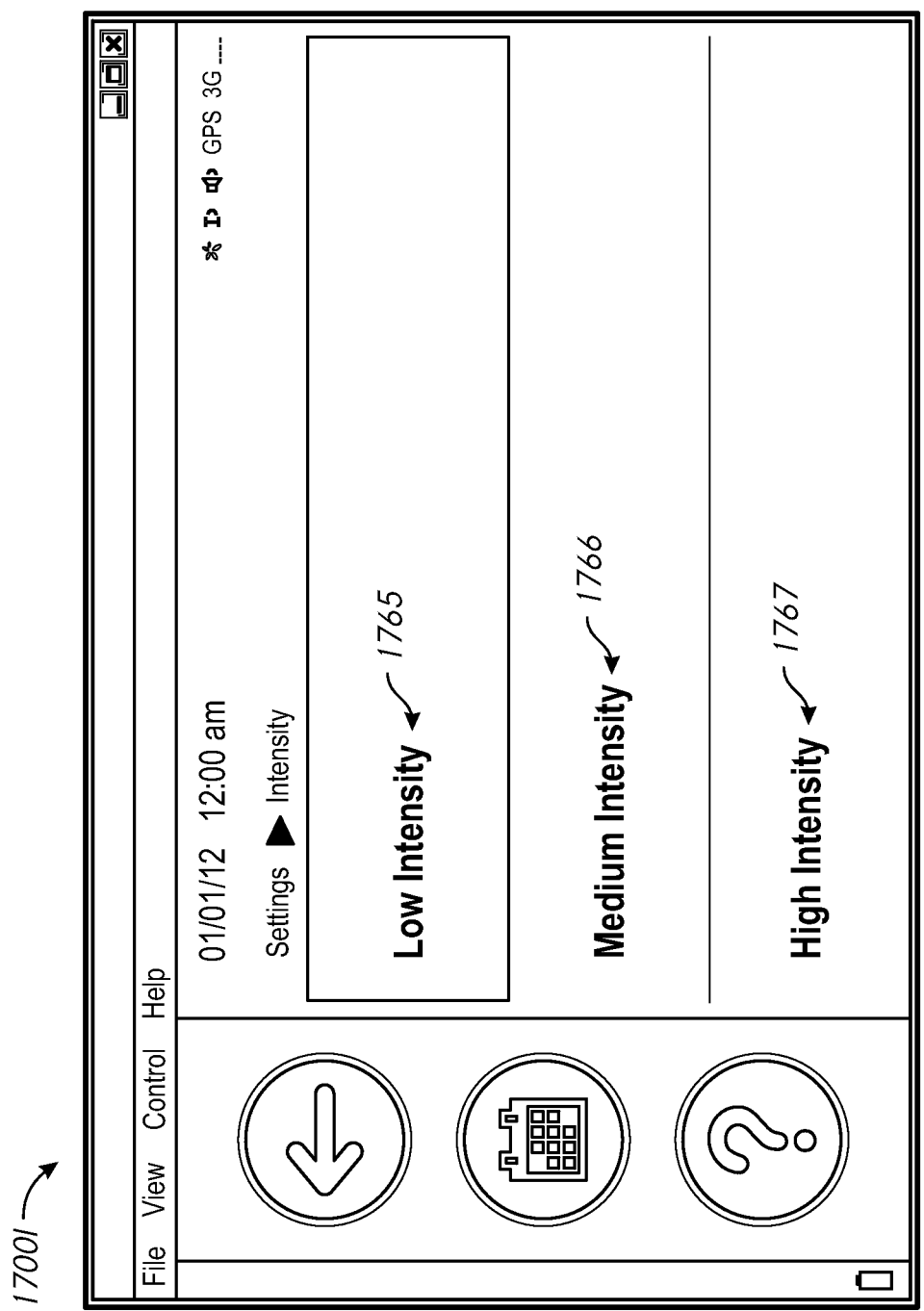
Figure 17J:
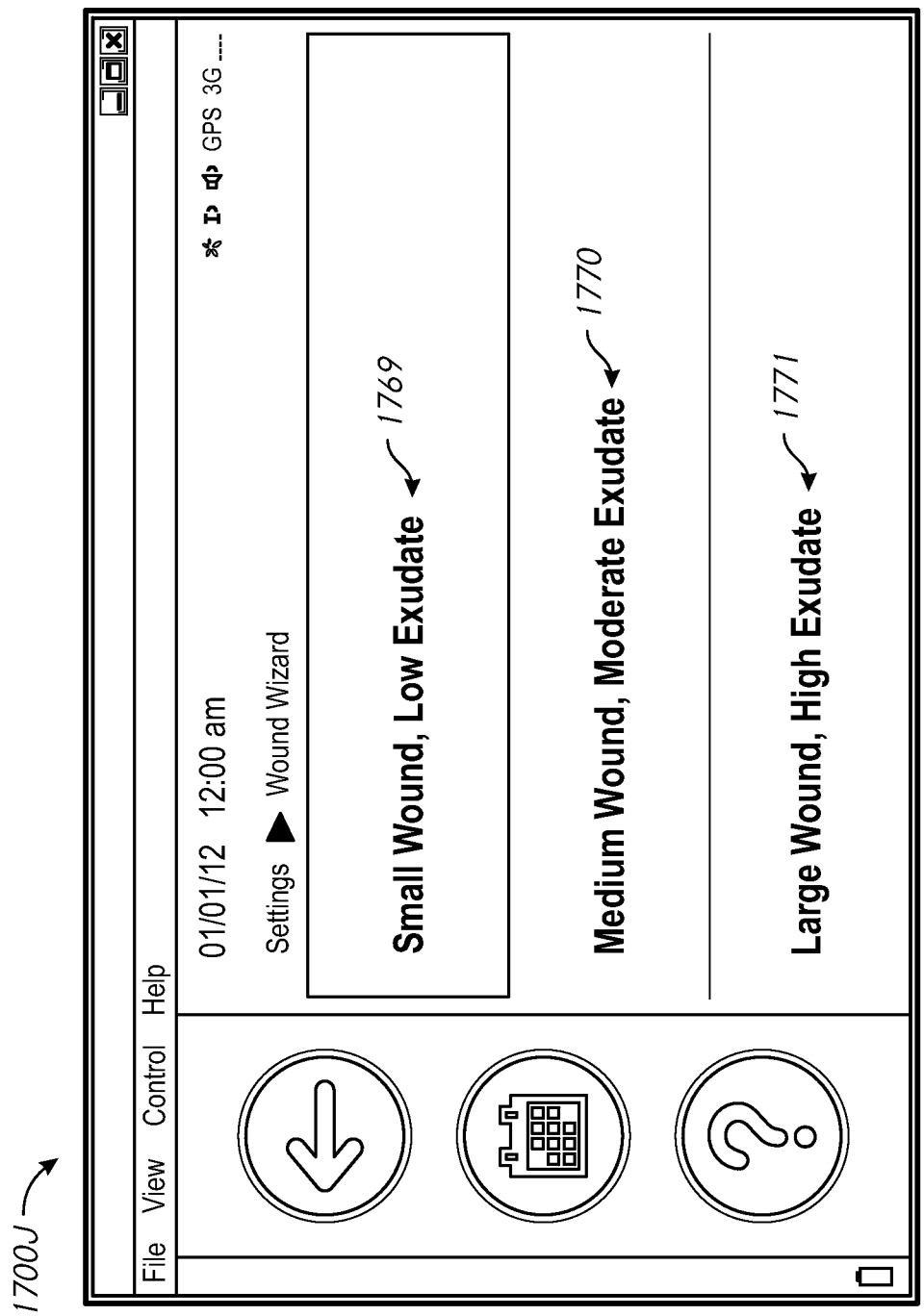
Figure 17K:
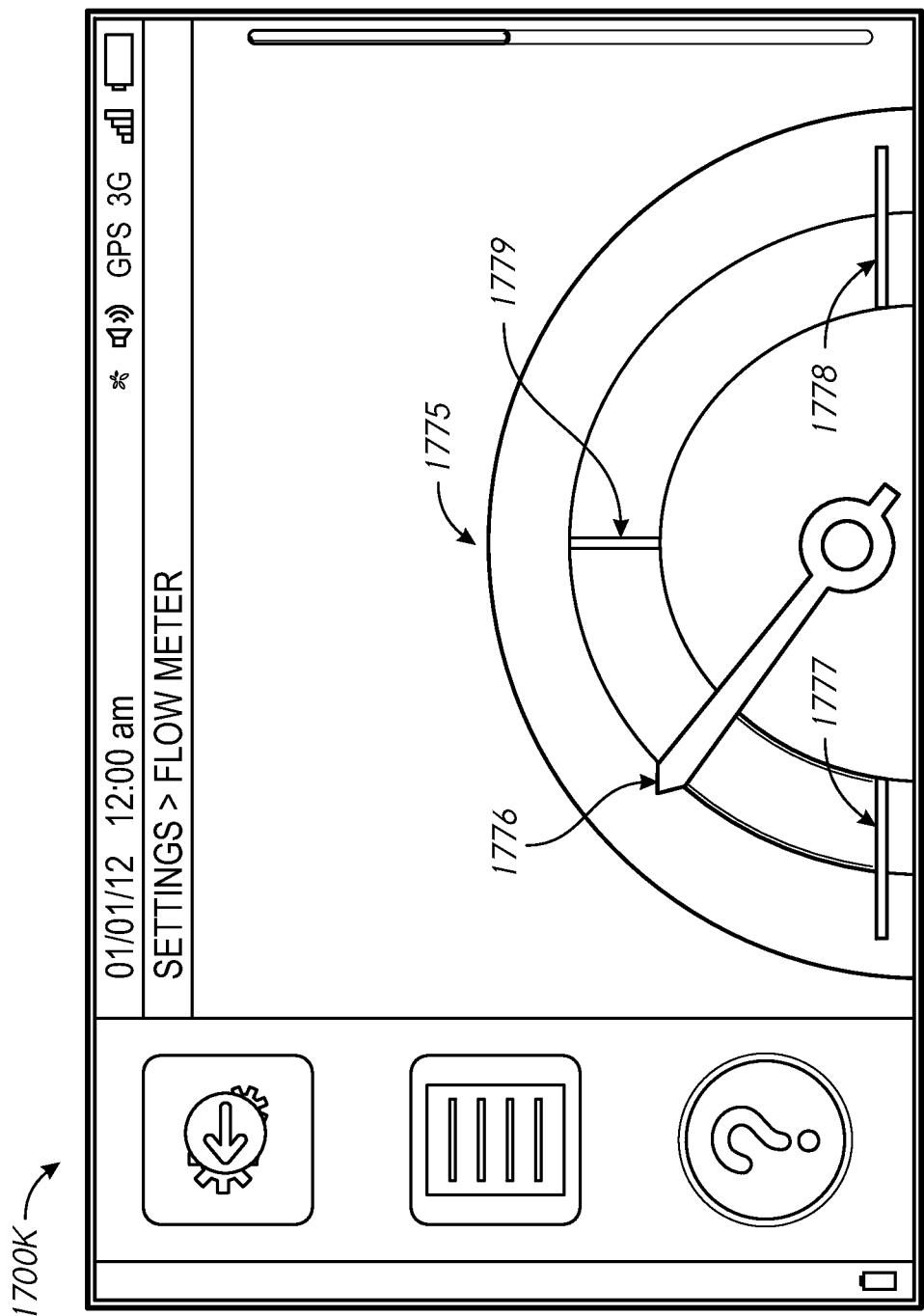
Figure 17L:
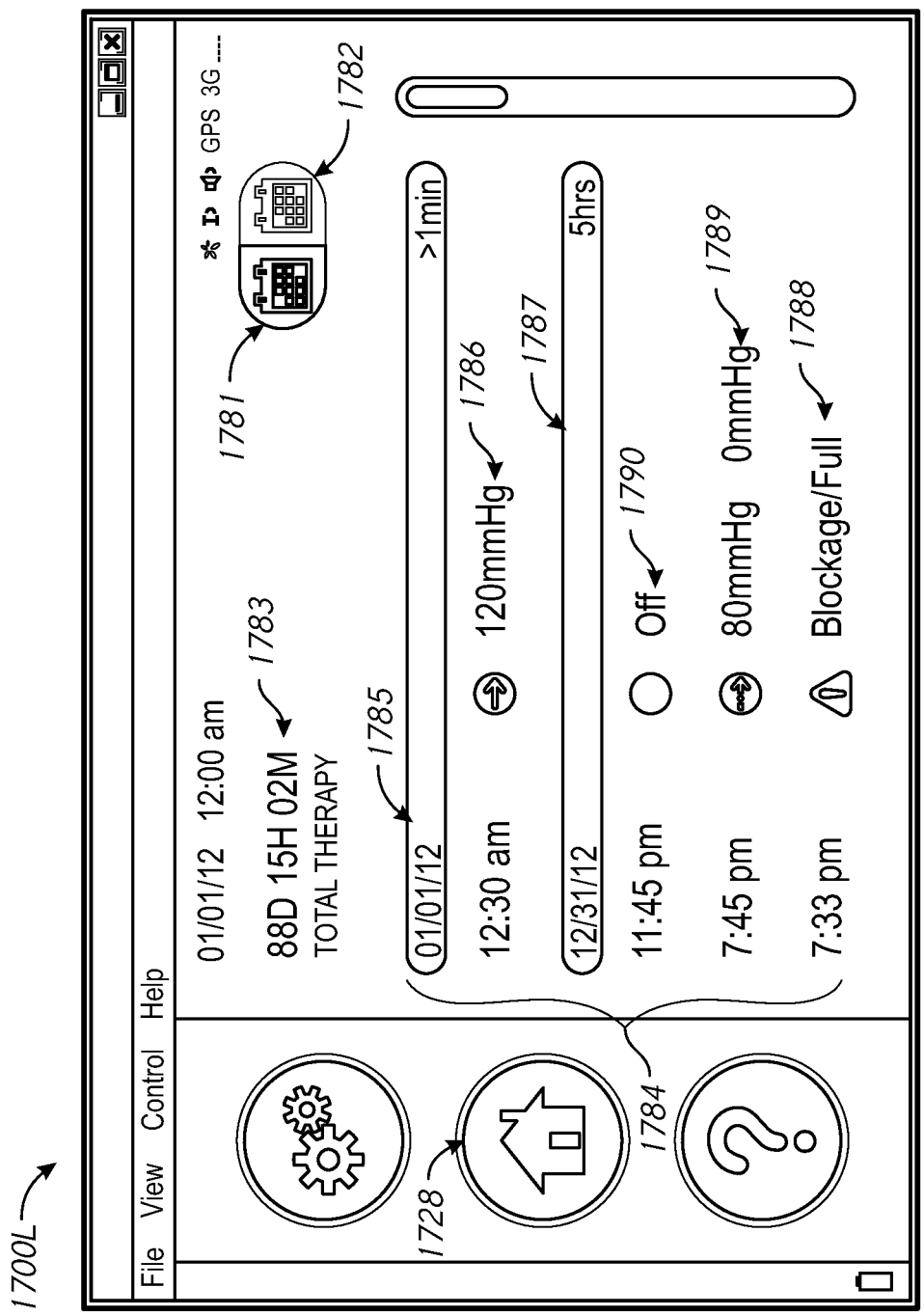
Figure 17M:
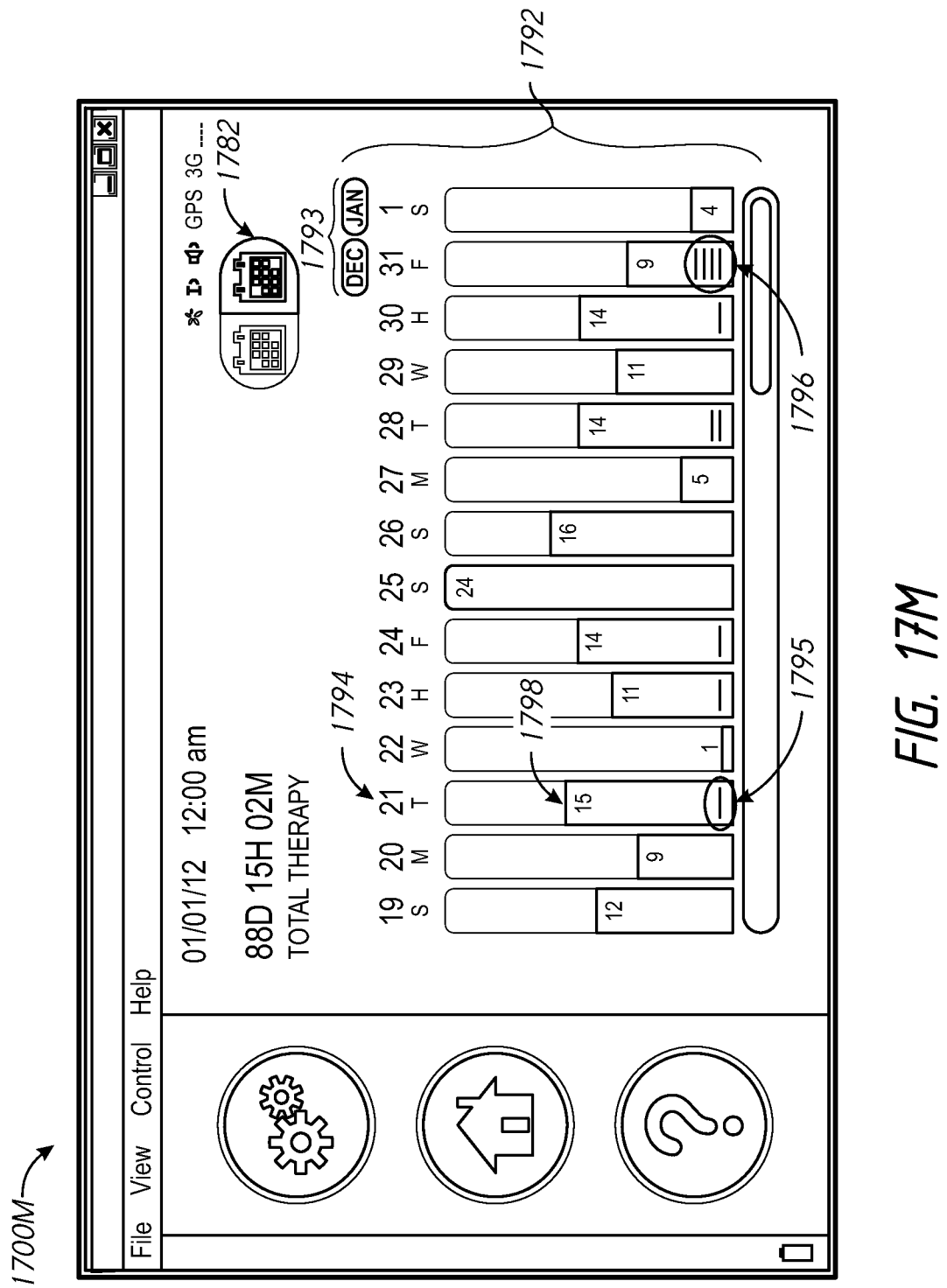
Figure 17N:
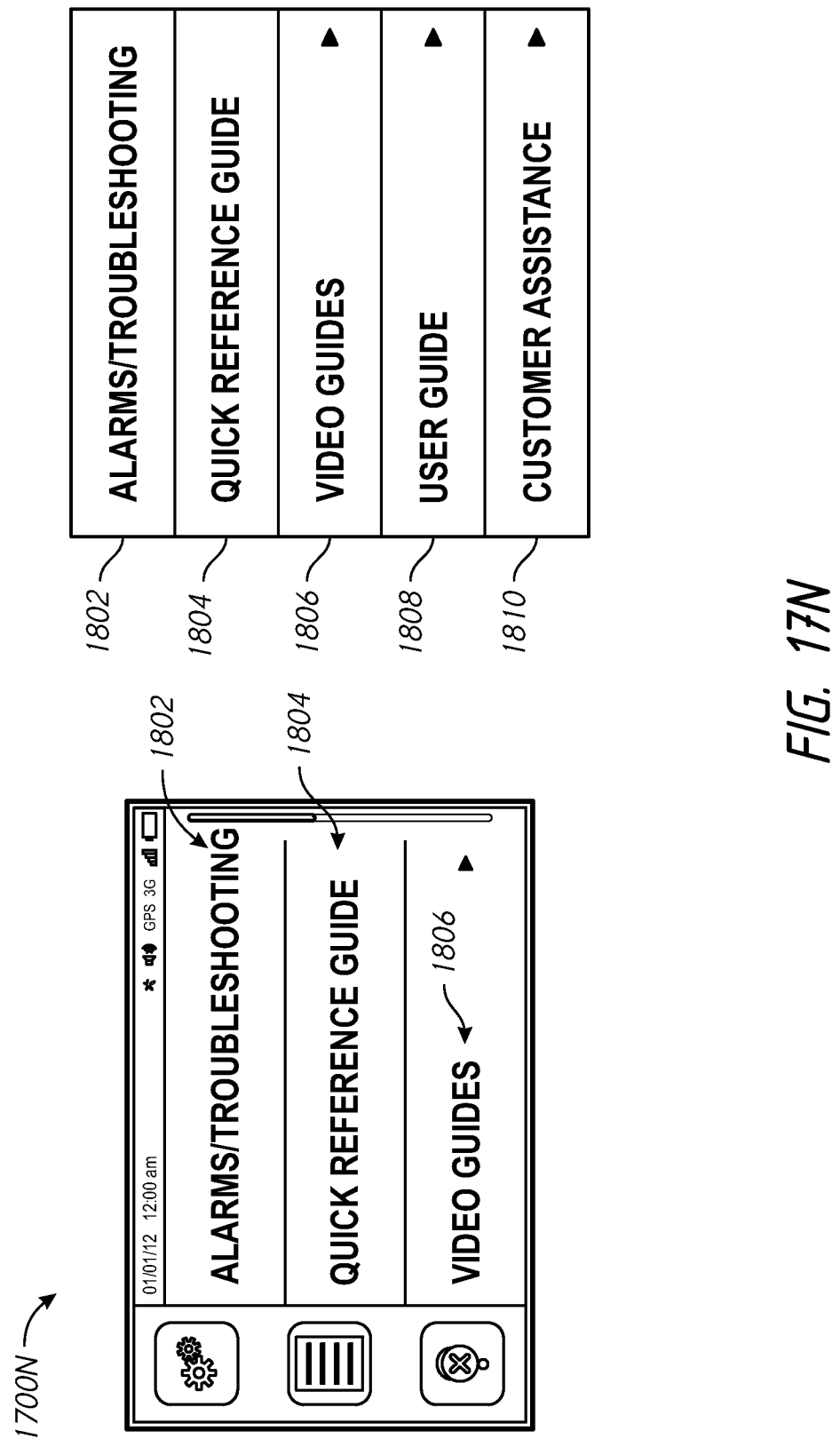
Figure 170:
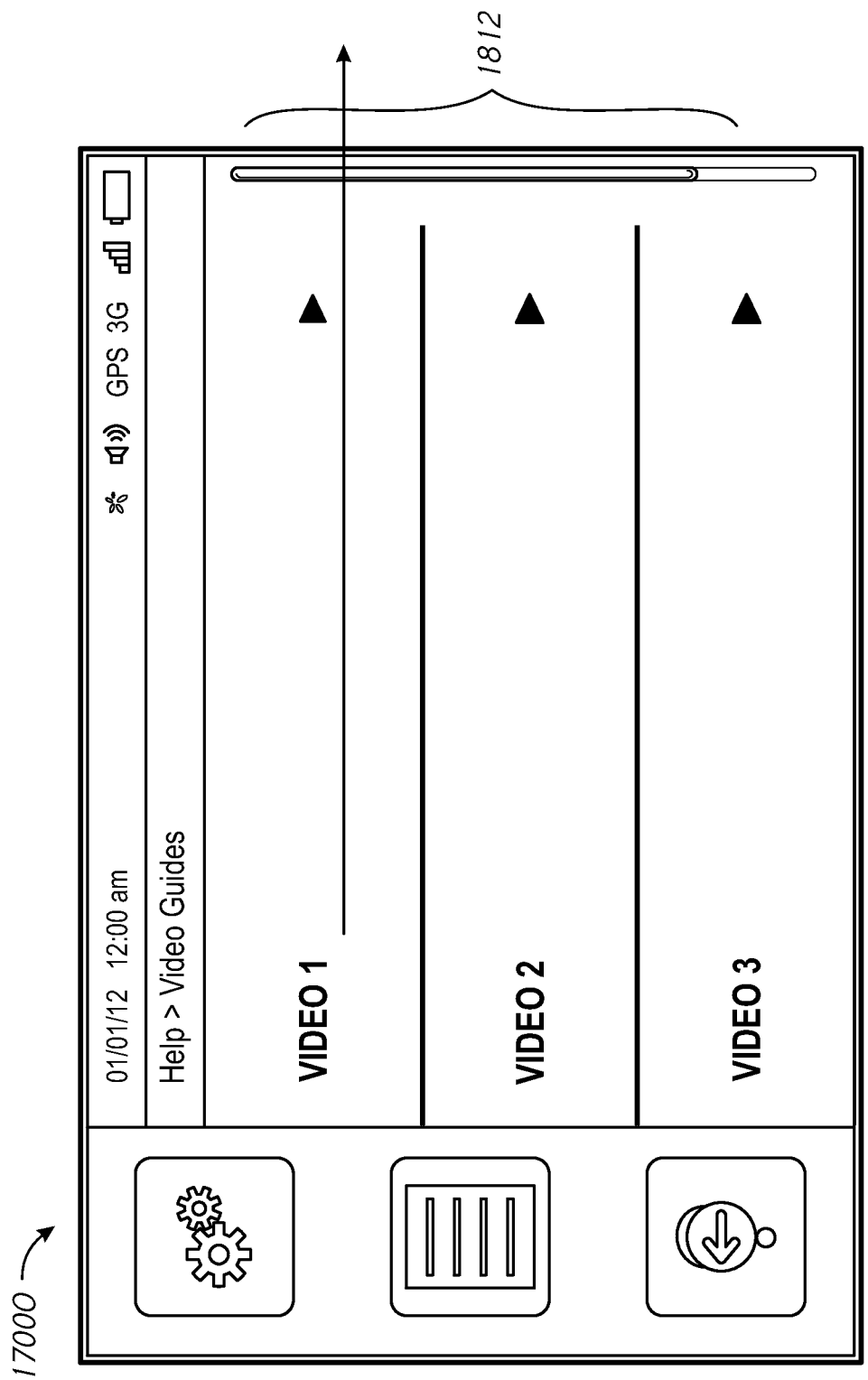
Figure 17P:
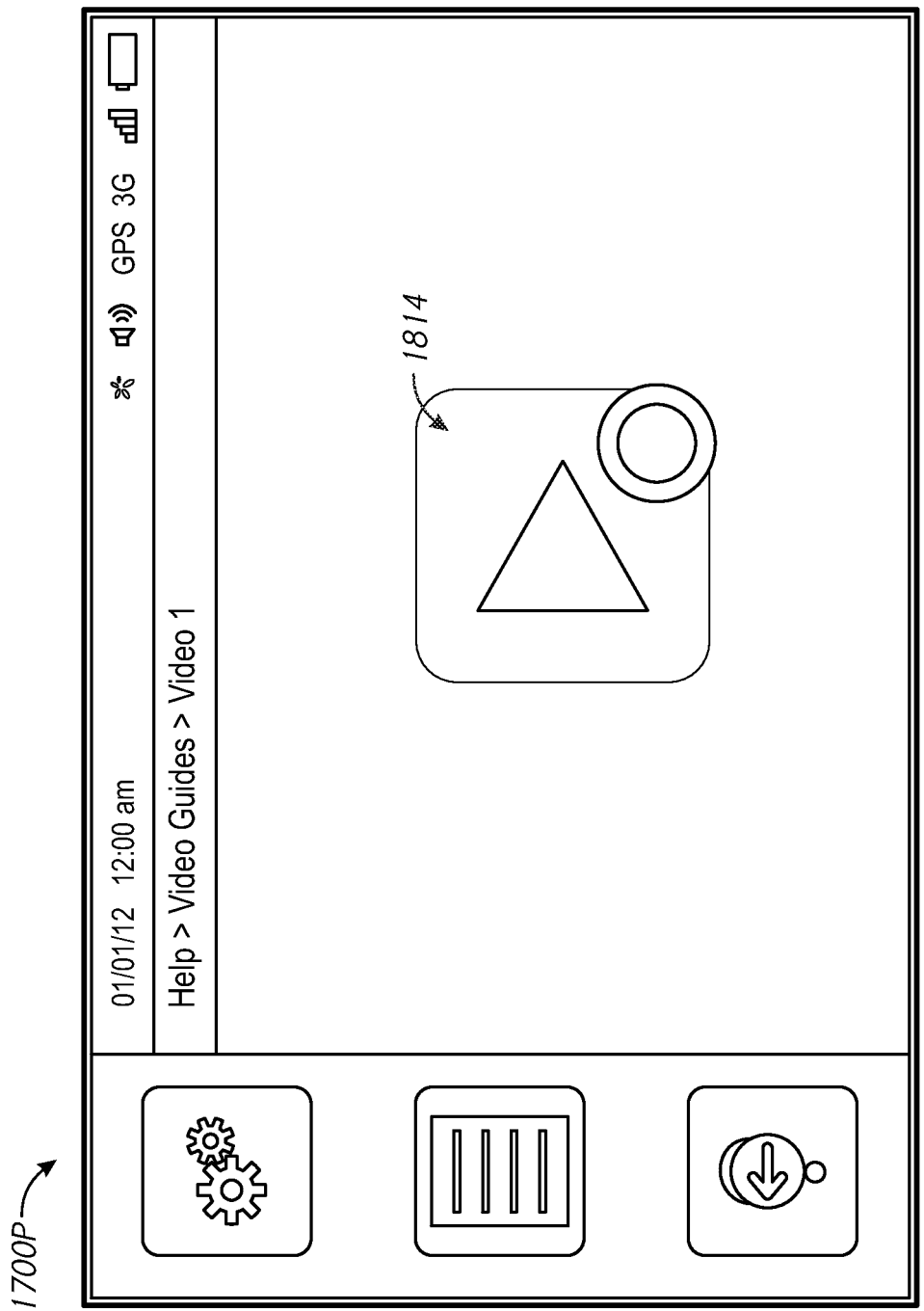
Figure 17Q:
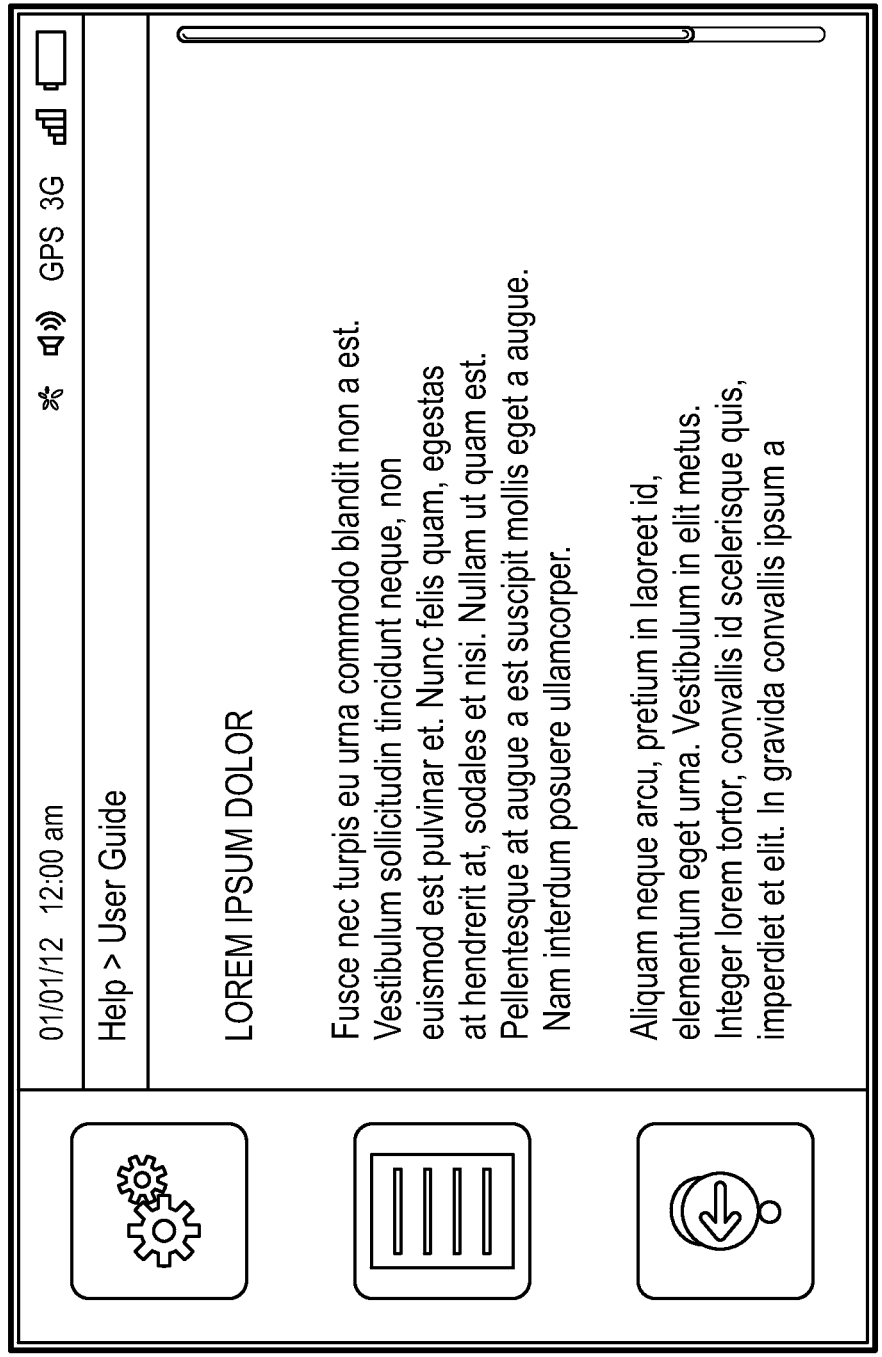
Figure 17R:
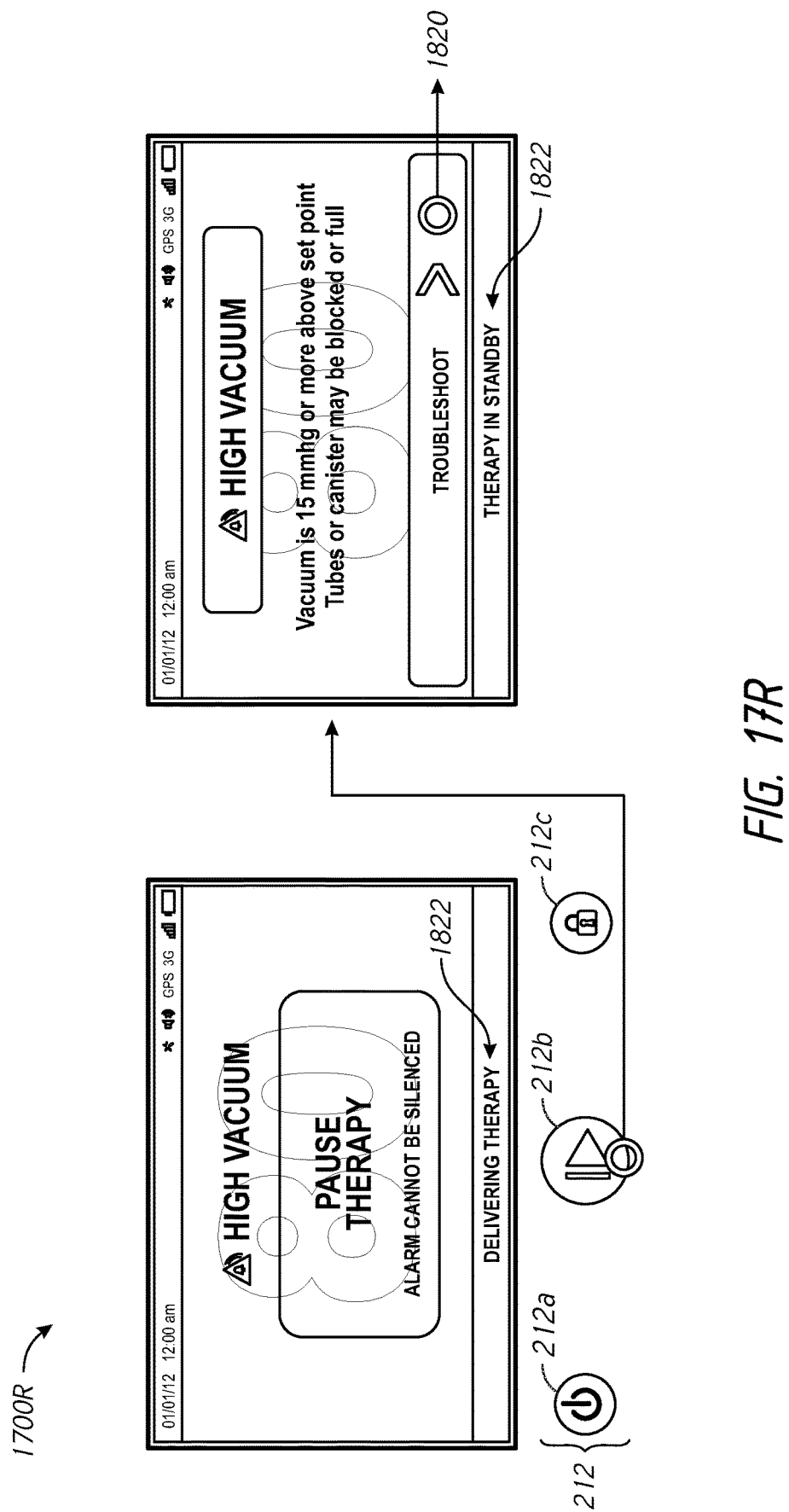
Figure 17S:
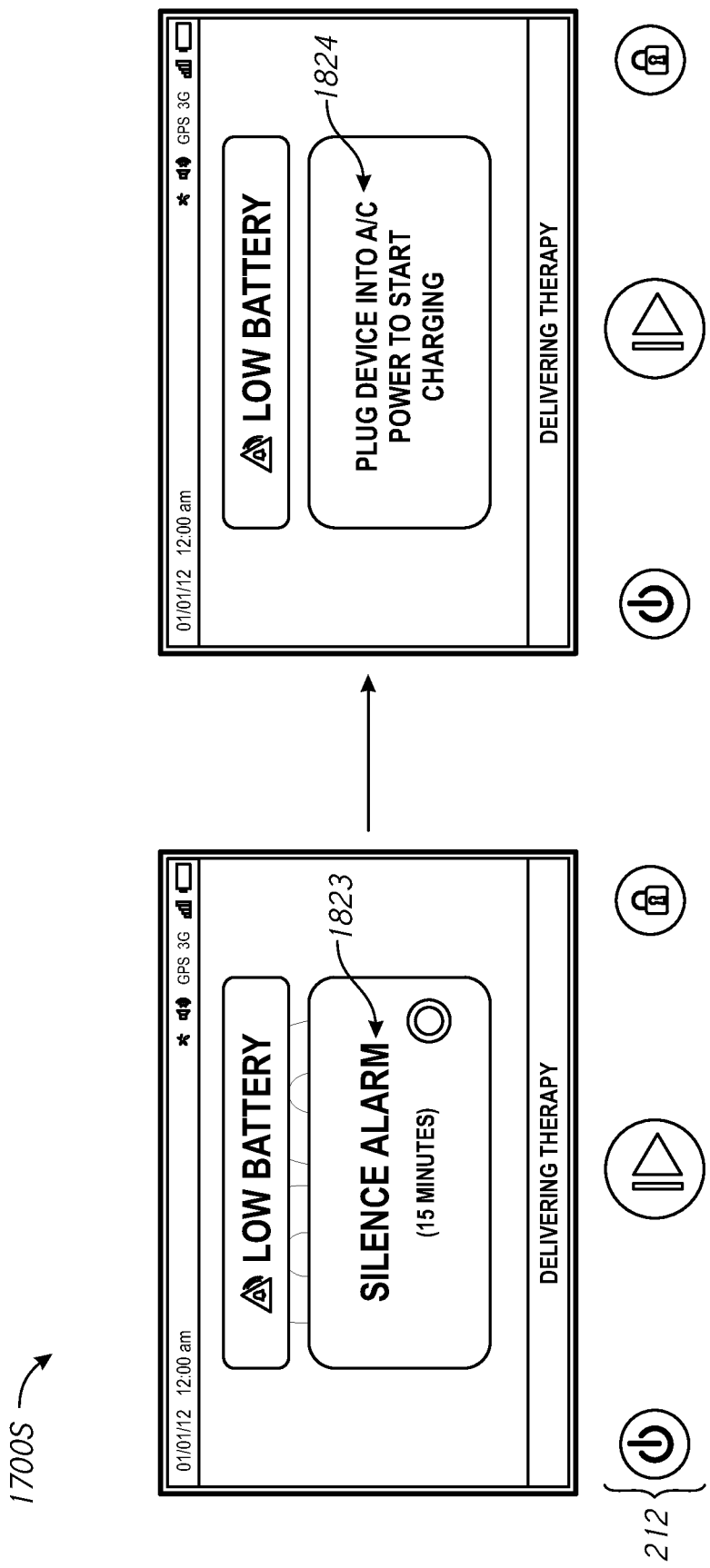
Figure 17T:
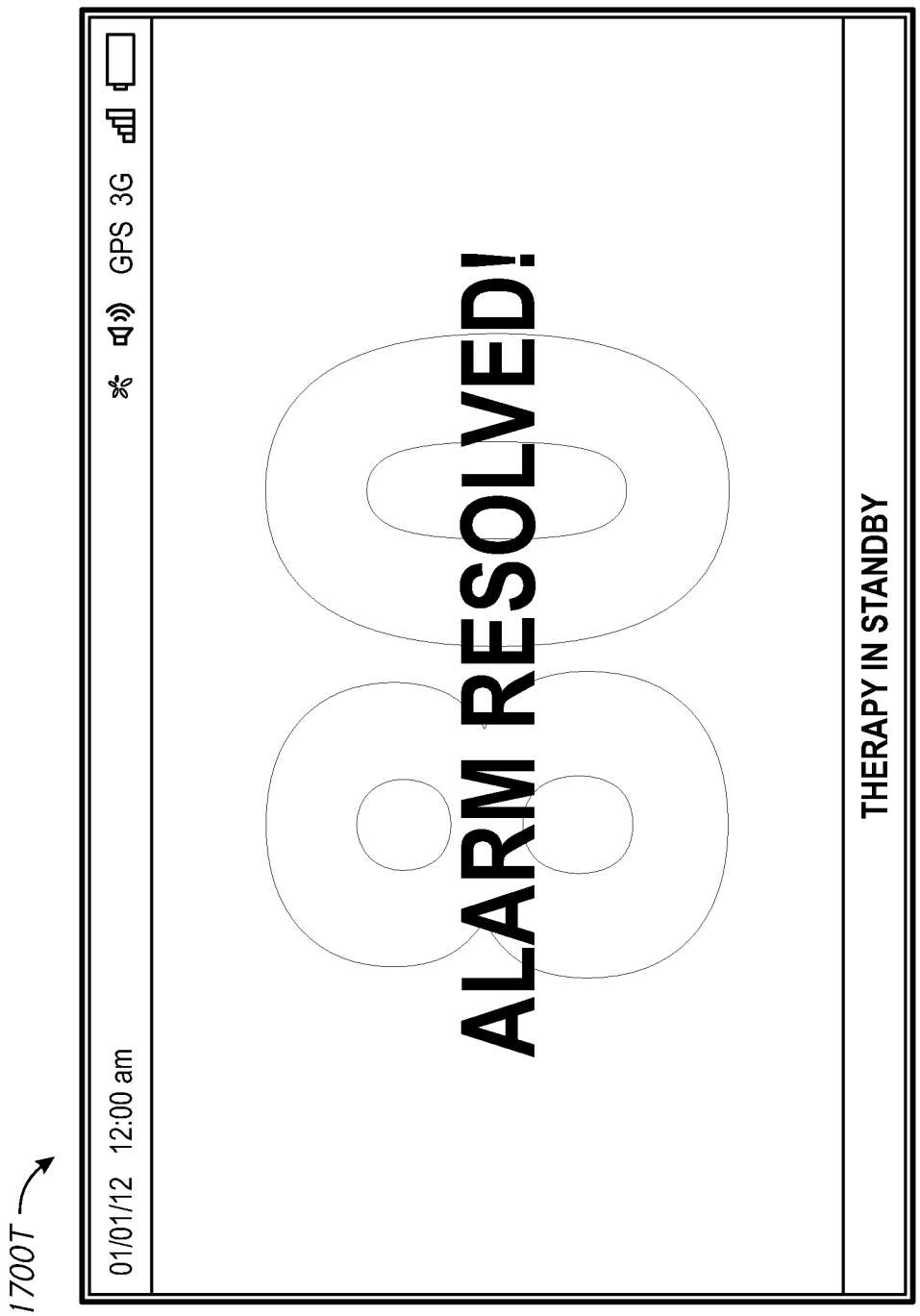
Figure 17U:
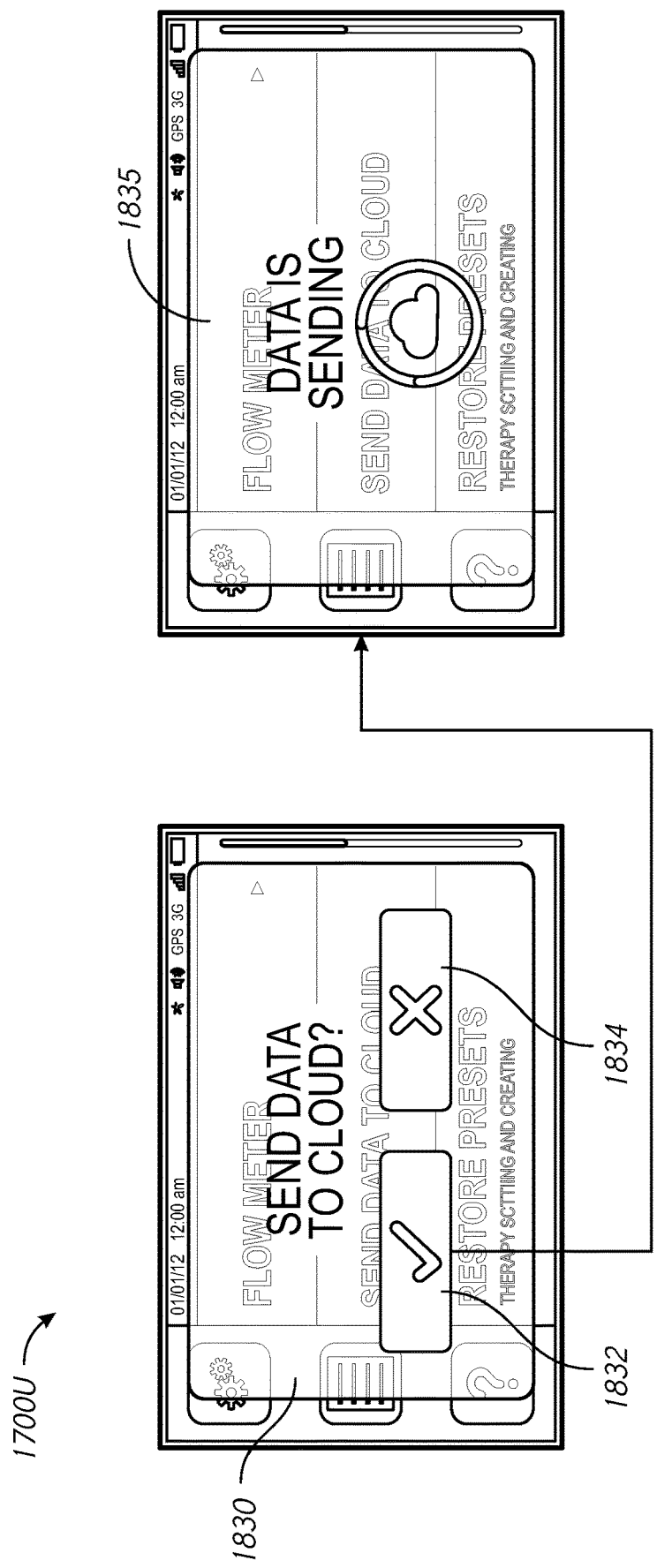
Figure 17V:
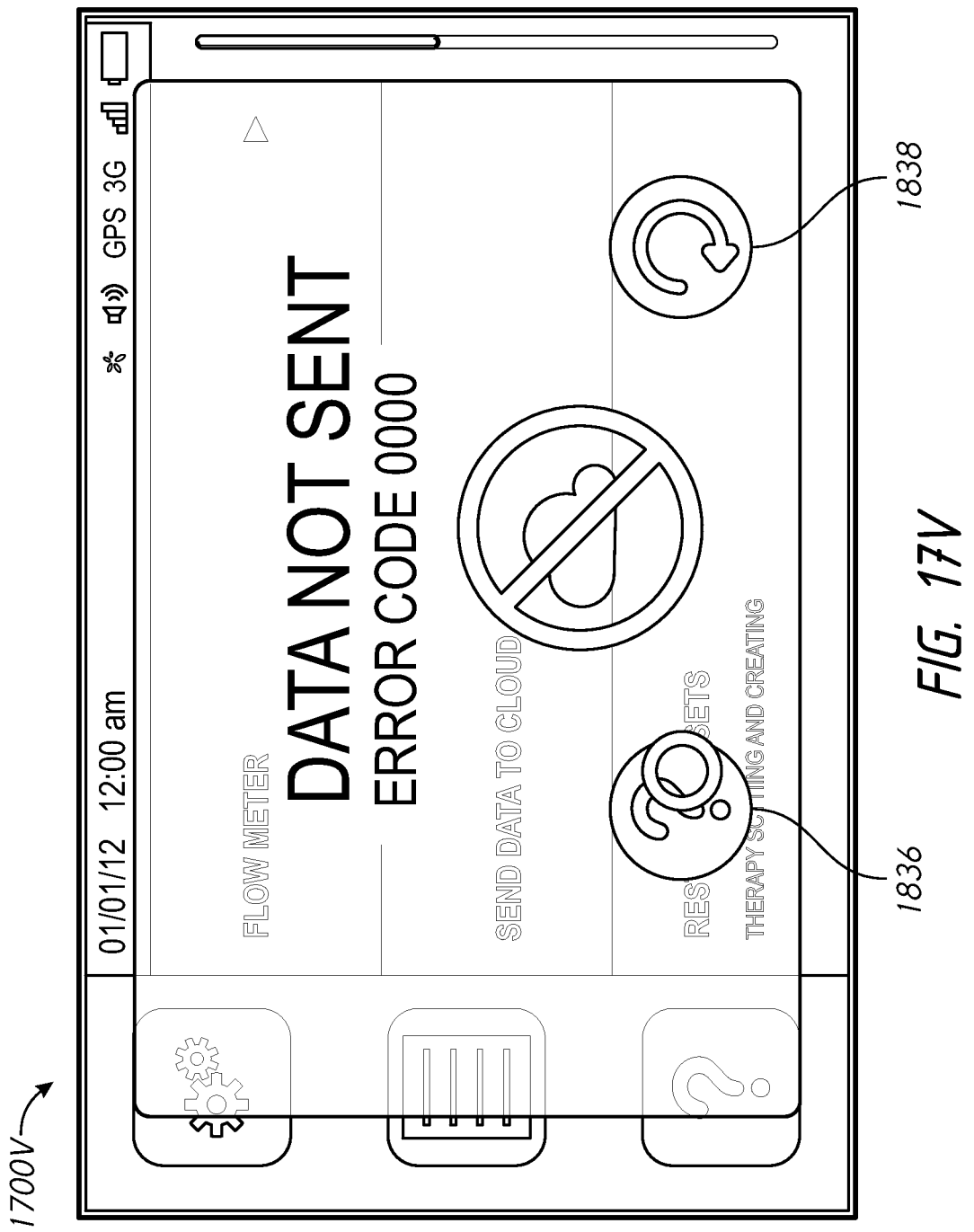

FIGS. 17A-17V illustrate graphical user interface (GUI) screens according to some embodiments. The GUI screens can be displayed on the screen 206, which can be configured as a touchscreen interface. Information displayed on the screens can be generated by and input received from the user can be processed by the processor 1410. The GUI screens can be utilized for initializing the device, selecting and adjusting therapy settings, monitoring device operation, uploading data to the cloud, and the like. Even though some of the screens 1700A-1700D include an outer Adobe Flash Player 10 window, the screens 1700A-1700D can be executed without Flash Player. In some embodiments, the screens 1700A-1700D can be generated directly by an operating system running on the processor 1410 and/or by a graphical user interface layer running on top of the operating system. For instance, the screens can be developed using Qt framework available from Digia.

FIGS. 17A-17D illustrated GUI screens 1700A-1700D for initializing the device according to various embodiments. In some embodiments, screens 1700A-1700D can be displayed when the device is powered on for the first time, after device reset, etc. Screen 1700A of FIG. 17A allows the user to select language in which the device will display and/or announce information to the user. The scroll bar 1702 allows the user to scroll through available languages. The user can select a desired language by pressing or tapping menu item 1701. After selecting the language, screen 1700B of FIG. 17B can be displayed to allow the user to select the time zone. The user can select the desired time zone by pressing menu item 1704. The user can return to the previous screen by pressing arrow 1703. In screen 1700C of FIG. 17C, the user can confirm the time zone selection by accepting it via button 1705 or rejecting it via button 1706. In screen 1700D of FIG. 17D, the user can complete the initialization by pressing the button 1707.

FIG. 17E illustrates a home screen 1700E according to some embodiments. The home screen 1700E can be displayed after the user has initialized the device. The home screen 1700E includes a status bar 1712 that comprises icons indicating operational parameters of the device. Animated icon 1713 is a therapy delivery indicator. In some embodiments, when therapy is not being delivered, icon 1713 is static and gray. When therapy is being delivered, icon 1713 turns orange and rotates (e.g., clockwise). Other status bar icons include volume indicator, and GPS and 3G connection indicator. The home screen includes a battery indicator 1716 for indicating battery charge level and date/time information 1718. The home screen 1700E includes a menu 1720 comprising menu items 1722 for accessing device settings, 1724 for accessing logs, 1726 for accessing help, and 1728 (see FIG. 17G) for returning to the home screen from other screens. In some embodiments, the device can be configured so that after a period of inactivity, such as not receiving input from the user, home screen 1700E is displayed.

The home screen 1700E includes therapy settings 1730 comprising negative pressure up and down controls 1732 and 1734 and scroll bar 1736 for adjusting the level of negative pressure. In some embodiments, up and down controls 1732 and 1734 adjust reduced pressure by a suitable step size, such as ±5 mmHg. As is indicated by label 1738, the current therapy selection is −80 mmHg. The home screen 1700E includes continuous/intermittent therapy selection 1740. Continuous therapy selection screen can be accessed via control 1742 and intermittent therapy selection screen can be accessed via control 1744. In certain embodiments, home screen 1700E illustrates continuous therapy selection screen. The home screen 1700E includes Y-connector selection 1745 for treating multiple wounds. Control 1746 selects treatment of a single wound, and control 1748 selects treatment of more than one wound by the device.

FIG. 17F illustrates home screen 1700F for selecting intermittent therapy according to some embodiments. Screen 1700F can be accessed via control 1744. Home screen 1700F includes intermittent therapy settings 1750 and 1755. As is illustrated by controls 1752, 1754, 1756, and 1758, current therapy selection is applying −80 mmHg for 5 minutes followed by 2 minutes of applying atmospheric pressure (or turning off the vacuum pump). Negative pressure levels and durations can be adjusted by selecting one of controls 1752, 1754, 1756, or 1758 and operating the up and down controls 1732 and 1736 or scroll bar 1736.

FIG. 17G illustrates settings screen 1700G according to some embodiments. Screen 1700G can be selected via menu item 1722. As is illustrated, wound volume 1760 can be adjusted (currently low wound volume corresponding to a small wound is selected), therapy intensity 1764 can be adjusted (currently low intensity is selected), and wound wizard 1768 can be activated (current selection is low/small). FIG. 17H illustrates wound volume selection screen 1700H, in which low volume (small wound) 1761, medium volume (medium wound) 1762, or high volume (large wound) 1763 can be selected. FIG. 17I illustrates therapy intensity selection screen 1700I, in which low intensity 1765, medium intensity 1766, or high intensity 1767 can be selected. In some embodiments, therapy intensity can be correspond to the volume of wound exudate and default negative pressure levels can be associated with various levels of therapy intensity. FIG. 17J illustrates wound wizard screen 1700J, in which small, low exudating wound 1769 can be selected, medium, moderately exudating wound 1770 can be selected, or large, high exudating wound 1771 can be selected. Therapy settings can be adjusted in accordance with user's selection of a wound type.

FIG. 17K illustrates a flow meter gauge screen 1700K according to some embodiments. The screen 1700K graphically indicates current leak rate in the system. The screen 1700K includes a dial 1775 with markings 1777, 1778, and 1779 and a gauge 1776. Low leak levels are illustrated by position of the gauge 1776. Higher leak rates may trigger an alarm.

FIG. 17L illustrates log screen 1700L for accessing therapy log data, alarm log data, and the like. The log screen 1700L can be selected via menu item 1724. The log screen 1700L includes therapy counter 1783 (e.g., relative to last device reset), log view selection controls 1781 and 1782, and log data viewer 1784. Control 1781 selects detailed view, and control 1782 selects overview presentation of log data. In some embodiments, screen 1700L illustrates detailed view of log data. Log data viewer 1784 illustrates events separated by calendar days 1785 and 1787. Calendar day 1785 shows that on Jan. 1, 2012, −120 mmHg of negative pressure therapy is being delivered starting at 12:30 am. Calendar day 1787 shows that on Dec. 31, 2012, the device experienced a blockage/canister full alarm at 7:33 pm (1788), at 7:45 pm intermitted therapy between −80 mmHg and atmospheric pressure (0 mmHg) was delivered (1789), and that delivery of the therapy was stopped at 11:45 pm (1790).

FIG. 17K illustrates log data overview screen 1700M according to some embodiments. The screen 1700M can be selected via control 1782. The overview screen 1700M includes a graph 1792 displaying log data corresponding to calendar days. Desired month can be selected using controls 1793. Bars, such as 1798, graphically illustrate therapy delivery time corresponding to a calendar day 1794. For example, on December 21 (1794) 15 hours of therapy (1798) was delivered. In addition, alarm events are indicated by lines on the bars, such as lines 1795 and 1796. In some embodiments, pressing or tapping on a particular bar, such as bar 1798, can bring up a detailed view (not shown) of logged events for the corresponding day.

FIG. 17N illustrates help screen 1700N according to some embodiments. The main help screen 1700N can be accessed via control 1726. Help screen 1726 includes a menu of help items for alarms/troubleshooting 1802, reference guide 1804, video guides 1806, user guide 1808, and customer assistance 1810. Each of these items can be selected by pressing on a corresponding control. FIG. 17O illustrates video guides screen 1700O, which can be accessed via control 1806. The screen 1700O includes a list of videos, such as instructional videos for operating the device and/or system. Videos, reference guides, user guides, and the like can be stored in the device memory (e.g., memory 1450), downloaded and/or streamed from a network using a wired or wireless connection. In some embodiments, a list of available videos, reference guides, user guides, etc. is downloaded from a remote server and, in response to the user selecting a particular video or guide for viewing, the selected material is downloaded from the network and/or streamed over the network. A desired video can be selected and viewed, as shown in screen 1700P of FIG. 17P. The selected video can be viewed, paused, stopped, etc. by operating control 1814. FIG. 17Q illustrates a user guide screen 1700Q, which can be accessed via control 1808. User can scroll through information displayed in the screen 1700Q.

FIG. 17R illustrates alarm screens 1700R according to some embodiments. For example, during therapy delivery the device can detect high vacuum condition (e.g., high levels of vacuum are being applied to the wound cavity 110). The device can display a high vacuum alarm as is shown in the left screen of FIG. 17R indicting that high vacuum was detected while delivering therapy (information bar 1822). Because in certain embodiments such alarm cannot be silenced, therapy is paused, as is indicated by information bar 1822 shown on the right screen in FIG. 17R. This screen is displayed after the user presses therapy pause button 212*b* as prompted by the screen on the left side of FIG. 17R. User can troubleshoot the system by selecting control 1820. If troubleshooting is successfully perform (e.g., leak is mitigated or eliminated), the device can display screen 1700T of FIG. 17T, and user can restart delivery of therapy.

FIG. 17S illustrates alarm screens 1700S according to certain embodiments. A low battery alarm is illustrated. In some embodiments, this alarm can be silenced for a period of time, during which delivery of therapy is being continued. The user can silence the alarm by selecting control 1823. Message 1824 can then be displayed alerting the user to charge the battery.

FIGS. 17U-17V illustrate data upload screens according to some embodiments. As is shown in screens 1700U, user can access data upload window 1830, which includes data upload controls 1832 (for starting the upload) and 1834 (for cancelling). If the user selects control 1832, message 1835 is displayed to the user indicating the data is being sent to the remote computer. If upload is successful, a confirmation screen (not shown) can be displayed. Such conformation screen can automatically fade away after a period of time. However, if the upload is not successful, screen 1700V of FIG. 17V can be displayed. The user can retry the upload by selecting control 1838 or access upload troubleshooting information by selecting control 1836.

Figure 18:
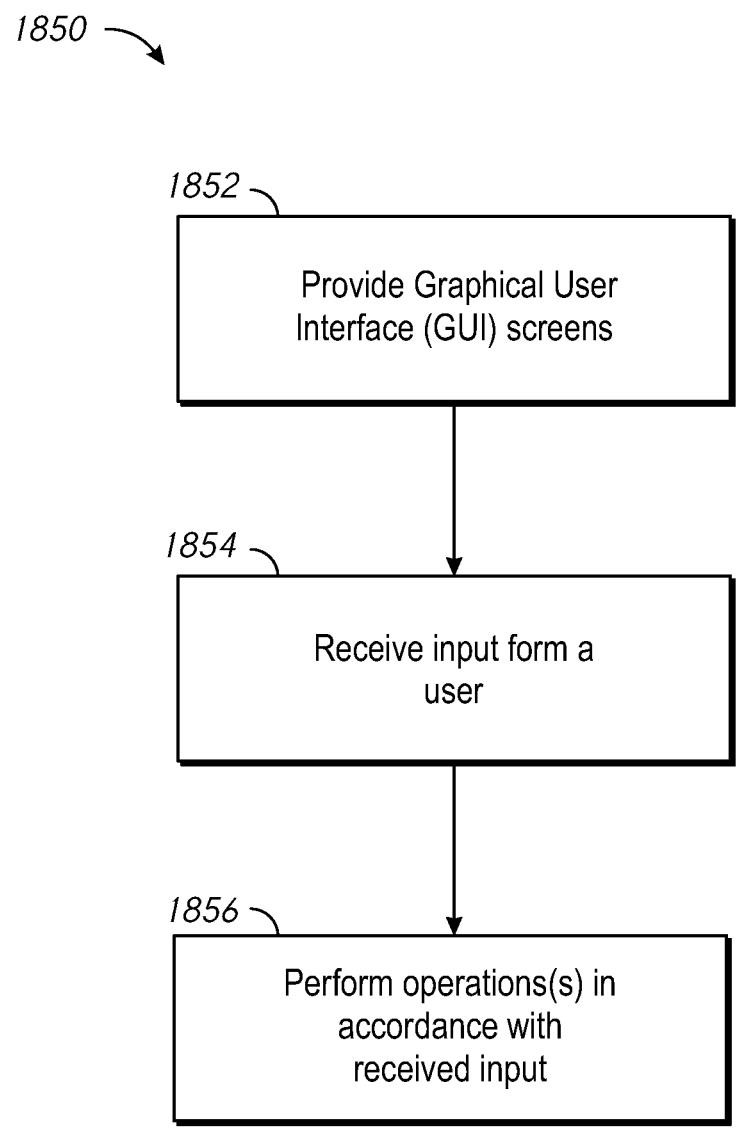
FIG. 18 illustrates a process of operating a device according to some embodiments.

FIG. 18 illustrates a process 1850 of operating a device according to some embodiments. The process 1850 can be executed by the processor 1410. In block 1852, the process 1850 provides GUI screens to the user. In block 1854, the process 1850 receives input from the user. In block 1856, the process 1856 performs one or more operations in accordance with input received from the user.

Flow Rate Monitoring

Some embodiments of the system monitor and/or determine a rate of flow of fluid in the system. In certain embodiments, flow rate monitoring can be performed by the pump control processor 1470 alone or in combination with the processor 1410. Monitoring the flow rate can be used, among other things, to ensure that therapy is properly delivered to the wound, to detect blockages, canister full conditions, and/or leaks in the fluid flow path, high pressure, ensure that the flow rate is not unsafe (e.g., dangerously high), etc.

In some embodiments, the system performs flow rate monitoring by measuring and/or monitoring speed of vacuum pump motor, such as, by using a tachometer. The pump control processor 1470 can continuously monitor voltage and/or current at which the pump is being driven using the tachometer feedback from the pump. Tachometer feedback can be used to determine the pump speed. If pump speed falls below a threshold value over a particular period of time, such as 2 minutes, it can be determined that a blockage is present in the flow path. The blockage can be due to a blockage in a tube or lumen, canister being full, etc. An alarm can be triggered and the system can wait for the user to take one or more actions to resolve the blockage.

In various embodiments, tachometer can be read periodically, such as every 100 msec, and periodic readings made over a time duration, such as 32 sec, can be combined (e.g., averaged). Combined tachometer readings can be used for leak detection, blockage detection, limiting the maximum flow rate, etc. Combined tachometer readings (e.g., in counts) can be converted to a flow rate (e.g., in mL/min) using one or more conversion equations and/or tables so that a current flow rate is determined. In some embodiments, the flow rate is determined according to the following equation:

$$FR=C_1*F*P+C_2$$

where FR is the flow rate, F is the frequency of the pump tachometer signal, P is pressure produced by the pump, and $C_1$ and $C_2$ are suitable constants. The determined flow rate can be compared to various flow rate thresholds, such as blockage threshold, leakage threshold, and maximum flow rate threshold, to determine a presence of a particular condition, such as a blockage, leakage, over-vacuum.

In some embodiments, a blockage condition is detected when the determined flow rate falls below a blockage threshold. A blockage alarm can be enabled if the blockage condition is present for a period of time, such as 30 seconds. The blockage alarm can be disabled when the determined flow rate exceeds the blockage threshold. In some embodiments, the system can differentiate between a blockage in a tube or lumen and canister full conditions. In some embodiments, a leakage condition is detected when the determined flow rate exceeds a leakage threshold. A leakage alarm can be enabled if the leakage condition is present for a period of time, such as 30 seconds. The leakage alarm can be disabled when the detected flow rate exceeds the leakage threshold. In some embodiments, in order to prevent an over-vacuum condition, a maximum flow rate is imposed, such as 1.6 liters/min. Pump drive signal, such as voltage or current signal, can be limited not exceed this flow rate threshold.

In certain embodiments, one or more pressure sensors can be placed in suitable locations in the fluid flow path. Pressure measured by the one or more sensors is provided to the system (e.g., pump control processor 1470) so that it can determine and adjust the pump drive signal to achieve a desired negative pressure level. The pump drive signal can be generated using PWM. Additional details of flow rate detection and pump control are provided in U.S. patent application Ser. No. 13/589,021, which is assigned to the assignee of the present application is incorporated by reference in its entirety.

In some embodiments, flow rate monitoring is performed by measuring flow through a flow restrictor placed in a portion of the fluid flow path. In certain embodiments, flow restrictor 278 illustrated in FIG. 2F can be used. The flow restrictor can be calibrated such that it can be used to reliably monitor flow rate for different types of wounds, dressings, and operating conditions. For example, a high precision silicon flow restrictor can be used. The flow restrictor can be located at any suitable location in the flow path, such as between the source of the negative pressure and the canister, such as upstream of the source of the negative pressure and downstream of the canister. A differential pressure sensor or two pressure sensors can be used to measure a pressure drop across the flow restrictor. For example, as explained above in connection with FIG. 2F, the pressure drop across the flow restrictor 278 can be measured using sensors 282 and 284. In certain embodiments, if the pressure drop falls below a pressure differential threshold, which indicates low flow, the measured flow rate is compared to a flow rate threshold. If the measured flow rate falls below the flow rate threshold, blockage condition is detected. Additional details of blockage detection are provided in U.S. Patent Publication No. 2011/0071483, which is assigned to the assignee of the present application is incorporated by reference in its entirety. In some embodiments, the measured flow rate is compared to a leakage threshold. If the measured flow rate exceeds the leakage threshold, a leak is detected. Additional details of leakage detection are provided in U.S. Pat. No. 8,308,714, which is assigned to a subsidiary of the assignee of the present application and is incorporated by reference in its entirety.

Figure 19A:
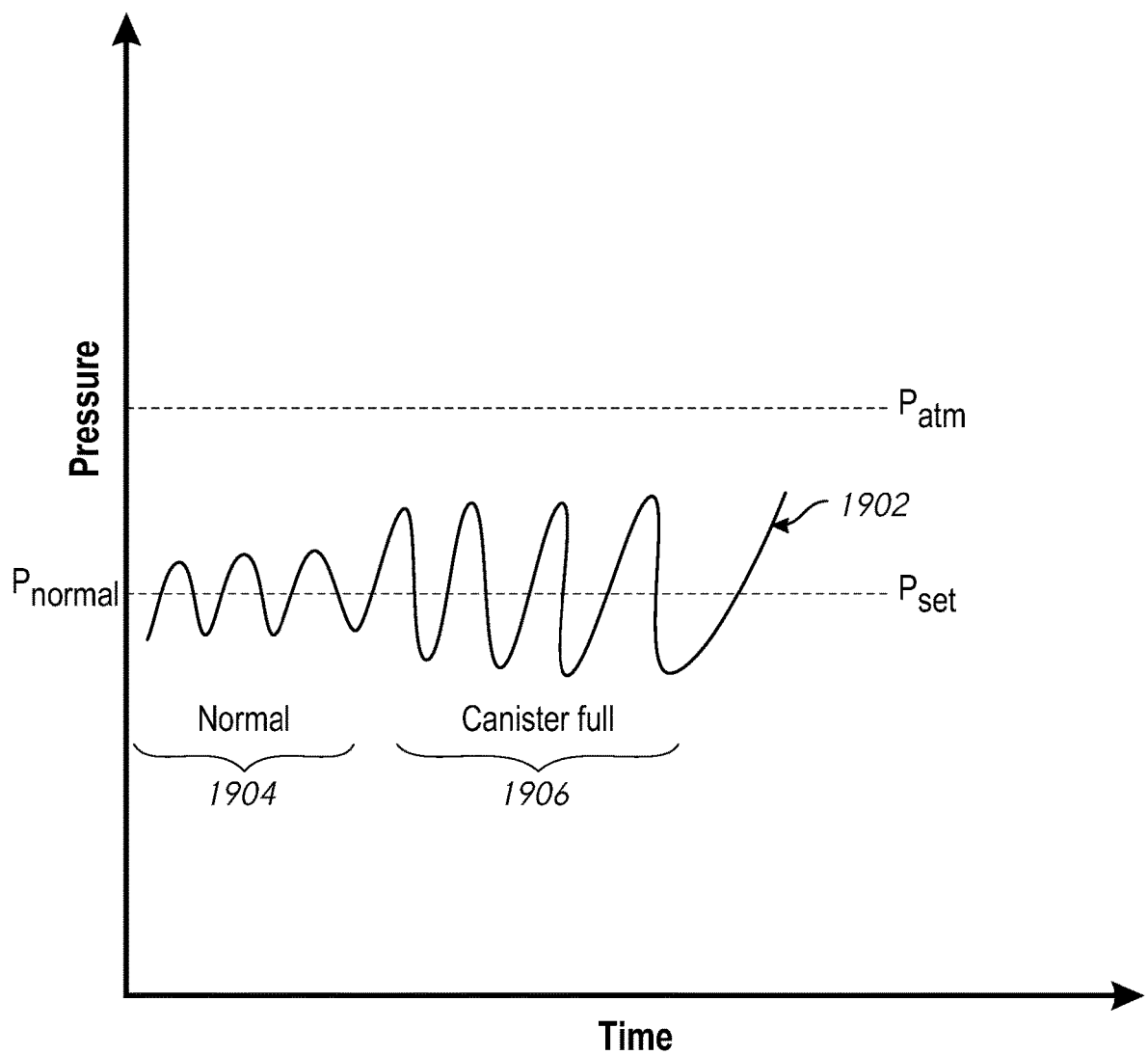
FIGS. 19A-19B illustrate graphs of pressure pulses according to some embodiments.

In some embodiments, blockages and presence of fluid in one or more tubes or lumens are detected by processing data from one or more pressure sensors, such as sensors 280, 282, and 284. This detection can be enhanced by changing one or more settings of the vacuum pump, such as increasing vacuum level delivered by the pump, decreasing the vacuum level, stopping the pump, changing the pump speed, changing a cadence of the pump, and the like. In some embodiments, as the pump operates, it generates pressure pulses that are propagated through the fluid flow path. The pressure pulses are illustrated in the pressure curve 1902 of FIG. 19A according to some embodiments. Region 1904 illustrates pressure pulses detected during normal operation of the system, and region 1906 illustrates pressure pulses detected when canister becomes full. As is illustrated, canister blockage causes a reduced volume to be seen upstream of the canister, and the amplitude of the pressure pulses increases. In certain embodiments, this change or "bounce" in the pressure pulse signal can be magnified or enhanced by varying the pump speed, varying the cadence of the pump, such as by adjusting PWM parameters, and the like. Such adjustments of pump operation can be performed over a short time duration and the changes can be small such that the operation of the system remains relatively unaffected.

Figure 19B:
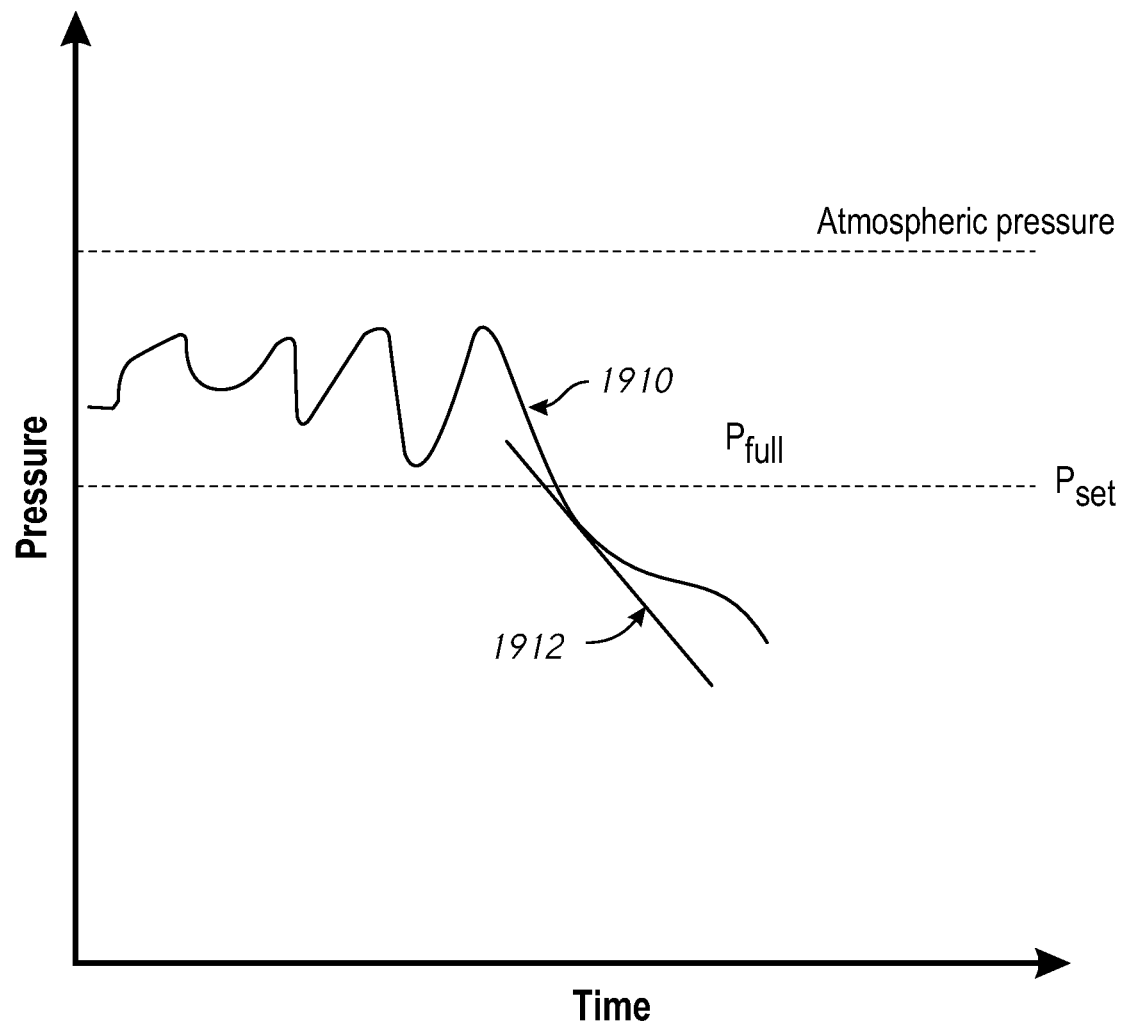

In some embodiments, the increase in the amplitude of pressure pulses (region 1906) can be detected and compared to a blockage threshold in order to determine whether a blockage condition exists. In certain embodiments, the frequency, rate of change of the amplitude (or slope), rate of change of the frequency, etc. of the pressure pulse signal can be monitored in place of or in addition to monitoring the amplitude. For example, curve 1910 of FIG. 19B illustrates pressure sensed by a pressure sensor downstream of the canister filter. As is shown, small or no pressure pulses are detected when the canister filter becomes blocked. A large negative change in the detected pressure signal is observed, as is illustrated by the slope 1912. In some embodiments, signal processing techniques can be utilized, such as converting the detected pressure pulse signal into frequency domain, for example by using the Fast Fourier Transform (FFT), and analyzing the pressure pulse signal in the frequency domain. Additional details of flow rate detection are described in U.S. Patent Publication No. 2012/0078539, which is assigned to the assignee of the present application is incorporated by reference in its entirety.

Figure 20:
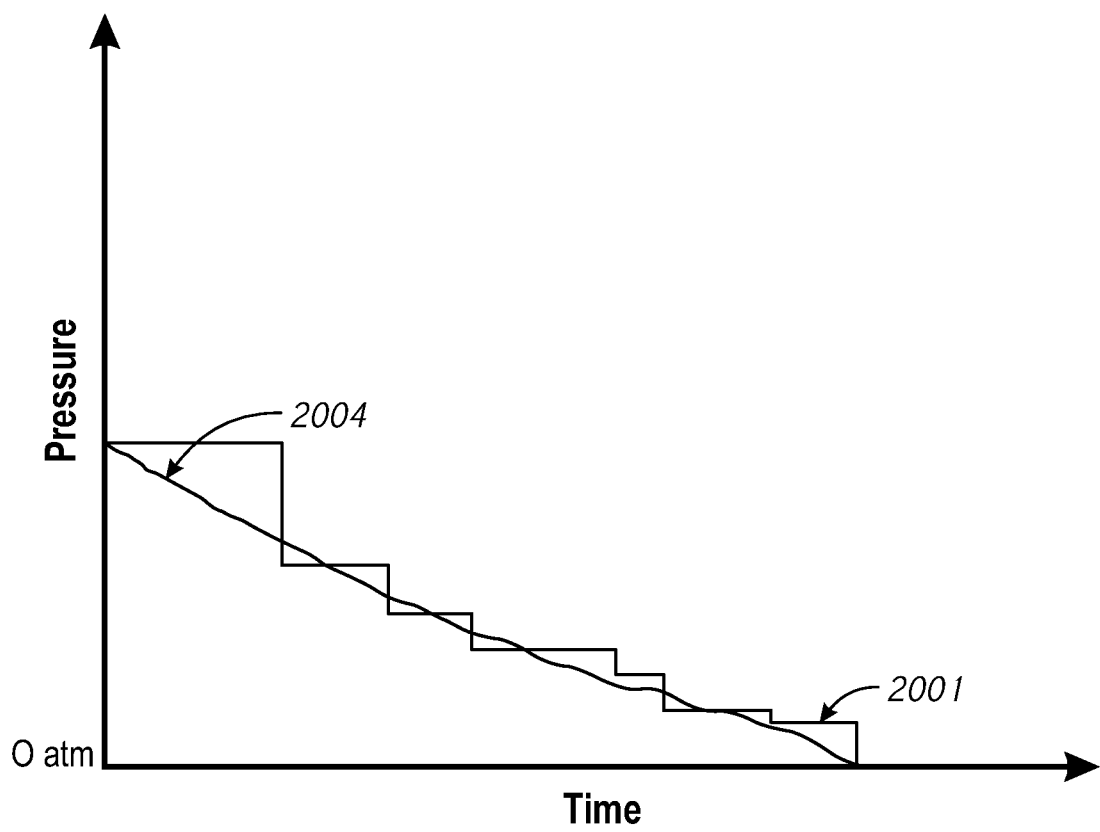
FIG. 20 illustrates a graph of vacuum level according to some embodiments.

In some embodiments, temporary blockages caused by slugs of fluid in tubes or lumens are detected by turning off the pump and monitoring the pressure change in the fluid flow path. The pump can be turned off for a short duration of time as to not affect the operation of the system. Presence of temporary blockages in the system due to slugs of fluid can cause vacuum level to decline in a discontinuous "stair and risers" pattern, such as that illustrated by curve 2002 of FIG. 20. This discontinuous decaying pattern is due to slugs of fluid moving through the fluid flow path and arriving at the canister inlet, which can suddenly change the volume seen by the pressure sensor (and the pump). When slugs of fluid are not present, a more continuous decaying pattern, such as illustrated in curve 2004, is observed. In certain embodiments, when the pattern illustrated in curve 2002 is detected, the system can increase the level of vacuum produced by the pump to clear the slugs.

In some embodiments, one or more flow sensors and/or flow meters can be used to directly measure the fluid flow. In some embodiments, the system can utilize one or more of the above flow rate monitoring techniques. The system can be configured to suitably arbitrate between flow rates determined using multiple flow rate monitoring techniques if one or more such techniques are executed in parallel. In certain embodiments, the system execute one of the techniques, such as the flow rate determination based on the pump speed, and utilize one or more other techniques as needed. In various embodiments, the system can utilize one or more other techniques in cases the determine flow rate is perceived to be inaccurate or unreliable.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated and/or disclosed may differ from those shown in the figures. Depending on the embodiment, certain of the steps described above may be removed, others may be added. For example, the actual steps and/or order of steps taken in the disclosed processes may differ from those shown in the figure. Depending on the embodiment, certain of the steps described above may be removed, others may be added. For instance, the various components illustrated in the figures may be implemented as software and/or firmware on a processor, controller, ASIC, FPGA, and/or dedicated hardware. Any disclosed hardware component or module can include logic circuitry. Furthermore, the features and attributes of the specific embodiments disclosed above may be combined in different ways to form additional embodiments, all of which fall within the scope of the present disclosure.

User interface screens illustrated and described herein can include additional and/or alternative components. These components can include menus, lists, buttons, text boxes, labels, radio buttons, scroll bars, sliders, checkboxes, combo boxes, status bars, dialog boxes, windows, and the like. User interface screens can include additional and/or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

What is claimed is:

1. An attachment system for mounting a negative pressure wound therapy pump, the attachment system comprising:
   a cradle comprising a back portion, a first side portion extending away from the back portion in a first direction, and a second side portion extending away from the back portion in the first direction, the cradle being configured to receive a negative pressure wound therapy pump between at least the first side portion and the second side portion;
   a first recess formed in the first side portion, the first recess comprising an open upper portion configured to slidably receive a first portion of the negative pressure wound therapy pump therein from above the first recess;
   a second recess formed in the second side portion, the second recess comprising an open upper portion configured to slidably receive a second portion of the negative pressure wound therapy pump therein from above the second recess;
   a clamp support projection extending away from the back portion of the cradle;
   a first clamp arm coupled with the cradle; and
   a second clamp arm configured to move along the clamp support projection relative to the first clamp arm between a clamped position and an unclamped position, the first clamp arm and the second clamp arm being configured to attach the cradle to a structure when the second clamp arm is in the clamped position;
   wherein:
      the open upper portion of the first recess is configured to receive the first portion of the negative pressure wound therapy pump therein from above the cradle when the cradle is in an operable position by at least lowering the first portion of the negative pressure wound therapy pump in a downward direction into the first recess;

the first recess formed in the first side portion has a wall portion that is configured to overlap with and block the first portion of the negative pressure wound therapy pump engaged with the first recess from moving in the first direction;

the open upper portion of the second recess is configured to receive the second portion of the negative pressure wound therapy pump therein from above the cradle when the cradle is in an operable position by at least lowering the second portion of the negative pressure wound therapy pump in a downward direction into the second recess; and the second recess formed in the second side portion has a wall portion that is configured to overlap with and block the second portion of the negative pressure wound therapy pump engaged with the second recess from moving in the first direction.

2. The attachment system of claim 1, wherein the back portion, the first side portion, the second side portion, and the clamp support projection are monolithically formed from plastic.

3. The attachment system of claim 1, wherein the first and second recesses are configured to prevent incorrect placement of the negative pressure wound therapy pump within the cradle.

4. The attachment system of claim 1, wherein the structure comprises a pole or a rail.

5. The attachment system of claim 1, wherein the negative pressure wound therapy pump is configured to be fluidically connected to a wound dressing, and the wound dressing is configured to be placed over a wound and to create a substantially fluid impermeable seal over the wound.

6. The attachment system of claim 1, further comprising a knob configured to move the second clamp arm between the clamped position and the unclamped position.

7. The attachment system of claim 1, wherein the cradle comprises a bumper positioned on a surface of the cradle, the bumper being configured to face the negative pressure wound therapy pump, wherein the bumper comprises an elastic material.

8. The attachment system of claim 1, wherein the back portion, the first side portion, and the second side portion are monolithically formed.

9. The attachment system of claim 1, wherein the first recess is formed on an inside surface of the first side portion and the second recess is formed on an inside surface of the second side portion such that the first recess faces the second recess.

10. The attachment system of claim 1, comprising a first screw having threads on an outside thereof and a second screw configured to cause the second clamp arm to move along the clamp support projection when the second screw is rotated, wherein the second screw has an opening therein that is threaded and configured to engage with the threads on the outside of the first screw.

11. A system for applying negative pressure to a wound, comprising a negative pressure wound therapy pump and the attachment system of claim 1.

12. An attachment system for mounting a negative pressure wound therapy device, the attachment system comprising:

a cradle comprising a plurality of recesses each comprising an open upper portion configured to receive a plurality of protrusions of the negative pressure wound therapy device therein from above the cradle when the cradle is in an operable position by at least lowering the plurality of protrusions of the negative pressure wound therapy pump in a downward direction into the plurality of recesses, the cradle being configured to selectively secure at least one of the plurality of protrusions within at least one of the plurality of recesses so that the cradle is removably attached to the negative pressure wound therapy device;

a first clamp arm attached to the cradle; and a second clamp arm configured to move between a clamped position and an unclamped position, the first clamp arm and the second clamp arm being configured to attach the cradle to a structure when the second clamp arm is in the clamped position;

wherein:

the plurality of recesses comprises a first recess and a second recess;

the first recess is formed in a first surface of the cradle and the second recess is formed in a second surface of the cradle; and the first surface faces the second surface.

13. The attachment system of claim 12, wherein, when the cradle is coupled with the negative pressure wound therapy pump, the cradle is configured to support the plurality of protrusions within the plurality of recesses to support at least a portion of a weight of the negative pressure wound therapy device.

14. The attachment system of claim 12, comprising a plurality of closures configured to selectively secure the plurality of protrusions within the plurality of recesses so that the cradle is removably attached to the negative pressure wound therapy pump and supports the negative pressure wound therapy pump.

15. The attachment system of claim 14, wherein the plurality of closures comprise one or more latches.

16. The attachment system of claim 14, wherein the plurality of closures comprise one or more locks.

17. The attachment system of claim 12, comprising a plurality of closures configured to selectively secure the plurality of protrusions within the plurality of recesses so that the cradle is removably attached to the negative pressure wound therapy pump and supports the negative pressure wound therapy pump.

18. The attachment system of claim 12, wherein the plurality of recesses is configured to prevent incorrect placement of the plurality of protrusions within the plurality of recesses.

* * * * *